(12) United States Patent
Nagano et al.

(10) Patent No.: US 10,183,949 B2
(45) Date of Patent: Jan. 22, 2019

(54) PYRIMIDINONE DERIVATIVE HAVING AUTOTAXIN-INHIBITORY ACTIVITY

(71) Applicants: The University of Tokyo, Tokyo (JP); TOHOKU UNIVERSITY, Miyagi (JP); Shionogi & Co., Ltd., Osaka (JP)

(72) Inventors: Tetsuo Nagano, Tokyo (JP); Takayoshi Okabe, Tokyo (JP); Hirotatsu Kojima, Tokyo (JP); Mitsuyasu Kawaguchi, Tokyo (JP); Osamu Nureki, Tokyo (JP); Ryuichiro Ishitani, Tokyo (JP); Hiroshi Nishimasu, Tokyo (JP); Junken Aoki, Sendai (JP); Nobuyuki Tanaka, Toyonaka (JP); Yasuhiko Kanda, Toyonaka (JP); Yoshiyuki Kioi, Toyonaka (JP); Yusuke Tateno, Toyonaka (JP); Shiro Kida, Toyonaka (JP); Junji Yamane, Toyonaka (JP)

(73) Assignees: THE UNIVERSITY OF TOKYO, Tokyo (JP); TOHOKU UNIVERSITY, Miyagi (JP); SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/441,385

(22) Filed: Feb. 24, 2017

(65) Prior Publication Data

US 2017/0158704 A1 Jun. 8, 2017

Related U.S. Application Data

(63) Continuation-in-part of application No. PCT/JP2015/074522, filed on Aug. 28, 2015.

(30) Foreign Application Priority Data

Aug. 29, 2014 (JP) .................. 2014-176147
Apr. 28, 2015 (JP) .................. 2015-091959

(51) Int. Cl.

| C07D 491/107 | (2006.01) |
|---|---|
| C07D 239/47 | (2006.01) |
| C07D 239/36 | (2006.01) |
| C07D 405/12 | (2006.01) |
| C07D 401/12 | (2006.01) |
| C07D 403/06 | (2006.01) |
| C07D 413/06 | (2006.01) |
| C07D 471/08 | (2006.01) |
| C07D 409/12 | (2006.01) |

(Continued)

(52) U.S. Cl.
CPC ....... *C07D 491/107* (2013.01); *C07D 239/36* (2013.01); *C07D 239/47* (2013.01); *C07D 401/04* (2013.01); *C07D 401/12* (2013.01); *C07D 403/04* (2013.01); *C07D 403/06* (2013.01); *C07D 403/12* (2013.01); *C07D 405/12* (2013.01); *C07D 409/12* (2013.01); *C07D 413/06* (2013.01); *C07D 413/12* (2013.01); *C07D 417/12* (2013.01); *C07D 471/08* (2013.01); *C07D 471/10* (2013.01)

(58) Field of Classification Search
CPC .............. C07D 491/107; C07D 239/36; C07D 239/47; C07D 401/04; C07D 401/12; C07D 403/04; C07D 403/06; C07D 403/12; C07D 405/12; C07D 409/12; C07D 413/06; C07D 413/12; C07D 417/12; C07D 471/08; C07D 471/10
See application file for complete search history.

(56) References Cited

U.S. PATENT DOCUMENTS 4,786,638 A 11/1988 Bagli et al.
9,051,320 B1 * 6/2015 Evans .................. A61K 31/405
(Continued)

FOREIGN PATENT DOCUMENTS

DE 196 12 101 10/1997
EP 0 123 402 10/1984
(Continued)

OTHER PUBLICATIONS

CAS Registry No. 10071466-7 (1960).*
(Continued)

*Primary Examiner* — Alexander R Pagano
(74) *Attorney, Agent, or Firm* — Wenderoth, Lind & Ponack, L.L.P.

(57) ABSTRACT

A compound according to any one of formula (Ia) to (Ic), or its pharmaceutically acceptable salt:

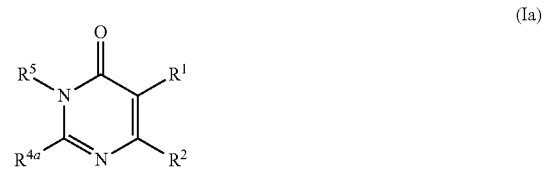

(Ia)

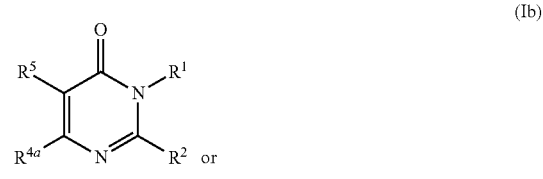

(Ib)

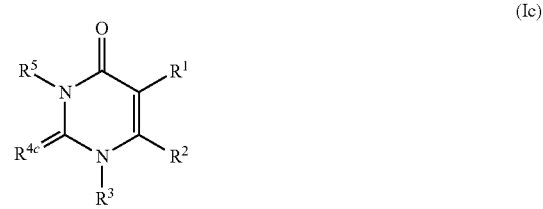

(Ic)

wherein $R^1$, $R^2$, $R^3$, $R^{4a}$, $R^{4c}$, $R^5$ are as defined in the description.

16 Claims, No Drawings

(51) Int. Cl.
*C07D 417/12* (2006.01)
*C07D 413/12* (2006.01)
*C07D 403/12* (2006.01)
*C07D 401/04* (2006.01)
*C07D 403/04* (2006.01)
*C07D 471/10* (2006.01)

(56) References Cited

U.S. PATENT DOCUMENTS

| | | |
|---|---|---|
| 2006/0025405 A1 | 2/2006 | Clark et al. |
| 2009/0069289 A1 | 3/2009 | Neagu et al. |
| 2016/0002247 A1 | 1/2016 | Nagano et al. |

FOREIGN PATENT DOCUMENTS

| | | |
|---|---|---|
| EP | 0 168 262 | 1/1986 |
| EP | 1 092 718 | 4/2001 |
| JP | 05043555 A * | 5/1993 |
| WO | 93/01198 | 1/1993 |
| WO | 00/29387 | 5/2000 |
| WO | 01/68613 | 9/2001 |
| WO | 03/039539 | 5/2003 |
| WO | 2007/062370 | 5/2007 |
| WO | 2007/146761 | 12/2007 |
| WO | 2008/043031 | 4/2008 |
| WO | 2010/022358 | 2/2010 |
| WO | 2011/015641 | 2/2011 |
| WO | 2012/129074 | 9/2012 |
| WO | 2015/064714 | 5/2015 |

OTHER PUBLICATIONS

CAS Registry Nos. (2006).*
CAS Registry Nos. (2011).*
CAS Res. Nos. (Nov. 2010).*
CAS Registry No. 1707605-33-1 (May 2015).*
International Search Report dated Dec. 1, 2015 in corresponding International (PCT) Application No. PCT/JP2015/074522.
Written Opinion dated Dec. 1, 2015 in corresponding International (PCT) Application No. PCT/JP2015/074522.

Elbashir et al., "Duplexes of 21-nucleotide RNAs mediate RNA interference in cultured mammalian cells", Nature, 411:494-498 (2001).
Stella et al., "Synthesis of a 2,4,6-trisubstituted 5-cyano-pyrimidine library and evaluation of its immunosuppressive activity in a Mixed Lymphocyte Reaction assay", Bioorganic & Medicinal Chemistry, 21(5):1209-1218 (2013).
Al Rawi et al., Journal de la Societe Chimique de Tunisie, 2(8):13-17 (1988).
Hajjem et al., Journal de la Societe Chimique de Tunisie, 2(2):15-21 (1985).
Nilov et al., "Oxidation of Adenosine and Inosine: The Chemistry of 8-Oxo-7,8-dihydropurines, Purine Iminoquinones, and Purine Quinones as Observed by Ultrafast Spectroscopy", Journal of the American Chemical Society, 135(9):3423-3438 (2013).
Cook et al., "Experiments in the Piperidine Series. Part I", Journal of the Chemical Society, pp. 399-402 (1945).
Andrews et al., "Design and synthesis of piperazinylpyrimidinones as novel selective 5-$HT_{2c}$ agonists", Bioorganic & Medicinal Chemistry Letters, 19(18):5346-5350 (2009).
Saito et al., "Thermal or Lewis acid-promoted electrocyclisation and hetero Diels-Alder cycloaddition of α,β unsaturated (conjugated) carbodiimides: a facile synthesis of nitrogen-containing heterocycles", Journal of the Chemical Society, Perkin Transactions 1: Organic and Bio-Organic Chemistry, 18:3065-3080 (1998).
Nugent et al., "New Anti-Inflammatory/Anti-Arthritic Heterocyclic Bisphosphonates", Phosphorus, Sulfur, and Silicon, 109-110:229-232 (1996).
Extended European Search Report dated Apr. 9, 2018 in European Application No. 15836638.5.
Cernova et al., "Regioselective Direct C-H Arylations of Protected Uracils. Synthesis of 5-and 6-Aryluracil Bases", The Journal of Organic Chemistry, vol. 76, 2011, pp. 5309-5319.
Cheng et al., "Regioselective acylation of uracil and 4-pyridone derivatives via copper(I) bromide mediated C-H bond activation", Tetrahedron, vol. 69, 2013, pp. 1387-1396.
Parrill et al., "Autotaxin inhibitors: a perspective on initial medicinal chemistry efforts", Expert Opinion on Therapeutic Patents, vol. 20, No. 12, 2010, pp. 1619-1625.

* cited by examiner

PYRIMIDINONE DERIVATIVE HAVING AUTOTAXIN-INHIBITORY ACTIVITY

TECHNICAL FIELD

The present invention provides pyrimidinone derivatives having autotaxin inhibitory activity, and a pharmaceutical composition comprising said pyrimidinone derivatives as an active ingredient.

BACKGROUND ART

Lysophosphatidic acid (LPA) is a lipid mediator that exhibits a variety of effects, such as cell proliferation, intracellular calcium influx, cytoskeletal changes, cell migration, via signal transduction through G protein-coupled receptor expressed on cell surface (LPA1-6). It has been reported that the lipid is involved in abnormalities of living body, such as fibrosis, pain, cancer, inflammation, arteriosclerosis (Non-Patent Document 1).

LPA can be biosynthesized by several metabolic pathways, primarily via hydrolysis of lysophosphatidylcholine by autotaxin (ENPP2, ATX). ATX is a secreted protein of ENPP (Ectonucleotide pyrophosphatase and phosphodiesterase) family (ENPP1-7) and referred to as ENPP2. ATX is the only one of this family that has a lysophospholipase D activity and thus is involved in LPA production. It has been reported that inhibiting the enzyme activity of ATX to inhibit LPA production is effective in the treatment of fibrotic diseases (Non-patent Document 1).

Fibrosis can occur in any organ, and the mechanism of its progression is common regardless of the trigger involved.

Animal tissues and organs maintain its structure with fibers such as collagen, and injured tissues and orgens are restored to the original condition through the process of wound healing with collagen production. However, in case where the tissue receives immunological, chemical, mechanical, metabolic or other injuries repeatedly or experiences a greater degree of injury, excessive accumulation of fibrous connective tissue may occur. Accumulation of such connective tissue is irreversible, and fibers abnormally increased cause fibrosis that is associated with dysfunction of tissues and organs.

Pathological feature of chronic kidney disease includes renal glomerular fibrosis and tubulointerstitial fibrosis. Dropout and fibrosis of parenchymal cells prevail in the pathology of end-stage renal failure. In chronic kidney disease patients having tubulointerstitial fibrosis, the progress to renal failure is faster as compared to chronic kidney disease patients without such fibrosis.

For preventing and treating chronic kidney disease, treatments with an antihypertensive drug, such as angiotensin receptor antagonists and calcium antagonists, have been practiced, as well as advice on daily living and dietary. However, the effect from such conventional treatments is not enough to be satisfied, and there still exists an ongoing need for new drugs to make prevention and treatment more effective.

Patent Documents 1 and 2 disclose pyrimidinone derivatives that are glucocorticoid modulators.

Patent Document 3 discloses pyrimidinone derivatives that are anti-HIV agents.

Patent Document 4 discloses pyrimidinone derivatives that are a calcium receptor inhibitor.

Patent Documents 5 and 6 disclose pyrimidinone derivatives that are an endothelin receptor inhibitor.

Patent Document 7 discloses pyrimidinone derivatives that are an aldose reductase inhibitor.

Non-Patent Document 2 discloses pyrimidinone derivatives having immunosuppressive activity.

Patent Document 8 disclosed dihydroprinon derivatives that are phosphodiesterase.

Patent Documents 9-11 disclose 2-(benzimidazole-yl) purinone derivatives as immunosuppressive agents.

Non-Patent Documents 3-5 disclose dihydropurinone derivatives.

Non-Patent Document 6 disclose tetrahydropyridinopyrimidine derivatives.

However, it is not described or suggested that such compounds inhibit autotaxin or may be a therapeutic agent for chronic kidney disease.

On the other hand, Patent Documents 12 and 13 discloses imidazopyridinone derivatives having an inhibitory activity on autotaxin.

PRIOR ART DOCUMENTS

Patent Documents

[Patent Document 1] WO2012/129074
[Patent Document 2] US Patent Application Publication 2006/025405
[Patent Document 3] WO2011/15641
[Patent Document 4] WO2007/62370
[Patent Document 5] WO2003/39539
[Patent Document 6] German Patent Application Publication 19612101.
[Patent Document 7] U.S. Pat. No. 4,786,638
[Patent Document 8] European Patent Application Publication 1092718
[Patent Document 9] US Patent Application Publication 2009/0069289
[Patent Document 10] WO2010/0022358
[Patent Document 11] WO2008/043031
[Patent Document 12] WO2014/133112
[Patent Document 13] WO2015/064714

Non-Patent Documents

[Non-Patent Document 1] Nature, vol. 411, pp. 494-498 (2001)
[Non-patent Document 2] Bioorganic & Medicinal Chemistry, vol. 21, issue: 4, pp. 1209-1218, 2013
[Non-patent Document 3] Journal de la Societe Chimique de Tunisie, Volume: 2, Issue: 8, Pages: 13-17, Journal, 1988
[Non-patent Document 4] Journal de la Societe. Chimique de Tunisie, Volume: 2, Issue: 2, Pages: 15-21, Journal, 1985
[Non-patent Document 5] Journal of the American Chemical Society, Volume: 135, Issue: 9, Pages: 3423-3438
[Non-patent Document 6] Journal of the Chemical Society, Pages: 399-402, Journal, 1945

SUMMARY OF INVENTION

Problem to be Solved by the Invention

The object of the present invention is to provide fused pyrazole derivatives having an excellent inhibitory activity on autotaxin.

Means for Solving the Problem

The present invention is based on the inventor's discovery of the fused pyrazole derivatives having an excellent inhibitory activity on autotaxin.

The present invention relates to the following.

(1') An autotaxin inhibitor comprising the compound according to any one of formula (Ia) to (Ic), or its pharmaceutically acceptable salt:

[Chemical Formula 1]

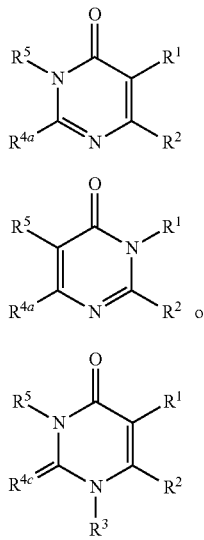

R[1] is hydrogen, halogen, hydroxy, cyano, formyl, carboxy, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl;

$R^2$, $R^3$ and $R^{4a}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted, alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfinyl or substituted or unsubstituted aromatic heterocyclylsulfinyl (provided that at least one of $R^1$, $R^2$ and $R^{4a}$ is not hydrogen);

$R^{4c}$ is O or N ($R^9$), $R^9$ is hydrogen, substituted or unsubstituted alkyl or substituted or unsubstituted alkyloxy, $R^5$ is a group represented by formula: $R^{11}$—$(C(R^{10a})(R^{10b}))_m$- wherein $R^{10a}$ and $R^{10b}$ are each independently hydrogen, halogen or substituted or unsubstituted alkyl, or $R^{10a}$ and $R^{10b}$ attached to the same carbon may be taken together to form substituted or unsubstituted carbocycle or substituted or unsubstituted heterocycle, m is integer of 1 to 6, and $R^{11}$ is hydrogen, carboxy, substituted or unsubstituted aromatic carbocyclyl, substituted or unsubstituted aromatic heterocyclyl, substituted or unsubstituted non-aromatic carbocyclyl, substituted or unsubstituted non aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, or substituted or unsubstituted sulfamoyl.

(1") An autotaxin inhibitor comprising the compound according to any one of formula (Ia) to (Ic), or its pharmaceutically acceptable salt:

[Chemical Formula 2]

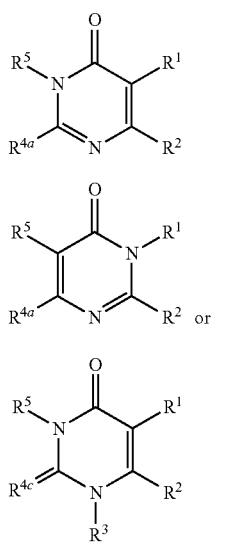

$R^1$ is hydrogen, halogen, hydroxy, cyano, formyl, carboxy, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl;

$R^2$, $R^3$ and $R^{4a}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfinyl (provided that at least one of $R^1$, $R^2$ and $R^{4a}$ is not hydrogen);

$R^{4c}$ is O or N ($R^9$), $R^9$ is hydrogen, substituted or unsubstituted alkyl or substituted or unsubstituted alkyloxy, $R^5$ is a group represented by formula: $R^{11}—(C(R^{10a})(R^{10b}))_m-$ wherein $R^{10a}$ are each independently hydrogen, halogen or substituted or unsubstituted alkyl, $R^{10b}$ are each independently hydrogen, halogen or substituted or unsubstituted alkyl, or $R^{10a}$ and $R^{10b}$ attached to the same carbon may be taken together to form substituted or unsubstituted carbocycle or a substituted or unsubstituted heterocycle, m is integer of 1 to 6, $R^{11}$ is hydrogen, carboxy, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, non-aromatic substituted or unsubstituted heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl, substituted or unsubstituted carbamoyl, substituted or unsubstituted sulfamoyl, or substituted or unsubstituted amino.

(2') The autotaxin inhibitor comprising the compound according to the above (1') to (1"), wherein $R^2$ is substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclyloxy, substituted or unsubstituted aromatic heterocyclyloxy, substituted or unsubstituted non-aromatic carbocyclyloxy, non-aromatic substituted or unsubstituted heterocyclyloxy, substituted or unsubstituted aromatic carbocyclylamino, substituted or unsubstituted aromatic heterocyclylamino, substituted or unsubstituted non-aromatic carbocyclylamino or substituted or unsubstituted non-aromatic heterocyclylamino, its pharmaceutically acceptable salt.

(3') The compound according to any one of formula (Ia) to (Ic), or its pharmaceutically acceptable salt:

[Chemical Formula 3]

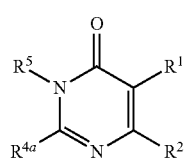

(Ia)

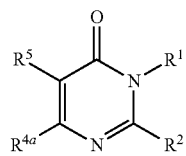

or (Ib)

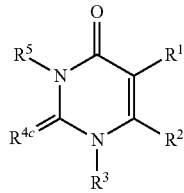

(Ic)

wherein $R^1$ is hydrogen, halogen, hydroxy, formyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl;

$R^2$ is a group represented by formula:

[Chemical Formula 4]

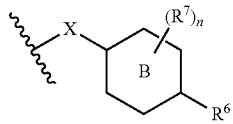

X is a single bond or O,

Ring B is a benzene ring, a 6-membered aromatic heterocycle, a non-aromatic carbocycle or 6-membered non-aromatic heterocycle, $R^6$ is halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, $R^7$ are each independently, halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, n is integer of 0 to 4, $R^3$ is substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted aromatic heterocyclylsulfonyl, substituted or unsubstituted non-aromatic carbocyclylsulfonyl or substituted or unsubstituted non-aromatic heterocyclylsulfonyl, $R^{4a}$ is halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclyl, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, a substituted or unsubstituted alkylsulfinyl, substituted or unsubstituted alkenylsulfinyl substituted, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, non-aromatic heterocyclylsulfonyl or substituted or unsubstituted aromatic heterocyclylsulfonyl, $R^{4c}$ is O or N ($R^9$), $R^9$ is hydrogen, substituted or unsubstituted alkyl or substituted or unsubstituted alkyloxy, $R^5$ is a group represented by formula: $R^{11}$—(C($R^{10a}$)($R^{10b}$))m- wherein $R^{10a}$ are each independently hydrogen, halogen or substituted or unsubstituted alkyl, $R^{10b}$ are each independently hydrogen, halogen or substituted or unsubstituted alkyl, or $R^{10a}$ and $R^{10b}$ attached to the same carbon may be taken together to form substituted or unsubstituted carbocycle or a substituted or unsubstituted heterocycle, m is integer of 1 to 6, $R^{11}$ is hydrogen, carboxy, substituted or unsubstituted aromatic carbocyclyl, substituted or unsubstituted aromatic heterocyclyl, substituted or unsubstituted non-aromatic carbocyclyl, substituted or unsubstituted non aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, non-aromatic substituted or unsubstituted heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, or substituted or unsubstituted sulfamoyl, provided that the following compounds (i) to (iii) are excluded.

(i) the compounds represented by formula (Ib), wherein (a) $R^1$ is hydrogen and $R^{11}$ is carboxy, unsubstituted methyloxycarbonyl or unsubstituted ethyloxycarbonyl, and wherein (b) $R^1$ is hydrogen, $R^{4a}$ is unsubstituted methyloxymethyl or unsubstituted methyl, and $R^{11}$ is substituted or unsubstituted phenyl, (ii) the compounds represented by formula (Ic), wherein (a) $R^2$ is methylphenyl, and $R^3$ is methylthiophenyl, and the compounds wherein (b) $R^3$ is methyl, and $R^{11}$ is piperazinyl substituted with naphthyl or isoquinolinyl, (iii) the compounds represented as follows:

[Chemical Formula 5]

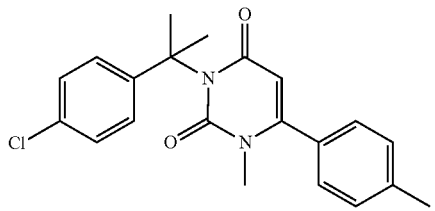

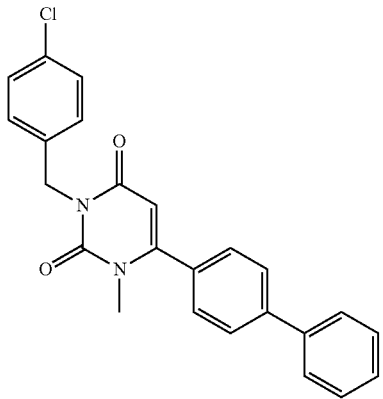

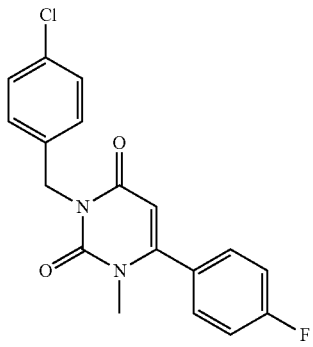

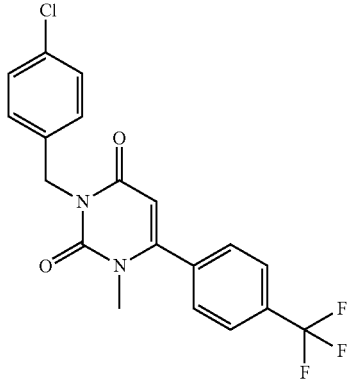

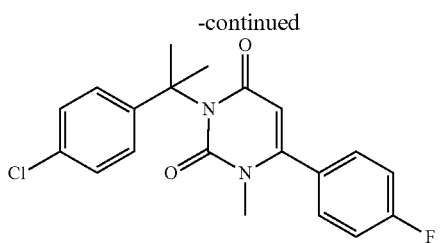

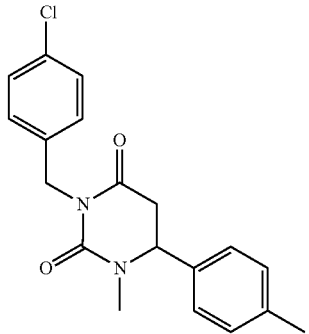

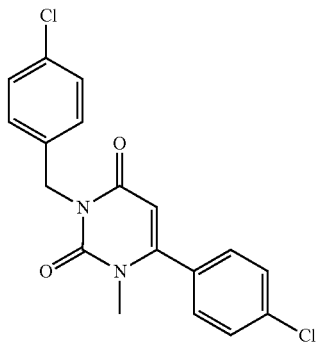

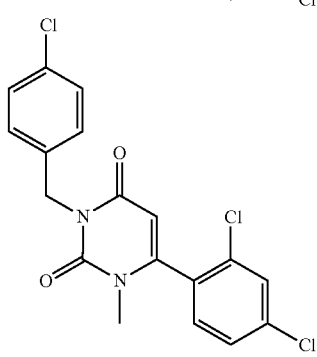

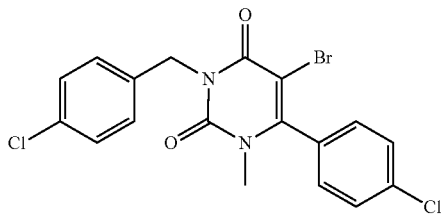

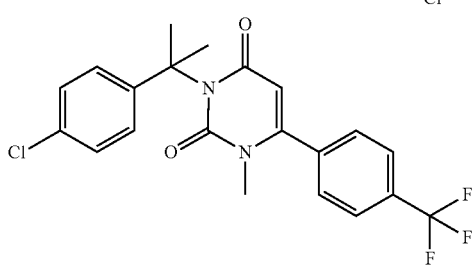

-continued
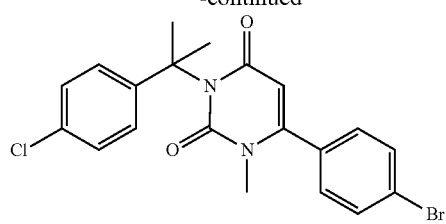
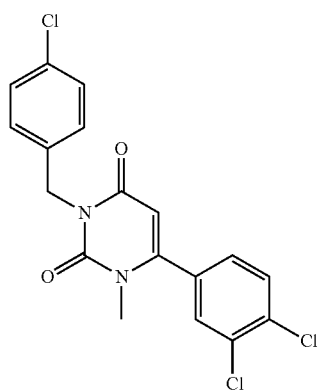
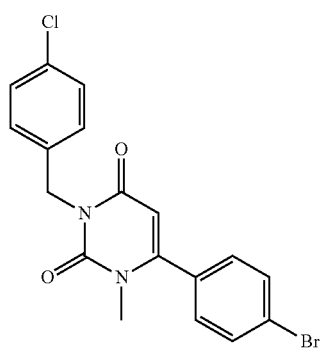
[Chemical Formula 6]
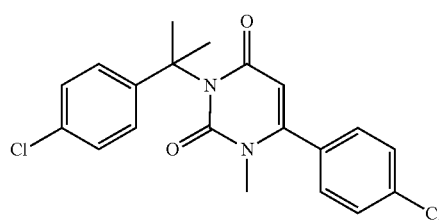
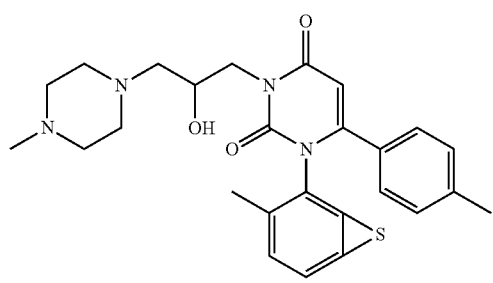
-continued
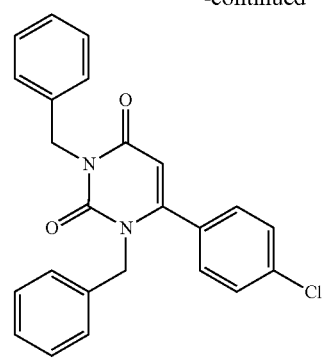
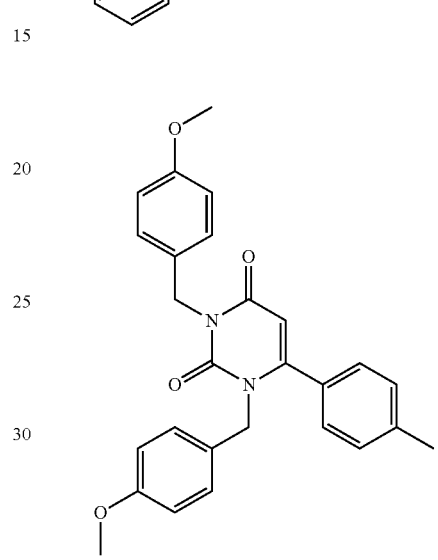
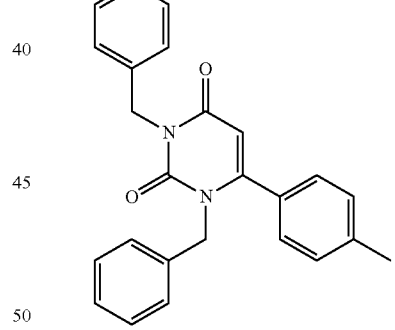
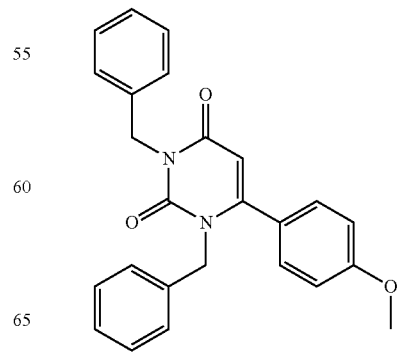

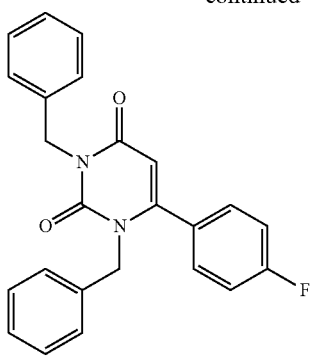

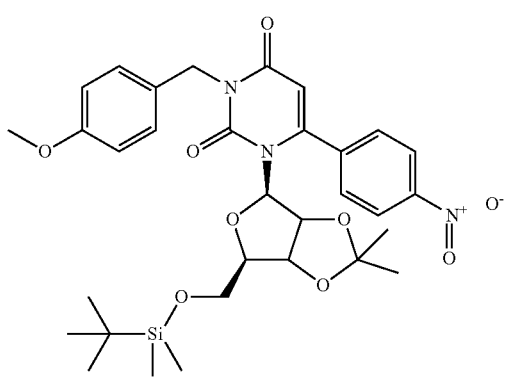

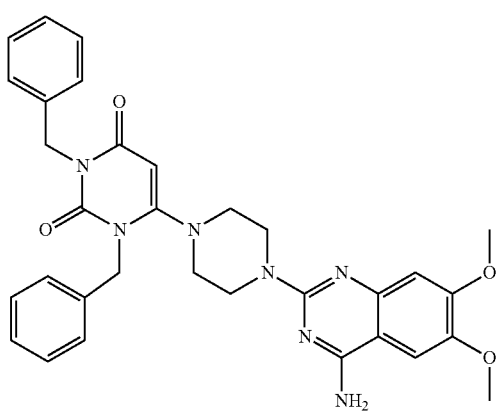

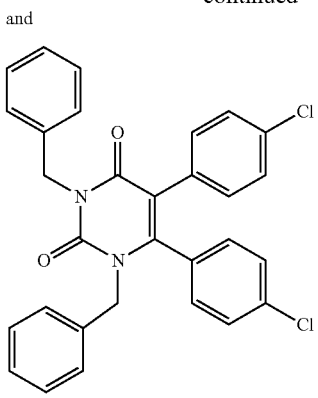

and (3″) A compound according to any one of formula (Ia) to (Ic), or its pharmaceutically acceptable salt:

[Chemical Formula 7]

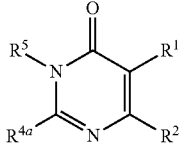
(Ia)

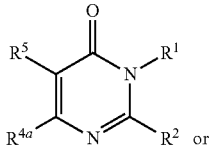
(Ib)

or

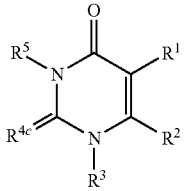
(Ic)

wherein $R^1$ is hydrogen, halogen, hydroxy, formyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl;

$R^2$ is a group represented by formula:

[Chemical Formula 8]

X is a single bond or O,

Ring B is a benzene ring, a 6-membered aromatic heterocycle, a non-aromatic carbocyclic or 6-membered non-aromatic heterocycle, $R^6$ is halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, $R^7$ are each independently, halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, n is integer of 0 to 4.

$R^3$ is substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted aromatic heterocyclylsulfonyl, substituted or unsubstituted non-aromatic carbocyclylsulfonyl or substituted or unsubstituted non-aromatic heterocyclylsulfonyl, $R^{4a}$ is halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted substituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclyl, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, a substituted or unsubstituted alkylsulfinyl, substituted or unsubstituted alkenylsulfinyl substituted, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, non-aromatic heterocyclylsulfonyl or substituted or unsubstituted aromatic heterocyclylsulfonyl, $R^{4c}$ is O or N ($R^9$), $R^9$ is hydrogen, substituted or unsubstituted alkyl or substituted or unsubstituted alkyloxy, $R^5$ is a group represented by formula: $R^{11}$—$(C(R^{10a})(R^{10b}))_m$- wherein $R^{10a}$ are each independently hydrogen, halogen or substituted or unsubstituted alkyl, $R^{10b}$ are each independently hydrogen, halogen or substituted or unsubstituted alkyl, or $R^{10a}$ and $R^{10b}$ attached to the same carbon may be taken together to form substituted or unsubstituted carbocycle or a substituted or unsubstituted heterocycle, m is integer of 1 to 6, $R^{11}$ is hydrogen, carboxy, substituted or unsubstituted aromatic carbocyclyl, substituted or unsubstituted aromatic heterocyclyl, substituted or unsubstituted non-aromatic carbocyclyl, substituted or unsubstituted non aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, non-aromatic substituted or unsubstituted heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, substituted or unsubstituted sulfamoyl or substituted or unsubstituted sulfamoyl, provided that the following compounds (i) to (iii) are excluded.

(i) the compounds represented by formula (Ib), wherein (a) $R^1$ is hydrogen and $R^{11}$ is carboxy, unsubstituted methyloxycarbonyl or unsubstituted ethyloxycarbonyl, and the compounds wherein (b) $R^1$ is hydrogen, $R^{4a}$ is unsubstituted methyloxymethyl or unsubstituted methyl, and $R^{11}$ is a substituted or unsubstituted phenyl, (ii) the compounds represented by formula (Ic), wherein (a) $R^2$ is unsubstituted methylphenyl, and $R^3$ is methylthiophenyl, and the compounds wherein (b) $R^3$ is unsubstituted methyl, and $R^{11}$ is piperazinyl substituted with unsubstituted naphthyl or unsubstituted isoquinolinyl, (iii) the compounds represented in the compounds represented by (iii) (Ia), wherein $R^1$ is hydrogen or cyano, $R^2$ is p-unsubstituted methyloxyphenyl, and $R^{4a}$ is unsubstituted methyl, (iv) the compounds represented as follows:

[Chemical Formula 9]

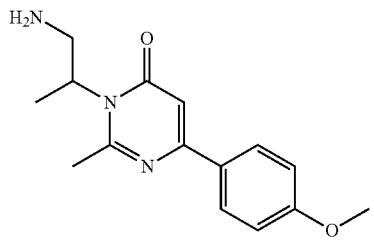

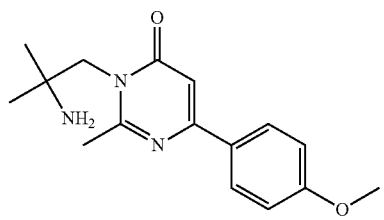

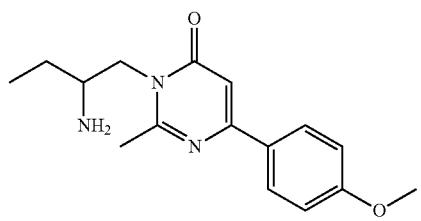

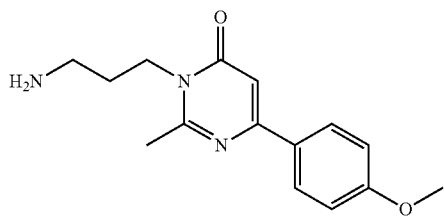

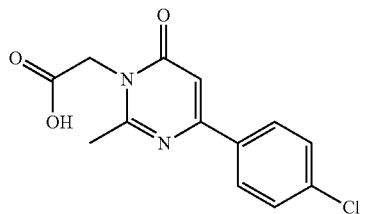

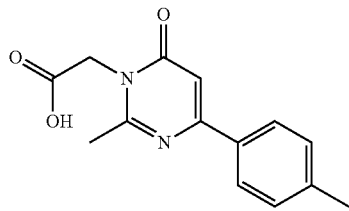

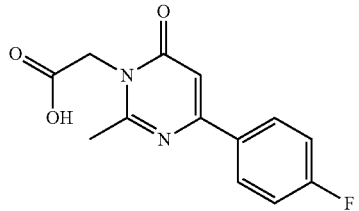

21
-continued
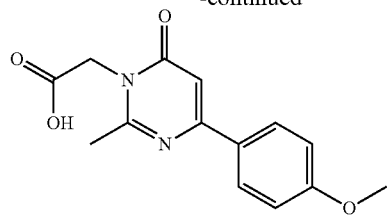
[Chemical Formula 10]
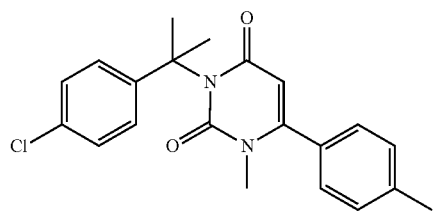
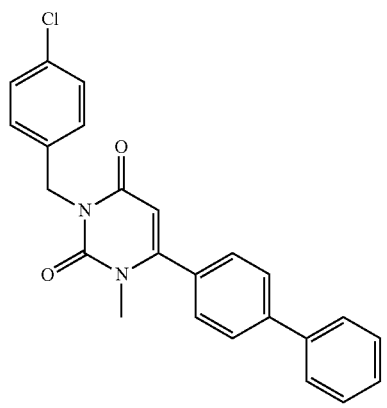
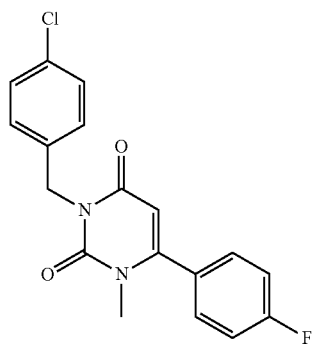
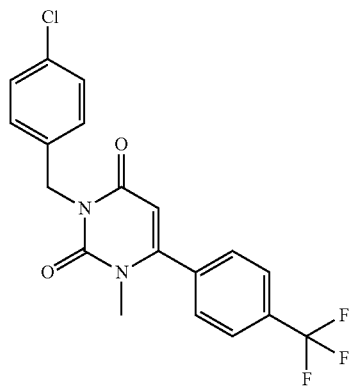
22
-continued
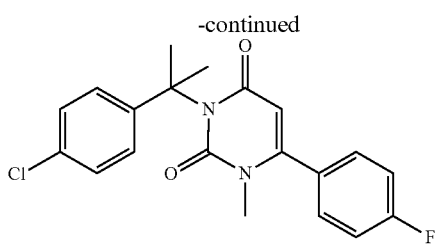
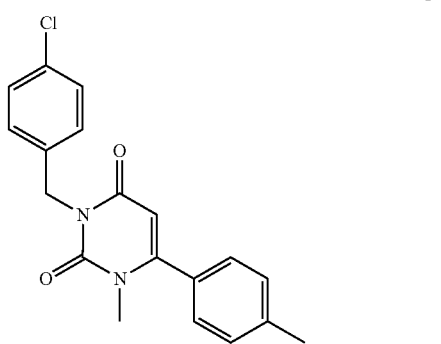
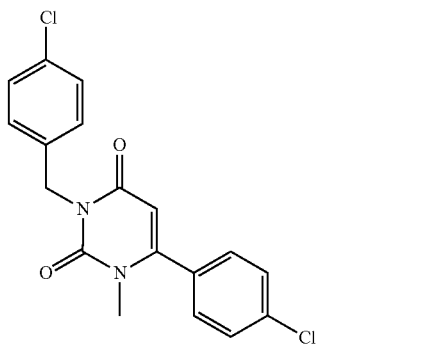
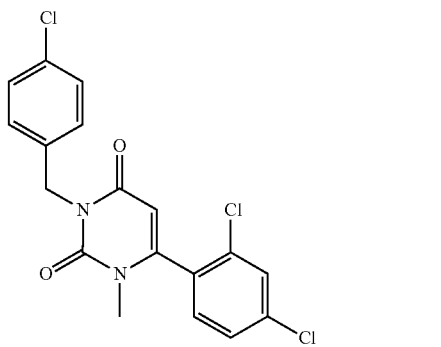
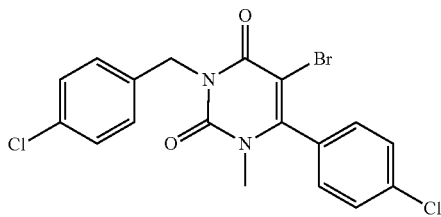
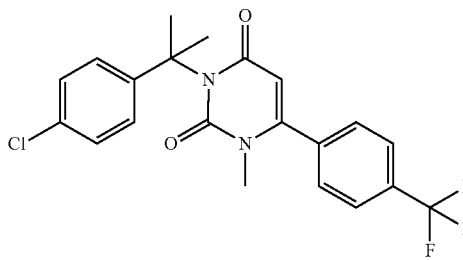

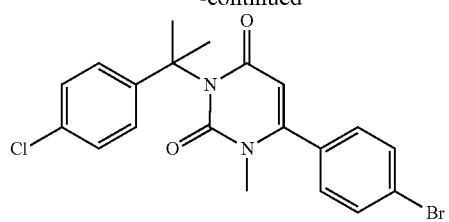
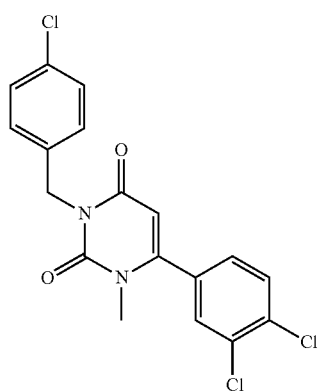
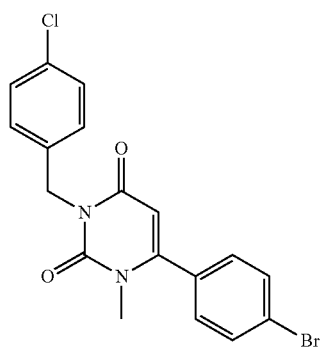
[Chemical Formula 11]
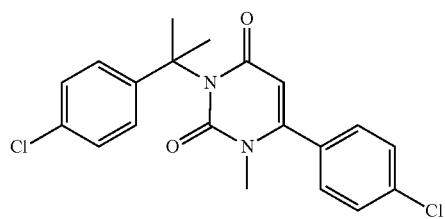
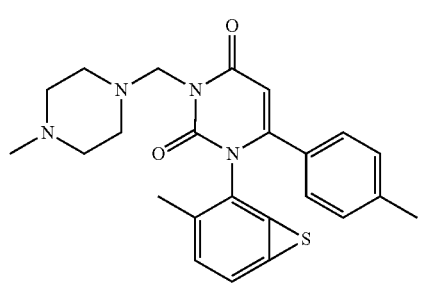
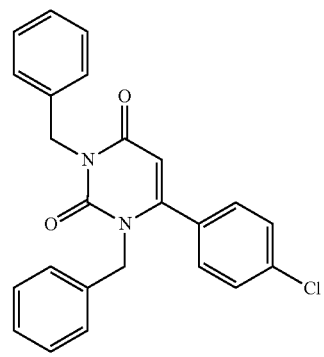
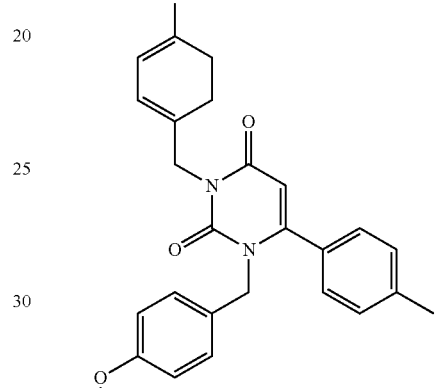
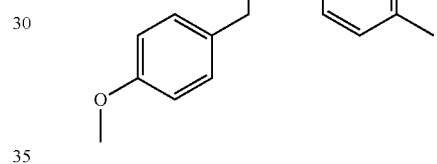
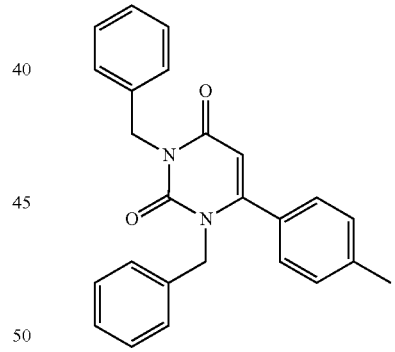
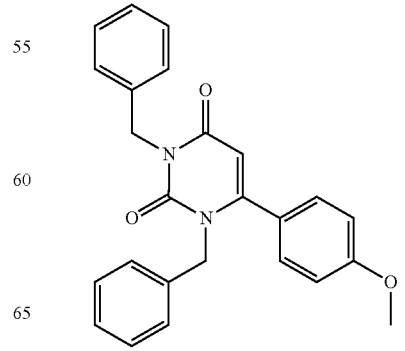

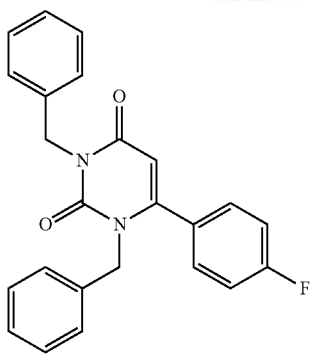

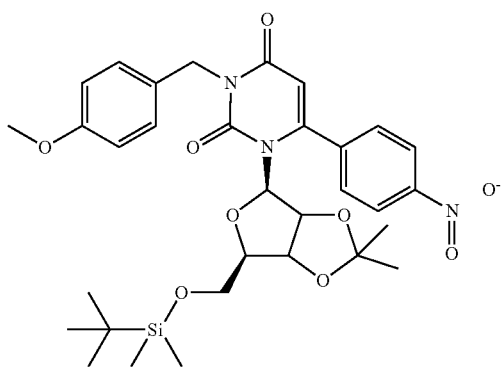

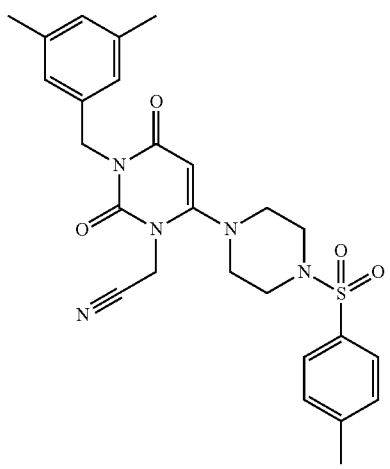

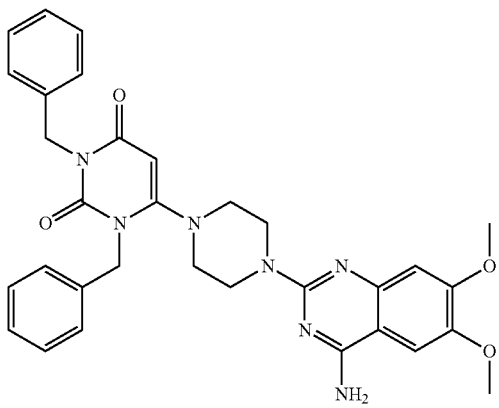

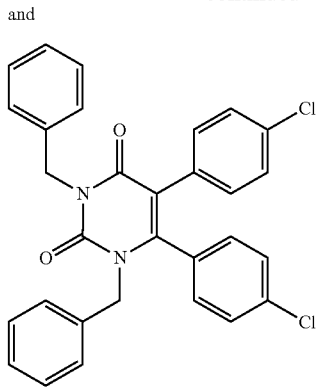

and (4') The compound according to the above (3') or (3"), represented by formula (Ia), or its pharmaceutically acceptable salt.

(5') The compound according to the above (3') or (3"), represented by formula (Ib), or its pharmaceutically acceptable salt.

(6') The compound according to the above (3') or (3"), represented by formula (Ic), or its pharmaceutically acceptable salt.

(7') The compound according to any one of the above (4') to (6'), wherein $R^1$ is hydrogen or halogen, or its pharmaceutically acceptable salt.

(8') The compound according to any one of the above (4') to (7'), wherein $R^{4a}$ is substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, or substituted or unsubstituted alkynylthio, its pharmaceutically acceptable salt.

(9') The compound according to the above (8'), wherein $R^{4a}$ is alkyl optionally substituted with one or more substitutent(s) selected from the Substituent group α (cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy, substituted or unsubstituted non-aromatic heterocyclylalkyloxy and substituted or unsubstituted aromatic heterocyclylalkyloxy), alkenyl optionally substituted with one or more substitutent(s) selected from the Substituent group α, alkynyl optionally substituted with one or more substitutent(s) selected from the Substituent group α, alkylamino optionally substituted with one or more substitutent(s) selected from the Substituent group α, alkenylamino optionally substituted with one or more substitutent(s) selected from the Substituent group α, alkynylamino optionally substituted with one or more substitutent(s) selected from the Substituent group α, alkyloxy optionally substituted with one or more substitutent(s) selected from the Substituent group α, alkenyloxy optionally substituted with one or more substitutent(s) selected from the Substituent group α, alkynyloxy optionally substituted with one or more substitutent(s) selected from the Substituent group α, alkylthio optionally substituted with one or more substitutent(s) selected from the Substituent group α, alkenylthio optionally substituted with one or more substitutent(s) selected from the Substituent group α, alkynylthio optionally substituted with one or more substitutent(s) selected from the Substituent group α, its pharmaceutically acceptable salt.

(10') The compound according to any one of the above (4') to (9'), wherein $R^{11}$ is carboxy, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl or substituted or unsubstituted sulfamoyl, its pharmaceutically acceptable salt.

(11') The compound according to the above (10'), wherein $R^{11}$ is substituted or unsubstituted aromatic carbocyclyl, substituted or unsubstituted aromatic heterocyclyl, substituted or unsubstituted non-aromatic carbocyclyl, or substituted or unsubstituted non-aromatic heterocyclyl, or its pharmaceutically acceptable salt.

(12') The compound according to the above (11'), wherein $R^{11}$ is aromatic carbocyclyl substituted with one or more substitutent(s) selected from the Substituent group β (carboxy, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, a substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, and substituted or unsubstituted aromatic carbocyclylsulfonyl), aromatic heterocyclyl substituted with one or more substitutent(s) selected from the Substituent group β, non-aromatic carbocyclyl substituted with one or more substitutent(s) selected from the Substituent group β, or non-aromatic heterocyclyl substituted with one or more substitutent(s) selected from the Substituent group β, or its pharmaceutically acceptable salt.

(13') The compound according to the above (10'), wherein $R^{11}$ is substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl or substituted or unsubstituted sulfamoyl, or its pharmaceutically acceptable salt.

(14') The compound according to the above (10'), wherein $R^{11}$ is carbamoyl optionally substituted with one or more substitutent(s) selected from the Substituent group α (substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl and substituted or unsubstituted non-aromatic heterocyclyl), or its pharmaceutically acceptable salt.

(15') The compound according to the above (5'), wherein $R^1$ is hydrogen, $R^{4a}$ is substituted or unsubstituted C2-C10 alkyl, substituted or unsubstituted alkenyl or substituted or unsubstituted alkynyl, or its pharmaceutically acceptable salt.

(16') The compound according to the above (6'), wherein $R^1$ is hydrogen, $R^3$ is substituted methyl, substituted or unsubstituted C2-C10 alkyl, substituted or unsubstituted alkenyl or substituted or unsubstituted alkynyl, or its pharmaceutically acceptable salt.

(17') A pharmaceutical composition comprising the compound according to any one of the above (3") and (3') to (16') or its pharmaceutically acceptable salt as an active ingredient.

(18') The pharmaceutical composition according to the above (17'), which is an autotaxin inhibitor.

(19') The pharmaceutical composition according to the above (17'), for the prevention or treatment of a disease related to autotaxin.

(20') Use of a compound according to any one of (2') to (16') or its pharmaceutically acceptable salt for the manufacture of a medicament for the prevention or treatment of a disease related to autotaxin.

(21') A method for the prevention or treatment of a disease related to autotaxin, which is characterized by administering the compound according to any one of (2') to (16') or its pharmaceutically acceptable salt.

Effect of the Invention

The compound of the present invention exhibits excellent autotaxin inhibitory activity, and is useful for the prevention or treatment of a disease, especially, related to autotaxin.

DESCRIPTION OF EMBODIMENTS

The definitions of the terms as used herein are as follows. Unless specified otherwise, these terms are used alone or in combination with another term in the meaning as defined.

"Halogen" includes fluorine, chlorine, bromine and iodine. Fluorine and chlorine are particularly preferable.

"Alkyl" means a straight or branched hydrocarbon group having 1 to 10 carbon atoms, and includes alkyl of 1 to 6 carbon atoms, alkyl of 1 to 4 carbon atoms, and alkyl of 1 to 3 carbon atoms and the like. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

Specific examples of "C1-C2 alkyl" include methyl, and ethyl.

Specific examples of "C3-C10 alkyl" include n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

Specific examples of "alkyl" for $R^3$ include methyl, ethyl, n-propyl, isopropyl, n-butyl, isobutyl, sec-butyl, tert-butyl, n-pentyl, hexyl and the like.

Specific examples of "alkyl" for $R^{4a}$ include methyl, ethyl, n-propyl, isopropyl, n-butyl, isobutyl, sec-butyl, tert-butyl, n-pentyl, hexyl and the like. In particular, methyl, ethyl, n-propyl, n-butyl, n-pentyl, n-hexyl and the like is preferred.

Specific examples of "alkyl" for $R^{12}$ include methyl, ethyl, n-propyl, isopropyl, n-butyl, isobutyl, sec-butyl, tert-butyl and the like.

Specific examples of "alkyl" for $R^{13}$ include methyl, ethyl, n-propyl, isopropyl, n-butyl, isobutyl, sec-butyl, tert-butyl and the like.

Specific examples of "C3-C10 alkyl" for $R^{12}$ include n-propyl, isopropyl, n-butyl, isobutyl, sec-butyl, tert-butyl, n-pentyl, n-hexyl and the like. In particular, n-propyl, n-butyl, n-pentyl, n-hexyl and the like is preferred.

The alkyl moiety of "alkyloxy", "alkyloxycarbonyl", "alkylcarbonyl", "alkylsulfinyl", "alkylsulfonyl", and "alkylthio" is as defined above "alkyl".

Examples of "alkyloxy" include methyloxy, ethyloxy, n-propyloxy, isopropyloxy, n-butyloxy, isobutyloxy, sec-butyloxy, tert-butyloxy, n-pentyloxy, n-hexyloxy, n-heptyloxy, n-octyloxy, isobutylmethylhexyloxy, n-nonyloxy and the like. In particular, methyloxy, ethyloxy, n-propyloxy, isopropyloxy and the like is preferred.

Specific examples of "alkyloxy" for $R^{4a}$ include n-propyloxy, n-pentyloxy, and n-hexyoxyl and the like.

Examples of "alkylthio" include methylthio, ethylthio, n-propylthio, isopropylthio, n-butylthio, isobutylthio, sec-butylthio, tert-butylthio, n-pentylthio, n-hexylthio, n-heptylthio, n-octylthio, isobutylmethylhexylthio, n-nonylthio and the like. In particular, methylthio, ethylthio, n-propylthio, isopropylthio and the like is preferred.

Specific examples of "alkylthio" for $R^{4a}$ include methylthio.

Specific examples of "alkyloxycarbonyl" for $R^{12}$ include methyloxycarbonyl, ethyloxycarbonyl, isopropyloxycarbonyl, tert-butyloxycarbonyl and the like.

Specific examples of "alkylcarbonyl" for $R^{12}$ include methylcarbonyl, ethylcarbonyl, n-propylcarbonyl, isopropylcarbonyl, n-butylcarbonyl and the like.

Specific examples of "alkylsulfonyl" for $R^{12}$ include methylsulfonyl, ethylsulfonyl and the like.

"Haloalkyl" and "haloalkyloxy" mean respectively the alkyl moiety of alkyl and alkyloxy "Haloalkyl" and "haloalkyloxy" mean respectively alkyl and alkyloxy substituted with 1 to 5, preferably 1 to 3, "halogen" at a substitutable position.

Specific examples of "haloalkyl" for $R^{4a}$ include monohaloalkyl, dihaloalkyl, and trihaloalkyl and the like. In particular, monofluoromethyl, monochrolomethyl, dichloromethyl, difluoromethyl, trufluoromonochloromethyl, trufluoromethyl, trifluoroethyl, trifluoropropyl, trifluorobutyl, trufluoropentyl are preferred.

"Alkenyl" means a linear or branched hydrocarbon group having 2 to 10 carbon atoms and one or more double bonds at any position, and includes alkenyl of 2 to 8 carbon atoms, alkenyl of 2 to 6. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

Specific examples of "C3-C10 alkenyl" include propenyl, isopropenyl, buteny), isobutenyl, prenyl, butadienyl, pentenyl, isopentenyl, pentadienyl, hexenyl, isohexenyl, hexadienyl, heptenyl, octenyl, nonenyl, decenyl and the like.

The alkenyl moiety of "alkenyloxy", "alkenyloxycarbonyl", "alkenyl carbonyl", "alkenylsulfinyl", "alkenylsulfonyl" and "alkenylthio" has the same meaning as defined above "alkenyl".

"Alkynyl" means a linear or branched hydrocarbon group having 2 to 10 carbon atoms and one or more triple bonds at any position, and includes alkynyl of 2 to 6 carbon atoms, alkynyl of 2 to 4 carbon atoms. Examples include ethynyl, propynyl, butynyl, pentynyl, hexynyl, heptynyl, octynyl, nonynyl, decynyl and the like. Also, the alkynyl may further have a double bond, as well as one or more triple bonds at anyl position.

Specific examples of "C3-C10 alkynyl" include propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

The alkynyl moiety of "alkynyloxy", "alkynyloxycarbonyl", "alkynylcarbonyl", "alkynylsulfinyl", "alkynylsulfonyl" and "alkynylthio" has the same meaning as defined above "alkynyl".

"Non-aromatic carbocycle" means a saturated or unsaturated aliphatic hydrocarbon cycle which is monocyclic or fused cyclic. Examples include cyclic saturated C3 to C8 hydrocarbon (cycloalkane) or cyclic unsaturated C3 to C8 hydrocarbon (cycloalkene), or a ring wherein such cyclic hydrocarbon is fused with further 3- to 8-membered rings one or two.

"Cycloalkane" includes monocyclic or polycyclic saturated carbocycle having 3 to 10 carbon atoms. Specific examples of the monocyclic cycloalkane include cyclopropane, cyclobutane, cyclopentane, cyclohexane, cycloheptane, cyclooctane, cycloonane, cyclodecane and the like. Specific examples of polycyclic cycloalkane include norbornane, tetrahydronaphthalene, adamantane and the like.

"Cycloalkene" includes monocyclic or polycyclic carbocycle having 3 to 10 carbon atoms and one or more double bonds at any position. Specific examples of the monocyclic cycloalkene include cyclopentene, cyclohexene and the like. Specific examples of polycyclic cycloalkene include norbornene, indene and the like.

The term "cycloalkyl" includes a monovalent group derived from "cycloalkane" as defined above. Monocyclic cycloalkyl includes, for example, cyclopropyl, cyclobutyl, cyclopentyl, cyclohexyl, cycloheptyl, cyclooctyl, cyclononyl, cyclodecyl, etc. Polycyclic cycloalkyl includes norbornyl, tetrahydronaphthalene-5-yl, tetrahydronaphthalene-6-yl, adamanty etc.

Examples of "cycloalkyl" are cyclopropyl, cyclobutyl, cyclopentyl, cyclohexyl cycloheptyl, cyclooctyl and the like. Especially preferable examples include C3 to C6 cycloalkyl, or C5 to C6 cycloalkyl.

The term "cycloalkenyl" includes a monovalent group derived from "cycloalkene" as defined above. Monocyclic cycloalkenyl includes cyclopentenyl, cyclohexenyl, etc. Polycyclic cycloalkenyl includes norbornenyl, indene-1-yl, indene-2-yl, indene-3-yl, etc. Especially preferable examples include C5 to C6 cycloalkenyl.

"Non-aromatic carbocyclyl" includes cyclic saturated hydrocarbon group having 3 to 8 carbon atoms, groups wherein such cyclic saturated hydrocarbon ring is fused with further one or two 3- to 8-membered rings and cyclic unsaturated aliphatic hydrocarbon groups having 3 to 8 carbon atoms, and groups wherein such cyclic unsaturated aliphatic hydrocarbon ring is fused with further one or two 3- to 8-membered rings.

Specific examples of the cyclic saturated hydrocarbon group having 3 to 8 carbon atoms include cyclopropyl, cyclobutyl, cyclopentyl, cyclohexyl, cycloheptyl, cyclooctyl. In particular, a cyclic saturated hydrocarbon group having 3 to 6 carbon atoms and a cyclic saturated hydrocarbon group having 5 or 6 carbon atoms are preferred.

Specific examples of the ring to be fused with the cyclic saturated hydrocarbon group having 3 to 8 carbon atoms include non-aromatic carbocyclic rings, such as cycloalkane ring (for example: cyclohexane, cyclopentane etc.) and cycloalkene ring (for example: cyclohexene, cyclopentene etc.); non-aromatic heterocyclic rings, such as piperidine ring, piperazine ring and morpholine ring etc. The cyclic saturated hydrocarbon group having 3 to 8 carbon atoms should be involved in the linkage of such fused ring.

Specific examples of the ring to be fused with the cyclic unsaturated aliphatic hydrocarbon group having 3 to 8 carbon atoms include carbocyclic rings: such as aromatic carbocyclic rings (for example: benzene ring, naphthalene ring) and non-aromatic carbocyclic rings (for example: cycloalkane rings such as cyclohexane ring and cyclopentane ring, cycloalkene rings such as cyclohexene ring and cyclopentene ring); and heterocyclic rings: such as aromatic heterocyclic rings (for example: pyridine ring, pyrimidine ring, pyrrole ring, imidazole ring) and non-aromatic heterocyclic rings (for example: piperidine ring, piperazine ring, morpholine ring). The cyclic unsaturated aliphatic hydrocarbon group having 3 to 8 carbon atoms should be involved in the linkage of such fused ring.

Examples of the non-aromatic carbocyclic group include the following groups. These groups may have a substituent at any substitutable position.

[Chemical Formula 12]

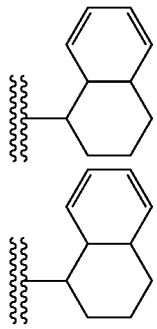
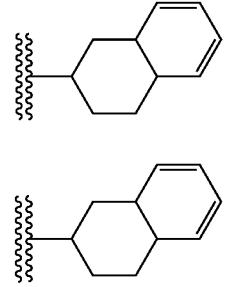

[Chemical Formula 13]

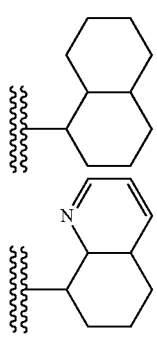
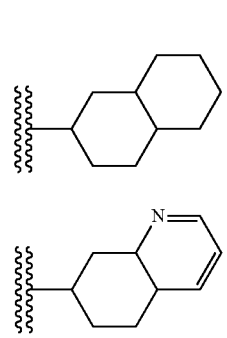

[Chemical Formula 14]

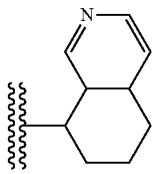
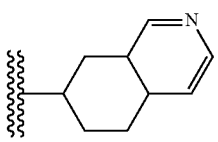

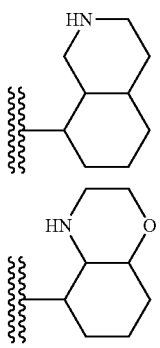
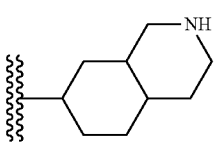

[Chemical Formula 15]

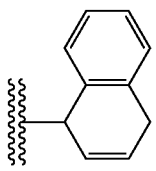
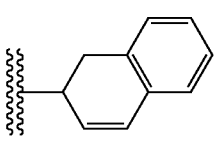

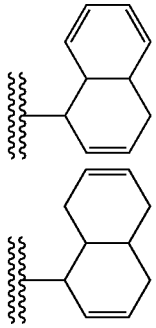
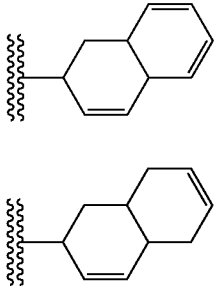

[Chemical Formula 16]

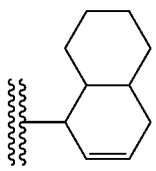
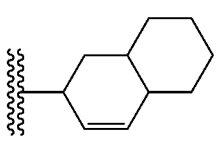

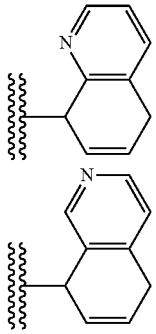
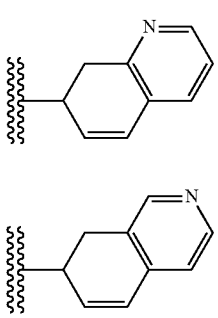

[Chemical Formula 17]

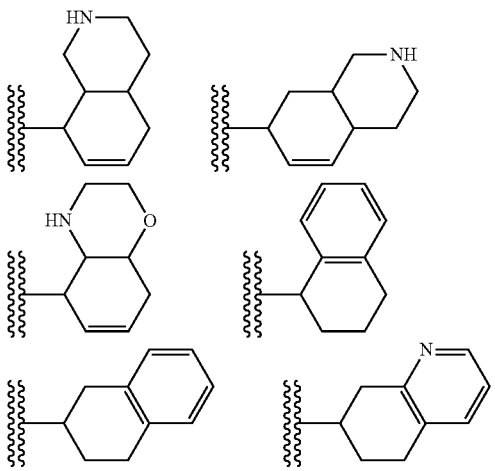

[Chemical Formula 18]

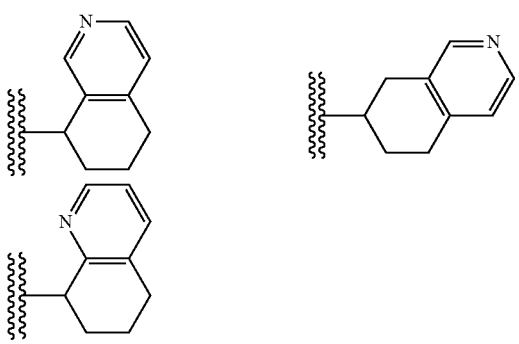

The non-aromatic carbocyclic ring moiety of "non-aromatic carbocyclyloxy", "non-aromatic carbocyclyloxycarbonyl", "non-aromatic carbocyclylcarbonyl", "non-aromatic amino", "non-aromatic carbocyclylsulfinyl", "non-aromatic carbocyclylsulfonyl", "non-aromatic carbocyclylthio", and the like is as defined above "non-aromatic carbocycle".

Specific examples of "non-aromatic carbocyclyl" for $R^2$ include, cyclopropyl, cyclobutyl, cyclopentyl, cyclohexyl, cyclohexenyl and the like are preferable. In particular, cyclohexyl, cyclohexenyl are preferable.

Specific examples of "non-aromatic carbocyclyloxy" for $R^2$ include, cyclopropyloxy, cyclobutyloxy, cyclopentyloxy, cyclohexyloxy, cyclohexenyloxy and the like are preferable. In particular, cyclohexyloxy, cyclohexenyloxy are preferable.

Specific examples of "non-aromatic carbocyclylcarbonyl" for $R^{11}$ include, cyclopropylcarbonyl, cyclobutylcarbonyl, cyclopentylcarbonyl, cyclohexylcarbonyl, cyclohexenylcarbonyl and the like are preferable. In particular, cyclohexylcarbonyl, cyclohexenylcarbonyl are preferable.

Specific examples of "non-aromatic carbocyclylcarbonyl" for $R^{13}$ include, cyclopropylcarbonyl, cyclobutylcarbonyl, cyclopentylcarbonyl, cyclohexylcarbonyl, and the like are preferable.

"Aromatic carbocycle" includes monocyclic or polycyclic aromatic carbocycle. Specific examples include benzene ring, naphthalene ring, anthracene ring and phenanthrene ring. Particularly, benzene ring is preferred.

"Aromatic carbocyclyl" includes monocyclic or polycyclic aromatic carbocyclic groups and groups wherein such monocyclic or polycyclic aromatic carbocyclic ring is fused with further one or two 3- to 8-membered rings. Specific examples of the monocyclic or polycyclic aromatic carbocyclic group include phenyl, naphthyl, anthryl and phenanthryl. Particularly, phenyl is preferred.

Specific examples of the ring to be fused with the monocyclic or polycyclic aromatic carbocyclic group include non-aromatic carbocycle such as cycloalkane rings (for example: cyclohexane ring, cyclopentane ring etc.), cycloalkene rings (for example: cyclohexene ring, cyclopentene ring etc.), and non-aromatic heterocycle (for example: piperidine ring, piperazine ring, morpholine ring etc). The monocyclic or polycyclic aromatic carbocyclyl should be involved in the linkage of such fused ring.

Examples of the aromatic carbocyclic groups include the following groups. These groups may have a substituent at any possible position.

[Chemical Formula 19]

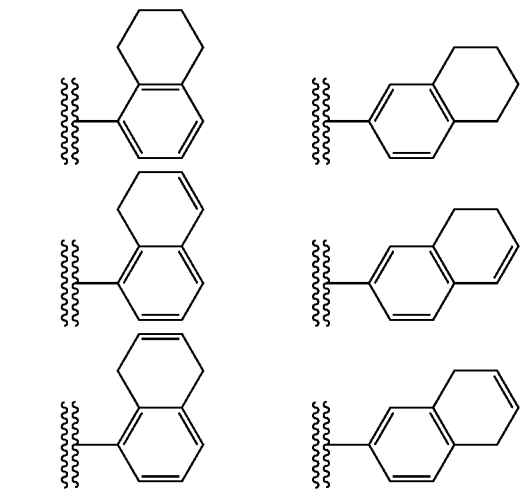

[Chemical Formula 20]

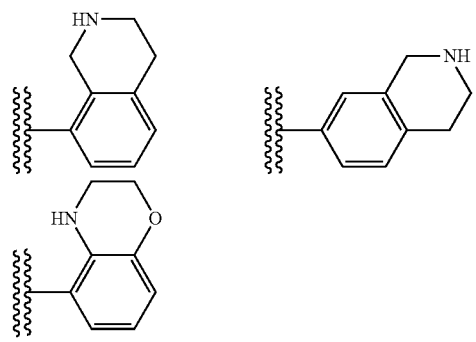

Specific examples of "aromatic carbocyclyl" for $R^2$ include phenyl, naphthyl, anthryl and phenanthryl and the like. In particular, phenyl is preferred.

Specific examples of "aromatic carbocyclyl" for $R^{11}$ include phenyl, naphthyl, anthryl and phenanthryl and the like. In particular, phenyl is preferred.

Specific examples of "aromatic carbocyclylcarbonyl" for $R^{11}$ include phenylcarbonyl, naphthylcarbonyl, anthrylcarbonyl and phenanthrylcarbonyl and the like. In particular, phenylcarbonyl is preferred.

The aromatic carbocycle moiety of "aromatic carbocyclyloxy", "aromatic carbocyclyloxycarbonyl", "aromatic carbocyclylcarbonyl", "aromatic carbocyclylamino", "aromatic carbocyclylsulfinyl", "aromatic carbocyclylsulfonyl", and "aromatic carbocyclylthio" and the like is as defined above "aromatic carbocycle".

Specific examples of "aromatic carbocyclylcarbonyl" for $R^{13}$ include phenylcarbonyl and the like.

"Aromatic heterocycle" means 5-6 membered aromatic ring having one or more heteroatoms selected from O, S and N in the ring.

Preferred examples of the aromatic heterocycle include monocyclic aromatic heterocycle such as pyrazole, tetrazole, furan, thiophene, pyridine, imidazole, triazole, triazine, pyridazine, pyrimidine, pyrazine, isoxazole, thiazole, isothiazole, thiadiazole, oxazole, oxadiazole and the like, fused aromatic heterocycle such as indole, isoindole, indazole, indolizine, quinoline, isoquinoline, cinnoline, phthalazine, quinazoline, naphthyridine, quinoxaline, purine, pteridine, benzimidazole, benzisoxazole, benzoxazole, benzimidazole oxadiazole, benzisothiazole, benzothiazole, benzothiadiazole, benzofuran, isobenzofuran, benzothiophene, benzotriazole, imidazopyridine, triazolopyridine, imidazothiazole, pyradinopyridazine, benzimidazoline and the like.

Specific examples of "aromatic heterocyclyl" for $R^{13}$ include pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like. Pyridyl are preferred, particularly 2-pyridyl, 3-pyridyl is more preferred.

"Non-aromatic heterocycle" includes 5-7 membered non-aromatic ring having at least one heteroatoms selected from O, S and N in the ring, non-aromatic ring wherein such non-aromatic heterocyclic rings are fused with further two or more rings, and fused ring wherein aromatic ring having 5-7 membered aromatic ring having at least one heteroatoms selected from O, S and N in the ring is fused with one or more the above "cycloalkane" or the above "cycloalkene", fused ring wherein non-aromatic ring having 5-7 membered aromatic ring having at least one heteroatoms selected from O, S and N in the ring is fused with one or more the above "aromatic carbocycle" or the above "aromatic heterocycle".

For example, preferred examples of the monocyclic non-aromatic heterocycle include pyrroline, pyrrolidine, imidazoline, imidazolidine, pyrazoline, pyrazolidine, piperidine, piperazine, morpholine, thiomorpholine, tetrahydropyran, dihydropyridine, dihydropyridazine, dihydropyrazine, dioxane, oxathiolane, thiane, tetrahydrofuran, tetrahydrothiazoline, tetrahydroisothiazolin.

For example, preferred examples of the fused non-aromatic heterocycle include indoline, isoindoline, benzopyran, benzodioxane, tetrahydroquinoline, benzo[d]oxazole-2(3H)-on, tetrahydrobenzothiophene.

"Aromatic heterocyclyl" means monocyclic or polycyclic aromatic heterocyclic groups having one or more heteroatoms selected from O, S and N in the ring and groups wherein such monocyclic or polycyclic aromatic heterocyclyl is fused with further one or two 3- to 8-membered rings.

Preferred examples of the monocyclic aromatic heterocyclyl include 5- or 6-membered aromatic heterocyclyl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like.

Preferred examples of the polycyclic aromatic heterocyclyl include aromatic heterocyclyl fused with a 5- or 6-membered ring, such as bicyclic aromatic heterocyclyl (for example: indolyl, isoindolyl, indazolyl, indolizinyl, quinolinyl, isoquinolinyl, cinnolinyl, phthalazinyl, quinazolinyl, naphthyridinyl, quinoxalinyl, purinyl, puteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyradinopyridazinyl, oxazolopyridyl, thiazolopyridyl etc.); and tricyclic aromatic heterocyclyl (for example: carbazolyl, acridinyl, xanthenyl, phenothiazinyl, phenoxathiinyl, phenoxazinyl, dibenzofuryl etc.). Any ring of the polycyclic aromatic heterocyclyl may be involved in the linkage.

Specific examples of the ring to be fused the monocyclic or polycyclic aromatic heterocyclic groups include non-aromatic carbocycle such as cycloalkane rings (for example: cyclohexane ring, cyclopentane ring etc.), cycloalkene rings (for example: cyclohexene ring, cyclo pentene ring etc.), non-aromatic heterocycle (for example, piperidine ring, piperazine ring, morpholine ring etc.). The monocyclic or polycyclic aromatic heterocyclyl should be involved in the linkage of such fused ring.

Examples of the aromatic heterocyclic groups include the following groups. These groups may have a substituent at any possible position.

[Chemical Formula 21]

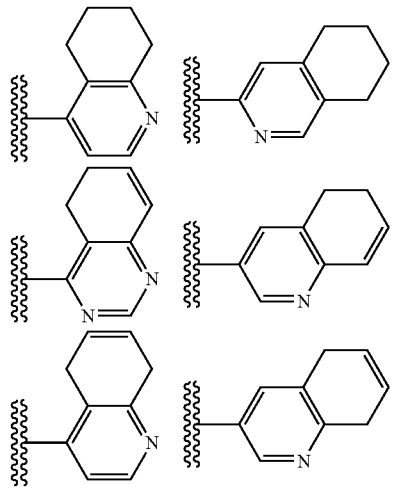

[Chemical Formula 22]

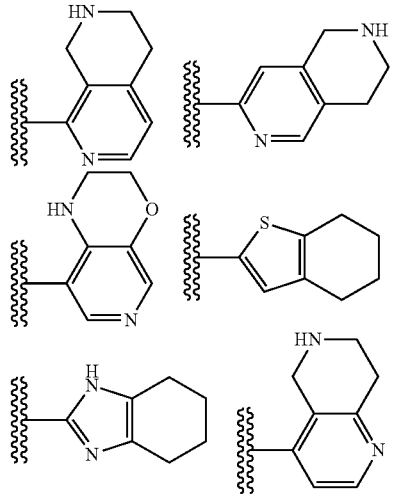

Specific examples of "aromatic heterocyclyl" for $R^2$ include pyrrolyl, imidazolyl, pyrazolyl, pyridyl, pyridadinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like. In particular, pyridyl is preferred.

Specific examples of "aromatic heterocyclyl" for $R^{11}$ include pyrrolyl, imidazolyl, pyrazolyl, pyridyl, pyridadinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like. In particular, pyridyl is preferred.

Specific examples of "aromatic heterocyclyl" for $R^{15}$ include pyrrolyl, imidazolyl, pyrazolyl, pyridyl, pyridadinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like. In particular, pyridyl is preferred. Moreover, 2-pyridyl and 3-pyridyl are more preferred.

Specific examples of "aromatic heterocyclylcarbonyl" for $R^{11}$ include pyrrolylcarbonyl, imidazolylcarbonyl, pyrazolylcarbonyl, pyridylcarbonyl, pyridadinylcarbonyl, pyrimidinylcarbonyl, pyrazinylcarbonyl, triazolylcarbonyl, triazinylcarbonyl, tetrazolylcarbonyl, isoxazolylcarbonyl, oxazolylcarbonyl, oxadiazolylcarbonyl, isothiazolylcarbonyl, thiazolylcarbonyl, thiadiazolylcarbonyl, furylcarbonyl, thienylcarbonyl and the like. In particular, pyridylcarbonyl is preferred.

Preferable examples of "aromatic heterocyclylcarbonyl" for $R^{13}$ are pyrazolylcarbonyl, thienylcarbonyl is preferred.

The aromatic heterocyclyl moiety of "aromatic heterocyclyloxy", "aromatic heterocyclyloxycarbonyl", "aromatic heterocyclylcarbonyl", "aromatic heterocyclylamino", "aromatic heterocyclylsulfinyl", "aromatic heterocyclylsulfonyl", and "aromatic heterocyclylthio" and the like is as defined above "aromatic heterocycle".

"Non-aromatic heterocyclyl" means non-aromatic heterocyclyl having one or more heteroatoms selected from O, S and N in the ring and non-aromatic group wherein such non-aromatic heterocyclyl is fused with further two 3- to 8-membered rings, and includes monocyclic non-aromatic hetelocyclyl or molycyclic non-aromatic hetelocyclyl.

Specific examples of the monocyclic non-aromatic heterocyclyl include dioxanyl, thiiranyl, oxiranyl, oxathioranyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperazino, morpholinyl, morpholino, oxadiadinyl, dihydropyridyl, thiomorpholinyl, thiomorpholino, tetrahydrofuryl, tetrahydropyranyl, tetrahydrothiazolyl, tetrahydroisothiazolyl, oxazolidyl, thiazolidyl and the like.

Specific examples of the polycyclic non-aromatic heterocyclyl include indolinyl, isoindolinyl, chromanyl, isochromanyl, isomannyl and the like. Any ring of the polycyclic non-aromatic heterocyclyl may be involved in the linkage.

Examples of the non-aromatic heterocyclyl include the following groups.

[Chemical Formula 23]

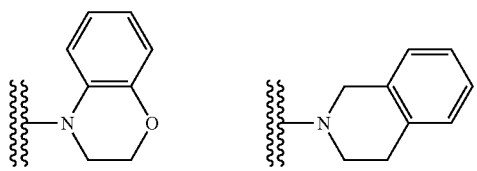

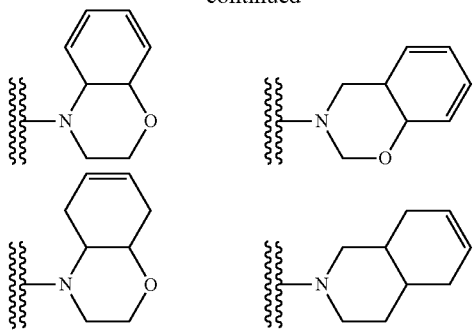

[Chemical Formula 24]

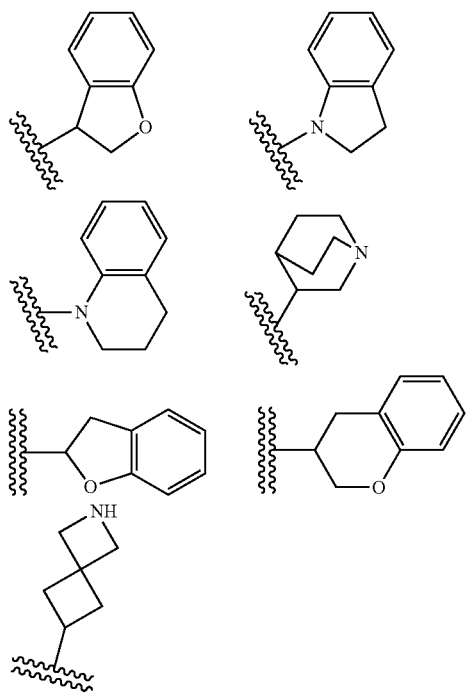

[Chemical Formula 25]

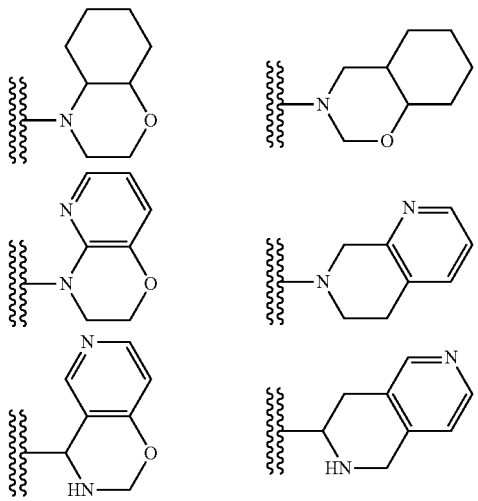

[Chemical Formula 26]

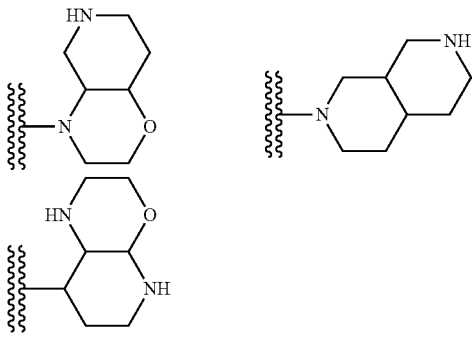

Specific examples of "non-aromatic heterocyclyl" for $R^1$ include azethidinyl, piperidyl, piperidino, piperazinyl, piperadino, morpholinyl, morpholino, pyrrolidinyl, azepanyl, isoindolinyl, 2-oxa-6-azaspiro[3.3] heptanyl etc. In particular, azethidinyl, piperidyl, piperidino, piperazinyl, piperadino and the like are preferred.

Specific examples of "non-aromatic heterocyclyl" for $R^2$ include azethidinyl, piperidyl, piperidino, piperazinyl, piperadino, morpholinyl, morpholino, 2-oxa-6-azaspiro[3.3] heptanyl and the like. In particular, azethidinyl, piperidyl, piperidino, piperazinyl, piperadino and the like are preferred.

Specific examples of "non-aromatic heterocyclylcarbonyl" for $R^{11}$ include, azethidinylcarbonyl, piperidylcarbonyl, piperidinocarbonyl, piperazinylcarbonyl, piperadinocarbonyl, morpholinylcarbonyl, morpholinocarbonyl and the like.

In particular, pyrrolidinylcarbonyl, piperidinylcarbonyl, piperazinylcarbonyl, morpholinylcarbonyl, morpholinocarbonyl, 2-oxa-6-azaspiro[3.3] hept-ylcarbonyl and the like are preferable.

In particular, pyrrolidinylcarbonyl, piperidinylcarbonyl, piperazinylcarbonyl, morpholinylcarbonyl, 2-oxa-6-azaspiro[3.3] hept-yl carbonyl and the like are preferable.

Specific examples of "non-aromatic heterocyclylcarbonyl" for $R^{13}$ include pyrrolidinylcarbonyl, imidazolidinylcarbonyl, tetrahydrothiophenylcarbonyl, piperidinylcarbonyl, piperazinylcarbonyl, morpholinylcarbonyl the like.

The non-aromatic heterocyclyl moiety of "non-aromatic heterocyclyloxy", "non-aromatic heterocyclyloxycarbonyl", "non-aromatic heterocyclylamino", "non-aromatic heterocyclylsulfinyl", "non-aromatic heterocyclylsulfonyl", and "non-aromatic heterocyclylthio" and the like is as defined above "aromatic heterocycle".

The substituted or unsubstituted non-aromatic carbocyclyl or substituted or unsubstituted non-aromatic heterocyclyl are optionally substituted with one or two oxo, thioxo or substituted or unsubstituted imino.

Examples of the substitutent for "substituted alkyl", "substituted alkenyl", "substituted alkynyl" include halogen, hydroxy, mercapto, nitro, nitroso, cyano, azido, formyl, carboxy, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylcarbonyloxy, substituted or unsubstituted alkenylcarbonyloxy, substituted or unsubstituted alkynylcarbonyloxy, substituted or unsubstituted alkylthio, substituted or unsubstituted substituted alkenylthio, substituted or unsubstituted alkynylthio, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted carbamoyl, substituted or unsubstituted sulfamoyl, substituted or unsubstituted amino, substituted or unsubstituted non-aromatic carbocyclyl, substituted or unsubstituted aromatic carbocyclyl, substituted or unsubstituted aromatic heterocyclyl, substituted or unsubstituted non-aromatic heterocyclyl, substituted or unsubstituted non-aromatic carbocyclyloxy, substituted or unsubstituted aromatic carbocyclyloxy, substituted or unsubstituted aromatic heterocyclyloxy, substituted or unsubstituted non-aromatic heterocyclyloxy, substituted or unsubstituted non-aromatic carbocyclylcarbonyl, substituted or unsubstituted aromatic carbocyclylcarbonyl, substituted or unsubstituted aromatic heterocyclylcarbonyl, substituted or non-aromatic heterocyclylcarbonyl substituted or unsubstituted non-aromatic carbocyclyloxycarbonyl, substituted or unsubstituted aromatic carbocyclyloxycarbonyl, substituted or unsubstituted aromatic heterocyclyloxycarbonyl, substituted or unsubstituted non-aromatic heterocyclyloxycarbonyl, substituted or unsubstituted non-aromatic carbocyclylcarbonyloxy, substituted or unsubstituted aromatic carbocyclylcarbonyloxy, substituted or unsubstituted aromatic heterocyclylcarbonyloxy, non-aromatic heterocyclylcarbonyloxy and the like. One or more of these substituents may occur at any substitutable position.

Furthermore, halogen, hydroxy, mercapto, nitro, nitroso, cyano, azido, formyl, carboxy, alkyloxy, alkenyloxy, alkynyloxy, alkylcarbonyl, alkenylcarbonyl, alkynylcarbonyl, alkyloxycarbonyl, alkenyloxycarbonyl, alkynyloxycarbonyl, alkylcarbonyloxy, alkenylcarbonyloxy, alkynylcarbonyloxy, alkylthio, alkenylthio, alkynylthio, alkylsulfinyl, alkenylsulfinyl, alkynylsulfinyl, alkylsulfonyl, alkenylsulfonyl, alkynylsulfonyl, carbamoyl, substituted carbamoyl, sulfamoyl, substituted sulfamoyl, amino, substituted amino, non-aromatic carbocyclyl, aromatic carbocyclyl, aromatic heterocyclyl, non-aromatic heterocyclyl, non-aromatic carbocyclyloxy, aromatic carbocyclyloxy, aromatic heterocyclyloxy, non-aromatic heterocyclyloxy, non-aromatic carbocyclylcarbonyl, aromatic carbocyclylcarbonyl, aromatic heterocyclylcarbonyl, non-aromatic heterocyclylcarbonyl, non-aromatic carbocyclyloxycarbonyl, aromatic carbocyclyloxycarbonyl, aromatic heterocyclyloxycarbonyl, non-aromatic heterocyclyloxycarbonyl, non-aromatic carbocyclylcarbonyloxy, aromatic carbocyclylcarbonyloxy, aromatic heterocyclylcarbonyloxy, non-aromatic heterocyclylcarbonyloxy and the like are preferable. One or more of these substituents may occur at any substitutable position.

Examples of the substitutent for "substituted C3-C10 alkyl", "substituted alkyloxy", "substituted C3-C10 alkenyl", "substituted alkynyloxy", "substituted alkenyloxy", "substituted C3-C10 alkynyl" is same.

Examples of the substitutent for "substituted non-aromatic carbocyclyl", "substituted aromatic carbocyclyl", "substituted aromatic heterocyclyl" or "substituted non-aromatic heterocyclyl" include halogen, cyano, hydroxy, formyl, carboxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or non-aromatic heterocyclylcarbonyl unsubstituted, substituted or unsubstituted alkyloxycarbonyl, substituted or unsubstituted alkenyloxycarbonyl, substituted or unsubstituted alkynyloxycarbonyl, substituted or non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted alkylcarbonyloxy, substituted or unsubstituted alkenylcarbonyloxy, substituted or unsubstituted alkynylcarbonyloxy, substituted or unsubstituted non-aromatic carbocyclylcarbonyloxy, substituted or unsubstituted aromatic carbocyclylcarbonyloxy, substituted or unsubstituted non-aromatic heterocyclylcarbonyloxy, substituted or unsubstituted aromatic heterocyclylcarbonyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, substituted or unsubstituted amino, substituted or unsubstituted carbamoyl and substituted or unsubstituted sulfamoyl, and the like. One or more of these substituents may occur at any substitutable position.

Examples of the substituent for "Substituted non-aromatic carbocyclyl", "substituted aromatic carbocyclyl", "substituted aromatic heterocyclyl" or "substituted non-aromatic heterocyclyl" include halogen, hydroxy, mercapto, nitro, nitroso, cyano, azido, formyl, carboxy, alkyl, alkenyl, alkynyl, alkyloxy, alkenyloxy, alkynyloxy, alkylcarbonyl, alkenylcarbonyl, alkynylcarbonyl, alkyloxycarbonyl, alkenyloxycarbonyl, alkynyloxycarbonyl, alkylcarbonyloxy, alkenylcarbonyloxy, alkynylcarbonyloxy, alkylthio, alkenylthio, alkynylthio, alkylsulfinyl, alkenylsulfinyl, alkynylsulfinyl, alkylsulfonyl, alkenylsulfonyl, alkynylsulfonyl, carbamoyl, substituted carbamoyl, sulfamoyl, substituted sulfamoyl, amino, substituted amino, non-aromatic carbocyclyl, aromatic carbocyclyl, aromatic heterocyclyl, non-aromatic heterocyclyl, non-aromatic carbocyclyloxy, aromatic carbocyclyloxy, aromatic heterocyclyloxy, non-aromatic heterocyclyloxy, non-aromatic carbocyclylcarbonyl, aromatic carbocyclylcarbonyl, aromatic heterocyclylcarbonyl, non-aromatic heterocyclylcarbonyl, non-aromatic carbocyclyloxycarbonyl, aromatic carbocyclyloxycarbonyl, aromatic heterocyclyloxycarbonyl, non-aromatic heterocyclyloxycarbonyl, non-aromatic carbocyclylcarbonyloxy, aromatic carbocyclylcarbonyloxy, aromatic heterocyclylcarbonyloxy, non-aromatic heterocyclylcarbonyloxy and the like. One or more of these substituents may occur at any substitutable position.

Examples of the substituent for "substituted alkyl" include cyano, hydroxy, formyl, carboxy, halogen, sulfanyl, alkyloxy, haloalkyloxy, alkylcarbonyl, carbamoyl, alkylcarbamoyl, non-aromatic carbocyclylalkyloxy and the like.

Specific examples of the substituent for "substituted alkyl" in $R^{4a}$ and $R^3$ include the Substituent group α (cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy, substituted or unsubstituted non-aromatic heterocyclylalkyloxy and substituted or unsubstituted aromatic heterocyclylalkyloxy) and the like.

Preferably, specific examples include Substituent group α' (cyano, halogen, alkyloxy, haloalkyloxy and non-aromatic carbocyclylalkyloxy) and the like.

Specific examples of the substituent for "substituted alkyl" in $R^7$ include hydroxy, formyl, carboxy, sulfanyl, alkylcarbonyl, carbamoyl, alkylcarbamoyl and the like.

Preferable examples include hydroxy and the like.

Specific examples of the substituent for "substituted alkyloxy" in $R^{4a}$ include Substituent group α (cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy, substituted or unsubstituted non-aromatic heterocyclylalkyloxy and substituted or unsubstituted aromatic heterocyclylalkyloxy) and the like.

Preferably, specific examples include Substituent group α' (cyano, halogen, alkyloxy, haloalkyloxy and non-aromatic carbocyclylalkyloxy) and the like.

Specific examples of the substituent for "substituted alkylthio" in $R^{4a}$ include include the Substituent group α (cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy, substituted or unsubstituted non-aromatic heterocyclylalkyloxy and substituted or unsubstituted aromatic heterocyclylalkyloxy) and the like.

Preferably, specific examples include Substituent group α' (cyano, halogen, alkyloxy, haloalkyloxy and non-aromatic carbocyclylalkyloxy) and the like.

Specific examples of the substituent of the substituent for "substituted amino", "substituted carbamoyl", "substituted sulfamoyl", "substituted amidino" or "substituted imino" include substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, substituted or unsubstituted aromatic heterocyclylsulfonyl, substituted or unsubstituted carbamoyl and substituted or unsubstituted sulfamoyl. One or two of these substituents may occur at any substitutable position.

Specific examples of the substituent of the substituent for "Substituted amino", "substituted carbamoyl", "substituted sulfamoyl", "substituted amidino" or "substituted imino" include halogen, hydroxy, mercapto, nitro, nitroso, cyano, azido, formyl, carboxy, alkyl, alkenyl, alkynyl, alkyloxy, alkenyloxy, alkynyloxy, alkylcarbonyl, alkenylcarbonyl, alkynylcarbonyl, alkyloxycarbonyl, alkenyloxycarbonyl, alkynyloxycarbonyl, alkylcarbonyloxy, alkenylcarbonyloxy, alkynyl carbonyloxy, alkylthio, alkenylthio, alkynylthio, alkylsulfinyl, alkenylsulfinyl, alkynylsulfinyl, alkylsulfonyl, alkenylsulfonyl, alkynylsulfonyl, carbamoyl, substituted carbamoyl, sulfamoyl, substituted sulfamoyl, amino, substituted amino, non-aromatic carbocyclyl, aromatic carbocyclyl, aromatic heterocyclyl, non-aromatic heterocyclyl, non-aromatic carbocyclyloxy, aromatic carbocyclyloxy, aromatic heterocyclyloxy, non-aromatic heterocyclyloxy, non-aromatic carbocyclylcarbonyl, aromatic carbocyclylcarbonyl, aromatic heterocyclylcarbonyl, non-aromatic heterocyclylcarbonyl, non-aromatic carbocyclyloxycarbonyl, aromatic carbocyclyloxycarbonyl, aromatic heterocyclyloxycarbonyl, non-aromatic heterocyclyloxycarbonyl, non aromatic carbocyclylcarbonyloxy, aromatic carbocyclylcarbonyloxy, aromatic heterocyclylcarbonyloxy, non-aromatic heterocyclylcarbonyloxy. One or two of these substituents may occur at any substitutable position.

Specific examples of the substituent for the "substituted amino" in $R^{4a}$ include alkyl optionally substituted with one or more substitutent(s) selected from the Substituent group α (cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy, substituted or unsubstituted non-aromatic heterocyclylalkyloxy and substituted or unsubstituted aromatic heterocyclylalkyloxy), alkenyl optionally substituted with one or more substitutent(s) selected from the Substituent group α, or alkynyl optionally substituted with one or more substitutent(s) selected from the Substituent group α and the like.

Specific examples of the substituent for the "substituted amino" include alkyl optionally substituted with one or more substitutent(s) selected from the Substituent group α' (cyano, halogen, alkyloxy, haloalkyloxy and non-aromatic carbocyclylalkyloxy), alkenyl optionally substituted with one or more substitutent(s) selected from the Substituent group α' alkynyl optionally substituted with one or more substitutent(s) selected from the Substituent group α' and the like.

Specific examples of the substituent for the "substituted amino" in $R^7$ include alkyl, alkenyl, alkynyl, alkylcarbonyl, alkenylcarbonyl, alkynylcarbonyl, alkyloxycarbonyl, alkenyloxycarbonyl, alkynyloxycarbonyl, non-aromatic carbocyclylcarbonyl, aromatic carbocyclylcarbonyl, non-aromatic heterocyclylcarbonyl, and aromatic heterocyclylcarbonyl and the like.

Preferable embodiments include alkyl, alkenyl, alkynyl, alkylcarbonyl, alkyloxycarbonyl, non-aromatic carbocyclylcarbonyl and the like.

Specific examples of the substituent for the "substituted amino" in $R^{11}$ alkyl, alkenyl, alkynyl, alkylcarbonyl, alkenylcarbonyl, alkynylcarbonyl, alkyloxycarbonyl, alkenyloxycarbonyl, alkynyloxycarbonyl, non-aromatic carbocyclylcarbonyl, aromatic carbocyclylcarbonyl, non-aromatic heterocyclylcarbonyl and aromatic heterocyclylcarbonyl and the like.

Specific examples of the substituent for the "substituted sulfamoyl" in $R^{12}$ include alkylsulfamoyl, non-aromatic carbocyclylsulfamoyl, aromatic carbocyclylsulfamoyl. In particular, methylsulfamoyl, ethylsulfamoyl, isopropylsulfamoyl, dimethylsulfamoyl, isopropyl(methyl)sulfamoyl, cyclohexylsulfamoyl, phenylsulfamoyl and the like are preferable. "Alkyl", "non-aromatic carbocyclyl" and "aromatic carbocyclyl" in "alkylsulfamoyl", "non-aromatic carbocyclylsulfamoyl", "aromatic carbocyclylsulfamoyl" may be further substituted with one or more substituents as defined herein.

Specific examples of the substituent for the "substituted carbamoyl" in $R^{12}$ include alkylcarbamoyl, non-aromatic carbocyclylcarbamoyl, aromatic carbocyclylcarbamoyl.

In particular, methylcarbamoyl, ethylcarbamoyl, isopropylcarbamoyl, dimethylcarbamoyl, isopropyl(methyl)carbamoyl, cyclohexylcarbamoyl, phenylcarbamoyl and the like are preferable. "Alkyl", "non-aromatic carbocyclyl" and "aromatic carbocyclyl" in "alkylcarbamoyl", "non-aromatic carbocyclylcarbamoyl", "aromatic carbocyclylcarbamoyl" may be further substituted with one or more substituents as defined herein.

Especially preferable embodiments of the compounds of the present invention are described below.

The compound represented by formula (Ia) and formula (Ib):

[Chemical Formula 27]

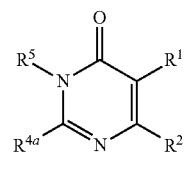

(Ia)

and

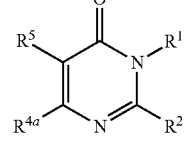

(Ib)

is preferable. The compound represented by formula (Ia):

[Chemical Formula 28]

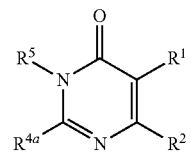

(Ia)

is especially preferable examples include

Preferred embodiments of $R^1$, $R^2$, $R^{4a}$ and $R^5$ in a compound represented by formula (Ia) and formula (Ib):

[Chemical Formula 29]

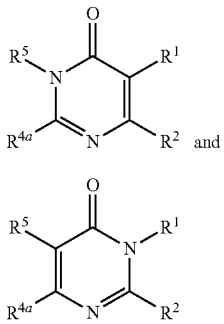

are described below. Compounds having possible combination of the substituents in the following embodiments are preferable.

R¹ includes hydrogen, halogen, hydroxy, formyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl;

Preferable embodiments of R¹ include hydrogen or halogen.

R² include a group represented by formula:

[Chemical Formula 30]

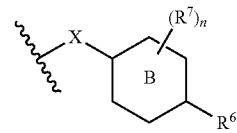

X is a single bond or O,

Ring B is a benzene ring, a 6-membered aromatic heterocycle, a non-aromatic carbocyclic or 6-membered non-aromatic heterocyclic ring, R⁶ is halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, R⁷ includes each independently, halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl.

Preferable embodiments of R² include a group represented by formula:

[Chemical Formula 31]

Preferable embodiments of x include a bond.
The other more preferable embodiments include O.
Preferable embodiments of Ring B include a benzene ring or 6-membered aromatic heterocycle.

The other more preferable embodiments include 6-membered non-aromatic carbocycle or 6-membered non-aromatic heterocycle.

Especially preferable embodiments include a benzene ring.

Preferable embodiments of $R^6$ include halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio.

The other more preferable embodiments of $R^6$ include substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl.

Especially preferable embodiments of $R^6$ include halogen, cyano, alkyl optionally substituted with halogen, or alkyloxy optionally substituted with halogen.

Preferable embodiments of $R^7$ include each independently, halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio or substituted or unsubstituted alkynylthio.

The other more preferable embodiment of $R^7$ include each independently substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl.

Especially preferable embodiments of $R^7$ include each independently, hydroxyalkyl, alkylcarbonylamino, non-aromatic carbocyclylcarbonylamino or alkyloxycarbonylamino.

Preferable embodiments of n include integer of 0 to 2.

The other preferable embodiments of n include integer of 1 to 2.

Preferable embodiments of $R^{4a}$ include each independently halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl substituted, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclyl.

The other more preferable embodiments of $R^{4a}$ include substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio or substituted or unsubstituted alkynylthio.

The other more preferable embodiments of $R^{4a}$ include alkyl optionally substituted with one or more substitutent(s) selected from the Substituent group α (cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy), alkenyl optionally substituted with one or more substitutent(s) selected from the Substituent group α, alkynyl optionally substituted with one or more substitutent(s) selected from the Substituent group α, alkylamino optionally substituted with one or more substitutent(s) selected from the Substituent group α, alkenylamino optionally substituted with one or more substitutent(s) selected from the Substituent group α, alkynylamino optionally substituted with one or more substitutent(s) selected from the Substituent group α, alkyloxy optionally substituted with one or more substitutent(s) selected from the Substituent group α, alkenyloxy optionally substituted with one or more substitutent(s) selected from the Substituent group α, alkynyloxy optionally substituted with one or more substitutent(s) selected from the Substituent group α, alkylthio optionally substituted with one or more substitutent(s) selected from the Substituent group α, alkenylthio optionally substituted with one or more substitutent(s) selected from the Substituent group α, alkynylthio optionally substituted with one or more substitutent(s) selected from the Substituent group α.

Especially preferable embodiments of $R^{4a}$ include alkyl optionally substituted with one or more substitutent(s) selected from the Substituent group α(cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy).

$R^5$ is a group represented by formula: $R^{11}$—$(C(R^{10a})(R^{10b}))$m-.

$R^{10a}$ are each independently hydrogen, halogen or substituted or unsubstituted alkyl, $R^{10b}$ are each independently hydrogen, halogen or substituted or unsubstituted alkyl, or $R^{10a}$ and $R^{10b}$ attached to the same carbon may be taken together to form substituted or unsubstituted carbocycle or substituted or unsubstituted heterocycle, Preferable embodiments of $R^{10a}$ and $R^{10b}$ include hydrogen, halogen or substituted or unsubstituted alkyl.

$R^{11}$ is hydrogen, carboxy, substituted or unsubstituted aromatic carbocyclyl, substituted or unsubstituted aromatic heterocyclyl, substituted or unsubstituted non-aromatic carbocyclyl, substituted or unsubstituted non aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, non-aromatic substituted or unsubstituted heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, substituted or unsubstituted sulfamoyl, or substituted or unsubstituted amino.

Preferable embodiments of $R^{11}$ include carboxy, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl, substituted or unsubstituted sulfamoyl, or substituted or unsubstituted amino.

The other more preferable embodiments of $R^{11}$ include substituted or unsubstituted aromatic carbocyclyl, substituted or unsubstituted aromatic heterocyclyl, substituted or unsubstituted non-aromatic carbocyclyl or substituted or unsubstituted non-aromatic heterocyclyl.

The other more preferable embodiments of $R^{11}$ include aromatic carbocyclyl optionally substituted with one or more substitutent(s) selected from the Substituent group β (carboxy, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or non-aromatic carbocyclyloxycarbonyl unsubstituted, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl and substituted or unsubstituted aromatic heterocyclylsulfonyl), aromatic heterocyclyl optionally substituted with one or more substitutent(s) selected from the Substituent group β, non-aromatic carbocyclyl optionally substituted with one or more substitutent(s) selected from the Substituent group β, or non-aromatic heterocyclyl optionally substituted with one or more substitutent(s) selected from the Substituent group β.

The other more preferable embodiments of $R^{11}$ include substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl or substituted or unsubstituted sulfamoyl.

The other more preferable embodiments of $R^{11}$ include carbamoyl optionally substituted with one or more substitutent(s) selected from the Substituent group γ (substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl and substituted or unsubstituted non-aromatic heterocyclyl).

m is integer of 1 to 6.

Preferable embodiments of m include integer of 1 to 3.

The other more preferable embodiments of m include 1.

Especially the following embodiments are preferable.

(i) A compound according to the formula (Ia'), or its pharmaceutically acceptable salt:

[Chemical Formula 32]

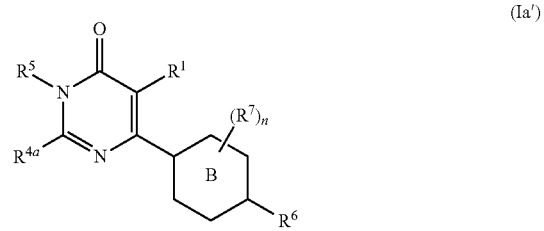

(Ia')

wherein
$R^1$ is hydrogen,
$R^6$ is halogen, cyano, substituted or unsubstituted alkyl, or substituted or unsubstituted alkyloxy,
$R^7$ are each independently, halogen, cyano, substituted or unsubstituted alkyl, substituted or unsubstituted amino, or substituted or unsubstituted alkyloxy,
n is integer of 0 to 4,
$R^5$ is a group represented by formula: $R^{11}$—$(C(R^{10a})(R^{10b}))$m-
wherein
$R^{10a}$ are each independently hydrogen, halogen or substituted or unsubstituted alkyl,
$R^{10b}$ are each independently hydrogen, halogen or substituted or unsubstituted alkyl,
$R^{11}$ is carboxy, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, substituted or unsubstituted sulfamoyl, or substituted or unsubstituted amino,
m is integer of 1 to 6, and
$R^{4a}$ is substituted or unsubstituted alkyl.

(ii) A compound according to the formula (Ia'), or its pharmaceutically acceptable salt:

[Chemical Formula 33]

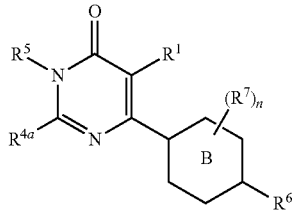

(Ia')

$R^1$ is hydrogen,
$R^6$ is halogen, cyano, substituted or unsubstituted alkyl, or substituted or unsubstituted alkyloxy,
$R^7$ are each independently, halogen, cyano, substituted or unsubstituted alkyl, substituted or unsubstituted amino, or substituted or unsubstituted alkyloxy,
n is integer of 0 to 4,
$R^5$ is a group represented by formula: $R^{11}$—$(C(R^{10a})(R^{10b}))$m-
wherein
$R^{10a}$ are each independently hydrogen, halogen or substituted or unsubstituted alkyl,
$R^{10b}$ are each independently hydrogen, halogen or substituted or unsubstituted alkyl,
$R^{11}$ is carboxy, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl
m is integer of 1 to 6, and
$R^{4a}$ is substituted or unsubstituted alkyl.

(iii) A compound according to the formula (Ia'), or its pharmaceutically acceptable salt:

[Chemical Formula 34]

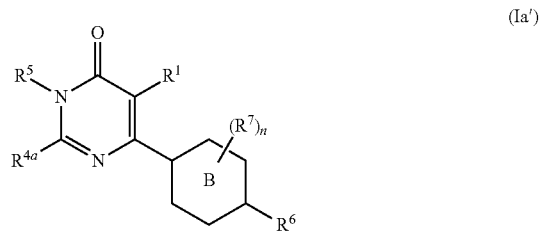

(Ia')

$R^1$ is hydrogen,
$R^6$ is halogen, cyano, substituted or unsubstituted alkyl, or substituted or unsubstituted alkyloxy,
$R^7$ are each independently, halogen, cyano, substituted or unsubstituted alkyl, substituted or unsubstituted amino, or substituted or unsubstituted alkyloxy,
n is integer of 0 to 4,
$R^5$ is a group represented by formula: $R^{11}$—$(C(R^{10a})(R^{10b}))$m-
wherein
$R^{10a}$ are each independently hydrogen, halogen or substituted or unsubstituted alkyl,
$R^{10b}$ are each independently hydrogen, halogen or substituted or unsubstituted alkyl,
$R^{11}$ is substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, substituted or unsubstituted sulfamoyl,
m is integer of 1 to 6, and
$R^{4a}$ is substituted or unsubstituted alkyl.

(iv) A compound according to the formula (Ia'), or its pharmaceutically acceptable salt:

[Chemical Formula 35]

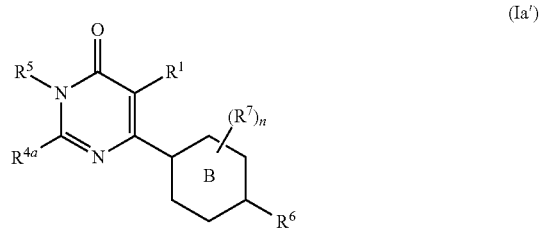

(Ia')

$R^1$ is hydrogen,
$R^6$ is halogen, cyano, substituted or unsubstituted alkyl, or substituted or unsubstituted alkyloxy,
$R^7$ are each independently, halogen, cyano, substituted or unsubstituted alkyl, substituted or unsubstituted amino, or substituted or unsubstituted alkyloxy, n is integer of 0 to 4, $R^5$ is a group represented by formula: $R^{11}$—$(C(R^{10a})(R^{10b}))m$- wherein $R^{10a}$ are each independently hydrogen, halogen or substituted or unsubstituted alkyl, $R^{10b}$ are each independently hydrogen, halogen or substituted or unsubstituted alkyl, $R^{11}$ is substituted or unsubstituted amino, m is integer of 1 to 6, and $R^{4a}$ is substituted or unsubstituted alkyl.

The compounds of this invention are not limited to a specific isomer but include all possible isomers (For example, imine-enamine isomer, geometrical isomer, diastereo isomer, optical isomer, rotamer etc.) and racemates or their mixture.

For example, the compounds of this invention include a tautomer as shown below.

[Chemical Formula 36]

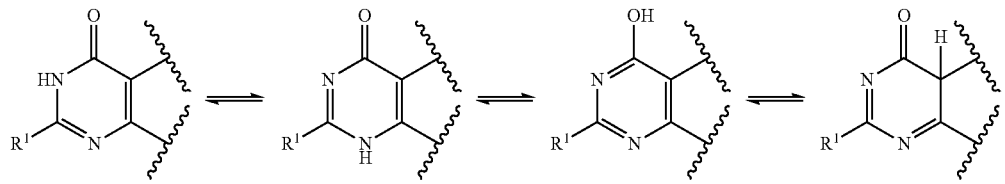

One or more hydrogen, carbon and/or other atoms in the compounds of the present invention may be replaced with isotopes of hydrogen, carbon and/or other atoms respectively. Examples of the isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds of the present invention include compounds replaced with these isotopes. The compounds replaced with the above isotopes are useful as pharmaceuticals and include all of radiolabeled compounds of the compound of the present invention. The present invention also includes a method of radiolabeling in the manufacture of the radiolabeled compounds. Such radiolabeled compounds are useful in the studies for metabolized drug pharmacokinetics and binding assay and also as a diagnostic tool.

A radiolabeled compound of the compounds of the present invention can be prepared using methods well-known in the art. For example, a tritium-labeled compound of formula (Ia), (Ib), (Ic) or (II) can be prepared by introducing a tritium into a compound of formula (Ia), (Ib), (Ic) or (II), through a catalytic dehalogenation using a tritium. This method comprises reacting with an appropriately-halogenated precursor of the compound of formula (Ia), (Ib), (Ic) or (II) with tritium gas in the presence of an appropriate catalyst, such as Pd/C, and in the presence or absent of a base. The other appropriate methods for preparing a tritium-labeled compound can be found in "Isotopes in the Physical and Biomedical Sciences, Vol. 1, Labeled Compounds (Part A), Chapter 6 (1987)". A $^{14}C$-labeled compound can be prepared by using a raw material having $^{14}C$ carbon.

Pharmaceutically acceptable salts of the compounds of the present invention include, for example, salts with alkaline metals such as lithium, sodium, potassium and the like; alkaline earth metals such as calcium, barium and the like; magnecium; transition metals such as zinc, iron and the like; ammonium; organic bases such as trimethylamine, trimethylamine, dicyclohexylamine, ethanolamine, diethanolamine, triethanolamine, meglumine, ethylenediamine, pyridine, picoline, quinolone and the like; amino acids; or inorganic acids such as hydrochloric acid, sulfuric acid, nitric acid, carbonic acid, hydrobromic acid, phosphoric acid, hydroiodic acid and the like; and organic acids such as formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethane sulfonic acid and the like, particularly salts with hydrochloric acid, sulfuric acid, phosphoric acid, tartaric acid and methanesulfonic acid. These salts can be formed according to conventional methods.

The compounds of the present invention or pharmaceutically acceptable salts thereof may exist in a form of solvate (e.g., hydrate and the like) and/or crystal polymorphs. The present invention encompasses those various solvates and crystal polymorphs. The "solvates" may be those wherein any numbers of solvent molecules (e.g. water molecules and the like) are coordinated with the compounds of the present invention. When the compounds of the present invention or pharmaceutically acceptable salts thereof are allowed to stand in the atmosphere, the compounds may absorb water, resulting in attachment of adsorbed water or formation of hydrates. Recrystallization of the compounds of the present invention or pharmaceutically acceptable salts thereof may produce crystal polymorphs.

The compounds of the present invention may form prodrugs. Such prodrugs are encompassed by the present invention. Prodrugs are derivatives of the compounds of the invention with a chemically or metabolically degradable group(s), and the compounds are converted to pharmaceutically active compounds of the invention through solvolysis or under physiological conditions in vivo. The prodrugs include compounds that are converted to a compound of the invention through enzymatic oxidation, reduction, hydrolysis or the like under physiological conditions in vivo, compounds that are converted to a compound of the invention through hydrolysis by gastric acid, and the like. Methods for selecting and preparing suitable prodrug derivatives are described in, for example, "Design of Prodrugs, Elsevier, Amsterdam, 1985". The prodrugs themselves may have some activity.

When the compound of the present invention or its pharmaceutically acceptable salt has hydroxyl group(s), the prodrugs may be acyloxy derivatives and sulfonyloxy derivatives that are prepared by, for example, reacting a compound having hydroxyl group(s) with suitable acyl halide, suitable acid anhydride, suitable sulfonyl chloride, suitable sulfonyl anhydride or mixed anhydride, or by reacting with a condensing agent. Examples include $CH_3COO$—, C₂H₅COO—, t-BuCOO—, C₁₅H₃₁COO—, PhCOO—, (m-NaOOCPh)COO—, NaOOCCH₂CH₂COO—, CH₃CH(NH₂)COO—, CH₂N(CH₃)₂COO—, CH₃SO₃—, CH₃CH₂SO₃—, CF₃SO₃—, CH₂FSO₃—, CF₃CH₂SO₃—, p-CH₃—O-PhSO₃—, PhSO₃—, and p-CH₃PhSO₃—.

"Chronic kidney disease" means a condition where either or both of (1) kidney disorder (urine abnormalities such as proteinuria, e.g. microalbuminuria, abnormal urinary sediment, abnormal finding of clinical imaging such as single kidney and polycystic kidney disease, decreased renal function such as increased serum creatinine, electrolyte abnormalities such as hypokalemia due to tubular damage, and abnormal finding of renal tissue biopsy) and (2) deterioration in renal function less than 60 mL/min/1.73 m² of GFR (glomerular filtration rate) is present for over three months.

The compounds of the present invention are produced according to general procedures as described below. Also, the compounds of the invention can be prepared according to other methods based on the knowledge in organic chemistry.

Preparation of Compound b2

[Chemical Formula 37]

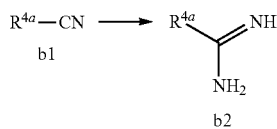

wherein $R^{4a}$ is hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyl, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted substituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfinyl.

The compound b2 can be obtained by reacting compound b1 with ammonium chloride or ammonium in the presence of an acid.

Examples of the solvent include toluene, methanol, ethanol, dichloroethane, DMF, THF and the like and these solvents may be used alone or in combination.

Ammonium hydroxide or ammonia may be used in 1 to 10 mole equivalents, preferably 1 to 3 mole equivalents of Compound b1.

Examples of the acid include trimethyl aluminum, hydrochloride and the like, acid may be used in 1 to 10 mole equivalents, preferably 1 to 3 mole equivalents of Compound b1.

The reaction temperature may be room temperature to 150° C., preferably 50° C. to 150° C.

The reaction time may be 1 to 24 hours, preferably 1 to 12 hours.

Preparation of Compound b4

[Chemical Formula 38]

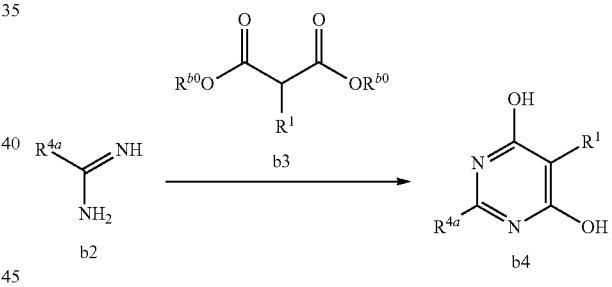

wherein $R^1$ is hydrogen, halogen, hydroxy, cyano, formyl, carboxy, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, $R^{b0}$ is substituted or unsubstituted alkyl, and the other symbols are as defined above.

Compound b4 can be obtained by reacting Compound b3 in the presence of base.

Examples of the reaction solvent include methanol, ethanol and the like, and the solvent may be used alone or in combination.

Examples of base may be tert-butoxy potassium, sodium methoxide, sodium ethoxide, potassium carbonate, sodium hydride and the like. The amount of the base may be 1 to 5 mole equivalents, preferably 1 to 3 mole equivalents of Compound b2.

The amount of Compound b3 may be 0.5 to 2 mole equivalents, preferably 0.5 to 1.5 mole equivalents of Compound b2.

The reaction temperature may be room temperature to 150° C., preferably 50 to 100° C.

The reaction time may be 0.1 to 12 hours, preferably 0.5 to 3 hours.

Preparation of Compound b5

[Chemical Formula 39]

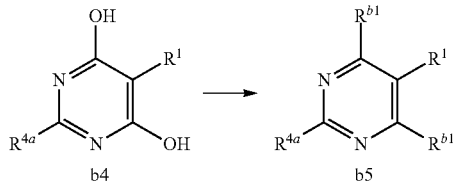

wherein $R^{b1}$ is halogen such as chloro and bromo and the like, and the other symbols are as defined above.

Compound b5 can be obtained by reacting Compound b4 with the halogenating agent.

Examples of the halogenating agent may be phosphorus oxychloride, phosphorus oxybromide and the like The amount of the halogenating agent may be 2 mole equivalents to a large excess, preferably 5 mole equivalents to a large excess of Compound b4.

The reaction temperature may be room temperature to 150° C., preferably 50 to 100° C.

The reaction time may be 0.5 to 6 hours, preferably 1 to 3 hours.

Preparation of Compound b7

[Chemical Formula 40]

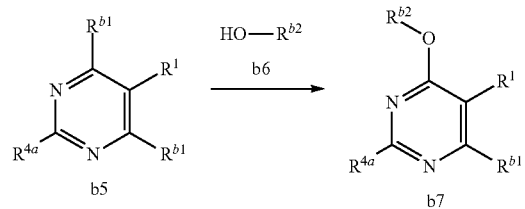

wherein $R^{b2}$ is substituted or unsubstituted alkyl and the like, and the other symbols are as defined above.

Compound b7 can be obtained by reacting Compound b5 with Compound b6 in the presence of a base.

Examples of the reaction solvent include DMF, THF, methanol, toluene, dichloromethane, acetonitrile and the like, and the solvent may be used alone or in combination.

Examples of base may be sodium hydride, potassium carbonate, cesium carbonate, triethylamine and the like. The amount of the base may be 1 to 5 mole equivalents, preferably 1 to 3 mole equivalents of Compound b5.

Examples of Compound b6 may be p-methoxybenzyl alcohol, methanol, benzyl alcohol and the like. The amount of Compound b6 may be 1 to 5 mole equivalents, preferably 1 to 3 mole equivalents of Compound b5.

The reaction temperature may be −50° C. to room temperature, preferably −30 to −10° C.

The reaction time may be 0.1 to 6 hours, preferably 0.1 to 1 hours.

Preparation of Compound b8

[Chemical Formula 41]

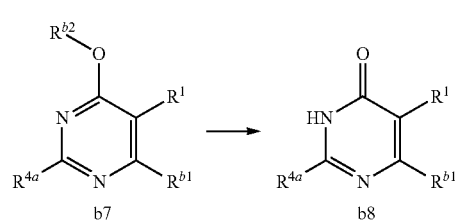

wherein each symbols is as defined above.

Compound b8 can be obtained by reacting Compound b7 with deprotecting agent.

Examples of the deprotecting agent include trifluoroacetic acid, hydrochloric acid, hydrobromic acid, ammonium hexanitratocerate (IV) and the like. The amount of the deprotecting agent may be 1 mole equivalents to a large excess, preferably 1 to 50 mole equivalents of Compound b7.

The reaction temperature may be −20° C. to reflux temperature, preferably under ice-cooling to room temperature.

The reaction time may be 0.1 to 6 hours, preferably 0.1 to 3 hours.

Preparation of Compound b10

[Chemical Formula 42]

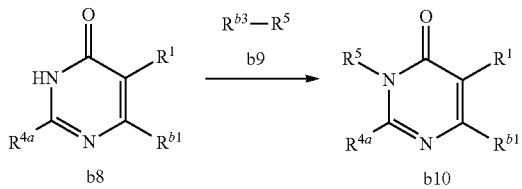

wherein $R^{b3}$ is halogen such as chloro, bromo and the like, leaving group such as mesyl group, tosyl group and the like, $R^5$ is a group of formula: $R^{11}$—$(C(R^{10a})(R^{10b}))$ m- (wherein, $R^{10a}$ and $R^{10b}$ are each independently hydrogen, halogen or substituted or unsubstituted alkyl, or $R^{10a}$ and $R^{10b}$ attached to the same carbon may be taken together to form substituted or unsubstituted carbocycle or substituted or unsubstituted heterocycle, m is integer of 1 to 6, $R^{11}$ is hydrogen, carboxy, substituted or unsubstituted aromatic carbocyclyl, substituted or unsubstituted aromatic heterocyclyl, substituted or unsubstituted non-aromatic carbocyclyl, substituted or unsubstituted non aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, non-aromatic substituted or unsubstituted heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted aromatic heterocyclyloxycarbonyl unsubstituted, substituted or unsubstituted carbamoyl, substituted or unsubstituted sulfamoyl, or substituted or unsubstituted amino, and the other symbols are as defined above.

Compound b10 can be obtained by reacting Compound b8 with Compound b9 in the presence of a base.

Examples of the reaction solvent include THF, DMF, acetone, acetonitrile and the like, and the solvent may be used alone or in combination.

Examples of base may be sodium hydride, potassium carbonate, cesium carbonate, sodium methoxide, sodium ethoxide, tert-butoxy potassium and the like. The amount of the base may be 1 to 5 mole equivalents, preferably 1 to 3 mole equivalents of Compound b8.

The amount of Compound b9 may be 1 to 5 mole equivalents, preferably 1 to 3 mole equivalents of Compound b8.

The reaction temperature may be under ice-cooling to room temperature, preferably under ice-cooling to 60° C.

The reaction time may be 0.5 to 24 hours, preferably 1 to 6 hours.

Preparation of Compound b15

[Chemical Formula 43]

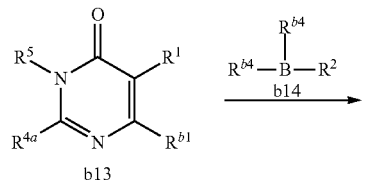

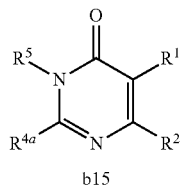

wherein $R^{b4}$ is hydroxy, substituted or unsubstituted alkyloxy or two $R^{b4}$ attached to the same carbon may be taken together to form substituted or unsubstituted alkylenedioxy, and the other symbols are as defined above.

Compound b15 can be obtained by reacting Compound b13 with Compound b14 in the presence of a metal catalyst and a base.

Examples of the solvent include DMF, toluene, methanol, ethanol, dioxane and the like and these solvents may be used alone or in combination.

Examples of the base include sodium carbonate, cesium carbonate, potassium carbonate, sodium hydroxide, potassium phosphate, tert-butoxy potassium and the like. The amount of the base may be 1 to 10 mole equivalents, preferably 1 to 3 mole equivalents of Compound b13.

The amount of Compound b14 may be 1 to 10 mole equivalents, preferably 1 to 3 mole equivalents of Compound b13.

Examples of the metal catalyst may be 1,1'-bis(diphenylphosphino)ferrocene-palladium (II) dichloride-dichloromethane complex, chloro (2-dicyclohexyl phosphino-2', 4',6'-triisopropyl-1,1'-biphenyl)[2-(2'-amino-1,1'-biphenyl)] palladium (II), tetrakis (triphenylphosphine) palladium and the like. The amount of the metal catalyst may be 0.01 to 1 mole equivalents, preferably 0.05 to 0.2 mole equivalents of Compound b13.

The reaction temperature may be 50 to 200° C., preferably 80 to 150° C.

The reaction time may be 0.1 to 12 hours, preferably 0.1 to 6 hours.

Preparation of Compound b11

[Chemical Formula 44]

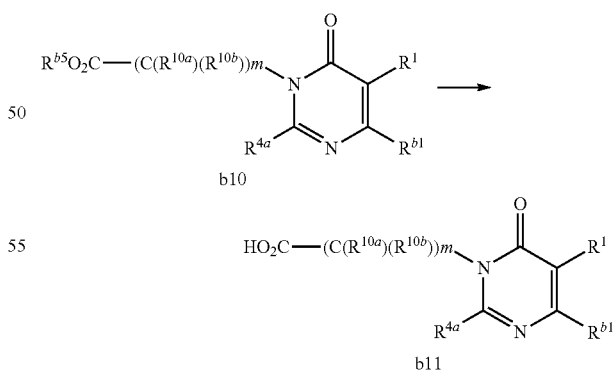

wherein $R^{5b}$ is substituted or unsubstituted alkyl, substituted or unsubstituted alkenyl, substituted or alkynyl or unsubstituted etc., and the other symbols are as defined above.

Compound b11 can be obtained by hydrolyzing Compound b10.

Examples of the reaction solvent include THF, ethanol, water, dichloromethane, DMF, methanol, 1,4-dioxane, acetonitrile, toluene, ethyl acetate and the like, these solvents may be used alone or in combination.

Examples of the additive include sodium hydroxide, lithium hydroxide, potassium hydroxide, trimethyltin, hydrochloric acid, sulfuric acid and the like. The amount of the acid may be 1 to 10 mole equivalents, preferably 1 to 5 mole equivalents of Compound b10.

The reaction temperature may be under ice-cooling to reflux temperature, preferably room temperature.

The reaction time may be 0.1 to 24 hours, preferably 0.1 to 5 hours.

Preparation of Compound b13

[Chemical Formula 45]

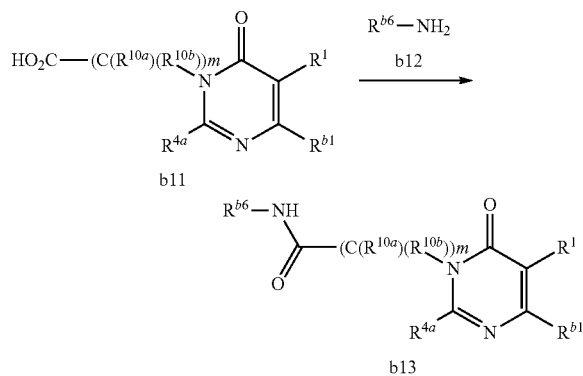

wherein $R^{b6}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or substituted aromatic heterocyclyl or substituted or unsubstituted non-aromatic heterocyclyl, and the other symbols are as defined above.

Compound b13 can be obtained by reacting Compound b11 with amine b12 in the presence of base and condensing agents.

Examples of the reaction solvent include DMF, ethanol, water, dichloromethane, THF, methanol, 1,4-dioxane, acetonitrile, toluene, ethyl acetate and the like, and these solvents may be used alone or in combination.

Examples of the base include triethylamine, tert-butoxy potassium, potassium carbonate, cesium carbonate, diisopropylethylamine, DBU and the like. The amount of the base may be 1 to 10 mole equivalents, preferably 1 to 5 mole equivalents of Compound b11.

Examples of the condensing agent include HATU, WSC, DCC and the like. The amount of the condensing agent may be 1 to 10 mole equivalents, preferably 1 to 5 mole equivalents of Compound b11.

The amine b12 may be used in 1 to 10 mole equivalents, preferably 1 to 5 mole equivalents of Compound b11.

The reaction temperature may be under ice-cooling to reflux temperature, preferably room temperature.

The reaction time may be 0.1 to 24 hours, preferably 1 to 5 hours.

Preparation of Compound b25

[Chemical Formula 46]

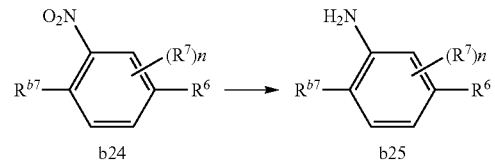

wherein $R^{b7}$ is halogen such as chloro, bromo etc., leaving group such as mesyl, tosyl etc., $R^6$ is halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, $R^7$ are each independently, halogen, hydroxy, cyano, formyl, carboxy, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl, n is integer of 0 to 4.

Compound b25 can be obtained by reacting Compound b24 with reductants.

Examples of the reaction solvent include ethanol, methanol, ethyl acetate, THF, dichloromethane and the like, and these solvents may be used alone or in combination.

Examples of the reductant include stannous chloride, iron, palladium-carbon and the like. The amount of the reductant may be 0.01 to 10 mole equivalents, preferably 0.05 to 5 mole equivalents of Compound b24.

The reaction temperature may be under ice-cooling to reflux temperature, preferably room temperature.

The reaction time may be 0.1 to 24 hours, preferably 0.5 to 6 hours.

Preparation of Compound b26

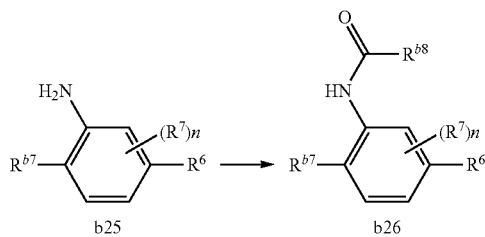

where $R^{b8}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, and the other symbols are as defined above.

Compound b26 can be obtained by reacting Compound b25 with an acyl halide in the presence of base.

Examples of the reaction solvent include pyridine, dichloromethane, THF, ethyl acetate and the like, and these solvents may be used alone or in combination.

Examples of the base include sodium hydride, sodium hydroxide, potassium carbonate and the like. The amount of the base may be 1 to 5 equivalents, preferably 1 to 3 mole equivalents of Compound b25.

The reaction temperature may be under ice-cooling to reflux temperature, preferably room temperature to reflux temperature.

The reaction time may be 0.1 to 12 hours, preferably 0.5 to 3 hours.

Preparation of Compound b28

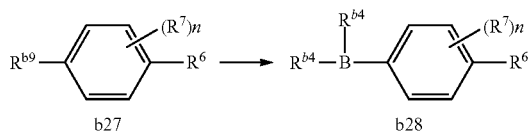

wherein $R^{b9}$ is halogen such as chloro, bromo, etc., mesyl, leaving group such as mesyl, tosyl, etc., and the other symbols are as defined above.

Compound b28 can be obtained by reacting Compound b27 with a boronic acid ester in the presence of a base and a metal catalyst.

Examples of the solvent include dioxane, THF, toluene, DMF, dichloromethane and the like and these solvents may be used alone or in combination.

The amount of the boronic acid ester may be 1 to 10 mole equivalents, preferably 1 to 3 mole equivalents of Compound b27.

The reaction temperature may be room temperature to reflux temperature, preferably 50° C. to reflux temperature.

The reaction time may be 0.5 to 12 hours, preferably 0.5 to 6 hours.

Preparation of Compound b30

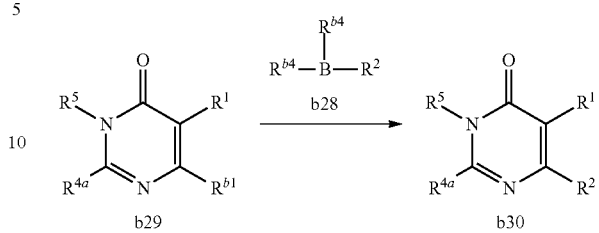

wherein $R^2$ is a group represented by formula:

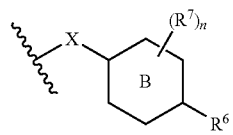

X is a single bond or O,

Ring B is a benzene ring, 6-membered aromatic heterocycle, non-aromatic carbocycle or 6-membered non-aromatic heterocycle, and the other symbols are as defined above.

Compound b30 can be obtained by reacting Compound b28 with Compound b29 in the presence of a metal catalyst and base.

Examples of the reaction solvent include DMF, THF, dioxane and the like, and the solvent may be used alone or in combination.

Examples of the base may be sodium carbonate, potassium carbonate, cesium carbonate and the like. The amount of the base may be 1 to 10 mole equivalents, preferably 1 to 3 mole equivalents of Compound b29.

Examples of the metal catalyst may be 1,1'-bis(diphenylphosphino) ferrocene-palladium (II) dichloride-dichloromethane complex, palladium acetate and the like. The amount of the metal catalyst may be 0.01 to 0.5 mole equivalents, preferably 0.05 to 0.2 mole equivalents of Compound b29.

The reaction temperature may be room temperature to reflux temperature, preferably room temperature to 100° C.

The reaction time may be 0.1 to 24 hours, preferably 1 to 12 hours.

Preparation of Compound b35

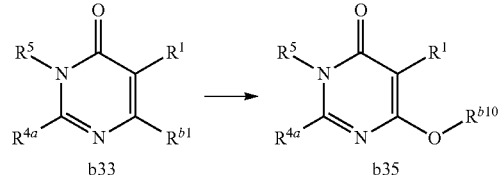

wherein $R^{b10}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, and the other symbols are the same meaning as defined above.

Compound b35 can be obtained by reacting Compound b33 with alcohol in the presence of a base.

Examples of the reaction solvent include DMF, THF, acetonitrile, dichloromethane and the like, and the solvent may be used alone or in combination.

Examples of the base may be sodium hydride, sodium hydroxide, potassium carbonate, tert-butoxy potassium, triethylamine, diisopropylethylamine and the like. The amount of the base may be 1 to 5 mole equivalents, preferably 1 to 3 mole equivalents of Compound b33.

The amount of the alcohol may be 1 to 5 mole equivalents, preferably 1 to 3 mole equivalents of Compound b33.

The reaction temperature may be room temperature to reflux temperature, preferably 50 to 100° C.

The reaction time may be 0.5 to 24 hours, preferably 1 to 6 hours.

Preparation of Compound b41

[Chemical Formula 52]

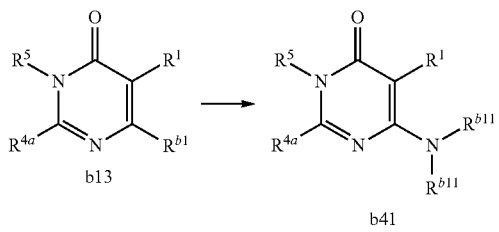

wherein $R^{b11}$ are each independently hydrogen, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl or the two $R^{b11}$ may be taken together to form substituted or unsubstituted non-aromatic heterocycle, and the other symbols are the same meaning as defined above.

Compound b41 can be obtained by reacting Compound b13 with amine in the presence of the base.

Examples of the reaction solvent include DMF, THF, acetonitrile, dichloromethane and the like, and the solvent may be used alone or in combination.

Examples of the base may be sodium hydride, sodium hydroxide, potassium carbonate, tert-butoxy potassium, triethylamine, diisopropylethylamine and the like. The amount of the base may be 1 to 5 mole equivalents, preferably 1 to 3 mole equivalents of Compound b13.

The amount of the amine may be 1 to 5 mole equivalents, preferably 1 to 3 mole equivalents of Compound b13.

The reaction temperature may be room temperature to reflux temperature, preferably 50 to 100° C.

The reaction time may be 0.5 to 24 hours, preferably 1 to 6 hours.

Preparation of Compound b49

[Chemical Formula 53]

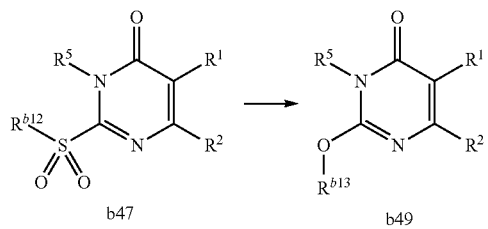

wherein $R^{b12}$ is substituted or unsubstituted alkyl, substituted or unsubstituted alkenyl, substituted or unsubstituted alkynyl, $R^{b13}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, and the other symbols are the same meaning as defined above.

Compound b49 can be obtained by reacting Compound b47 with alcohol in the presence of a base.

Examples of the reaction solvent include DMF, THF, acetonitrile, dichloromethane and the like, and the solvent may be used alone or in combination.

Examples of the base may be sodium hydride, sodium hydroxide, potassium carbonate, tert-butoxy potassium, triethylamine, diisopropylethylamine and the like. The amount of the base may be 1 to 5 mole equivalents, preferably 1 to 3 mole equivalents of Compound b47.

The amount of the alcohol may be 1 to 5 mole equivalents, preferably 1 to 3 mole equivalents of Compound b47.

The reaction temperature may be −78° C. to room temperature, preferably −78° C. to −20° C.

The reaction time may be 0.1 to 6 hours, preferably 0.5 to 3 hours.

Preparation of Compound b57

[Chemical Formula 54]

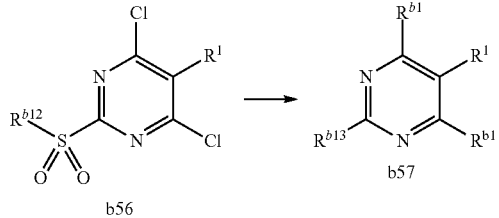

The symbols in the formula are the same meaning as defined above.

Compound b57 can be obtained by reacting Compound b56 with a metal catalyst.

Examples of the solvent include THF, benzene, toluene, acetonitrile, diethyl ether, dichloromethane and the like and these solvents may be used alone or in combination.

Examples of the metal catalyst may be alkyl magnesium bromide, aryl magnesium bromide, alkyl lithium and the like. The amount of the metal catalyst may be 1 to 5 mole equivalents, preferably 1 to 3 mole equivalents of Compound b56.

The reaction temperature may be under ice-cooling to reflux temperature, preferably under ice-cooling to room temperature.

The reaction time may be 0.1 to 6 hours, preferably 0.5 to 3 hours.

Preparation of Compound b68

[Chemical Formula 55]

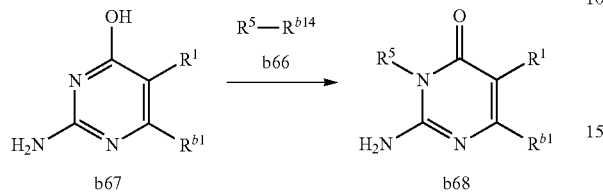

wherein $R^{b14}$ is halogen such as chloro, bromo and the like, leaving group such as mesyl group, tosyl group and the like, and the other symbols are as defined above.

Compound b67 can be obtained by reacting Compound b67 with Compound b66 in the presence of base.

Examples of the reaction solvent include THF, DMF, acetone, acetonitrile and the like, and these solvents may be used alone or in combination.

Examples of the base include sodium hydride, potassium carbonate, cesium carbonate, sodium methoxide, sodium ethoxide, tert-butoxy potassium and the like. The amount of the base may be 1 to 5 equivalents, preferably 1 to 3 mole equivalents of Compound b67.

The reaction temperature may be under ice-cooling to 100° C., preferably under ice-cooling to 60° C.

The reaction time may be 0.5 to 24 hours, preferably 1 to 6 hours.

Preparation of Compound b70

[Chemical Formula 56]

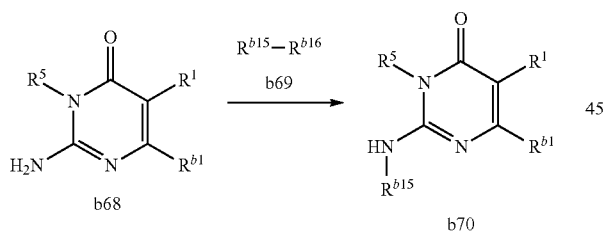

wherein $R^{b15}$ is substituted or unsubstituted alkyl, substituted or unsubstituted alkenyl, substituted or unsubstituted alkynyl, substituted or unsubstituted aromatic carbocyclic group, a substituted or unsubstituted non-aromatic carbocyclic ring Shikimoto, a substituted or unsubstituted aromatic heterocyclic group, or a substituted or unsubstituted non-aromatic heterocyclic group, $R^{b16}$ is chloro, halogen bromo or mesyl leaving group, and other symbols tosyl, etc. it is as defined above.

Compound b70 can be obtained by reacting Compound b68 with Compound b69 in the presence of a base.

Examples of the reaction solvent include THF, DMF, acetone, acetonitrile and the like, and the solvent may be used alone or in combination.

Examples of the base may be sodium hydride, potassium carbonate, cesium carbonate, sodium methoxide, sodium ethoxide, tert-butoxy potassium and the like. The amount of the base may be 1 to 5 mole equivalents, preferably 1 to 3 mole equivalents of Compound b68.

The amount of Compound b69 may be 1 to 5 mole equivalents, preferably 1 to 3 mole equivalents of Compound b68.

The reaction temperature may be under ice-cooling to 100° C., preferably under ice-cooling to 60° C.

The reaction time may be 0.5 to 24 hours, preferably 1 to 6 hours.

Preparation of Compound b70

[Chemical Formula 57]

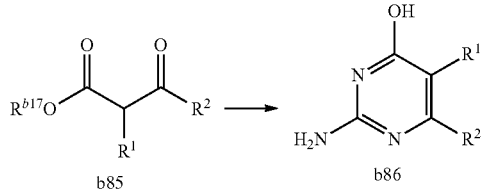

wherein $R^{b17}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, and the other symbols are as defined above.

Compound b86 can be obtained by reacting Compound b85 with guanidine.

Examples of the reaction solvent include methanol, ethanol and the like, and these solvents may be used alone or in combination.

The amount of the guanidine may be 0.5 to 2 equivalents, preferably 1 to 2 mole equivalents of Compound b85.

The reaction temperature may be room temperature to 150° C., preferably 50 to 100° C.

The reaction time may be 0.1 to 12 hours, preferably 0.5 to 6 hours.

Preparation of Compound b60

[Chemical Formula 58]

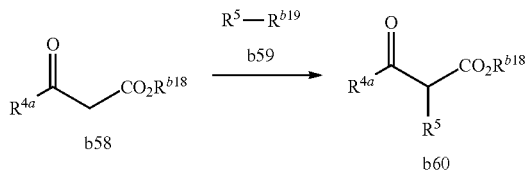

wherein $R^{b18}$ is substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $R^{b19}$ is halogen such as chloro, bromo, leaving group such as mesyl, and the other symbols are as defined above.

Compound b60 can be obtained by reacting Compound b58 with Compound b59 in the presence of base.

Examples of the reaction solvent include THF, DMF, dichloromethane and the like, and these solvents may be used alone or in combination.

Examples of the base include potassium carbonate, sodium hydride, tert-butoxy potassium, n-butyl lithium and the like. The amount of the base may be 1 to 5 equivalents, preferably 1 to 3 mole equivalents of Compound b58.

The reaction temperature may be under ice-cooling to reflux temperature, preferably room temperature to 50° C.

The reaction time may be 1 to 24 hours, preferably 3 to 18 hours.

Preparation of Compound b62

[Chemical Formula 59]

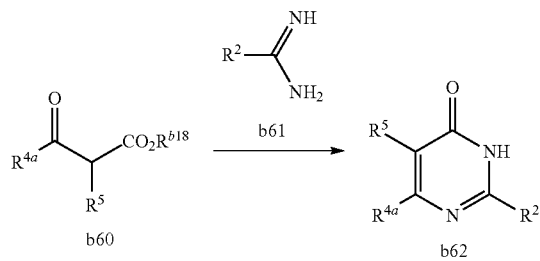

wherein each symbols is as defined above.

Compound b62 can be obtained by reacting Compound b60 with Compound b61 in the presence of base.

Examples of the reaction solvent include methanol, ethanol and the like, and these solvents may be used alone or in combination.

Examples of the base include sodium tert-butoxy potassium, sodium methoxide, sodium ethoxide, potassium carbonate, sodium hydride and the like. The amount of the base may be 1 to 5 equivalents, preferably 1 to 3 mole equivalents of Compound b60.

The reaction temperature may be room temperature to 150° C., preferably 50 to 100° C.

The reaction time may be 0.1 to 12 hours, preferably 0.5 to 3 hours.

Preparation of Compound b91

[Chemical Formula 60]

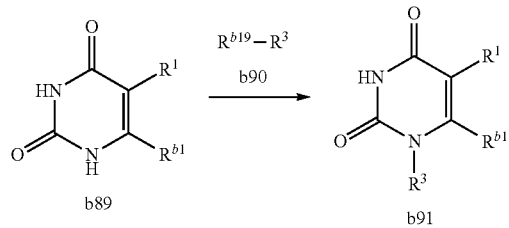

wherein $R^{b19}$ is halogen such as chloro, bromo etc., leaving group such as tosyl, etc., $R^3$ is substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted aromatic heterocyclylsulfonyl, substituted or unsubstituted non-aromatic carbocyclylsulfonyl or substituted or unsubstituted non-aromatic heterocyclylsulfonyl, and the other symbols are as defined above.

Compound b91 can be obtained by reacting Compound b89 with Compound b90 in the presence of base.

Examples of the reaction solvent include THF, DMF, acetone, acetonitrile and the like, and these solvents may be used alone or in combination.

Examples of the base include sodium hydride, potassium carbonate, cesium carbonate, sodium methoxide, sodium ethoxide, tert-butoxy potassium and the like. The amount of the base may be 1 to 5 equivalents, preferably 1 to 3 mole equivalents of Compound b90.

The reaction temperature may be under ice-cooling to 100° C., preferably under ice-cooling to 60° C.

The reaction time may be 0.5 to 24 hours, preferably 1 to 6 hours.

Preparation of Compound b93

[Chemical Formula 61]

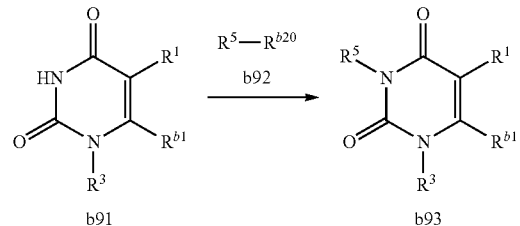

wherein $R^{b20}$ is halogen such as chloro, bromo etc., leaving group such as mesyl, tosyl, etc., and the other symbols are as defined above.

Compound b93 can be obtained by reacting Compound b91 with Compound b92 in the presence of base.

Examples of the reaction solvent include THF, DMF, acetone, acetonitrile and the like, and these solvents may be used alone or in combination.

Examples of the base include sodium hydride, potassium carbonate, cesium carbonate, sodium methoxide, sodium ethoxide, tert-butoxy potassium and the like. The amount of the base may be 1 to 5 equivalents, preferably 1 to 3 mole equivalents of Compound b91.

The reaction temperature may be under ice-cooling to 100° C., preferably under ice-cooling to 60° C.

The reaction time may be 0.5 to 24 hours, preferably 1 to 6 hours.

Preparation of Compound b94

[Chemical Formula 62]

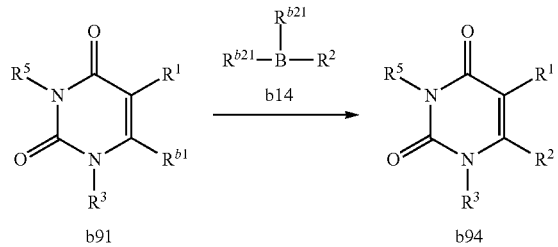

wherein $R^{b21}$ is hydroxy, substituted or unsubstituted alkyloxy or two $R^{b21}$ may be taken together to form substituted or unsubstituted alkylenedioxy, and the other symbols are as defined above.

Compound b94 can be obtained by reacting Compound b91 with Compound b14 in the presence of a metal catalyst and a base.

Examples of the solvent include DMF, THF, dioxane and the like and these solvents may be used alone or in combination.

Examples of the base include sodium carbonate, potassium carbonate, cesium carbonate and the like. The amount of the base may be 1 to 10 mole equivalents, preferably 1 to 3 mole equivalents of Compound b91.

The amount of Compound b14 may be 1 to 10 mole equivalents, preferably 1 to 3 mole equivalents of Compound b91.

Examples of the metal catalyst may be 1,1'-bis(diphenylphosphino) ferrocene-palladium (II) dichloride-dichloromethane complex, palladium acetate and the like. The amount of the metal catalyst may be 0.01 to 0.5 mole equivalents, preferably 0.05 to 0.2 mole equivalents of Compound b91.

The reaction temperature may be room temperature to reflux temperature, preferably room temperature to 100° C.

The reaction time may be 0.1 to 24 hours, preferably 1 to 12 hours.

Preparation of Compound b97

[Chemical Formula 63]

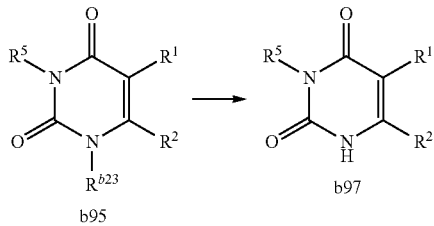

wherein $R^{b23}$ is a protecting group such as substituted or unsubstituted phenylmethyl etc., and the other symbols are as defined above.

Compound b97 can be obtained by reacting Compound b95 with deprotecting agent.

Examples of the reaction solvent include acetonitrile, water, trifluoroacetic acid, dichloromethane, methanol, ethanol and the like, and the solvent may be used alone or in combination.

Examples of the deprotecting agent include ammonium hexanitratocerate (IV) palladium-carbon, trifluoroacetic acid, tetrabutylammonium fluoride and the like. The amount of the deprotecting agent may be 0.01 mole equivalents to a large excess, preferably 0.05 to a large excess of Compound b95.

The reaction temperature may be under ice-cooling to 100° C., preferably room temperature to 70° C.

The reaction time may be 0.5 to 12 hours, preferably 1 to 6 hours.

Preparation of Compound b99 and b100

[Chemical Formula 64]

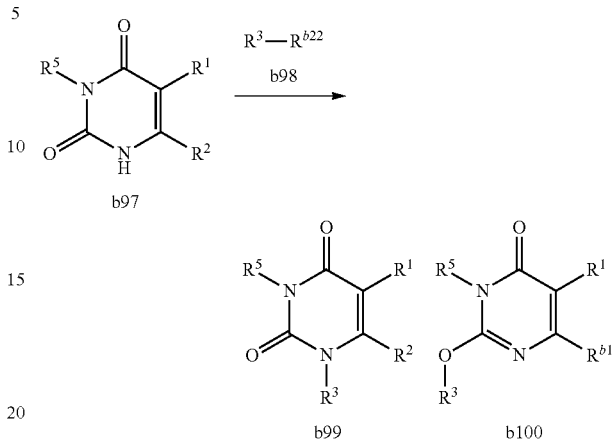

wherein each symbols is as defined above.

Compound b99 and b100 can be obtained by reacting Compound b97 with Compound b98 in the presence of a base.

Examples of the solvent include THF, DMF, acetone, acetonitrile and the like and these solvents may be used alone or in combination.

Examples of the base include triethylamine, sodium hydride, potassium carbonate, cesium carbonate, sodium methoxide, sodium ethoxide, tert-butoxy potassium and the like. The amount of the base may be 1 to 5 mole equivalents, preferably 1 to 3 mole equivalents of Compound b97.

The amount of Compound b98 may be 1 to 5 mole equivalents, preferably 1 to 3 mole equivalents of Compound b97.

The reaction temperature may be under ice-cooling to 60° C.

The reaction time may be 0.5 to 24 hours, preferably 1 to 6 hours.

The compound of the present invention thus obtained may be purified and crystallized in a variety of solvents. Examples of the solvent to be used include alcohols (methanol, ethanol, isopropylalcohol, n-butanol etc.), ether (diethylether, diisopropylether etc.), methyl acetate, ethyl acetate, chloroform, methylene chloride, tetrahydrofuran, N,N-dimethylformamide, toluene, benzene, xylene, acetonitrile, hexane, dioxane, dimethoxyethane, water or a mixture thereof. The compound may be dissolved in the solvent under heating, and the impurities are removed. The solution is then gradually cooled and filtered to collect the precipitated solid or crystal.

The compound of the present invention has autotaxin inhibitory activity. Accordingly, the pharmaceutical composition containing the compound of the present invention is useful as a therapeutic and/or prophylactic agent for diseases related to autotaxin. The diseases related to autotaxin include, for example, urinary extraction failure, chronic kidney disease or renal fibrosis, interstitial pneumonitis or pulmonary fibrosis, scleroderma, pain, fibromyalgia, rheumatoid arthritis, angiogenesis, cancer, formation, growth and propagation of tumor, arteriosclerosis, ocular diseases, choroidal neovascularization and diabetic retinopathy, inflammatory diseases, arthritis, neurodegeneration, restenosis, wound healing, transplant rejection, endometriosis and the like. The pharmaceutical composition containing the compound the present invention is useful as a therapeutic agent and/or preventive agent for these diseases. More preferably, the pharmaceutical composition containing the compound of the present invention is useful as a therapeutic agent and/or preventive agent for urinary extraction failure, interstitial lung disease or fibroid lung, renal fibrosis, hepatic fibrosis, pachyderma, pain, fibromyalgia syndrome, arthsitis and rheumatism, disseminated sclerosis or endometriosis and the like. The compound of the present invention may have a utility as pharmaceutical, as well as autotaxin inhibitory effect, characterized by any of or all of the features as follows:

a) weak inhibitory effect on CYP enzyme (e.g. CYP1A2, CYP2C9, CYP3A4, etc.);
b) good pharmacokinetics, such as high bioavailability and appropriate clearance;
c) low toxicity (e.g. anemia-induced action);
d) high metabolic stability;
e) high water solubility;
f) high brain migration;
g) free of gastrointestinal disorders (e.g., hemorrhagic enteritis, gastrointestinal ulcers, gastrointestinal bleeding, etc.).

Also, the compound of the present invention has low affinity for ENPP1, ENPP3 to 7 receptors and high selectivity for ENPP2 receptor.

The pharmaceutical composition of the present invention may be administered orally in a formulation as conventionally used including tablets, granules, powders, capsules, pills, solution, syrups, buccal or sublingual. The pharmaceutical composition may be administered parentally in a formulation as conventionally used including injections such as intramuscular or intravenous injection, suppositories, transdermal absorbents, inhalants, etc.

The pharmaceutical composition may be prepared by mixing an effective amount of the compound of the invention with various pharmaceutical additives suitable for the formulation, such as excipients, binders, moistening agents, disintegrants, lubricants, diluents and the like. For injections, an active ingredient together with a suitable carrier may be sterilized to obtain a pharmaceutical composition.

Examples of the excipients include lactose, saccharose, glucose, starch, calcium carbonate, crystalline cellulose and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, agar, sodium lauryl sulfate and the like. Examples of the lubricants include talc, magnesium stearate, macrogol and the like. For base materials of suppositories, cacao oil, macrogol, methylcellulose and the like may be used. Solubilizing agents, suspending agents, emulsifiers, stabilizers, preservatives, isotonic agents and the like, which are commonly used, may be added when the composition is prepared as solutions, emulsified or suspended injections. Sweetening agents, flavors and the like, which are commonly used, may be added for oral formulation.

The dosage of the pharmaceutical composition of the invention is determined in the light of the age and weight of the patient, the type and severity of the disease to be treated, and the route for administration and the like. In the case of oral administration to adults, the dosage is usually in the range of 0.05 to 100 mg/kg/day, preferably 0.1 to 10 mg/kg/day. In the case of parenteral administration, the dosage is variable depending on the administration route, but is usually 0.005 to 10 mg/kg/day, preferably in the range of 0.01 to 1 mg/kg/day. The dosage may be administered in single or divided doses.

EXAMPLES

The present invention is further explained by the following Examples and Test Examples, which are not intented to limit the scope of the present invention.

The abbreviations as used herein represent the following meaning.

Me: methyl
Et: ethyl
Bu: butyl
Ph: phenyl
$PPh_3$, TPP: triphenylphosphine
AcOEt: ethyl acetate
DMF: N,N-dimethylformamide
TFA: trifluoroacetic acid
DMSO: dimethyl sulfoxide
THF: tetrahydrofuran
DIEA, Hunig's Base: N,N-diisopropylethylamine
TBAF: tetrabutylammonium fluoride
SEM: 2-(trimethylsilyl) ethoxymethyl
OAc: acetic acid group
mCPBA: metachloroperbenzoic acid
NMP: 1-methylpyrrolidin-2-one
LAH: lithium aluminum hydride
DBU: 1,8-diazabicyclo[5.4.0] undec-7-ene
DCM: methylene chloride
TEA: trimethylamine
TMS: tetramethylsilane
HATU: O-(7-azabenzotriazol 1-yl)-N,N,N',N',-tetramethyluronium hexafluorophosphate
DPPA: diphenylphosphoryl azide NMR analysis of the compounds obtained in the Example was carried out at 400 MHz, using deuterated dimethyl sulfoxide ($d_6$-DMSO) or deuterochloroform ($CDCl_3$).

LC/MS was measured under the following conditions.
(Method A)
Column: ACQUITY UPLC BEH C18 (1.7 μm i.d.2.1×50 mm) (Waters)
Flow rate: 0.8 mL/min
UV detection wavelength: 254 nm
Mobile phase:
[A] 0.1% formic acid in water
[B] 0.1% formic acid in acetonitrile
Gradient: linear gradient from 10% to 100% [B] over 3.5 minutes, and then 100% [B] was maintained for 0.5 minutes.
(Method B)
Column: Shim-pack XR-ODS (2.2 μm, i.d.50×3.0 mm) (Shimadzu)
Flow rate: 1.6 mL/min
UV detection wavelength: 254 nm
Mobile phase:
[A] 0.1% formic acid in water
[B] 0.1% formic acid in acetonitrile
Gradient: linear gradient from 10% to 100% [B] over 3 minutes, and then 100% [B] was maintained for 0.5 minute.
(Method C)
Column: Boston ODS-3 250×4.6 mm
flow rate: 1.0 mL/min
UV detection wavelength: 246 nm
Mobile phase:
[A] water
[B] acetonitrile
Gradient: linear gradient from 10% to 100% [B] over 3 minutes, and then 100% [B] was maintained for 0.5 minute.

(Method D)
Column: Waters X Bridge C18 (3.5 μm 50×4.6 mm)
Flow rate: 2.0 mL/min
UV detection wavelength: 254 nm
Mobile phase:
[A] 0.05% TFA in water
[B] 0.05% TFA in acetonitrile
Gradient: linear gradient from 5% to 100% [B] over 1.6 minutes, and then 100% [B] was maintained for 1.4 minutes.
(Method E)
Column: ACQUITY UPLC BEH C18 (1.7 μm i.d.2.1×50 mm) (Waters)
Flow rate: 0.55 mL/min
UV detection wavelength: 254 nm
Mobile phase:
[A] 0.1% formic acid in water
[B] 0.1% formic acid in acetonitrile
Gradient: linear gradient from 5% to 100% [B] over 3.5 minutes, and then 100% [B] was maintained for 0.5 minutes.
(Method F)
Column: Waters X Bridge C18 (3.5 μm 50×4.6 mm)
Flow rate: 2.0 mL/min
UV detection wavelength: 254 nm
Mobile phase:
[A] 0.01% NH$_4$HCO$_3$aq in water
[B] acetonitrile
Gradient: linear gradient from 5% to 100% [B] over 1.6 minutes, and then 100% [B] was maintained for 1.4 minutes.

Example 1

Preparation of Compound a15 (I-0218)

Step 1: Preparation of Compound a2

[Chemical Formula 65]

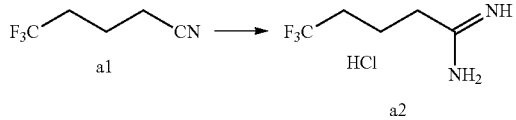

To a solution of ammonium chloride (6.73 g, 126 mmol) in toluene (93 mL) was dropped 2 mol/L trimethyl aluminum n-hexane solution (58.5 mL, 117 mmol) under ice-cooling, and the mixture was stirred for 30 minutes under ice-cooling. After Compound a1 (9.32 g, 68 mmol) was added under ice-cooling, the solution was stirred at 80° C. overnight. The reaction solution was filtered, washed with methanol (150 mL)/methylene chloride (150 mL) solution, and concentrated under reduced pressure to yield Compound a2 hydrochloride (9.5 g, yield: 73%) as white oil.

$^1$H-NMR (DMSO-D$_6$) δ: 4.17 (s, 1H), 3.16 (s, 3H), 2.50-2.46 (m, 3H), 2.32-2.27 (m, 2H), 1.85-1.83 (m, 2H).

Step 2: Preparation of Compound a4

[Chemical Formula 66]

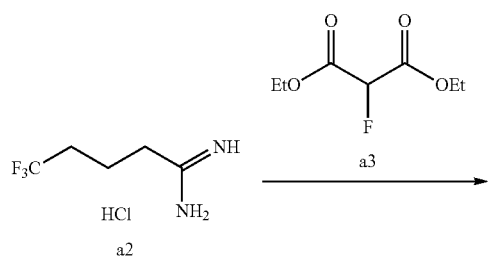

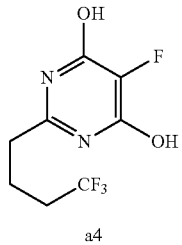

To a solution of Compound a2 hydrochloride (1.0 g, 5.25 mmol) in methanol (10 mL) was added potassium tert-butoxide (1.07 g, 9.54 mmol), the mixture was stirred 10 minutes under ice-cooling. After added Compound a3 (739 ul, 4.77 mmol), the solution was stirred at 60° C. for 1 hour. After added 2 mol/L hydrochloric acid aqueous solution, methanol was removed under reduced pressure. The precipitated solid was filtered, washed with water, and concentrated under reduced pressure to yield Compound a4 (648.8 mg, yield: 57%) as pale pink solid.

LC-MS: m/z=241. [M+H]$^+$

LC/MS method: Method A, retention time: 0.74 min

Step 3: Preparation of Compound a5

[Chemical Formula 67]

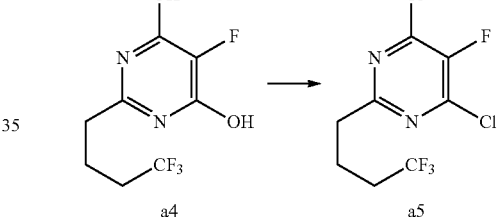

A solution of Compound a4 (648 mg, 2.70 mmol) in phosphorus oxychloride (6 mL) was stirred at 80° C. for one and a half hours. After removed the excess phosphorus oxychloride, to the reaction solution was added ice. To the residue was added water, the solution was extracted with ethyl acetate twice. The organic layer was washed with water, saturated sodium bicarbonate aqueous solution and brine, dried over anhydrous sodium sulfate, and concentrated under reduced pressure to yield Compound a5 (519.3 mg, yield: 70%) as pale brown oil.

$^1$H-NMR (CDCl$_3$) δ: 2.56 (t, 2H, J=7.5 Hz), 2.33-2.29 (m, 2H), 1.86-1.84 (m, 2H).

Step 4: Preparation of Compound a7

[Chemical Formula 68]

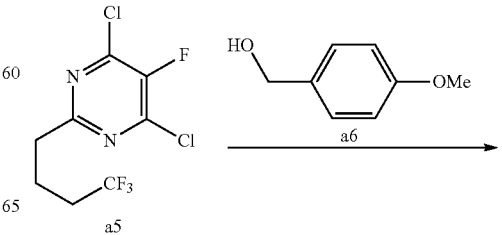

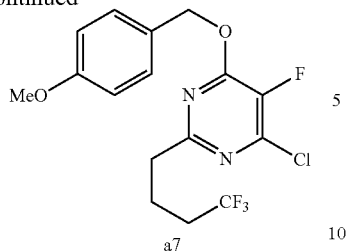

a7

To a solution of Compound a6 (252 uL, 2.03 mmol) in DMF (2 mL) was added sodium hydride (81 mg, 2.025 mmol) under salt ice bath cooling to prepare the solution A. To a solution of Compound a5 (510 mg, 1.84 mmol) in DMF (3 mL) was dropped the solution A under salt ice bath cooling, and the mixture was stirred for 30 minutes. To the reaction solution was added to ice-water, and the solution was extracted with ethyl acetate twice. The organic layer was washed with water and brine, dried over anhydrous sodium sulfate and concentrated under reduced pressure. The obtained residue was purified by silica gel column chromatography (ethyl acetate/hexane) to yield Compound a7 (343 mg, yield: 49%).

LC-MS: m/z=379. [M+H]$^+$
LC/MS method: Method A, retention time: 2.84 min
Step 5: Preparation of Compound a8

[Chemical Formula 69]

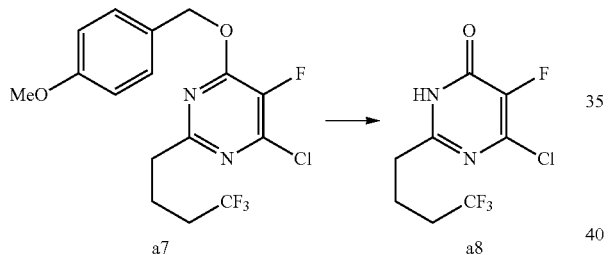

A solution of Compound a7 (343 mg, 1.84 mmol) in trifluoroacetic acid (3 mL) was stirred for 20 minutes under ice-cooling. To the reaction solution was added water, and the solution was extracted with chloroform twice. The organic layer was washed with water, dried over anhydrous sodium sulfate and concentrated under reduced pressure to yield Compound a8 (351.5 mg, yield: quant) as a white solid.

LC-MS: m/z=259. [M+H]$^+$
LC/MS method: Method A, retention time: 1.65 min
Step 6: Preparation of Compound a10

[Chemical Formula 70]

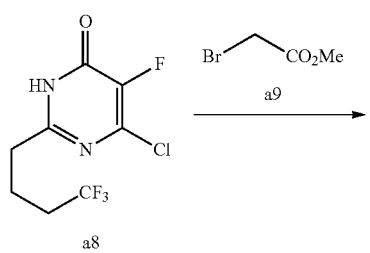

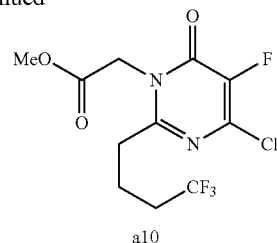

a10

To a solution of Compound a8 (350 mg, 1.35 mmol) in THF (3.5 mL) was added sodium hydride (70.4 mg, 1.759 mmol) under ice-cooling, and the solution was stirred for 10 minutes. After Compound a9 (162 ul, 1.76 mmol) was added to the reaction solution, the solution was stirred for 60° C. for 2 hours. To the reaction solution was added water, and the solution was extracted with ethyl acetate twice. The organic layer was washed with water and brine, dried over anhydrous sodium sulfate and concentrated under reduced pressure. The obtained residue was purified by silica gel column chromatography (ethyl acetate/hexane) to yield Compound a10 (243 mg, yield: 54%) as colorless oil.

LC-MS: m/z=331. [M+H]$^+$
LC/MS method: Method A, retention time: 2.05 min
Step 7: Preparation of Compound a11

[Chemical Formula 71]

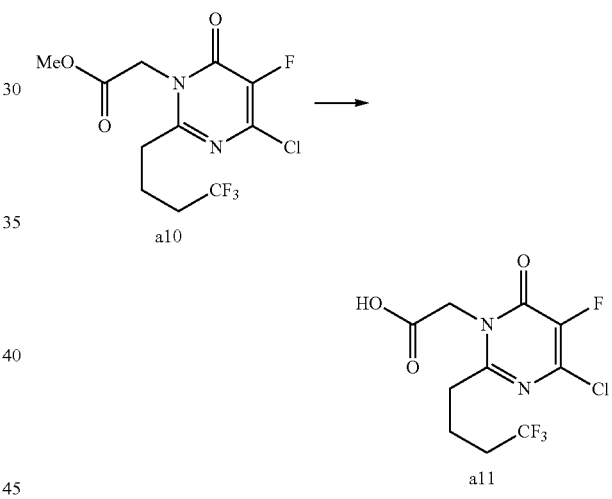

To a solution of Compound a10 (233 mg, 0.71 mmol) in methanol/THF (1:1, 2.3 mL) was added 2 mol/L sodium hydroxide aqueous solution (1.06 ml, 2.11 mmol), and the solution was stirred at room temperature for 20 minutes. To the reaction solution was added water, and the solution was extracted with chloroform twice. The organic layer was washed with brine, anhydrous sodium sulfate, and concentrated under reduced pressure. The obtained crude product was directly used in the next step.

Step 8: Preparation of Compound a13

[Chemical Formula 72]

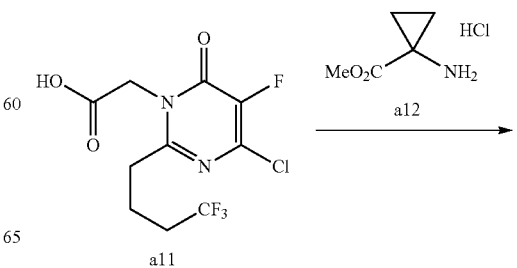

-continued

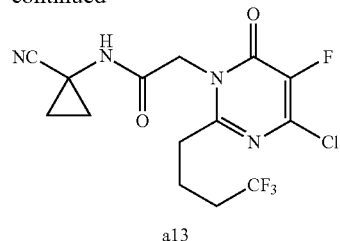
a13

To a solution of Compound a11 in DMF (2.3 mL) was added HATU (322 mg, 0.85 mmol), and added Compound a12 hydrochloride (100 mg, 0.85 mmol) and trimethylamine (147 ul, 1.06 mmol) under ice-cooling, and the mixture was stirred for 3 hours under ice-cooling. To the reaction solution was added water, and the solution was extracted with ethyl acetate twice. The organic layer was washed with water and brine, dried over anhydrous sodium sulfate and concentrated under reduced pressure. The residue was purified by silica gel column chromatography (ethyl acetate/hexane) to yield Compound a13 (178.3 mg, yield: 67%) as a pale brown solid.

LC-MS: m/z=381. [M+H]$^+$

LC/MS method: Method A, retention time: 1.87 min

Step 9: Preparation of Compound a15 (I-0218)

[Chemical Formula 73]

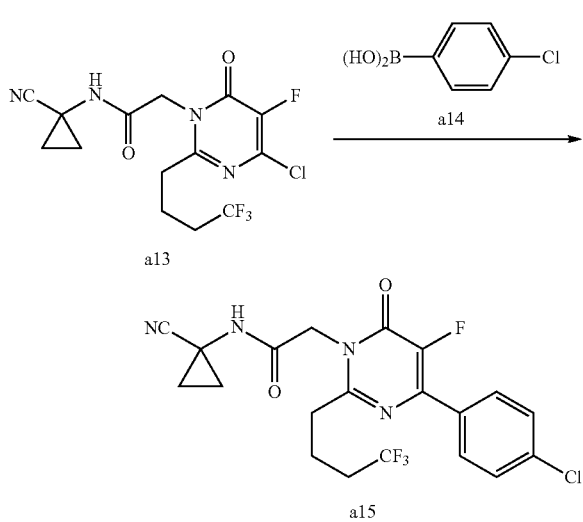

To a solution of Compound a13 (65 mg, 0.17 mmol) in DMF (650 ul) was added Compound a14 (29.4 mg, 0.19 mmol), 1, 1'-bis(diphenylphosphino)ferrocen-palladium(II) dichloride-dichloromethane complex (13.9 mg, 0.017 mmol) and 2 mol/L sodium carbonate aqueous solution (94 μl, 0.188 mmol), and the mixture was stirred at 150° C. for 10 minutes under microwave irradiation. To the reaction solution was added water, and the solution was extracted with chloroform twice. The organic layer was washed with water and brine, dried over anhydrous sodium sulfate and concentrated under reduced pressure. The obtained residue was purified by reversed phase silica gel column chromatography to yield Compound a15 (I-0218) (2.4 mg, yield: 3%) as a pale brown solid.

$^1$H-NMR (CDCl$_3$) δ: 7.99 (d, 2H, J=7.8 Hz), 7.69 (s, 1H), 7.47 (d, 2H, J=7.8 Hz), 4.73 (s, 2H), 2.97-2.93 (m, 2H), 2.33-2.18 (m, 4H), 1.57-1.56 (m, 2H), 1.31-1.29 (m, 2H).

Example 2

Preparation of Compound a23 (I-0112)

Step 1: Preparation of Compound a 17

[Chemical Formula 74]

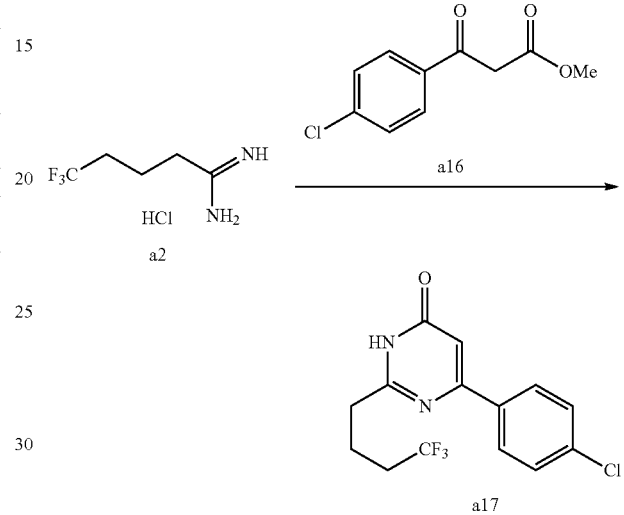

Compound a17 was obtained by the method similar to the preparation of Compound a4.

LC-MS: m/z=317. [M+H]$^+$

Step 2: Preparation of Compound a18 (I-0254)

[Chemical Formula 74]

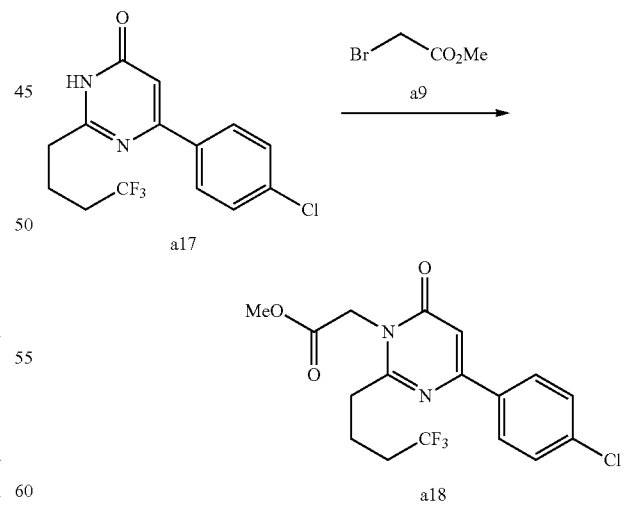

To a solution of Compound a17 (1.0 g, 3.16 mmol) in THF (10 mL) was added potassium carbonate (655 mg, 4.74 mmol), and added Compound a9 (389 ul, 4.10 mmol) under ice-cooling, and the mixture was stirred for 7 hours under ice-cooling. The reaction solution was added water, and extracted with ethyl acetate. The organic layer was washed with brine, dried over anhydrous sodium sulfate, and concentrated under reduced pressure. The obtained residue was purified by silica gel column chromatography (ethyl acetate/hexane) to yield Compound a18 (I-025.1) (134.2 mg, yield: 86%) as a pale brown solid.

LC-MS: m/z=389. [M+H]$^+$

Step 3: Preparation of Compound a19 (I-0110)

[Chemical Formula 76]

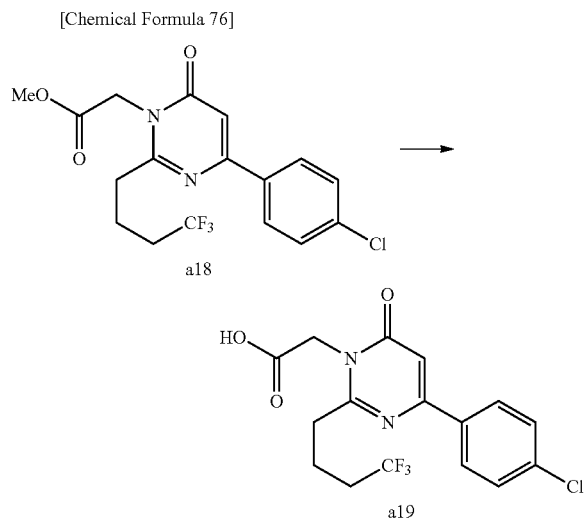

Compound a19 (I-0110) was obtained by the method similar to the preparation of Compound a11.

$^1$H-NMR (DMSO-D$_6$) δ: 8.11 (d, 2H, J=7.3 Hz), 7.57 (d, 2H, J=7.3 Hz), 6.94 (s, 1H), 4.64 (s, 2H), 2.86 (t, 2H, J=7.0 Hz), 2.43-2.36 (m, 2H), 2.07-2.00 (m, 2H).

Step 4: Preparation of Compound a21 (I-0111)

[Chemical Formula 77]

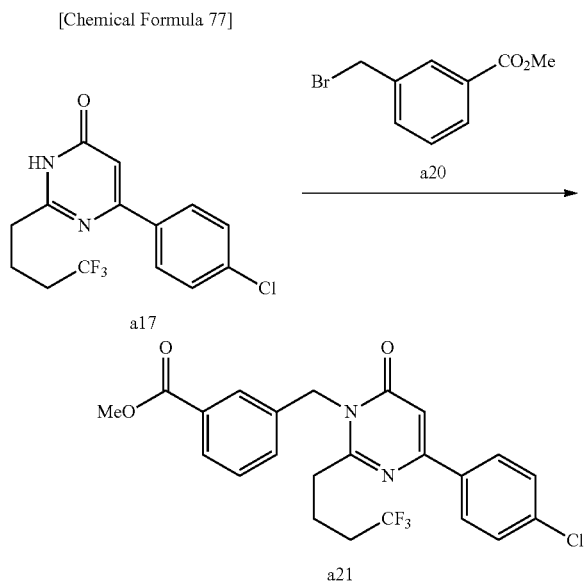

Compound a21 (I-0111) was obtained by the method similar to the preparation of Compound a18.

$^1$H-NMR (CDCl$_3$) δ: 7.97 (dd, 3H, J=14.4, 7.7 Hz), 7.89 (s, 1H), 7.46-7.38 (m, 4H), 6.89 (s, 1H), 5.38 (s, 2H), 3.91 (s, 3H), 2.79 (t, 2H, J=6.5 Hz), 2.24-2.11 (m, 4H).

Step 5: Preparation of Compound a23 (I-0112)

[Chemical Formula 78]

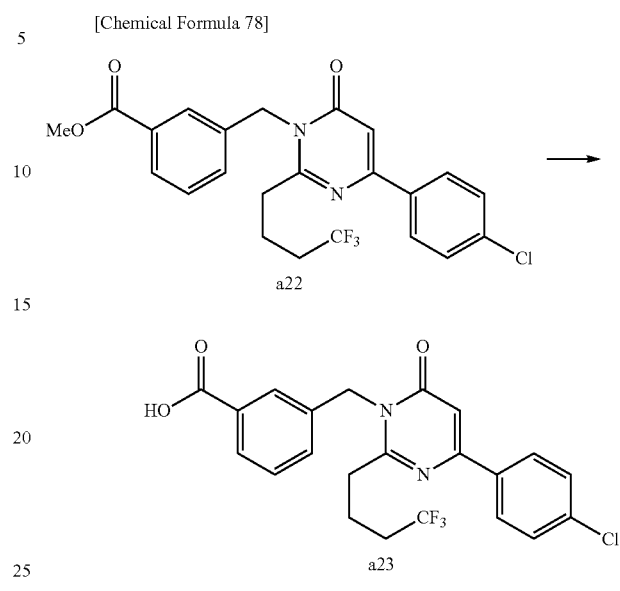

Compound a23 (I-0112) was obtained by the method similar to the preparation of Compound a11.

$^1$H-NMR (DMSO-D$_6$) δ: 8.15 (d, 2H, J=8.5 Hz), 7.86 (d, 1H, J=7.4 Hz), 7.76 (s, 1H), 7.58 (d, 2H, J=8.5 Hz), 7.50-7.42 (m, 2H), 7.08 (s, 1H), 5.38 (s, 2H), 2.87 (t, 2H, J=7.0 Hz), 2.39-2.27 (m, 2H), 2.01-1.93 (m, 2H).

Example 3

Preparation of Compound a32 (I-0205)

Step 1: Preparation of Compound a25

[Chemical Formula 79]

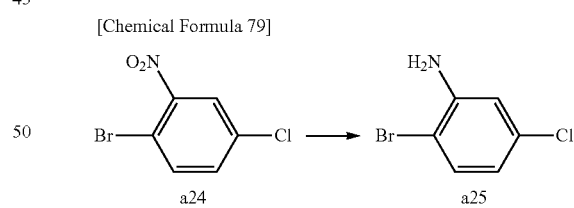

To a solution of Compound a24 (1.5 g, 6.34 mmol) in ethanol (15 mL) was added tin chloride dihydrate (5.73 g, 25.4 mmol), and the solution was stirred at 60° C. for 1 hour. To the reaction solution was added ethyl acetate and 4 mol/L sodium hydroxide aqueous solution (12.69 ml, 50.8 mmol), the precipitated solid was filtered. The organic layer was concentrated under reduced pressure to yield Compound a25 (1.29 g, yield: 98%) as a pale brown solid.

$^1$H-NMR (CDCl$_3$) δ: 7.30 (d, 1H, J=8.5 Hz), 6.75 (s, 1H), 6.59 (d, 1H, J=8.5 Hz), 4.15 (br s, 2H).

Step 2: Preparation of Compound a26

[Chemical Formula 80]

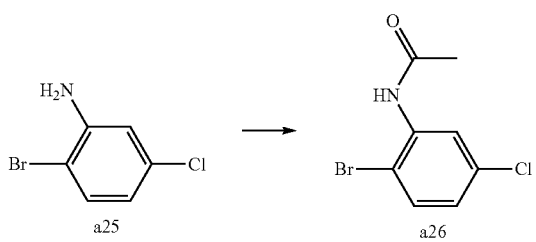

To a solution of Compound a25 (1 g, 4.84 mmol) in pyridine (8 mL) was added sodium hydride (0.21 g, 5.33 mmol) and acetyl chloride (0.42 ml, 5.81 mmol), and the solution was stirred at 80° C. for 1 hour. To the reaction solution was added water, and the solution was extracted with ethyl acetate twice. The organic layer was washed with water and brine, dried over anhydrous sodium sulfate and concentrated under reduced pressure. To a solution of the obtained residue in THF/methanol (1:1, 9 ml) was added 2 mol/L sodium hydroxide aqueous solution (2.6 ml, 5.16 mmol), and the solution was stirred at room temperature for 30 minutes. To the reaction solution was added water, and the solution was extracted with ethyl acetate twice. The organic layer was washed with water and brine, dried over anhydrous sodium sulfate and concentrated under reduced pressure. To the obtained residue was added ethyl acetate (5 ml), and the mixture was dissolved in a water bath of 80° C. After cooled to room temperature, hexane (5 ml) was added to the solution, and the precipitated solid was filtered, washed with isopropyl ether (5 ml), and dried under reduced pressure to Compound a26 (674.4 mg, yield: 53%) as a pale brown solid.

$^1$H-NMR (CDCl$_3$) δ: 8.46 (s, 1H), 7.59 (s, 1H), 7.45 (d, 1H, J=8.5 Hz), 6.97 (d, 1H, J=8.5 Hz), 2.25 (s, 3H).

Step 3: Preparation of Compound a28

[Chemical Formula 81]

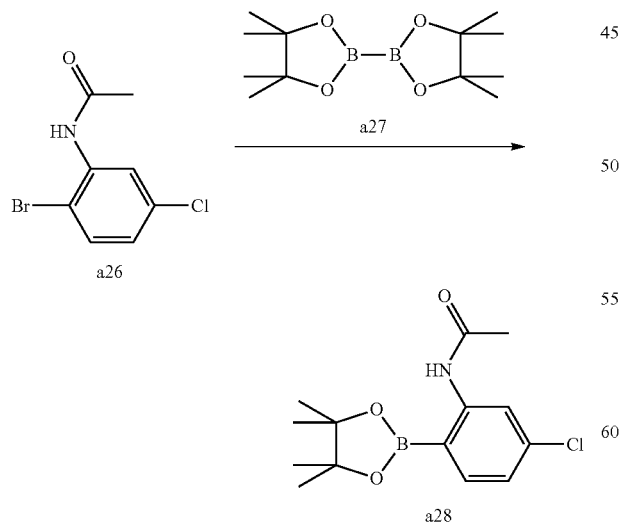

To a solution of Compound a26 (300 mg, 1.21 mmol) in 1,4-dioxane (3 mL) was added Compound a27 (368 g, 1.45 mmol), potassium acetate (355 mg, 3.62 mmol) and 1,1'-bis(diphenylphosphino)ferrocene-palladium(II) dichloride-dichloromethane complex (99 mg, 0.121 mmol), and the mixture was stirred at 100° C. for 5 hours. The reaction mixture was purified by silica gel column chromatography (ethyl acetate/hexane) to yield Compound a28 (101 mg, yield: 29%) as a broen oil.

$^1$H-NMR (CDCl$_3$) δ: 9.50 (s, 1H), 8.50 (s, 1H), 7.66 (d, 1H, J=8.3 Hz), 7.04 (d, 1H, J=8.0 Hz), 2.15 (s, 3H), 1.37 (s, 13H).

Step 4: Preparation of Compound a30

[Chemical Formula 82]

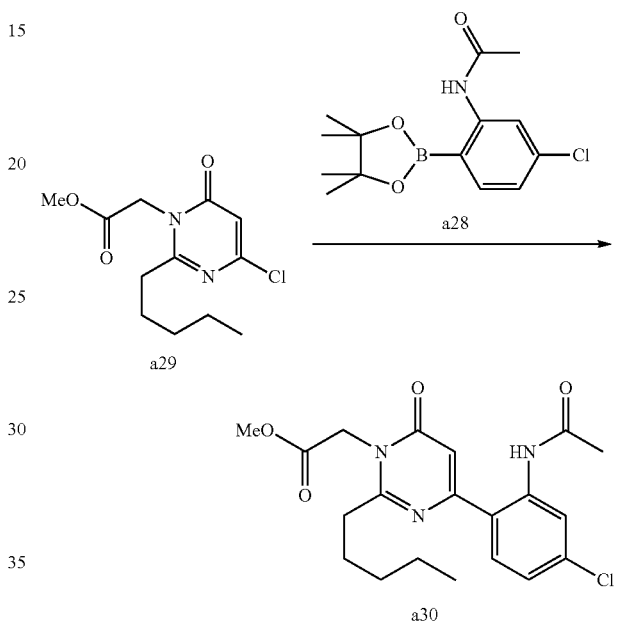

Compound a30 was obtained by the method similar to the preparation of Compound a11 and a15.

LC/MS method: Method A, retention time: 2.31 min

Step 5: Preparation of Compound a31

[Chemical Formula 83]

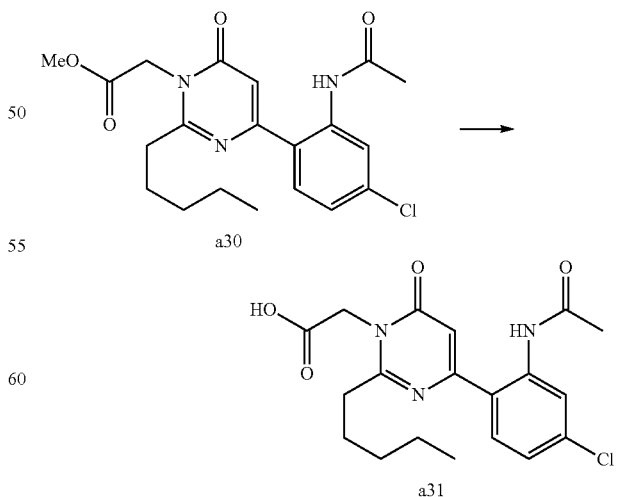

Compound a31 was obtained by the method similar to the preparation of Compound a11.

85

Step 6: Preparation of Compound a32 (I-0205)

[Chemical Formula 84]

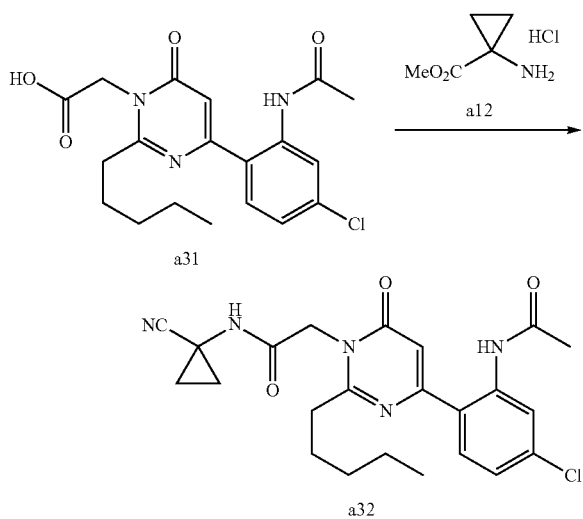

Compound a32 (I-0205) was obtained by the method similar to the preparation of Compound a13.
LC/MS method: Method A, retention time: 2.11 min

Example 4

Preparation of Compound a35 (I-0208)

Step 1: Preparation of Compound a33

[Chemical Formula 85]

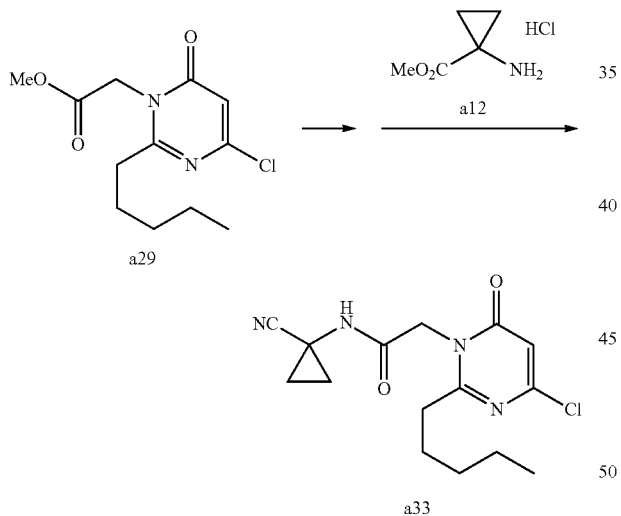

Compound a33 was obtained by the method similar to the preparation of Compound a13.
LC/MS method: Method A, retention time: 1.77 min Step 2: Preparation of Compound a35 (I-0208)

[Chemical Formula 86]

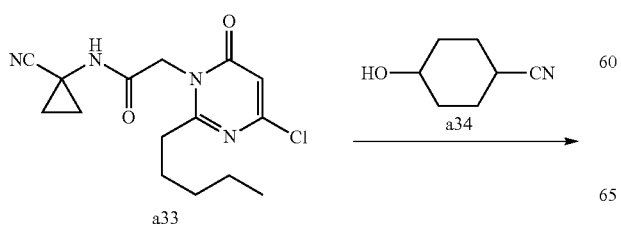

86

-continued

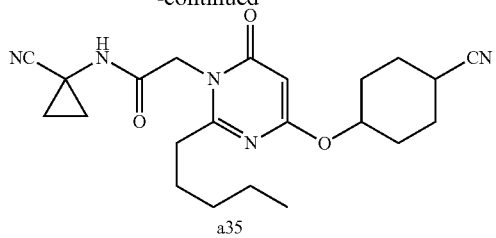

To a solution of Compound a34 (80 mg, 0.64 mmol) in DMF (200 ul) was added sodium hydride (30.7 mg, 0.77 mmol) under ice-cooling, and the mixture was stirred for 10 minutes. Compound a33 (206 mg, 0.64 mmol) and DMF (600 ul) was added to the solution, and the solution was stirred at 60° C. for 2 hours, and stirred at 80° C. for 1 hour. To the reaction solution was added water, and the solution was extracted with ethyl acetate twice. The organic layer was washed with water and brine, dried over anhydrous sodium sulfate and concentrated under reduced pressure. The obtained residue was purified by reversed-phase silica gel column chromatography to yield Compound a35 (5.1 mg, yield: 2%) as a white solid.

LC/MS method: Method A, retention time: 1.85 min

Example 5

Preparation of Compound a39 (I-0255)

Step 1: Preparation of Compound a38 (I-0254)

[Chemical Formula 87]

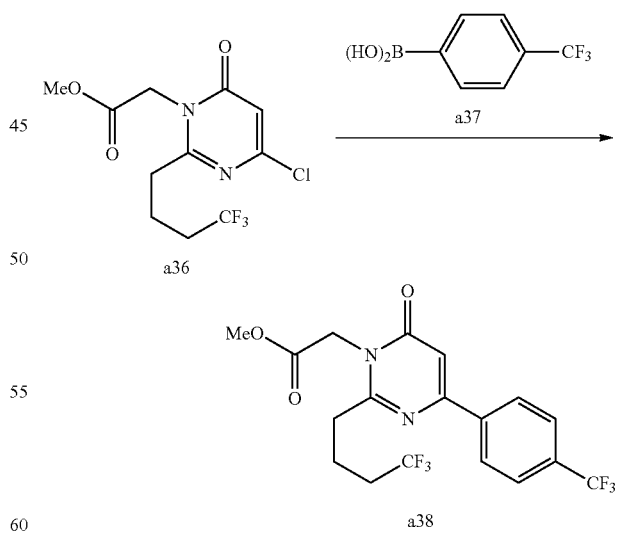

Compound a38 (I-0254) was obtained by the method similar to the preparation of Compound a15.

LC-MS: m/z=423. [M+H]$^+$

LC/MS method: Method B, retention time: 2.37 min

Step 2: Preparation of Compound a39 (I-0255)

[Chemical Formula 88]

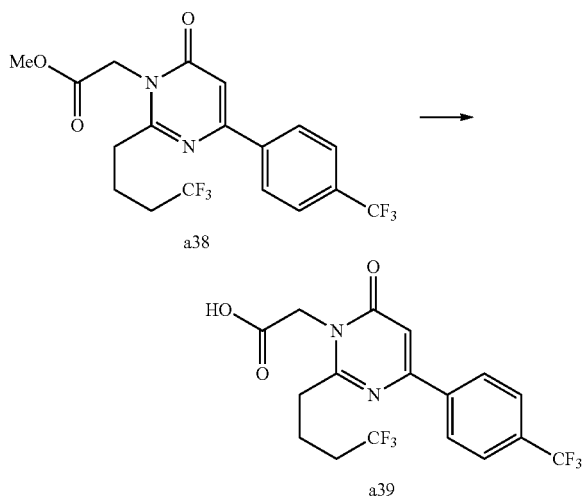

Compound a39 (I-0255) was obtained by the method similar to the preparation of Compound a11.
LC-MS: m/z=409. [M+H]$^+$
LC/MS method: Method B, retention time: 2.18 min Example 6

Preparation of Compound a41 (I-0254)

[Chemical Formula 89]

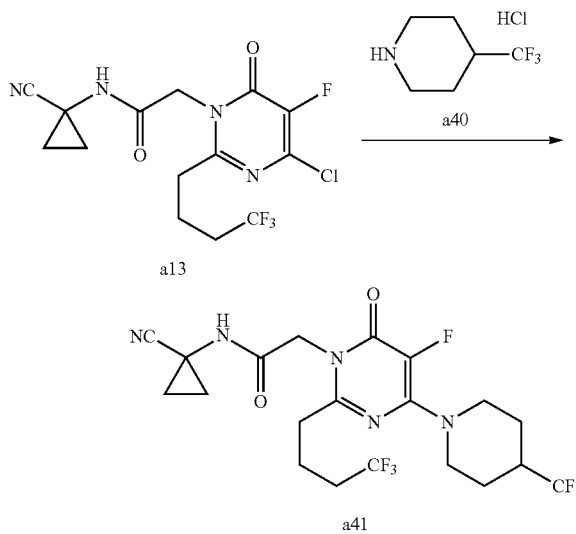

To a solution of Compound a40 hydrochloride (112 mg, 0.59 mmol) in DMF (200 ul) was added sodium hydride (47.1 mg, 1.18 mmol) under ice-cooling, and the solution was stirred for 10 minutes. Compound a13 (112 mg, 0.29 mmol) in DMF (1 ml) was added to the solution under ice-cooling, and the solution was stirred at 60° C. for 1 hour. To the reaction solution was added water, and the solution was extracted with ethyl acetate twice. The organic layer was washed with water and brine, dried over anhydrous sodium sulfate and concentrated under reduced pressure. The obtained residue was purified by reversed-phase silica gel column chromatography to yield Compound a41 (15.8 mg, yield: 11%) as a white solid.

LC/MS method: Method A, retention time: 2.19 min

Example 7

Preparation of Compound a52 (I-0242)

Step 1: Preparation of Compound a43

[Chemical Formula 90]

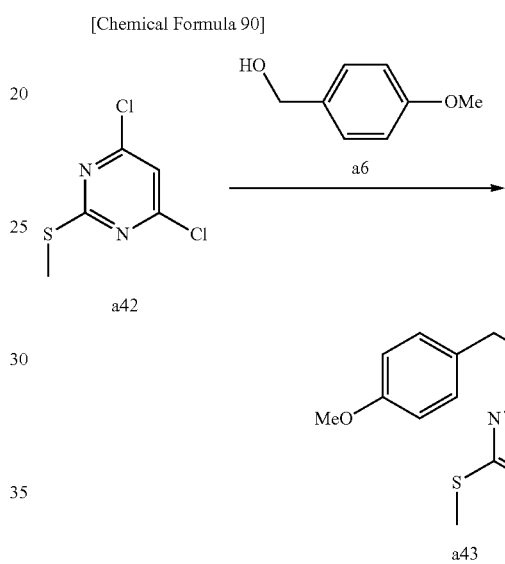

Compound a43 was obtained by the method similar to the preparation of Compound a7.

$^1$H-NMR (CDCl$_3$) δ: 7.35 (2H, d, J=8.4 Hz), 6.91 (2H, d, J=8.4 Hz), 6.42 (1H, s), 5.35 (2H, a), 3.82 (3H, s), 2.56 (3H, s).

LC-MS: m/z=297. [M+H]$^+$

Step 2: Preparation of Compound a44

[Chemical Formula 91]

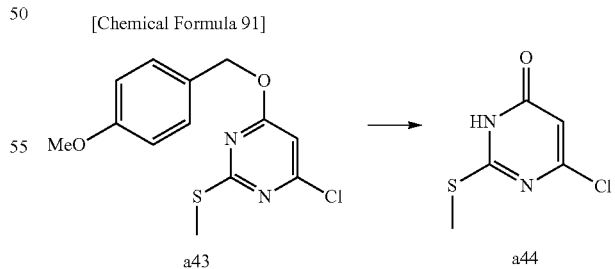

Compound a44 was obtained by the method similar to the preparation of Compound a8.

$^1$H-NMR (DMSO-D$_6$) δ: 8.26 (1H, s), 6.30 (1H, s), 2.49 (3H, a).

LC-MS: m/z=177. [M+H]$^+$

Step 3: Preparation of Compound a45

[Chemical Formula 92]

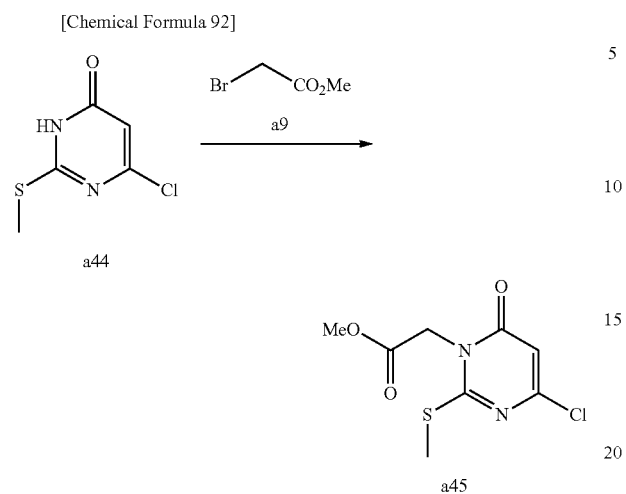

Compound a45 was obtained by the method similar to the preparation of Compound a10.
$^1$H-NMR (CDCl$_3$) δ: 6.31 (1H, s), 4.81 (2H, s), 3.80 (3H, s), 2.62 (3H, s).
LC-MS: m/z=249. [M+H]$^+$ Step 4: Preparation of Compound a46

[Chemical Formula 93]

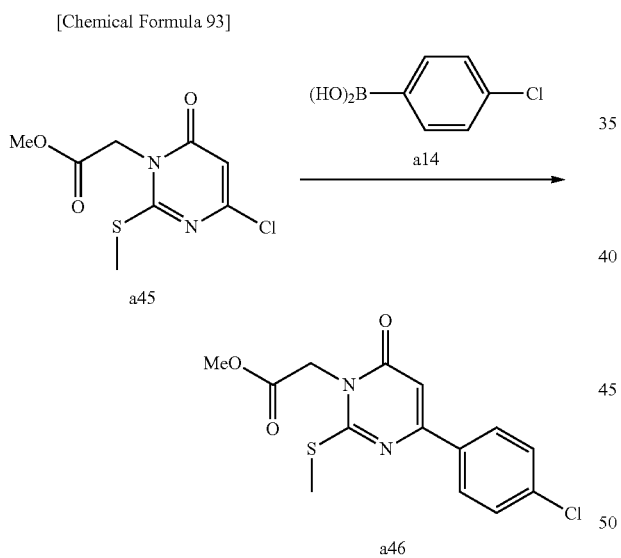

To a solution of Compound a45 (500 mg, 2.01 mmol) in THF (4 mL) was added Compound a14 (472 mg, 3.02 mmol), chloro(2-dicyclohexylphosphino-2',4',6'-triisopropyl-1,1'-biphenyl)[2-(2'-amino-1,1'-biphenyl)]palladium(II) (31.7 mg, 0.040 mmol) and 2 mol/L potassium phosphate aqueous solution (8.04 ml), and the mixture was stirred at 60° C. for 1 hour. To the reaction solution was added water, and the solution was extracter with ethyl acetate twice. The organic layer was washed with water and brine, dried over anhydrous sodium sulfate and concentrated under reduced pressure. The residue was purified by silica gel column chromatography (ethyl acetate/hexane) to yield Compound a46 (580 mg, yield: 89%) as a white solid.
$^1$H-NMR (CDCl$_3$) δ: 7.93 (2H, d, J=8.4 Hz), 7.43 (2H, d, J=8.3 Hz), 6.68 (1H, s), 4.89 (2H, s), 3.81 (3H, s), 2.71 (3H, s).

LC-MS: m/z=325. [M+H]$^+$
LC/MS method: Method B, retention time: 1.85 min

Step 5: Preparation of Compound a47

[Chemical Formula 94]

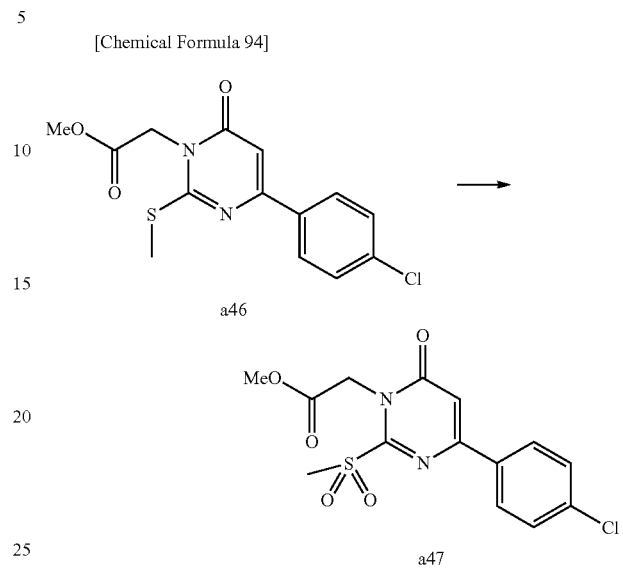

To a solution of Compound a46 (200 mg, 0.62 mmol) in dichloromethane (5 mL) was added m-chloroperbanzoic acid (425 mg, 1.85 mmol), and the mixture was stirred at room temperature for 3 hours. To the reaction solution was added 10% sodium bisulfite aqueous solution, and the solution was extracted with chloroform twice. The organic layer was washed with water and brine, dried over anhydrous sodium sulfate and concentrated under reduced pressure. The residue was purified by silica gel column chromatography (ethyl acetate/hexane) to yield Compound a47 (110 mg, yield: 50%) as colorless oil.
$^1$H-NMR (CDCl$_3$) δ: 7.83 (2H, d, J=8.4 Hz), 7.48 (2H, d, J=8.3 Hz), 6.90 (1H, s), 5.19 (2H, s), 3.80 (3H, s), 3.56 (3H, s).
LC-MS: m/z=357. [M+H]$^+$
LC/MS method: Method B, retention time: 1.90 min Step 6: Preparation of Compound a49

[Chemical Formula 95]

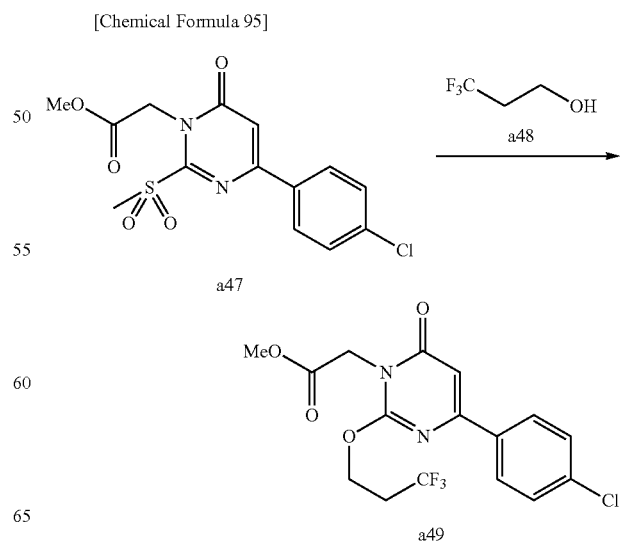

To a solution of Compound a48 (19.2 mg, 0.17 mmol) in THF (250 uL) was added potassium tert-butoxide (18.9 mg, 0.17 mmol), and the solution was stirred for 30 minutes under ice-cooling. To the reaction solution was added a solution of Compound a47 (50 mg, 0.14 mmol) in THF (250 ul), and the solution was stirred at −78° C. for 1 hour. To the reaction solution was added 1 mol/L hydrochloric acid aqueous solution, the solution was extracted with ethyl acetate twice. The organic layer was washed with water and brine, dried over anhydrous sodium sulfate and concentrated under reduced pressure. The residue was purified by silica gel column chromatography (ethyl acetate/hexane) to yield Compound a49 (42 mg, yield: 77%) as a white solid.

$^1$H-NMR (CDCl$_3$) δ: 7.88 (2H, d, J=8.4 Hz), 7.43 (2H, d, J=8.3 Hz), 6.63 (1H, s), 4.82-4.75 (4H, m), 3.78 (3H, s), 2.68-2.62 (2H, m).

LC-MS: m/z=391. [M+H]$^+$

LC/MS method: Method B, retention time: 2.25 min

Step 7: Preparation of Compound a50

[Chemical Formula 96]

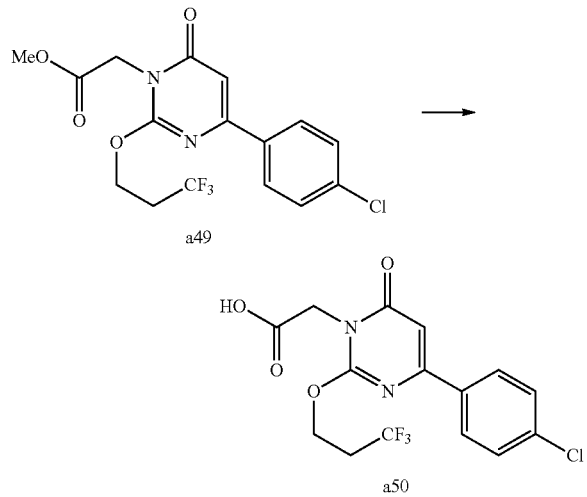

Compound a50 was obtained by the method similar to the preparation of Compound a11.

Step 8: Preparation of Compound a52 (I-0242)

[Chemical Formula 97]

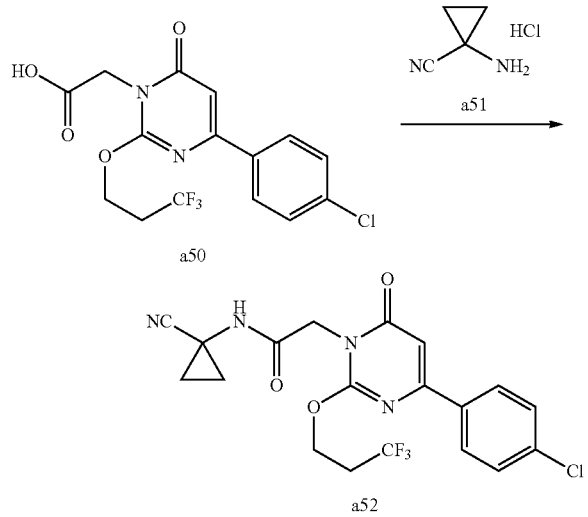

Compound a52 (I-0242) was obtained by the method similar to the preparation of Compound a13.

$^1$H-NMR (CDCl$_3$) δ: 7.86 (2H, d, J=7.8 Hz), 7.43 (1H, d, J=7.8 Hz), 6.84 (2H, d, J=7.9 Hz), 6.61 (1H, s), 4.70 (1H, t, J=7.8 hz), 4.66 (1H, s), 2.70 (2H, t, J=7.8 Hz), 1.57-1.56 (m, 2H), 1.31-1.29 (m, 2H).

LC-MS: m/z=441. [M+H]$^+$

LC/MS method: Method B, retention time: 1.77 min

Example 8

Preparation of Compound a55 (I-0243)

Step 1: Preparation of Compound a53

[Chemical Formula 98]

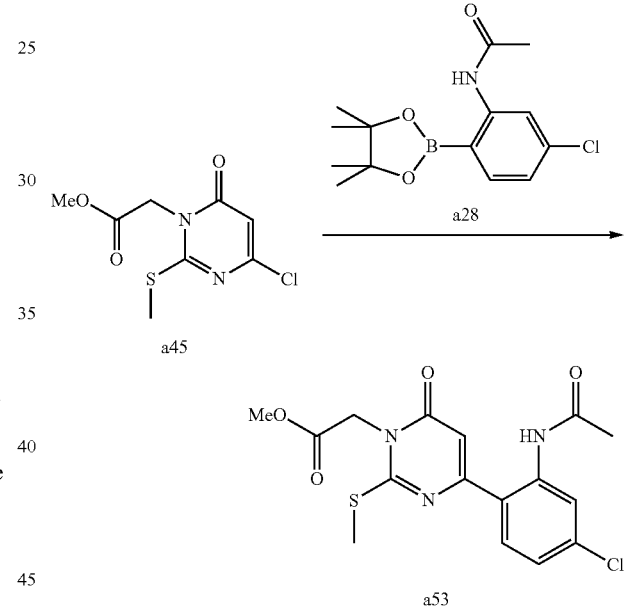

Compound a53 was obtained by the method similar to the preparation of Compound a46.

LC/MS method: Method B, retention time: 1.60 min

Step 2: Preparation of Compound a54

[Chemical Formula 99]

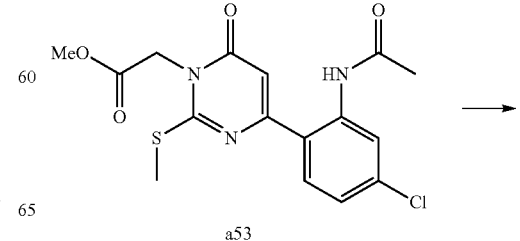

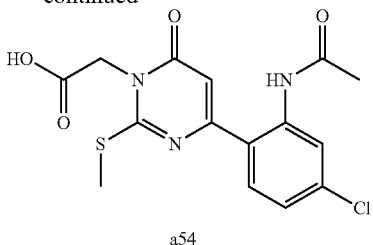

a54

To a solution of Compound a53 (20 mg, 0.052 mmol) in 1,2-dichloroethane (1 ml) was added hydroxy trimethyltin (95 mg, 0.52 mmol), and the solution was stirred at 70° C. for 2 hours. To the reaction solution was added 1 mol/L hydrochloric acid aqueous solution, and the solution was extracted with ethyl acetate, dried over anhydrous sodium sulfate and concentrated under reduced pressure. The obtained Compound a54 was directly used in the next step.

Step 3: Preparation of Compound a55 (I-0243)

[Chemical Formula 100]

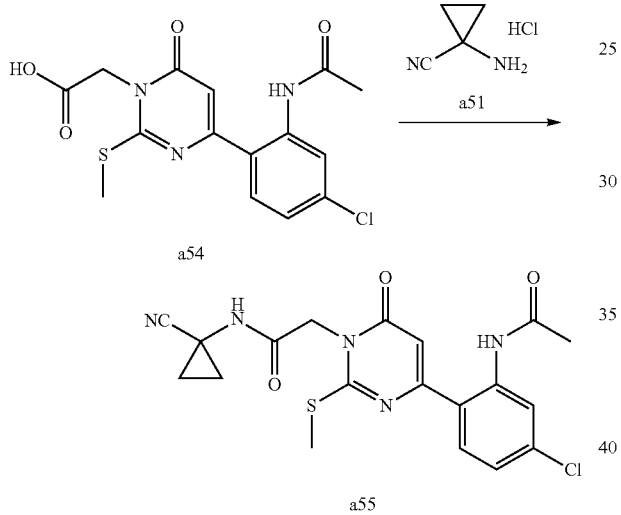

Compound a55 (I-0243) was obtained by the method similar to the preparation of Compound a13.

$^1$H-NMR (DMSO-D$_6$) δ: 9.88 (1H, s), 9.29 (1H, s), 8.01 (1H, s), 7.65 (1H, d, J=8.5 Hz), 7.30 (1H, d, J=8.5 Hz), 6.46 (1H, s), 4.66 (2H, s), 2.58 (3H, s), 2.01 (3H, s), 1.52-1.51 (2H, m), 1.16-1.14 (2H, m).

LC-MS: m/z=432. [M+H]$^+$

Example 9

Preparation of Compound a57

[Chemical Formula 101]

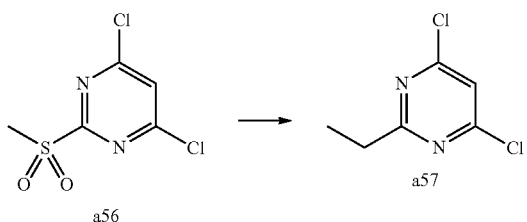

To a solution of Compound a56 (1 g, 4.40 mmol) in THF (7 ml) was added 3 mol/L ethyl magnesium bromide diethyl ether solution (2.9 ml, 8.81 mmol) under ice-cooling, and the solution was stirred for 1 hour under ice-cooling. To the reaction solution was added 1 mol/L hydrochloric acid aqueous solution, and the solution was extracted with ethyl acetate. The organic layer was washed saturated sodium hydrogen carbonate solution, dried over anhydrous sodium sulfate and concentrated under reduced pressure to yield Compound a57 (730 mg, yield: 94%) as yellow oil.

LC/MS method: Method B, retention time: 1.97 min

Example 10

Preparation of Compound a63 (I-0002)

Step 1: Preparation of Compound a60

[Chemical Formula 102]

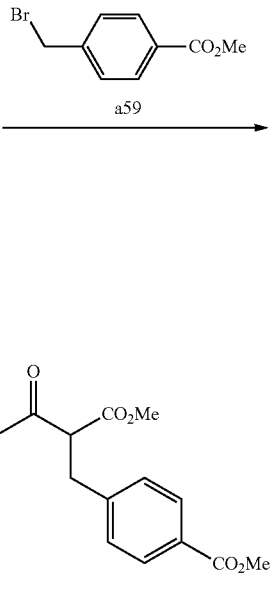

To a solution of Compound a58 (1.0 g, 5.81 mmol) in acetone (20 mL) was added potassium carbonate (1.6 g, 11.6 mmol) and Compound a59 (1.46 g, 6.39 mmol), and the solution was stirred at 40° C. for 18 hours. To the reaction solution was added saturated ammonium chloride aqueous solution, and the solution was extracted with ethyl acetate three times. The organic layer was concentrated under reduced pressure, the residue was purified by silica gel column chromatography (ethyl acetate/petroleum ether) to yield Compound a60 (530 mg, yield: 28%) as colorless oil.

Step 2: Preparation of Compound a62

[Chemical Formula 103]

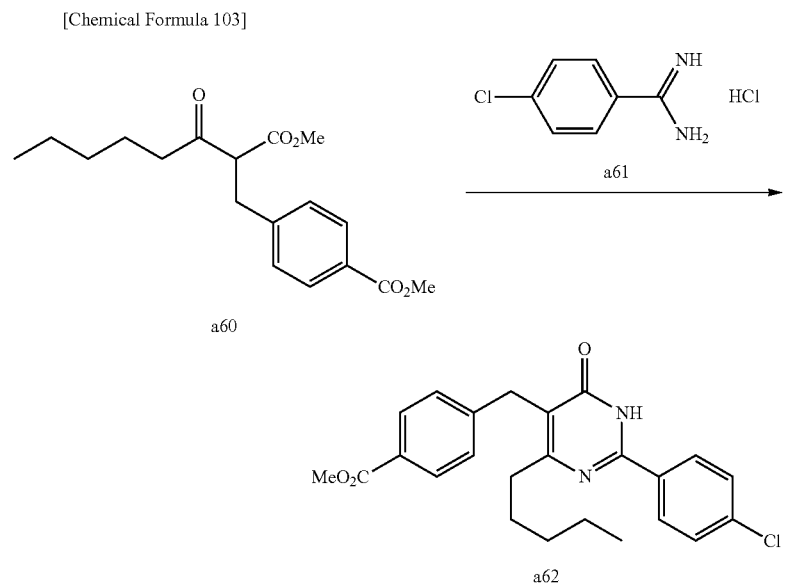

Compound a62 was obtained by the method similar to the preparation of Compound a4.

Step 3: Preparation of Compound a63 (I-0002)

[Chemical Formula 104]

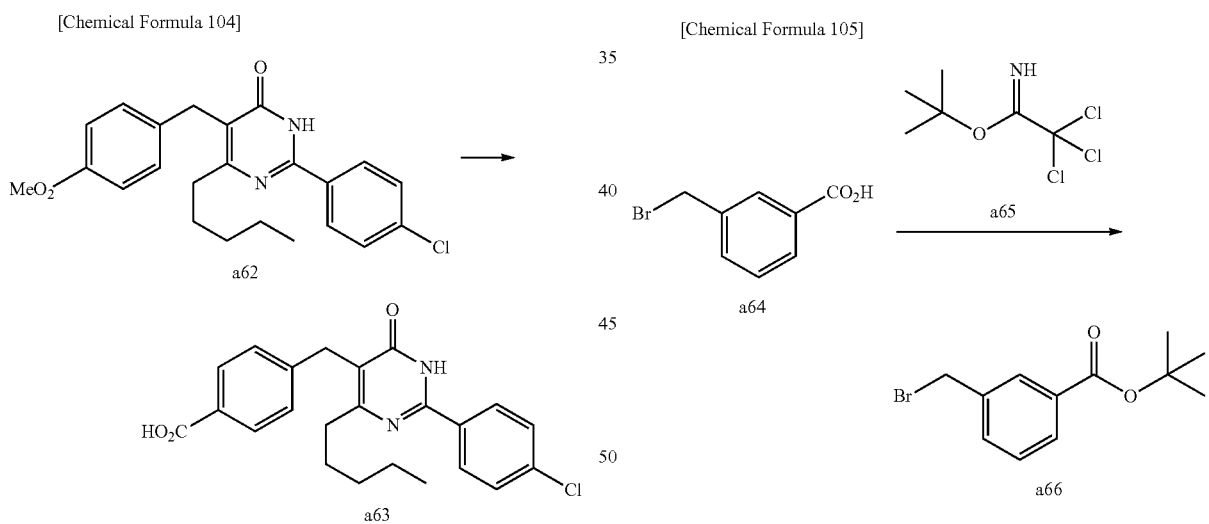

To a solution of Compound a62 (150 mg, 0.35 mmol) in 1,4-dioxane/water (3:1, 4 mL) was added lithium hydroxide (14.7 mg, 0.61 mmol), and the mixture was stirred at 40° C. for 18 hours. The solvent was removed under reduced pressure and the residue was adjusted to pH5 to 7 by adding 1 mol/L hydrochloric acid aqueous solution. To the reaction solution was added water, and the solution was extracted with dichloromethane three times. The organic layer was washed with brine, dried over anhydrous sodium sulfate and concentrated under reduced pressure to yield Compound a63 (I-0002) (33 mg, yield: 23%) as colorless oil.

LC-MS: m/z=411. [M+H]$^+$

Example 11

Preparation of Compound a68

Step 1: Preparation of Compound a66

[Chemical Formula 105]

To a solution of Compound a64 (2.0 g, 9.3 mmol) in dichloromethane (10 mL), cyclohexane (18.5 ml) and THF (1 ml) was added a solution of Compound a65 (4.07 g, 18.6 mmol) in cyclohexane (6 ml) under ice-cooling. To the reaction solution was dropped boron trifluoride-diethyl ether complex (0.26 g, 1.86 mmol) under ice-cooling, and the mixture was stirred at room temperature overnight. To the reaction solution was added sodium hydrogen carbonate (2 g), and the mixture was stirred at room temperature for 30 minutes. The insoluble material was filtered out, and the filtrate was concentrated under reduced pressure. The residue was purified by silica gel column chromatography (ethyl acetate/petroleum ether) to yield Compound a66 (2.2 g, yield: 88%) as colorless oil.

LC-MS: m/z=271. [M+H]$^+$

Step 2: Preparation of Compound a68

[Chemical Formula 106]

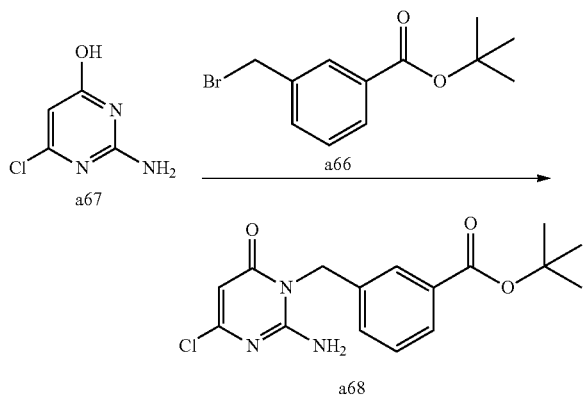

To a solution of Compound a67 (2.0 g, 13.8 mmol) in DMF (18 mL) was added sodium hydride (0.55 g, 13.8 mmol) slowly, and the solution was added at room temperature for 30 minutes. A solution of Compound a66 (3.73 g, 13.8 mmol) in DMF (11 mL) was dropped into the reaction solution, and the mixture was stirred at room temperature overnight. To the reaction solution was added saturated ammonium chloride aqueous solution and water, and the solution was extracted with ethyl acetate three times. The organic layer was washed with water and brine, dried over anhydrous sodium sulfate and concentrated under reduced pressure. The residue was purified by silica gel column chromatography (ethyl acetate/petroleum ether) to yield Compound a68 (1 g, yield: 22%) as a white solid.

LC-MS: m/z=336. [M+H]$^+$

Example 12

Preparation of Compound a74 (I-0014)

Step 1: Preparation of Compound a70

[Chemical Formula 107]

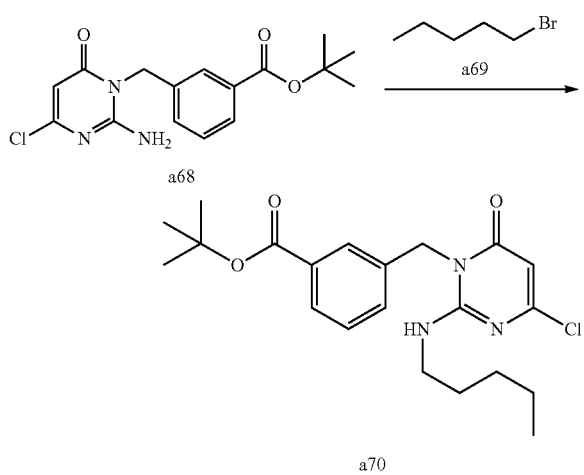

To a solution of Compound a68 (1.0 g, 2.98 mmol) in DMF (10 mL) was added sodium hydride (0.14 g, 3.57 mmol) slowly, and the solution was added at room temperature for 15 minutes. To the reaction solution was added Compound a69 (0.47 g, 3.13 mmol), and the solution was stirred at 60° C. overnight. To the reaction solution was added saturated ammonium chloride aqueous solution, and the solution was extracted with ethyl acetate three times. The organic layer was washed with water and brine, dried over anhydrous sodium sulfate and concentrated under reduced pressure to yield Compound a70 (305 mg, yield: 25%) as a gray solid.

LC-MS: m/z=406 [M+H]$^+$ $^1$H-NMR (CDCl$_3$): 7.96 (d, J=8.0 Hz, 1H), 7.89 (s, 1H), 7.44 (t, J=7.6 Hz, 1H), 7.36 (d, J=7.6 Hz, 1H), 6.03 (s, 1H), 5.21 (s, 2H), 4.59 (b, 1H), 3.31 (q, J=6.8 Hz, 2H), 1.43-1.38 (m, 2H), 1.21-1.16 (m, 2H), 1.02-0.96 (m, 2H), 0.79 (t, J=7.2 Hz, 3H)

Step 2: Preparation of Compound a71

[Chemical Formula 108]

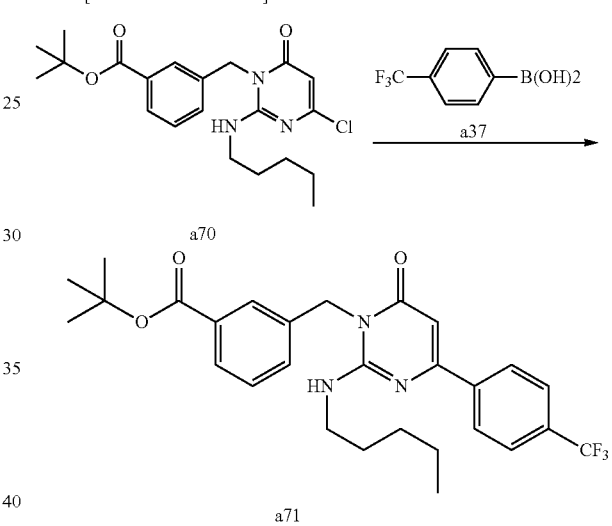

Compound a71 was obtained by the method similar to the preparation of Compound a15.

LC-MS: m/z=516. [M+H]$^+$ $^1$H-NMR (CDCl$_3$): 8.09 (d, J=8.0 Hz, 2H), 7.95 (d, J=8.4 Hz, 2H), 7.70 (d, J=8.0 Hz, 2H), 7.47-7.41 (m, 2H), 6.51 (s, 1H), 5.31 (s, 2H), 4.60 (b, 1H), 3.44 (q, J=6.8 Hz, 2H), 1.60 (s, 9H), 1.52-1.45 (m, 2H), 1.25-1.18 (m, 2H), 1.09-1.02 (m, 2H), 0.81 (t, J=7.2 Hz, 3H)

Step 3: Preparation of Compound a72

[Chemical Formula 109]

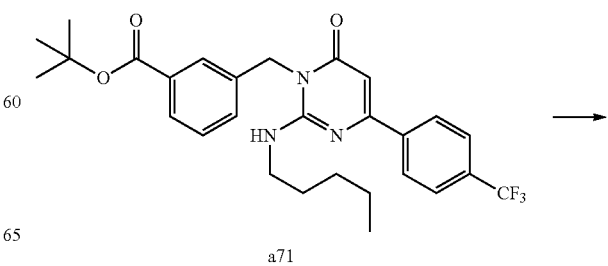

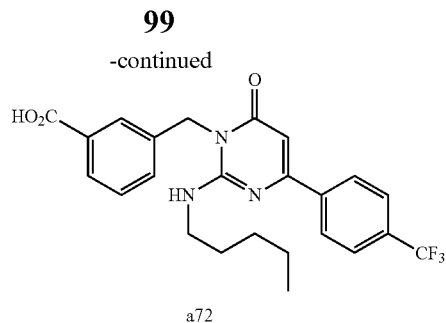

a72

To a solution of Compound a71 (418 mg, 0.81 mmol) in chloroform (13 mL) was dropped trifluoroacetic acid (5 mL) under ice-cooling, and the solution was stirred at room temperature for 4 hours. The reaction solution was concentrated under reduced pressure to yield Compound a72 (317 mg, yield: 85%) as a brown solid.

LC-MS: m/z=460. [M+H]$^+$ $^1$H-NMR (CDCl$_3$): 8.26 (d, J=8.0 Hz, 2H), 7.83 (J=7.6 Hz, 4H), 7.48 (t, J=8.4 Hz, 2H), 7.36 (b, 1H), 6.48 (s, 1H), 5.31 (s, 2H), 3.42 (d, J=5.6 Hz, 2H), 1.55-1.49 (m, 2H), 1.23-1.16 (m, 2H), 1.11-1.05 (m, 2H), 0.76 (t, J=7.2 Hz, 3H)

Step 4: Preparation of Compound a74 (I-0014)

[Chemical Formula 110]

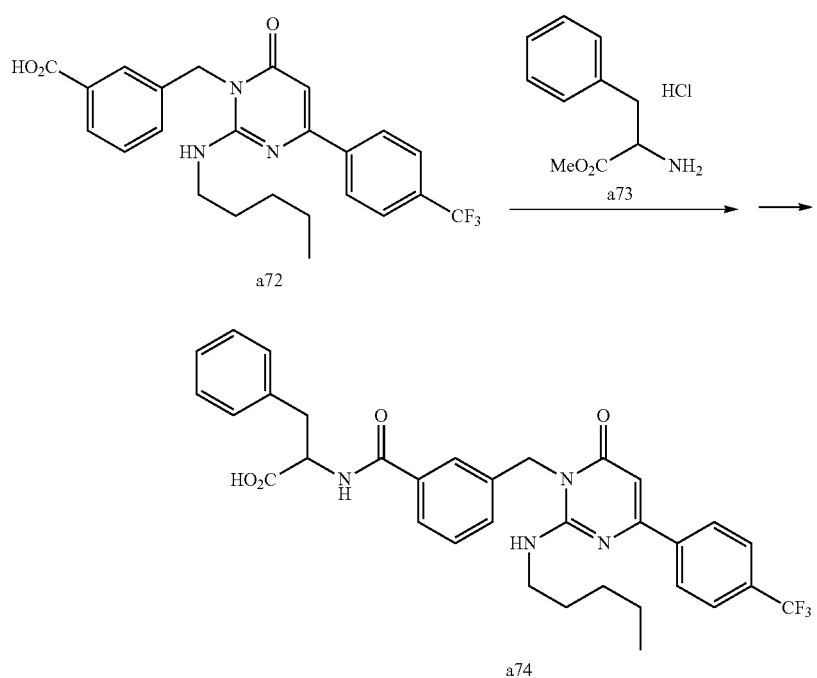

Compound a74 (I-0014) was obtained by the method similar to the preparation of Compound a11 and a13.

$^1$H-NMR (DMSO-D$_6$) δ: 12.7 (brs, 1H), 8.65 (d, 1H, J=8.0 Hz), 8.25 (d, 2H, J=8.2 Hz), 7.83 (d, 2H, J=8.3 Hz), 7.69 (t, 2H, J=6.8 Hz), 7.41 (t, 1H, J=7.7 Hz), 7.28-7.22 (m, 6H), 7.14 (t, 1H, J=7.0 Hz), 6.45 (s, 1H), 5.27 (s, 2H), 4.59-4.57 (m, 1H), 3.39 (q, 1H, J=6.2 Hz), 3.17 (dd, 1H, J=13.7, 4.5 Hz), 3.07-3.04 (m, 1H), 1.51-1.50 (m, 2H), 1.19-1.12 (m, 4H), 0.76 (t, 3H, J=7.2 Hz). LC-MS: m/z=607. [M+H]$^+$ Example 13

Preparation of Compound a80 (I-0205)

Step 1: Preparation of Compound a77

[Chemical Formula 111]

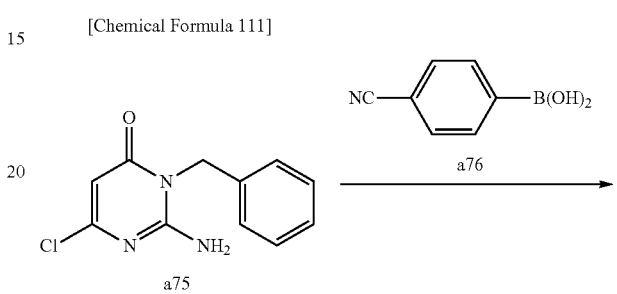

-continued

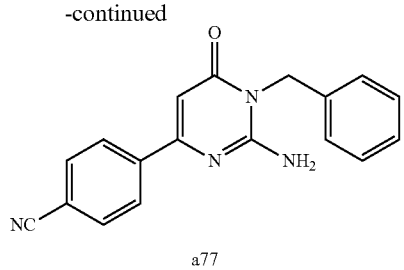

a77

Compound a77 was obtained by the method similar to the preparation of Compound a15.

LC-MS: m/z=303. [M+H]$^+$
LC/MS method: Method B, retention time: 1.61 min

Step 2: Preparation of Compound a80 (I-0205)

[Chemical Formula 112]

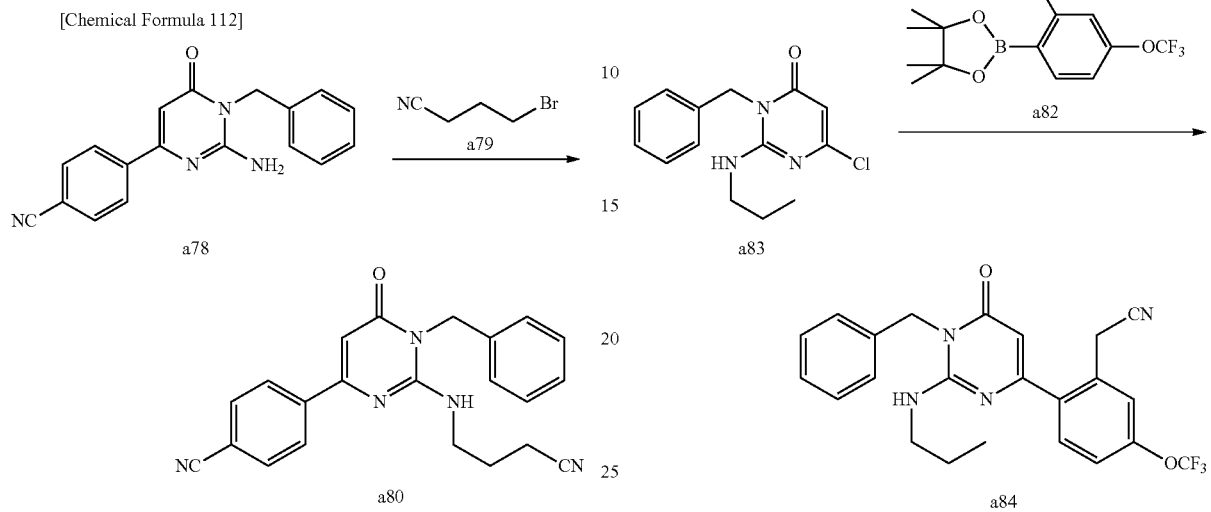

Compound a80 (I-0205) was obtained by the method similar to the preparation of Compound a70.

$^1$H-NMR (CDCl$_3$) δ: 8.06 (d, 2H, J=8.4 Hz), 7.73 (d, 2H, J=8.4 Hz), 7.43-7.36 (m, 3H), 7.28 (d, 3H, J=6.9 Hz), 6.54 (s, 1H), 5.30 (s, 2H), 4.84 (s, 1H), 3.61 (q, 2H, J=6.2 Hz), 2.11 (t, 2H, J=6.9 Hz), 1.89-1.87 (m, 2H).
LC-MS: m/z=370 [M+H]$^+$

Example 14

Preparation of Compound a84 (I-0201)

Step 1: Preparation of Compound a82

[Chemical Formula 113]

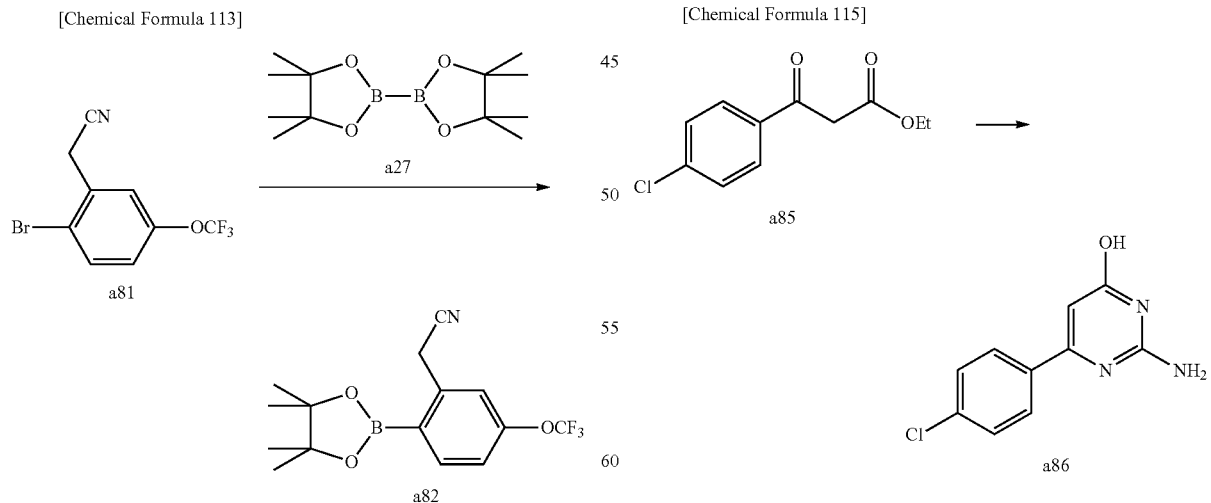

Compound a81 was obtained by the method similar to the preparation of Compound a28.

$^1$H-NMR (CDCl$_3$) δ: 7.92 (d, 1H, J=8.3 Hz), 7.30 (s, 1H), 7.19 (s, 1H), 4.11 (s, 2H), 3.74 (s, 1H), 1.35 (s, 13H).

Step 2: Preparation of Compound a84 (I-0201)

[Chemical Formula 114]

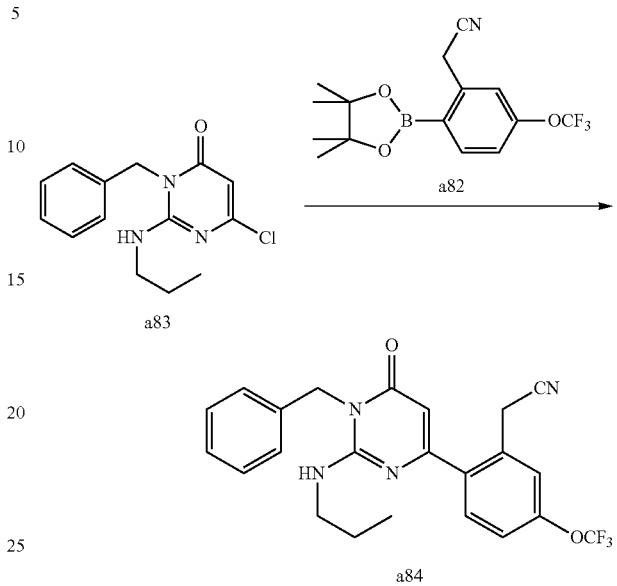

Compound a84 (I-0201) was obtained by the method similar to the preparation of Compound a15.

$^1$H-NMR (CDCl$_3$) δ: 7.56 (d, 1H, J=8.3 Hz), 7.42-7.37 (m, 4H), 7.30-7.27 (m, 4H), 6.13 (s, 1H), 5.27 (s, 2H), 4.64 (s, 1H), 4.11 (s, 2H), 3.34-3.32 (m, 2H), 1.38-1.37 (m, 2H), 1.11-1.08 (m, 1H), 0.81 (t, 3H, J=7.3 Hz).

Example 15

Preparation of Compound a88 (I-0001)

Step 1: Preparation of Compound a86

[Chemical Formula 115]

To a solution of Compound a85 (3 g, 13.24 mmol) in ethanol (24 mL) was added guanidine hemi-carbonate (2.39 g, 13.24 mmol), and the solution was refluxed for 5 hours. After ethanol was removed under reduced pressure, water was added to the reaction solution, and the precipitated solid was filtered. The solid washed with water and hexane, and dried under reduced pressure to yield Compound a86 (1.41 g, yield: 48%) as a yellow solid.

$^{1}$H-NMR (DMSO-D$_6$) δ: 10.94 (1H, br s), 7.97 (2H, d, J=8.8 Hz), 7.49 (2H, d, J=8.5 Hz), 6.67 (2H, br s), 6.13 (1H, s).

LC-MS: m/z=222. [M+H]$^{+}$

Step 2: Preparation of Compound a87

[Chemical Formula 116]

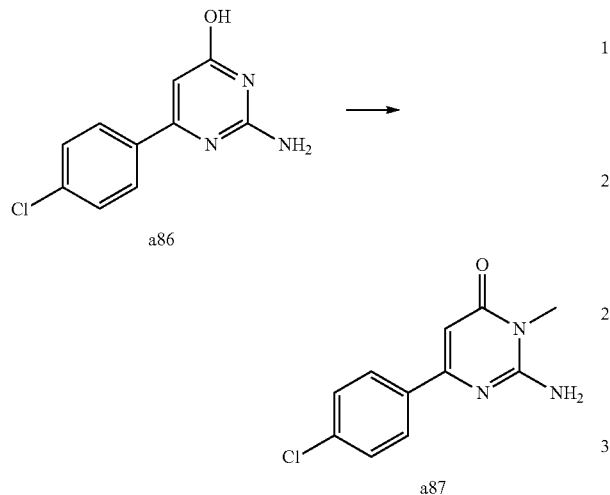

Compound a87 was obtained by the method similar to the preparation of Compound a68.

$^{1}$H-NMR (DMSO-D$_6$) δ: 7.99 (2H, d, J=8.3 Hz), 7.51 (2H, d, J=8.4 Hz), 7.28 (2H, br s), 6.24 (1H, s), 3.29 (3H, s).

LC-MS: m/z=236. [M+H]$^{+}$

Step 3: Preparation of Compound a88 (I-0001)

[Chemical Formula 117]

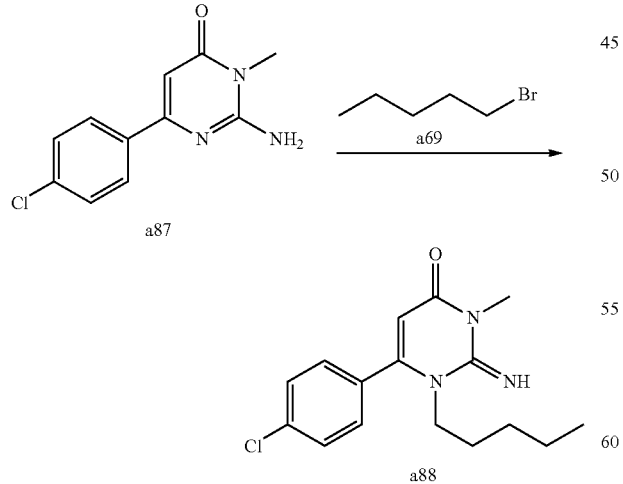

Compound a88 (I-0001) was obtained by the method similar to the preparation of Compound a70.

LC-MS: m/z=306 [M+H]$^{+}$

LC/MS method: Method B, retention time: 2.49 min

Example 16

Preparation of Compound a96 (I-0107)

Step 1: Preparation of Compound a91

[Chemical Formula 118]

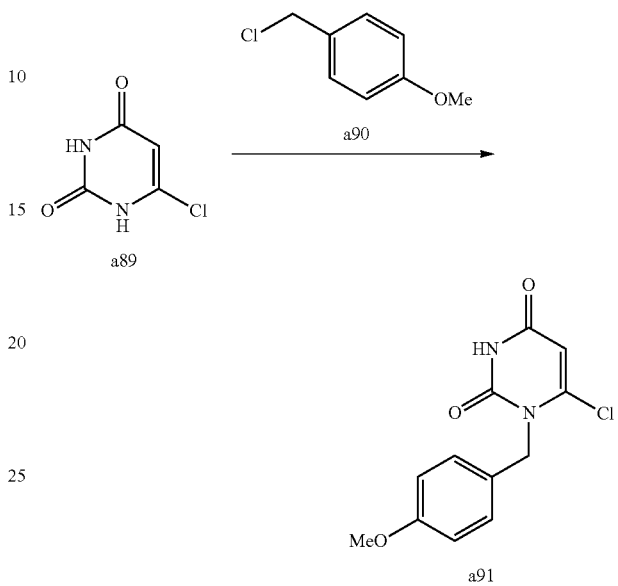

To a solution of Compound a89 (400 mg, 2.73 mmol) in DMF (4 mL) was added potassium carbonate (189 mg, 1.37 mmol) and Compound a90 (483 ul, 3.55 mmol), and the solution was stirred at 70° C. for 2 hours. After DMF was removed under reduced pressure, the residue was purified by silica gel column chromatography (chloroform/methanol) to yield Compound a91 (287.7 mg, yield: 40%) as a white solid.

LC-MS: m/z=265 [M−H]$^{+}$

LC/MS method: Method B, retention time: 1.52 min

Step 2: Preparation of Compound a92

[Chemical Formula 119]

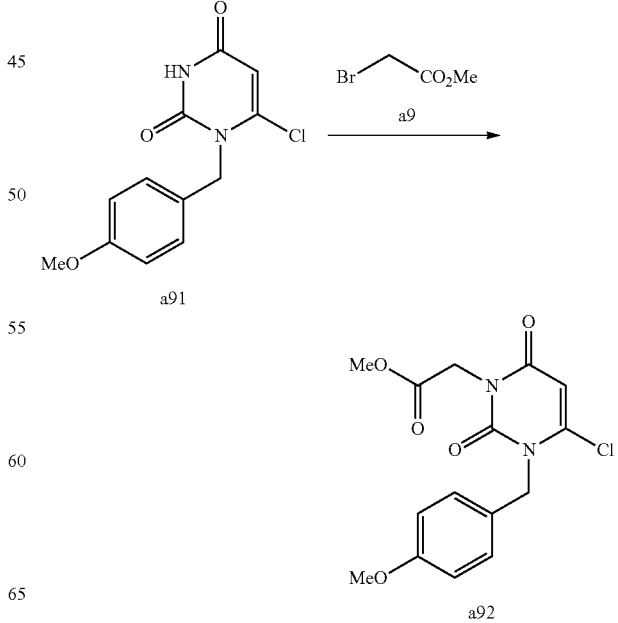

Compound a92 was obtained by the method similar to the preparation of Compound a18.
LC-MS: m/z=339 [M+H]⁺
LC/MS method: Method B, retention time: 1.84 min Step 3: Preparation of Compound a93

[Chemical Formula 120]

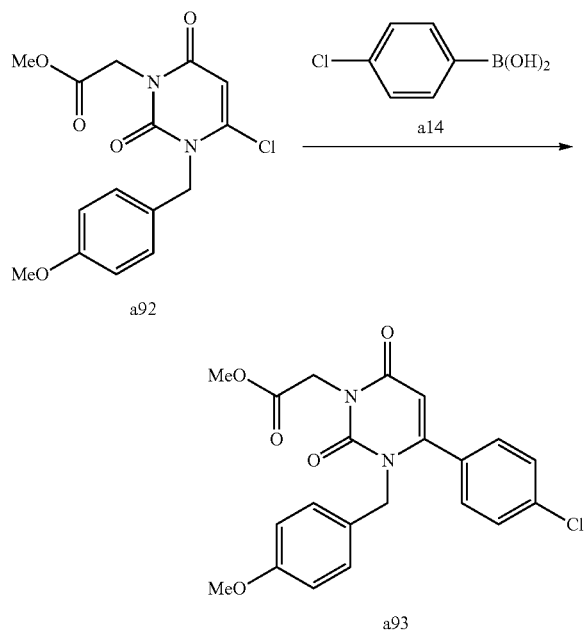

Compound a93 was obtained by the method similar to the preparation of Compound a15.
LC-MS: m/z=415 [M+H]⁺
LC/MS method: Method B, retention time: 2.17 min Step 4: Preparation of Compound a94

[Chemical Formula 121]

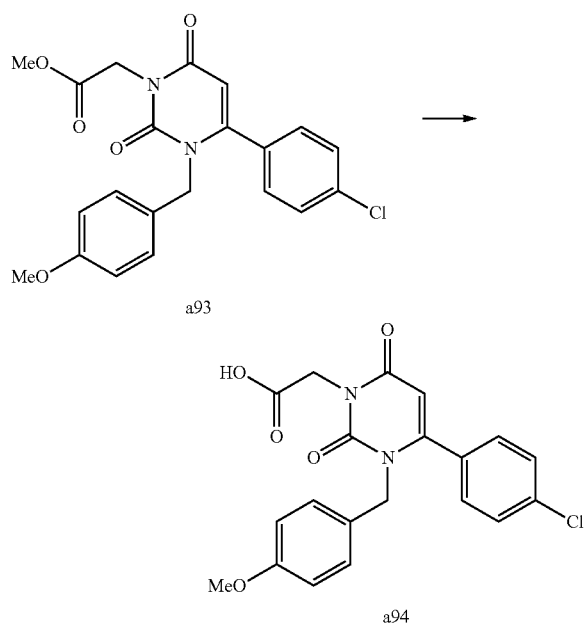

Compound a94 was obtained by the method similar to the preparation of Compound a11.
LC-MS: m/z=401. [M+H]⁺
LC/MS method: Method B, retention time: 2.00 min Step 5: Preparation of Compound a95

[Chemical Formula 122]

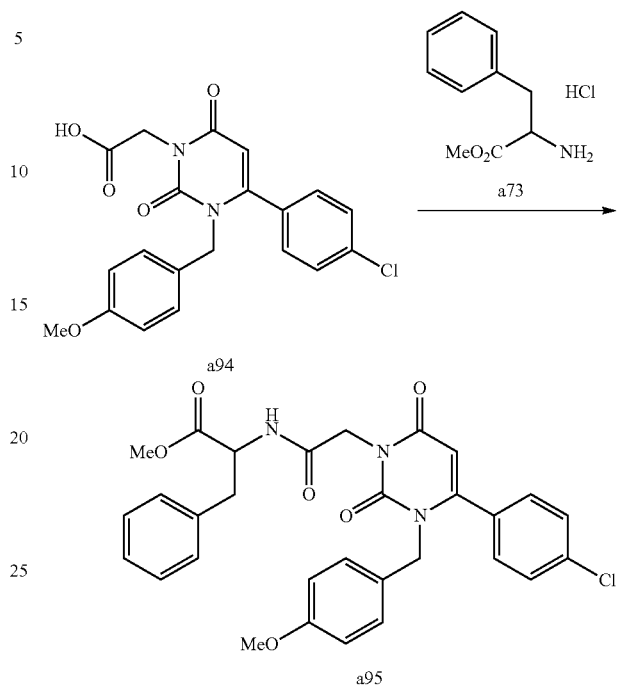

Compound a95 was obtained by the method similar to the preparation of Compound a13.
LC-MS: m/z=562 [M+H]⁺
LC/MS method: Method B, retention time: 2.32 min Step 6: Preparation of Compound a96 (I-0107)

[Chemical Formula 123]

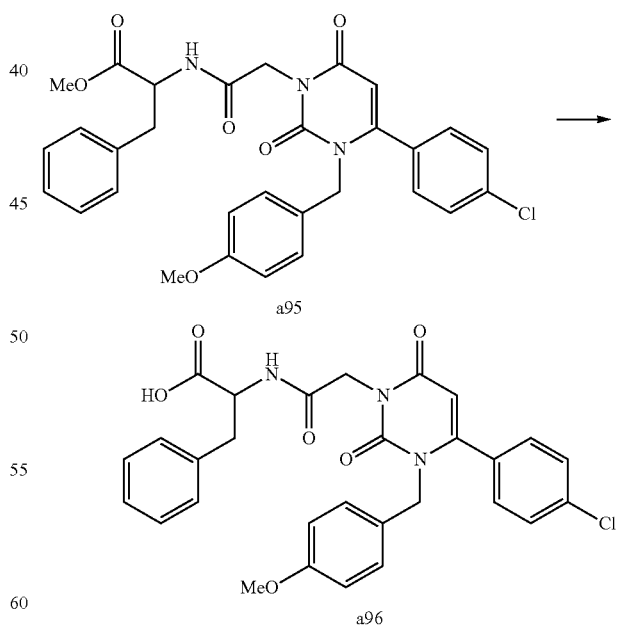

Compound a96 (I-0107) was obtained by the method similar to the preparation of Compound a11.
LC-MS: m/z=548 [M+H]⁺
LC/MS method: Method B, retention time: 2.13 min
$^1$H-NMR (CDCl$_3$) δ: 7.35 (d, 2H, J=7.8 Hz), 7.21-7.19 (m, 3H), 7.08 (d, 2H, J=7.8 Hz), 6.79-6.74 (m, 4H), 6.51 (br s, 1H), 5.67 (s, 1H), 4.86 (s, 3H), 4.69 (s, 2H), 3.75 (s, 3H), 3.25-3.13 (m, 2H), 1.26 (s, 4H), 0.88 (t, 2H, J=6.3 Hz).

Example 17

Preparation of Compound a100 (I-0115) and a101 (I-0116)

Step 1: Preparation of Compound a97

[Chemical Formula 124]

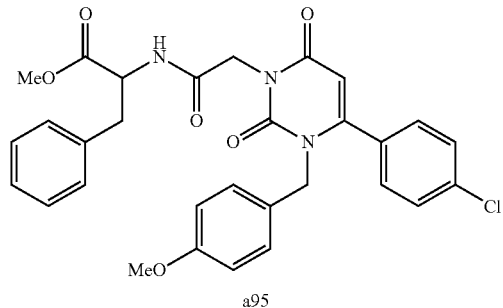

a95

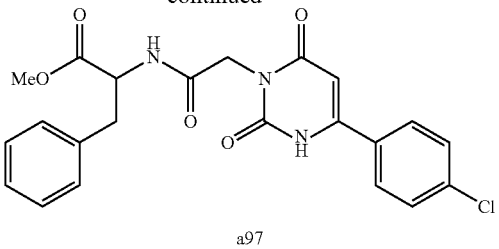

a97

To a solution of Compound a95 (150 mg, 0.27 mmol) in acetonitrile/water (9:1, 1.5 mL) was added ammonium hexanitrate cerium(IV) (293 mg, 0.53 mmol), and the mixture was stirred at 50° C. for 3 hours. To the reaction solution was added water, and the solution was extracted with ethyl acetate twice. The organic layer was washed with water and brine, dried over anhydrous sodium sulfate and concentrated under reduced pressure. Diisopropyl ether was added to the residue, and the precipitated solid was filtered to yield Compound a97 (64 mg, yield: 54%) as a pale brown solid.
$^1$H-NMR (DMSO-D$_6$) δ: 8.57 (s, 1H), 7.80 (d, 2H, J=8.3 Hz), 7.57-7.55 (m, 2H), 7.29-7.27 (m, 2H), 7.23 (s, 3H), 5.96 (s, 1H), 4.46-4.42 (m, 4H), 3.58 (s, 3H), 3.17 (d, 1H, J=4.8 Hz), 3.00-2.94 (m, 2H), 2.09 (s, 3H).

Step 2: Preparation of Compound a98 and a99

[Chemical Formula 125]

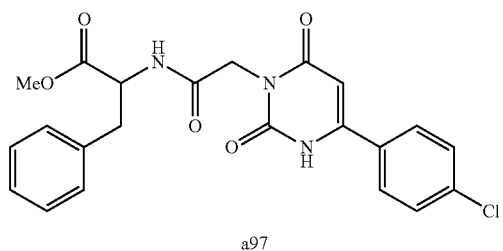

a97

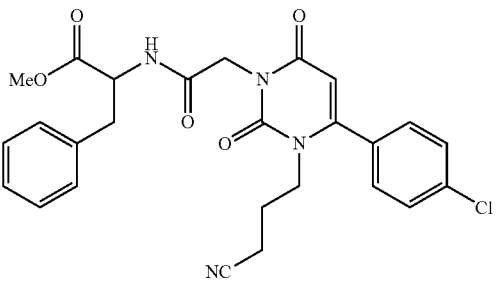

a98

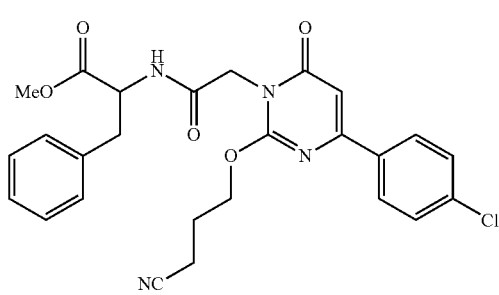

a99

To a solution of Compound a97 (45 mg, 0.10 mmol) in DMF (450 uL) was added triethylamine (16.9 ul, 0.12 mmol) and 4-bromobutane nitrile (12.1 ul, 0.12 mmol), and the solution was stirred at 80° C. for 2 hours. The reaction solution was purified by silica gel column chromatography (chloroform/methanol) to yield a mixture of Compound a98 and a99 (100 mg) as a brown oil.
LC-MS: m/z=509 [M+H]$^+$
Compound a98
LC/MS method: Method B, retention time: 1.95 min
Compound a99
LC/MS method: Method B, retention time: 2.16 min Step 3: Preparation of Compound a100 (I-0115) and a101 (I-0116)

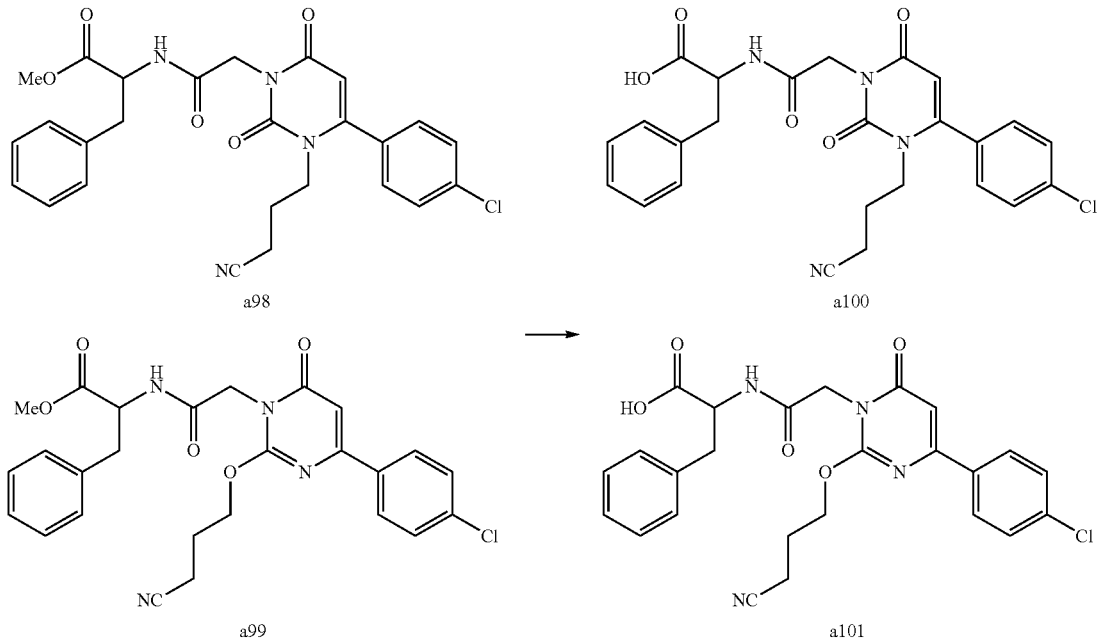

Compound a 100 (I-0115) and a101 (I-0116) was obtained by the method similar to the preparation of Compound a54.

a compound a100

$^1$H-NMR (CDCl$_3$) δ: 7.47 (d, 2H, J=7.8 Hz), 7.25-7.20 (m, 8H), 7.08 (br s, 1H), 5.63 (s, 1H), 4.75-4.73 (m, 1H), 4.63-4.57 (m, 2H), 4.18 (br s, 2H), 3.76-3.74 (m, 2H), 3.48 (s, 1H), 3.21-3.19 (m, 1H), 3.08-3.06 (m, 1H), 2.64 (s, 1H), 2.19 (t, 2H, J=6.8 Hz), 1.75 (t, 2H, J=6.9 Hz).

Compound a101

$^1$H-NMR (CDCl$_3$) δ: 7.72 (d, 3H, J=60.5 Hz), 7.24-7.19 (m, 9H), 6.40 (s, 1H), 4.71 (s, 2H), 4.48-4.27 (m, 4H), 3.26 (s, 1H), 2.94 (s, 1H), 2.63 (s, 1H), 2.26 (s, 2H), 1.87 (s, 2H).

Similarly, the following compounds were synthesized.

TABLE 1

| Example No | Structure |
|---|---|
| I-0001 | 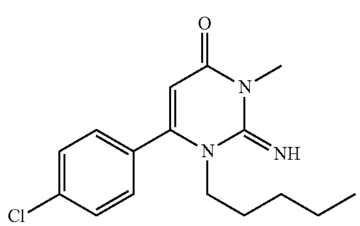 [SMILES: CCCCCn1c(-c2ccc(Cl)cc2)cc(=O)n(C)c1=N] |
| I-0002 | 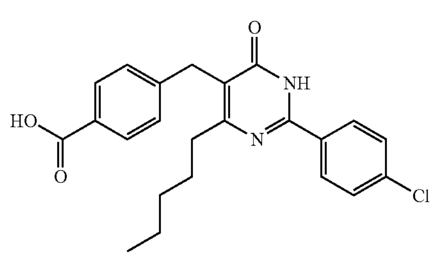 [SMILES: CCCCCc1nc(-c2ccc(Cl)cc2)[nH]c(=O)c1Cc1ccc(C(=O)O)cc1] |

TABLE 1-continued

| Example No | Structure |
|---|---|
| I-0003 | 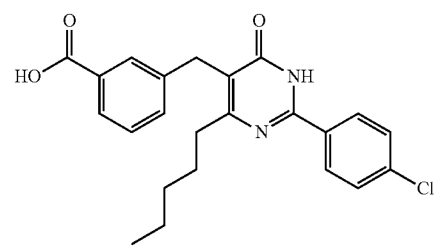 [SMILES: CCCCCc1nc(-c2ccc(Cl)cc2)[nH]c(=O)c1Cc1cccc(C(=O)O)c1] |
| I-0004 | 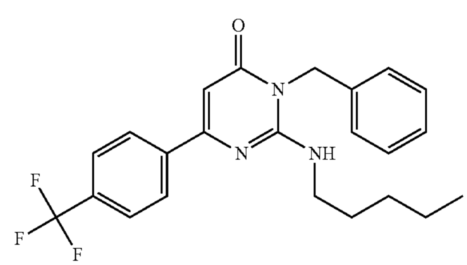 [SMILES: CCCCCNc1nc(-c2ccc(C(F)(F)F)cc2)cc(=O)n1Cc1ccccc1] |
| I-0005 | 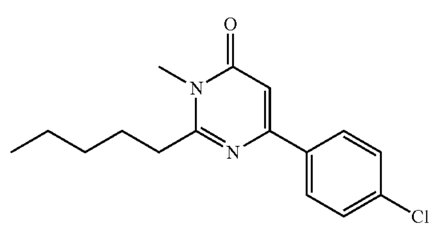 [SMILES: CCCCCc1nc(-c2ccc(Cl)cc2)cc(=O)n1C] |

TABLE 1-continued
| Example No | Structure |
|---|---|
| I-0006 | 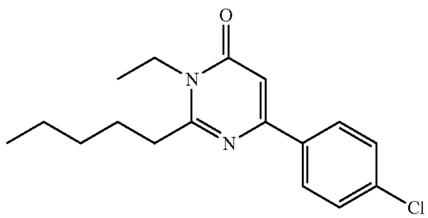 [SMILES: CCCCCc1nc(-c2ccc(Cl)cc2)cc(=O)n1CC] |
TABLE 2
| | |
|---|---|
| I-0007 | |
| I-0008 | |
| I-0009 | |
| I-0010 | |
| I-0011 | |
| I-0012 | |
TABLE 3
| | |
|---|---|
| I-0013 | |

TABLE 3-continued
I-0014
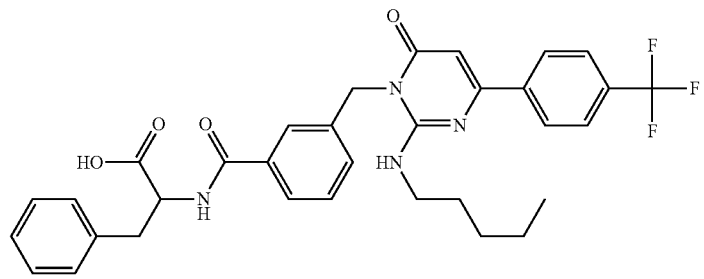 [SMILES: CCCCCNc1nc(-c2ccc(C(F)(F)F)cc2)cc(=O)n1Cc1cccc(C(=O)NC(Cc2ccccc2)C(=O)O)c1]
I-0015
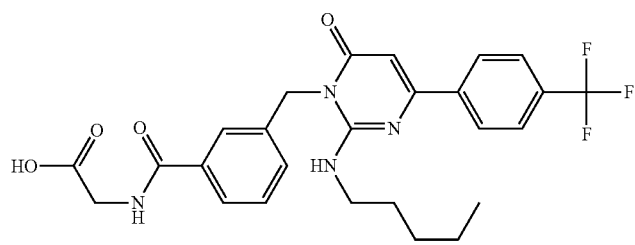 [SMILES: CCCCCNc1nc(-c2ccc(C(F)(F)F)cc2)cc(=O)n1Cc1cccc(C(=O)NCC(=O)O)c1]
I-0016
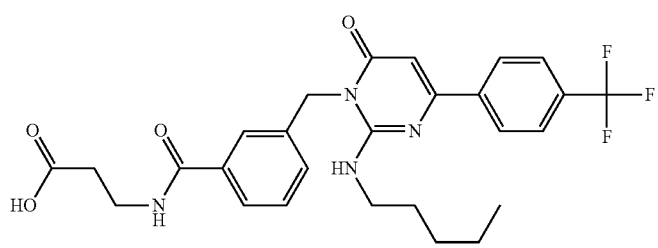 [SMILES: CCCCCNc1nc(-c2ccc(C(F)(F)F)cc2)cc(=O)n1Cc1cccc(C(=O)NCCC(=O)O)c1]
I-0017
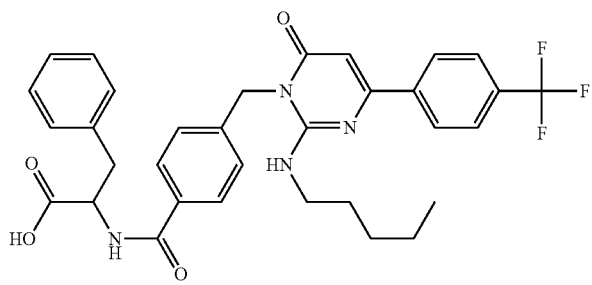 [SMILES: CCCCCNc1nc(-c2ccc(C(F)(F)F)cc2)cc(=O)n1Cc1ccc(C(=O)NC(Cc2ccccc2)C(=O)O)cc1]
I-0018
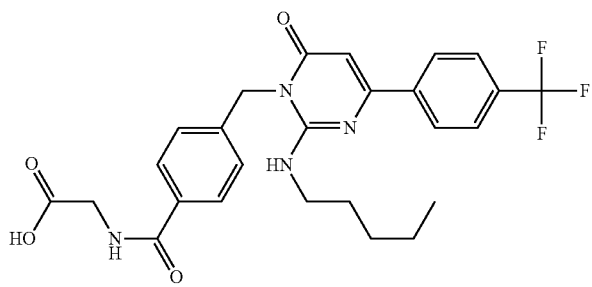 [SMILES: CCCCCNc1nc(-c2ccc(C(F)(F)F)cc2)cc(=O)n1Cc1ccc(C(=O)NCC(=O)O)cc1]

TABLE 4
I-0019
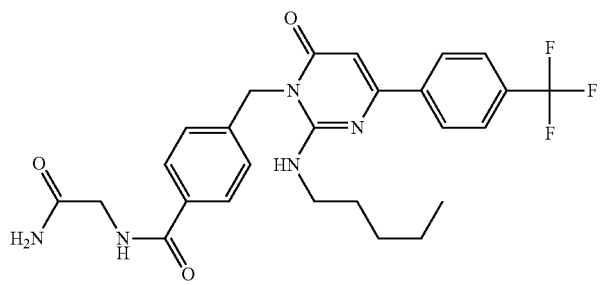 [SMILES: CCCCCNc1nc(-c2ccc(C(F)(F)F)cc2)cc(=O)n1Cc1ccc(C(=O)NCC(N)=O)cc1]
I-0020
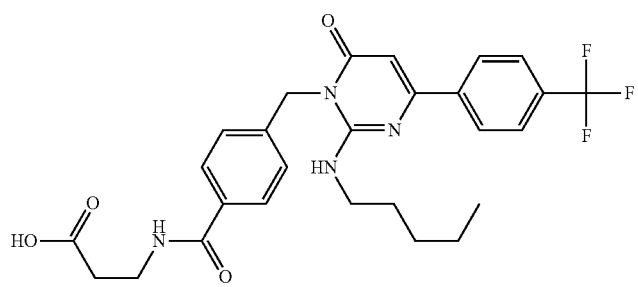 [SMILES: CCCCCNc1nc(-c2ccc(C(F)(F)F)cc2)cc(=O)n1Cc1ccc(C(=O)NCCC(=O)O)cc1]
I-0021
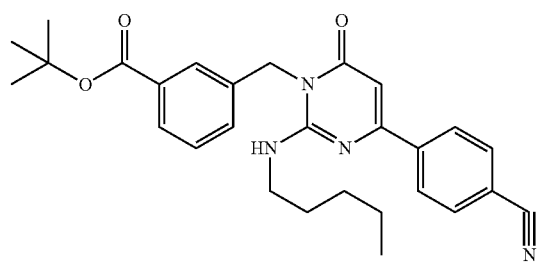 [SMILES: CCCCCNc1nc(-c2ccc(C#N)cc2)cc(=O)n1Cc1cccc(C(=O)OC(C)(C)C)c1]
I-0022
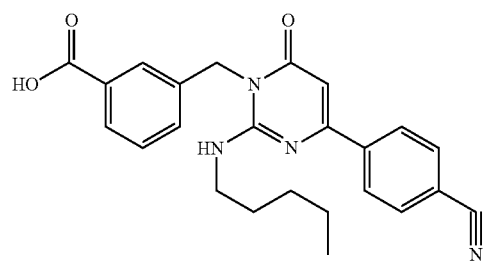 [SMILES: CCCCCNc1nc(-c2ccc(C#N)cc2)cc(=O)n1Cc1cccc(C(=O)O)c1]
I-0023
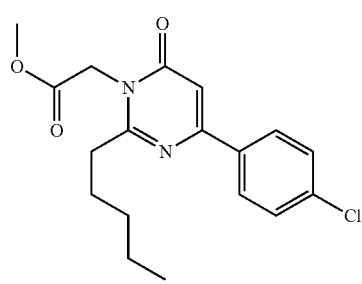 [SMILES: CCCCCc1nc(-c2ccc(Cl)cc2)cc(=O)n1CC(=O)OC]

TABLE 4-continued
I-0024
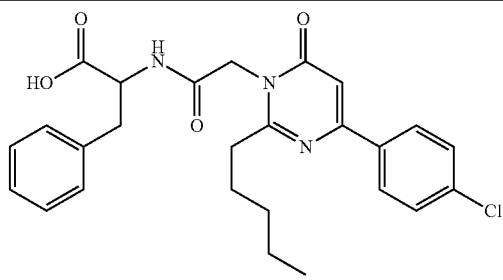
TABLE 5
I-0025
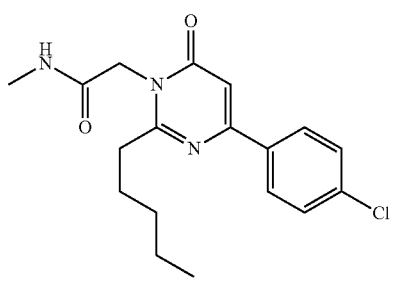 [SMILES: CCCCCc1nc(-c2ccc(Cl)cc2)cc(=O)n1CC(=O)NC]
I-0026
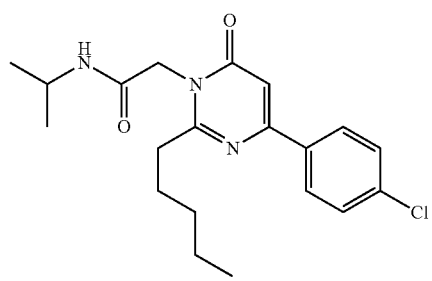 [SMILES: CCCCCc1nc(-c2ccc(Cl)cc2)cc(=O)n1CC(=O)NC(C)C]
I-0027
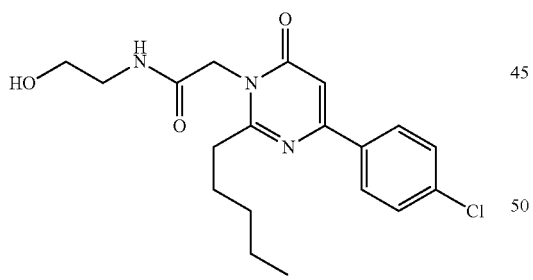
I-0028
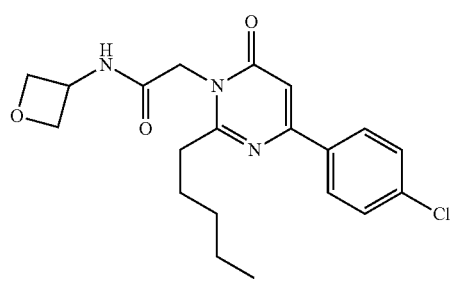 [SMILES: CCCCCc1nc(-c2ccc(Cl)cc2)cc(=O)n1CC(=O)NC1COC1]
TABLE 5-continued
I-0029
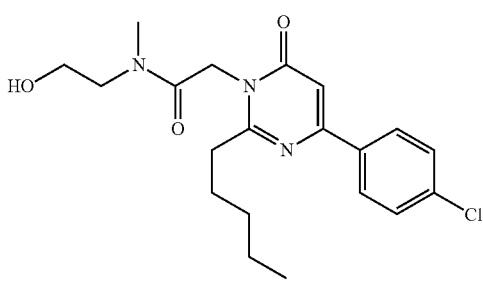 [SMILES: CCCCCc1nc(-c2ccc(Cl)cc2)cc(=O)n1CC(=O)N(C)CCO]
I-0030
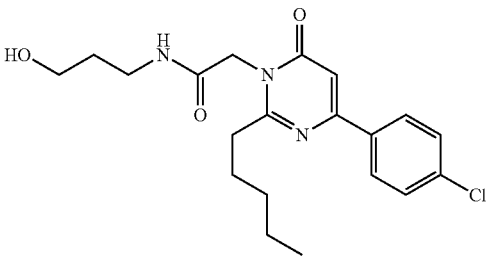 [SMILES: CCCCCc1nc(-c2ccc(Cl)cc2)cc(=O)n1CC(=O)NCCCO]
TABLE 6
I-0031
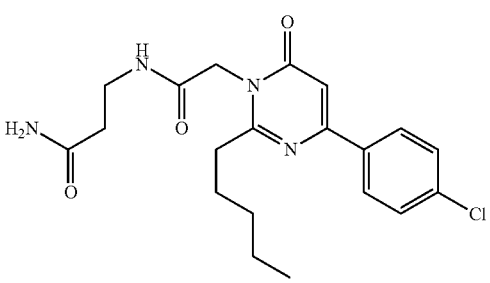 [SMILES: CCCCCc1nc(-c2ccc(Cl)cc2)cc(=O)n1CC(=O)NCCC(N)=O]
I-0032
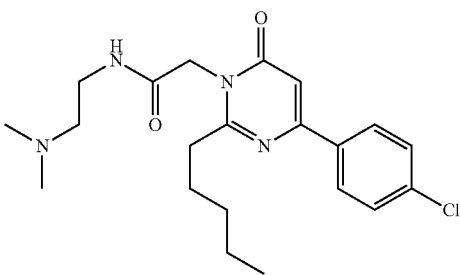 [SMILES: CCCCCc1nc(-c2ccc(Cl)cc2)cc(=O)n1CC(=O)NCCN(C)C]

TABLE 6-continued
I-0033 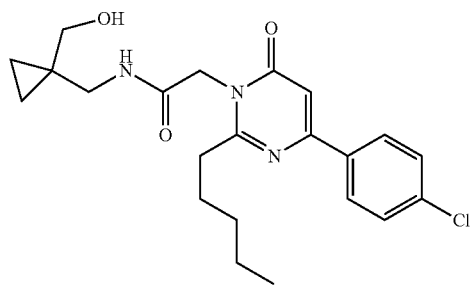 [SMILES: CCCCCc1nc(-c2ccc(Cl)cc2)cc(=O)n1CC(=O)NCC1(CO)CC1]
I-0034 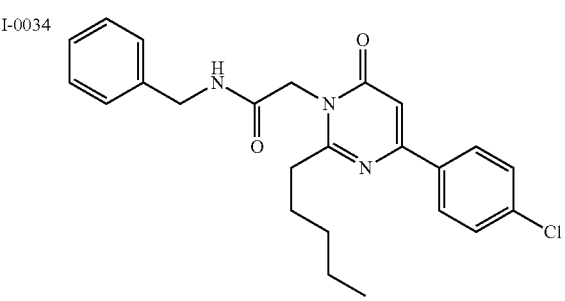
TABLE 6-continued
I-0035 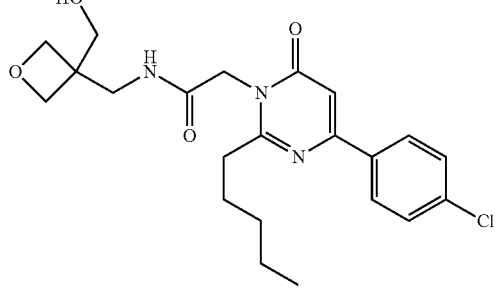
I-0036 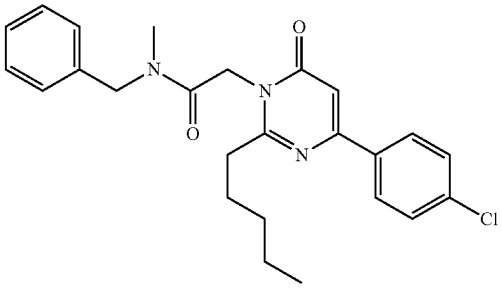 [SMILES: CCCCCc1nc(-c2ccc(Cl)cc2)cc(=O)n1CC(=O)N(C)Cc1ccccc1]
TABLE 7
I-0037 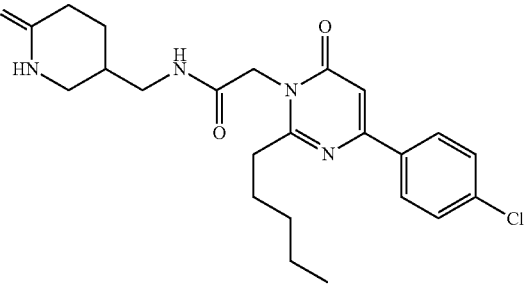
I-0038 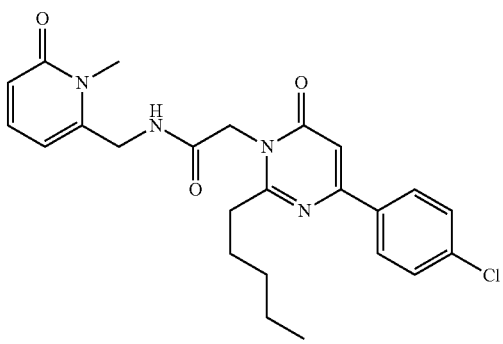 [SMILES: CCCCCc1nc(-c2ccc(Cl)cc2)cc(=O)n1CC(=O)NCc1cccc(=O)n1C]
I-0039 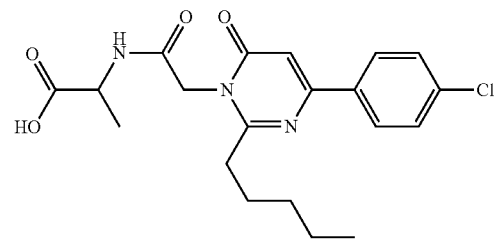 [SMILES: CCCCCc1nc(-c2ccc(Cl)cc2)cc(=O)n1CC(=O)NC(C)C(=O)O]

TABLE 7-continued
I-0040 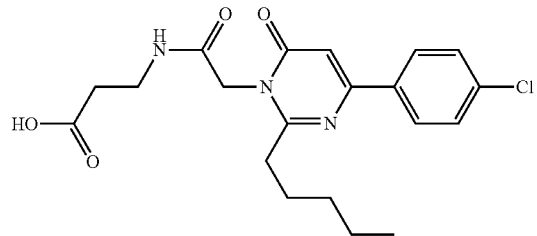 [SMILES: CCCCCc1nc(-c2ccc(Cl)cc2)cc(=O)n1CC(=O)NCCC(=O)O]
I-0041 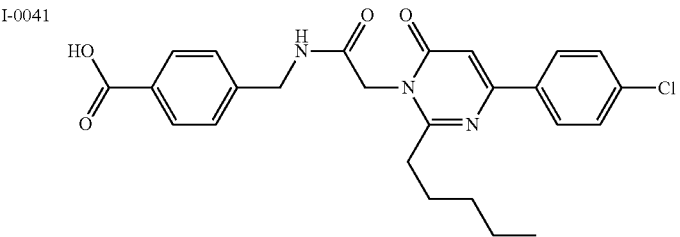
I-0042 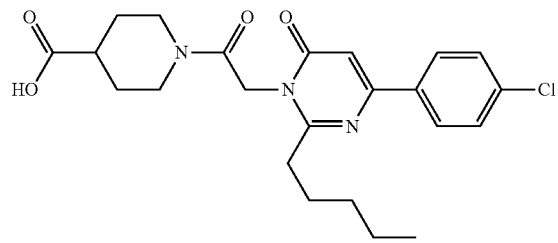 [SMILES: CCCCCc1nc(-c2ccc(Cl)cc2)cc(=O)n1CC(=O)N1CCC(C(=O)O)CC1]
TABLE 8
I-0043 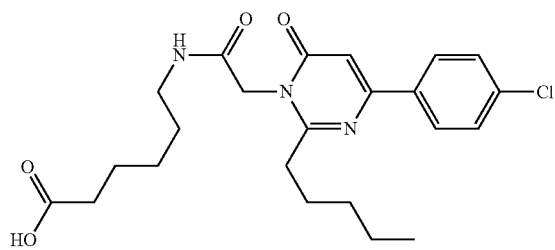 [SMILES: CCCCCc1nc(-c2ccc(Cl)cc2)cc(=O)n1CC(=O)NCCCCCC(=O)O]
I-0044 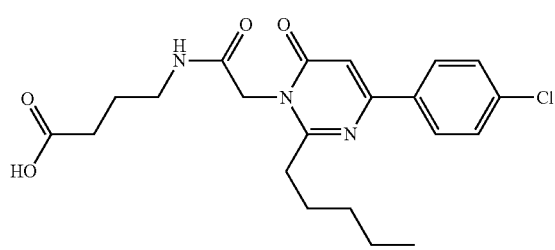 [SMILES: CCCCCc1nc(-c2ccc(Cl)cc2)cc(=O)n1CC(=O)NCCCC(=O)O]
I-0045 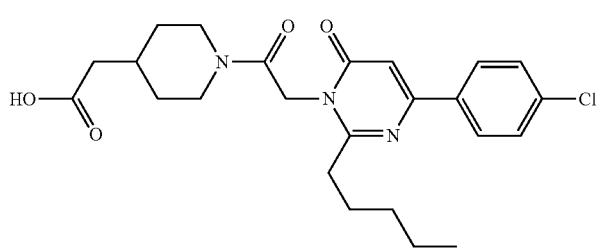

TABLE 8-continued
I-0046 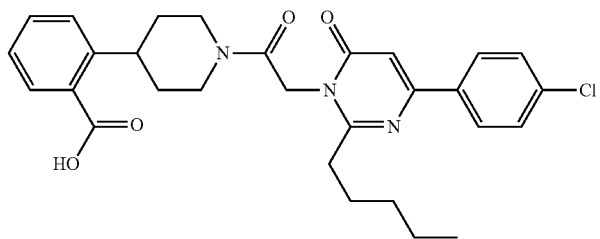 [SMILES: CCCCCc1nc(-c2ccc(Cl)cc2)cc(=O)n1CC(=O)N1CCC(c2ccccc2C(=O)O)CC1]
I-0047 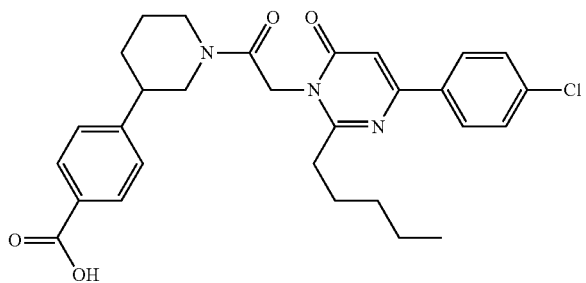 [SMILES: CCCCCc1nc(-c2ccc(Cl)cc2)cc(=O)n1CC(=O)N1CCCC(c2ccc(C(=O)O)cc2)C1]
I-0048 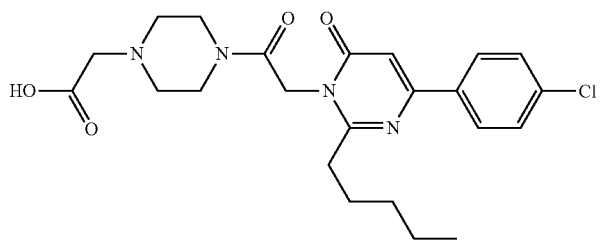 [SMILES: CCCCCc1nc(-c2ccc(Cl)cc2)cc(=O)n1CC(=O)N1CCN(CC(=O)O)CC1]
TABLE 9
I-0049 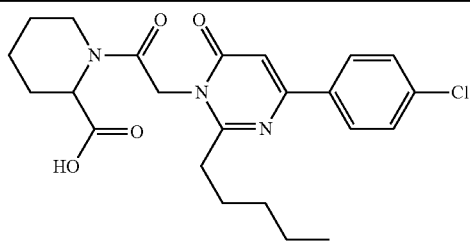
I-0050 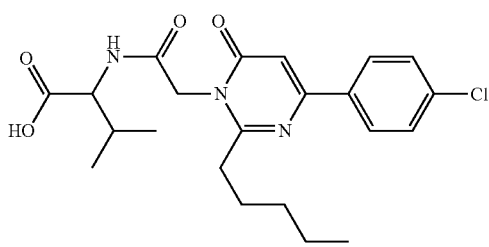
I-0051 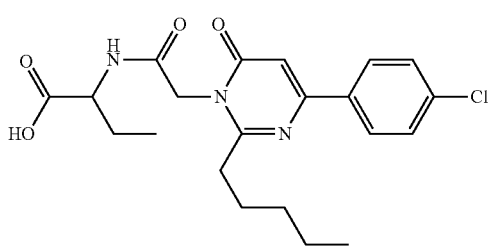 [SMILES: CCCCCc1nc(-c2ccc(Cl)cc2)cc(=O)n1CC(=O)NC(CC)C(=O)O]

TABLE 9-continued
I-0052 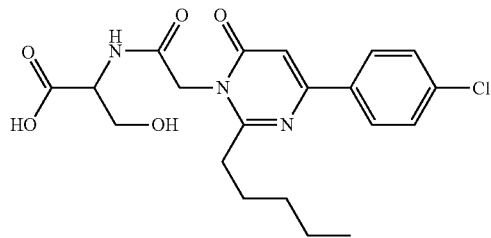 [SMILES: CCCCCc1nc(-c2ccc(Cl)cc2)cc(=O)n1CC(=O)NC(CO)C(=O)O]
I-0053 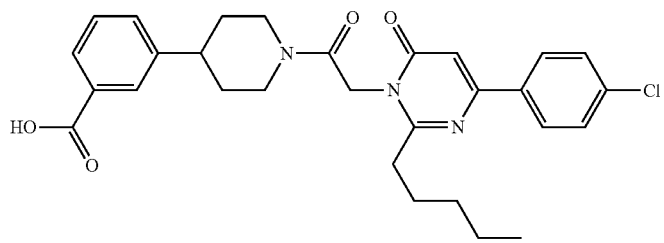 [SMILES: CCCCCc1nc(-c2ccc(Cl)cc2)cc(=O)n1CC(=O)N1CCC(c2cccc(C(=O)O)c2)CC1]
I-0054 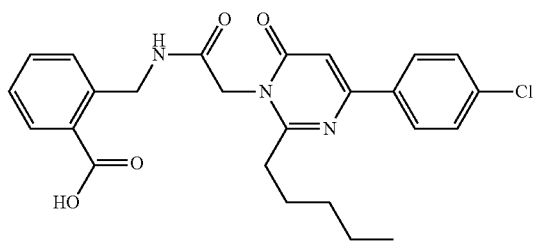 [SMILES: CCCCCc1nc(-c2ccc(Cl)cc2)cc(=O)n1CC(=O)NCc1ccccc1C(=O)O]
TABLE 10
I-0055 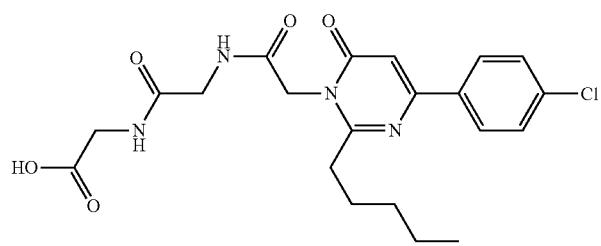 [SMILES: CCCCCc1nc(-c2ccc(Cl)cc2)cc(=O)n1CC(=O)NCC(=O)NCC(=O)O]
I-0056 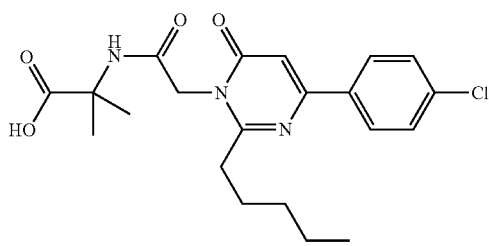 [SMILES: CCCCCc1nc(-c2ccc(Cl)cc2)cc(=O)n1CC(=O)NC(C)(C)C(=O)O]
I-0057 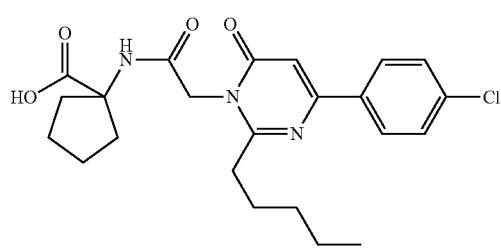 [SMILES: CCCCCc1nc(-c2ccc(Cl)cc2)cc(=O)n1CC(=O)NC1(C(=O)O)CCCC1]

TABLE 10-continued
I-0058 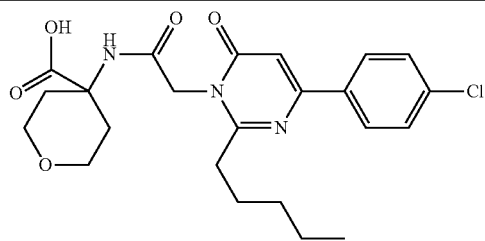
I-0059 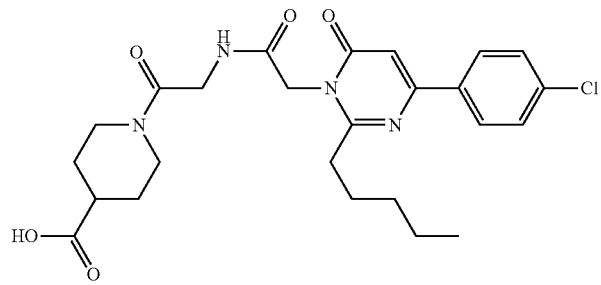 [SMILES: CCCCCc1nc(-c2ccc(Cl)cc2)cc(=O)n1CC(=O)NCC(=O)N1CCC(C(=O)O)CC1]
I-0060 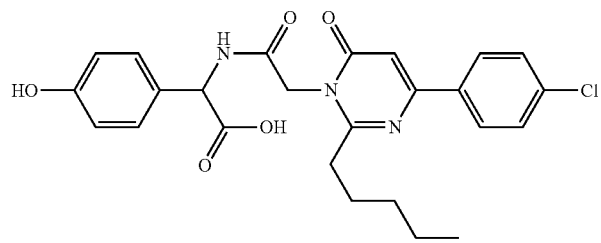 [SMILES: CCCCCc1nc(-c2ccc(Cl)cc2)cc(=O)n1CC(=O)NC(C(=O)O)c1ccc(O)cc1]
TABLE 11
I-0061 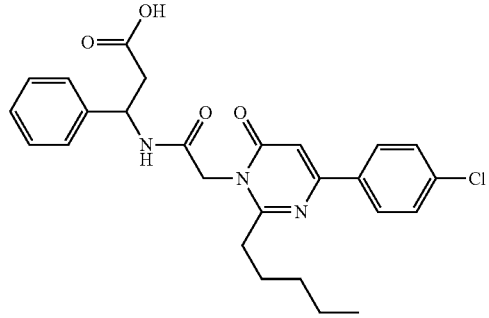 [SMILES: CCCCCc1nc(-c2ccc(Cl)cc2)cc(=O)n1CC(=O)NC(CC(=O)O)c1ccccc1]
I-0062 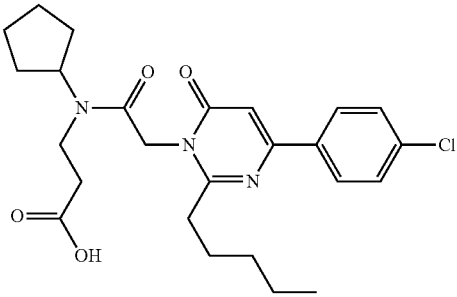 [SMILES: CCCCCc1nc(-c2ccc(Cl)cc2)cc(=O)n1CC(=O)N(CCC(=O)O)C1CCCC1]
TABLE 11-continued
I-0063 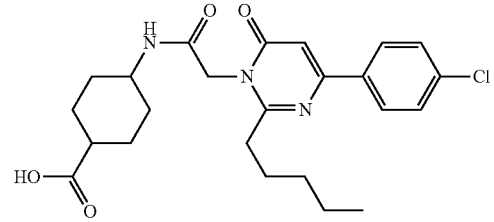 [SMILES: CCCCCc1nc(-c2ccc(Cl)cc2)cc(=O)n1CC(=O)NC1CCC(C(=O)O)CC1]
I-0064 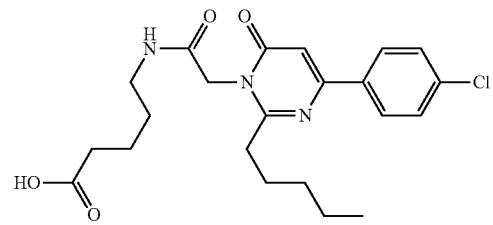 [SMILES: CCCCCc1nc(-c2ccc(Cl)cc2)cc(=O)n1CC(=O)NCCCCC(=O)O]
I-0065 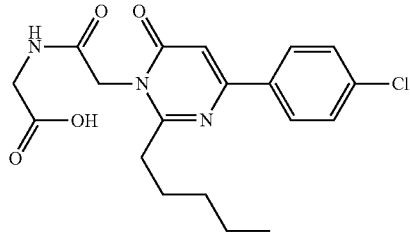 [SMILES: CCCCCc1nc(-c2ccc(Cl)cc2)cc(=O)n1CC(=O)NCC(=O)O]

TABLE 11-continued
I-0066 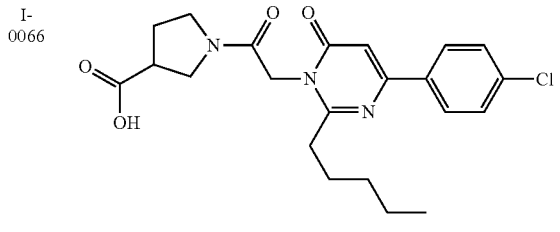
TABLE 12
I-0067 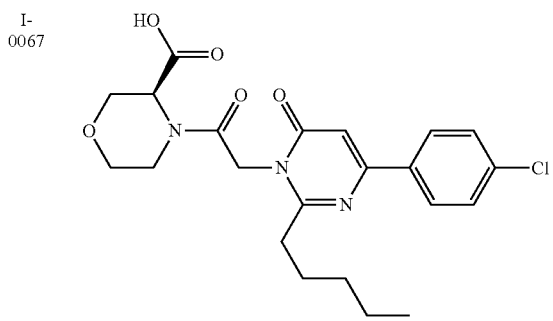
I-0068 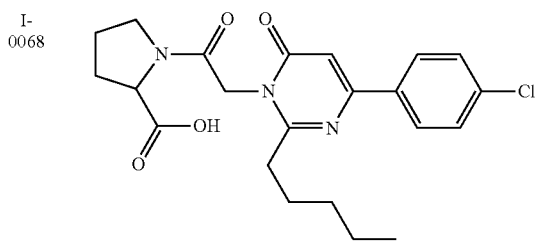
I-0069 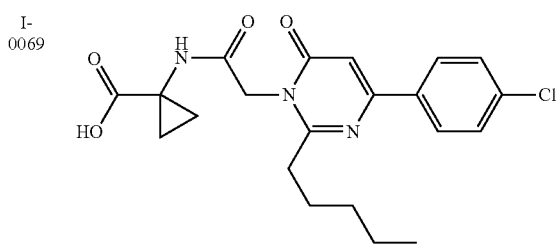
I-0070 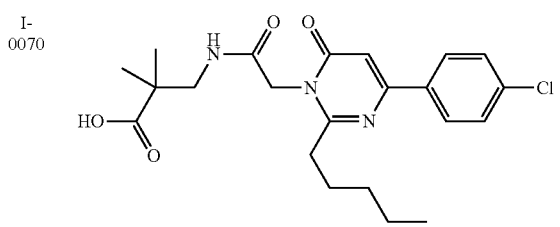
I-0071 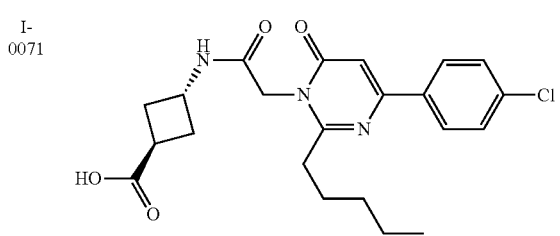
TABLE 12-continued
I-0072 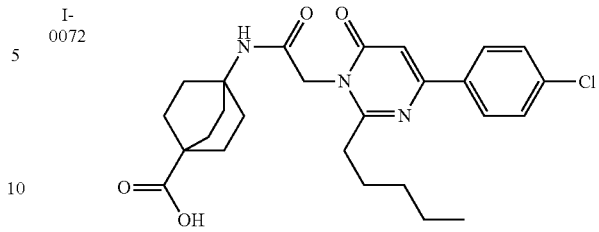
TABLE 13
I-0073 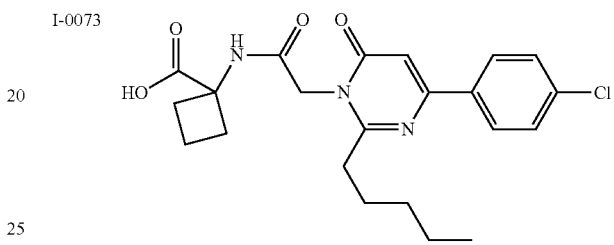
I-0074 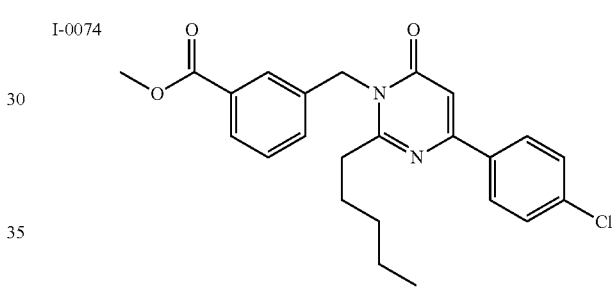
I-0075 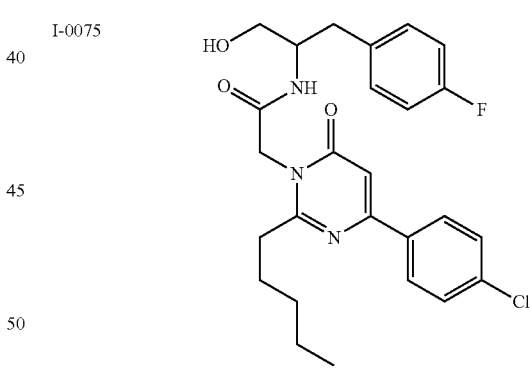
I-0076 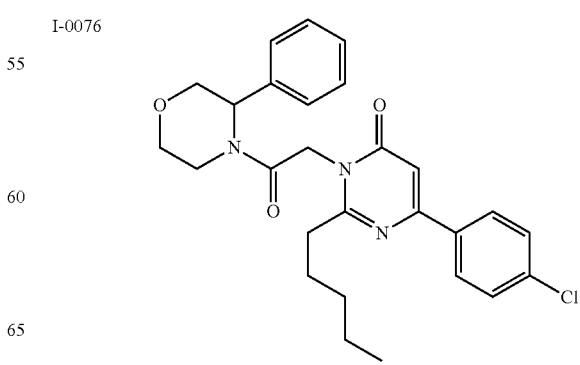

TABLE 13-continued
I-0077
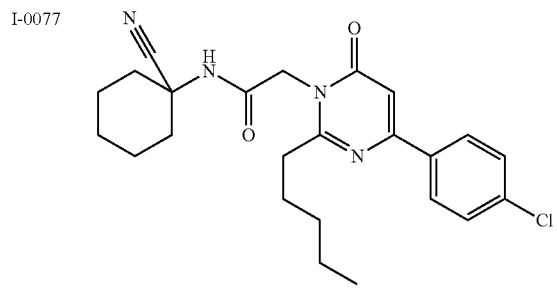
I-0078
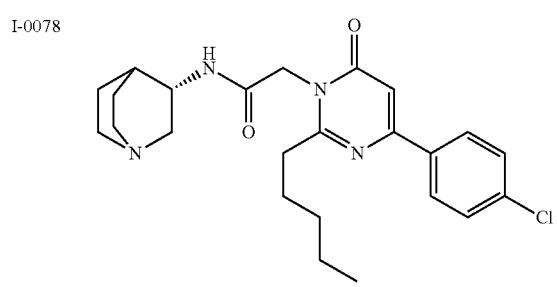
TABLE 14
I-0079
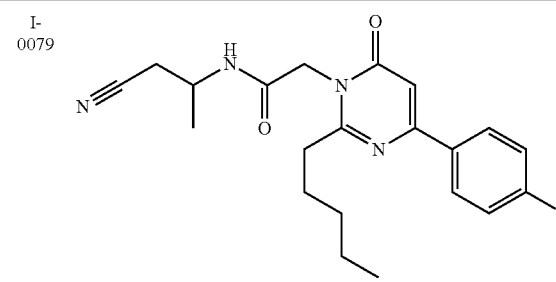
I-0080
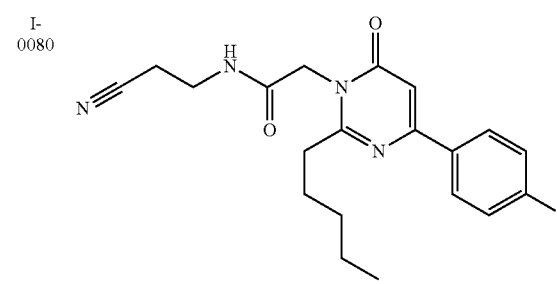
I-0081
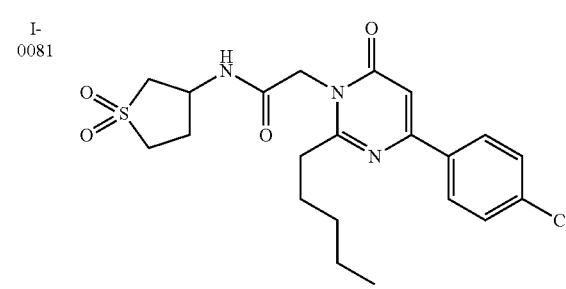
TABLE 14-continued
I-0082
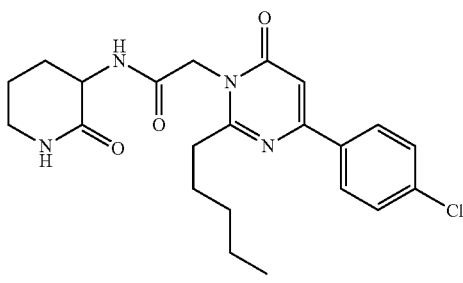 [SMILES: CCCCCc1nc(-c2ccc(Cl)cc2)cc(=O)n1CC(=O)NC1CCCNC1=O]
I-0083
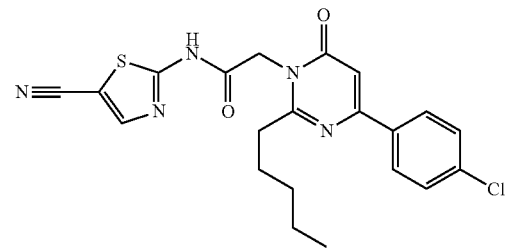 [SMILES: CCCCCc1nc(-c2ccc(Cl)cc2)cc(=O)n1CC(=O)Nc1ncc(C#N)s1]
I-0084
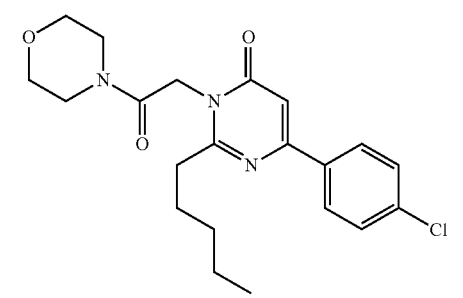 [SMILES: CCCCCc1nc(-c2ccc(Cl)cc2)cc(=O)n1CC(=O)N1CCOCC1]
TABLE 15
I-0085
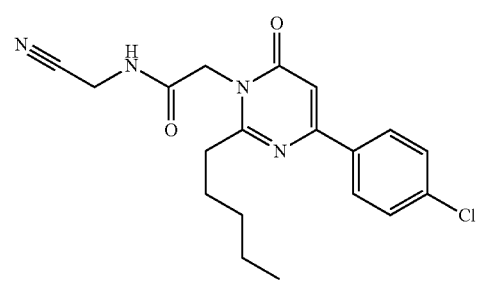 [SMILES: CCCCCc1nc(-c2ccc(Cl)cc2)cc(=O)n1CC(=O)NCC#N]
I-0086
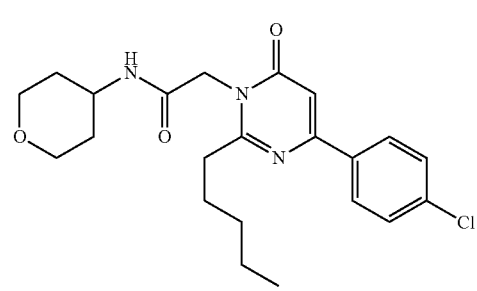 [SMILES: CCCCCc1nc(-c2ccc(Cl)cc2)cc(=O)n1CC(=O)NC1CCOCC1]

TABLE 15-continued
I-0087 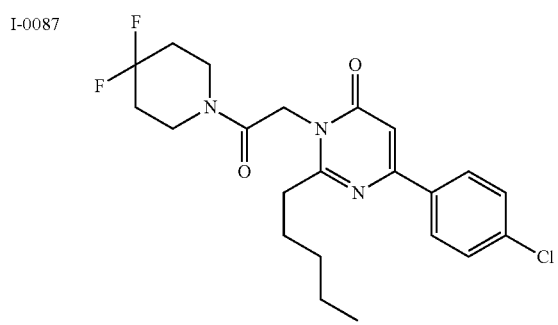
I-0088 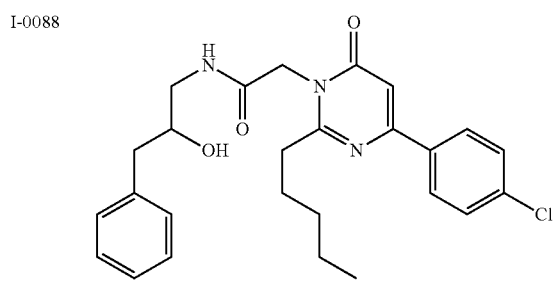
I-0089 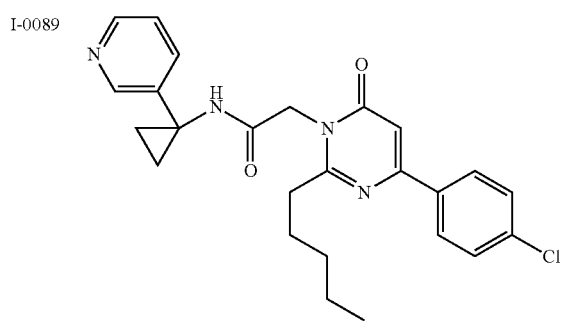
I-0090 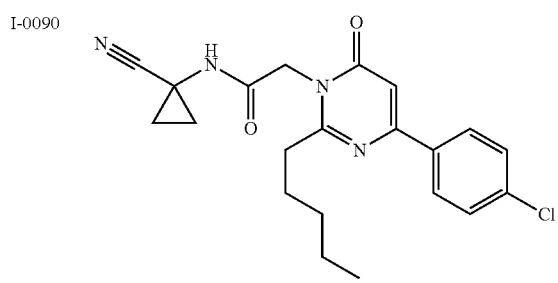
TABLE 16
I-0091 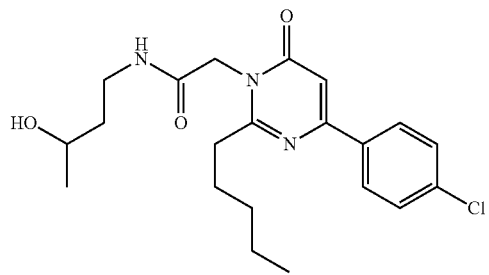 [SMILES: CCCCCc1nc(-c2ccc(Cl)cc2)cc(=O)n1CC(=O)NCCC(C)O]
TABLE 16-continued
I-0092 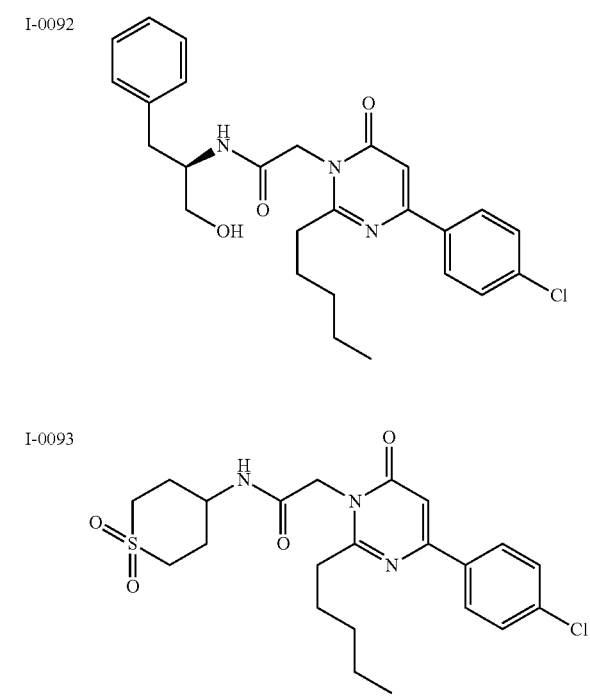
I-0093
I-0094
I-0095 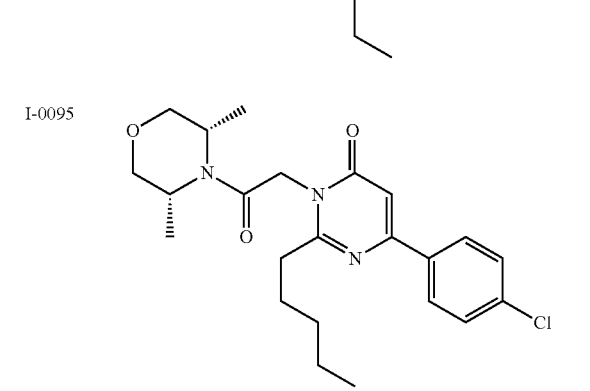
I-0096 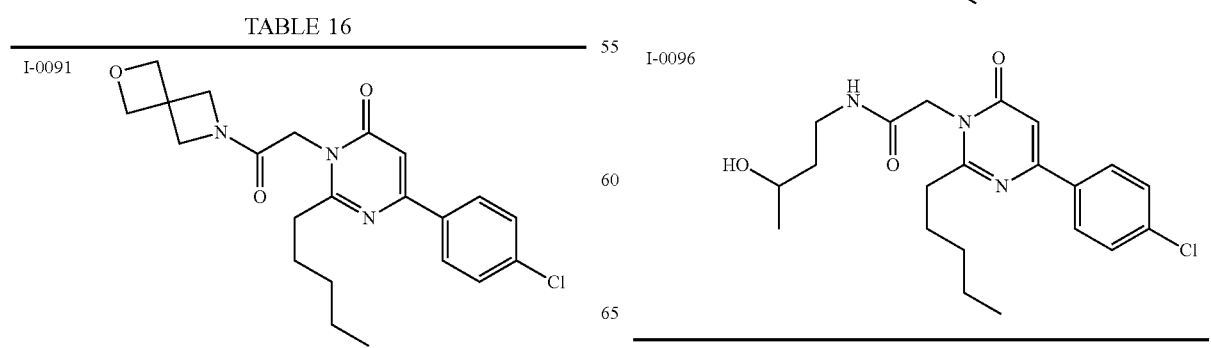

TABLE 17
I-0097
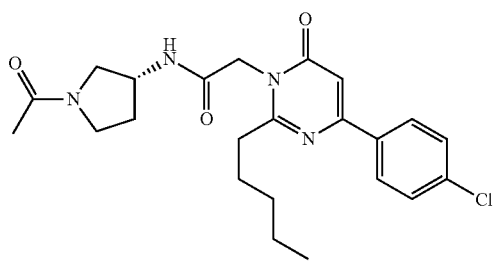 [SMILES: CCCCCc1nc(-c2ccc(Cl)cc2)cc(=O)n1CC(=O)N[C@@H]1CCN(C(C)=O)C1]
I-0098
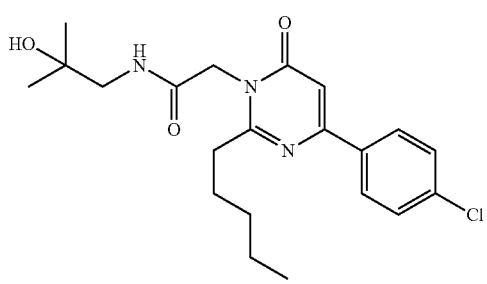 [SMILES: CCCCCc1nc(-c2ccc(Cl)cc2)cc(=O)n1CC(=O)NCC(C)(C)O]
I-0099
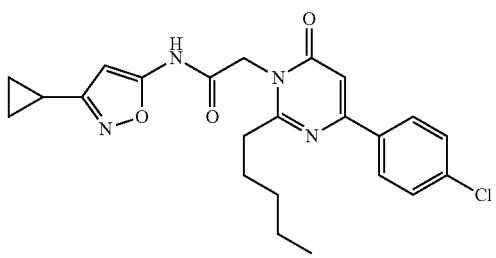 [SMILES: CCCCCc1nc(-c2ccc(Cl)cc2)cc(=O)n1CC(=O)Nc1cc(C2CC2)no1]
I-0100
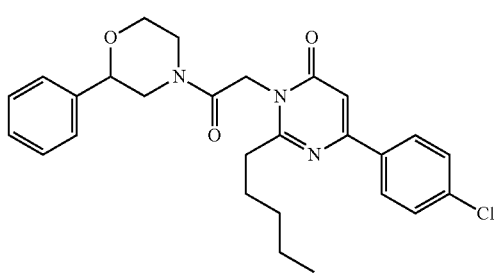 [SMILES: CCCCCc1nc(-c2ccc(Cl)cc2)cc(=O)n1CC(=O)N1CCOC(c2ccccc2)C1]
I-0101
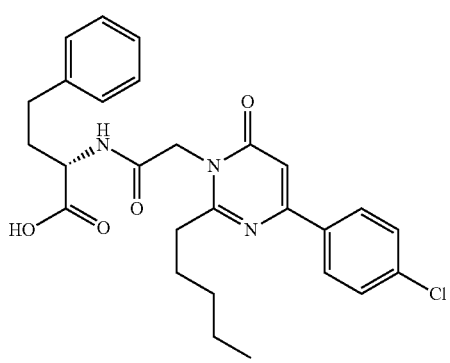 [SMILES: CCCCCc1nc(-c2ccc(Cl)cc2)cc(=O)n1CC(=O)N[C@@H](CCc1ccccc1)C(=O)O]
TABLE 17-continued
I-0102
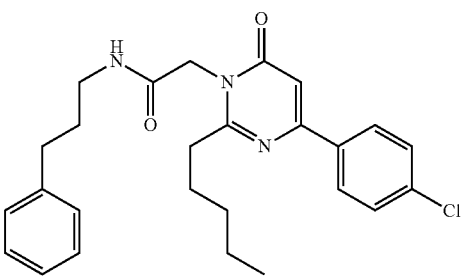 [SMILES: CCCCCc1nc(-c2ccc(Cl)cc2)cc(=O)n1CC(=O)NCCCc1ccccc1]
TABLE 18
I-0103
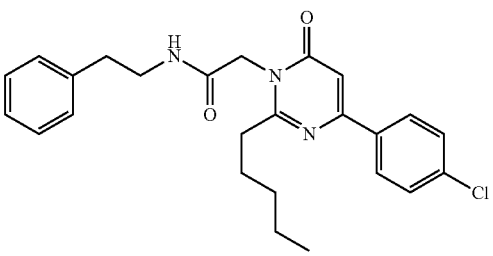 [SMILES: CCCCCc1nc(-c2ccc(Cl)cc2)cc(=O)n1CC(=O)NCCc1ccccc1]
I-0104
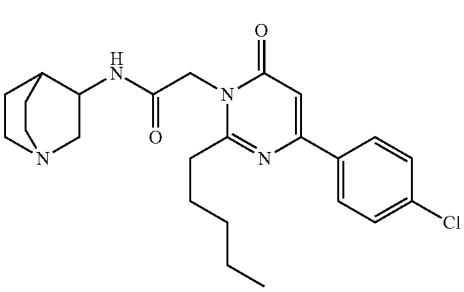 [SMILES: CCCCCc1nc(-c2ccc(Cl)cc2)cc(=O)n1CC(=O)NC1CN2CCC1CC2]
I-0105
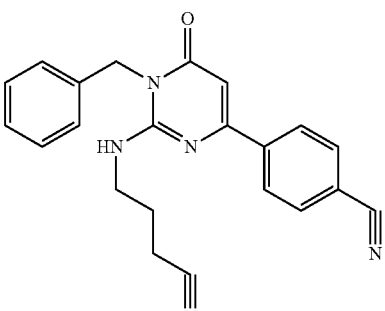
I-0106
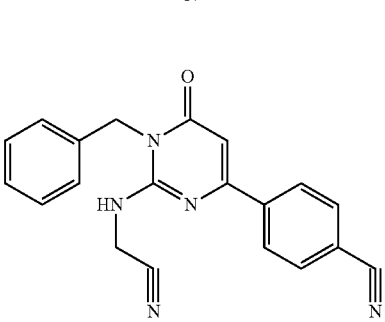

TABLE 18-continued
I-0107 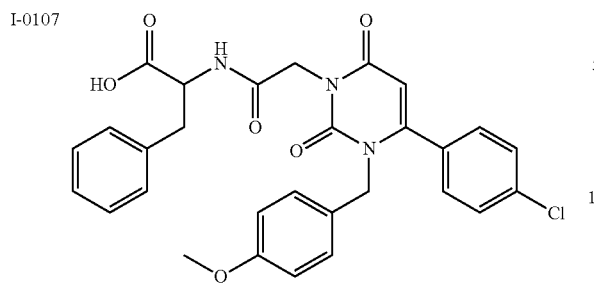
I-0108 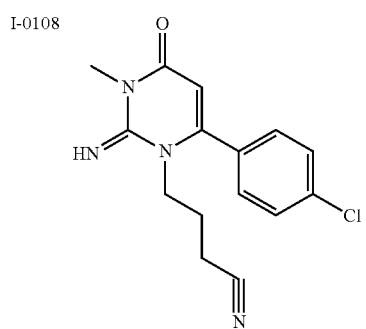
TABLE 19
I-0109 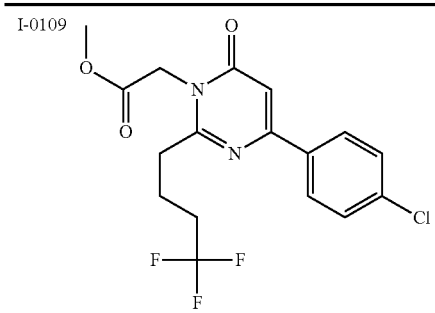
I-0110 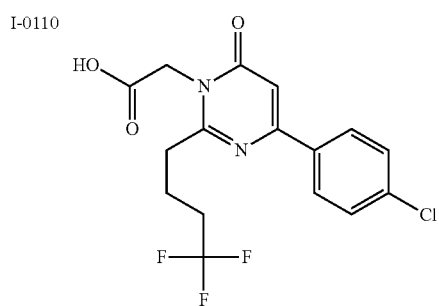
I-0111 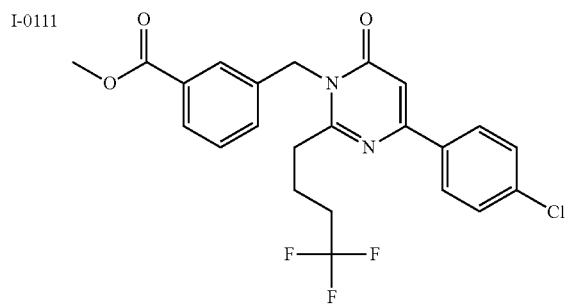
TABLE 19-continued
I-0112 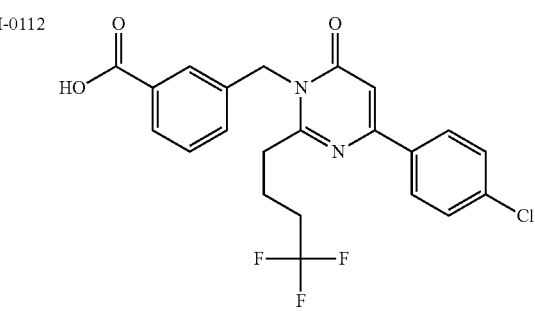
I-0113 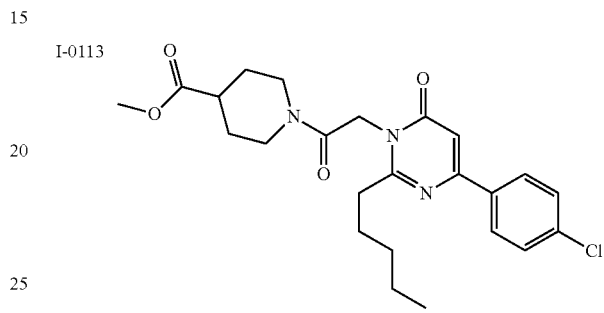
I-0114 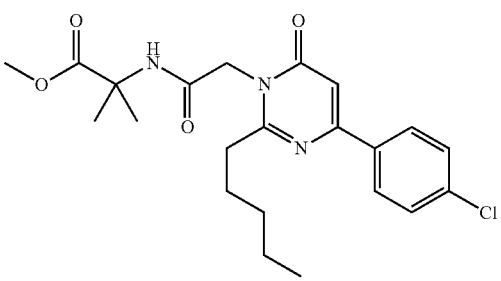 [SMILES: CCCCCc1nc(-c2ccc(Cl)cc2)cc(=O)n1CC(=O)NC(C)(C)C(=O)OC]
TABLE 20
I-0115 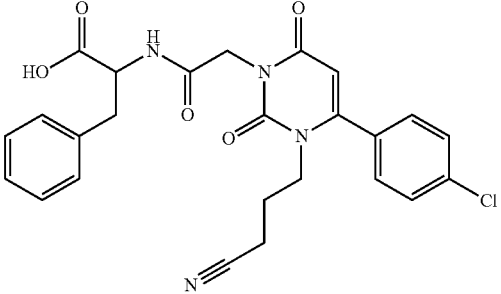 [SMILES: N#CCCCn1c(-c2ccc(Cl)cc2)cc(=O)n(CC(=O)NC(Cc2ccccc2)C(=O)O)c1=O]
I-0116 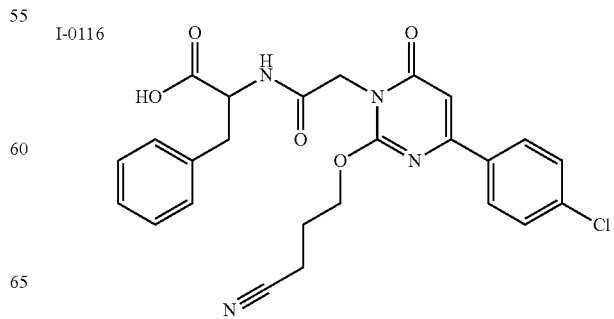

TABLE 20-continued
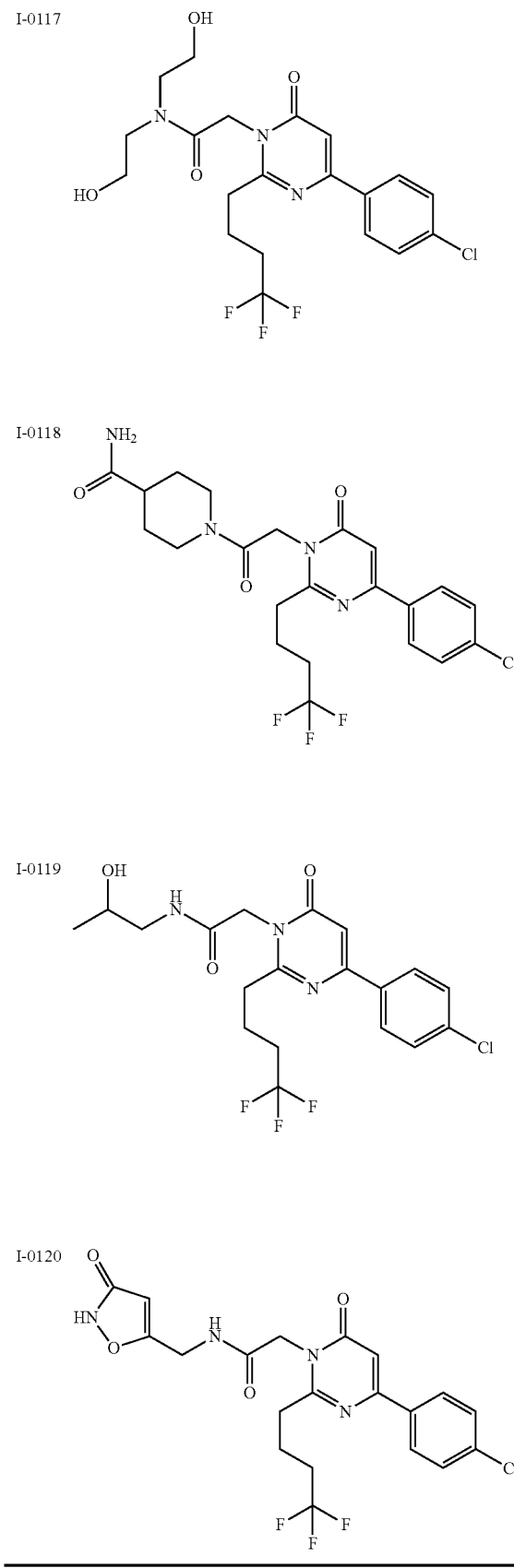
TABLE 21
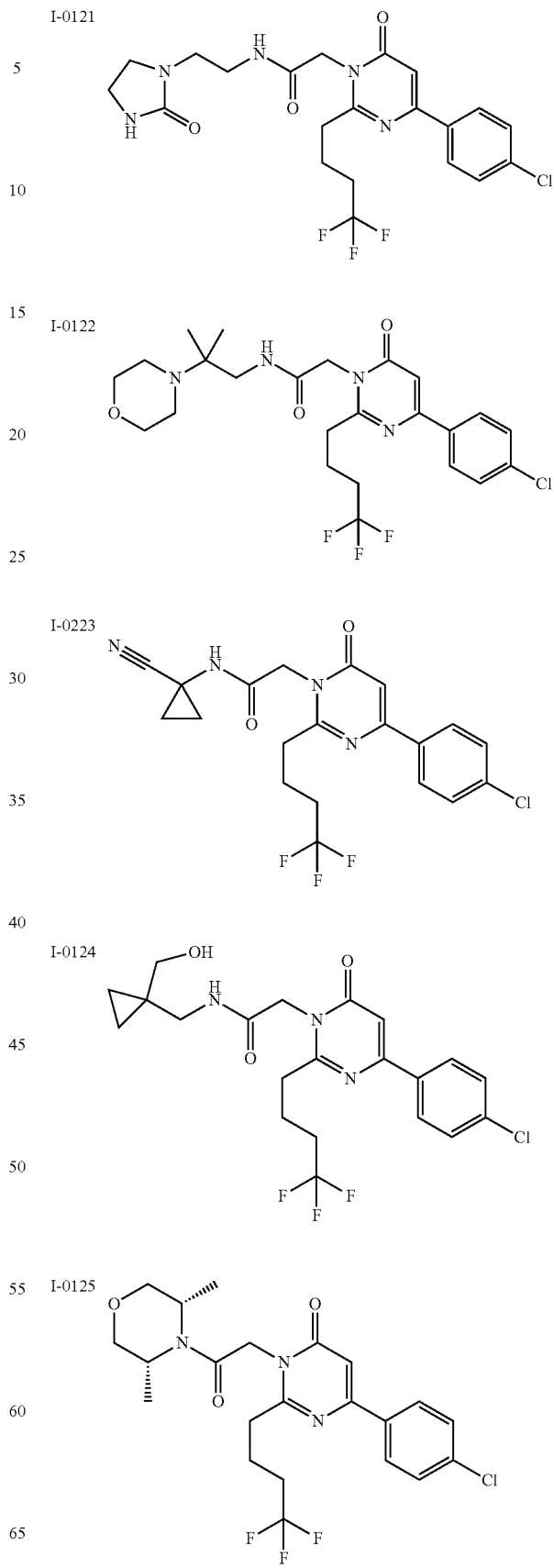

TABLE 21-continued
I-0126 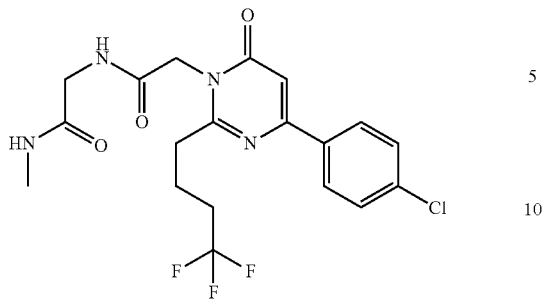
TABLE 22
I-0127 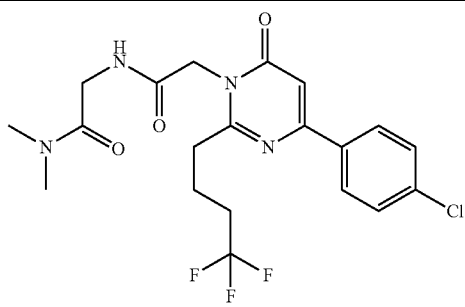
I-0128 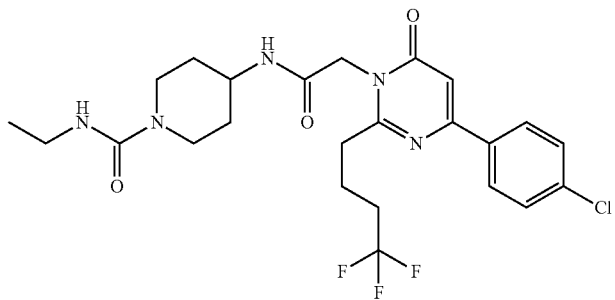 [SMILES: CCNC(=O)N1CCC(NC(=O)Cn2c(CCCC(F)(F)F)nc(-c3ccc(Cl)cc3)cc2=O)CC1]
I-0129 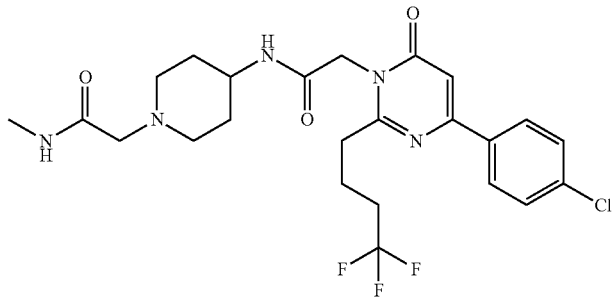 [SMILES: CNC(=O)CN1CCC(NC(=O)Cn2c(CCCC(F)(F)F)nc(-c3ccc(Cl)cc3)cc2=O)CC1]
I-0130 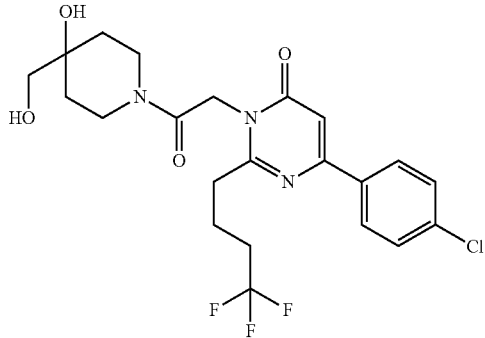 [SMILES: O=C(Cn1c(CCCC(F)(F)F)nc(-c2ccc(Cl)cc2)cc1=O)N1CCC(O)(CO)CC1]

TABLE 22-continued
I-0131 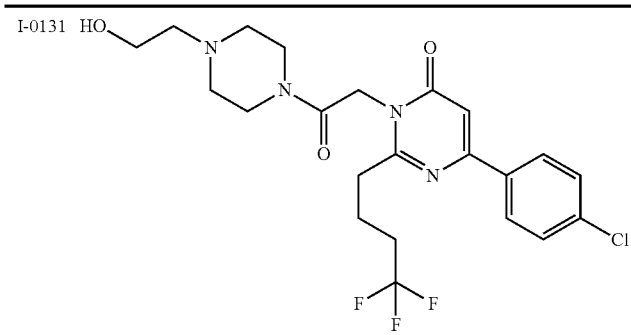
I-0132 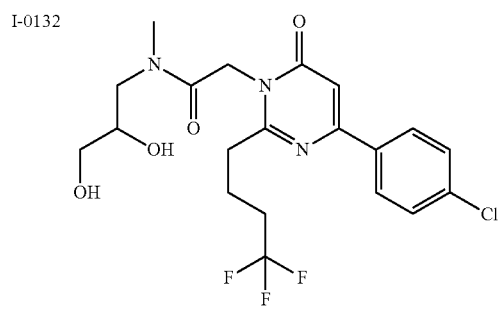
| TABLE 23 | TABLE 23-continued |
|---|---|
| I-0133 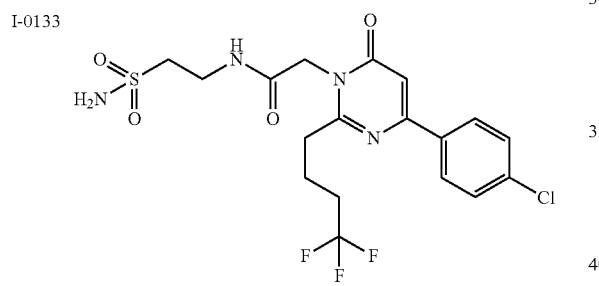 | I-0136 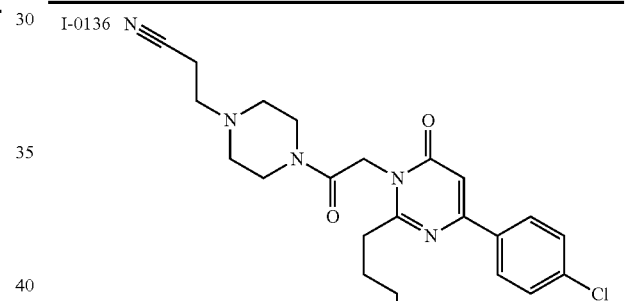 |
| I-0134 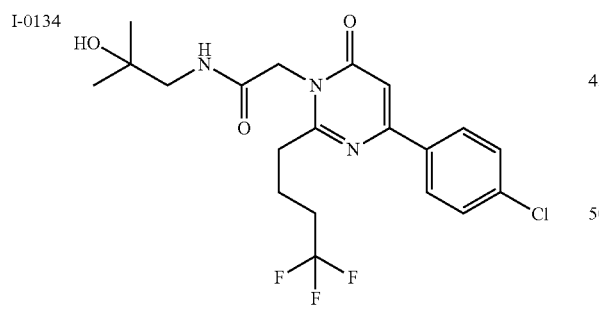 | I-0137 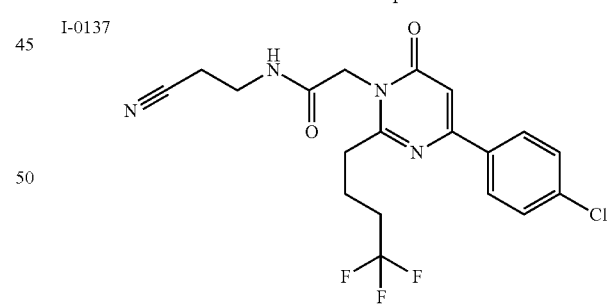 |
| I-0135 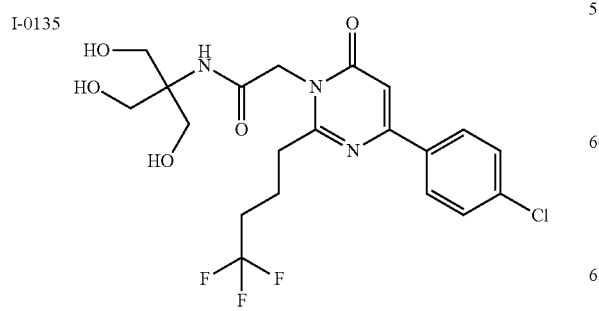 | I-0138 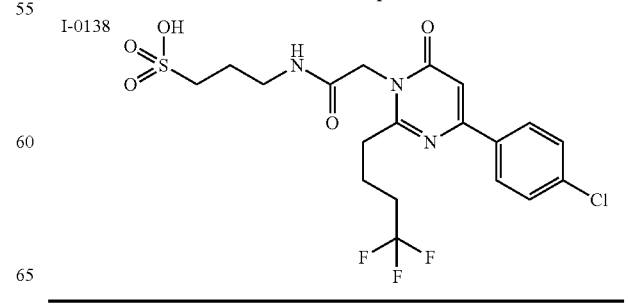 |

TABLE 24
I-0139
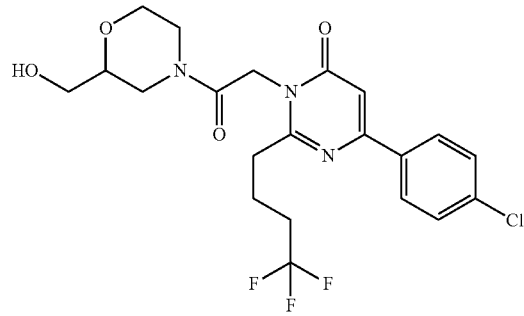 [SMILES: O=C(Cn1c(CCCC(F)(F)F)nc(-c2ccc(Cl)cc2)cc1=O)N1CCOC(CO)C1]
I-0140
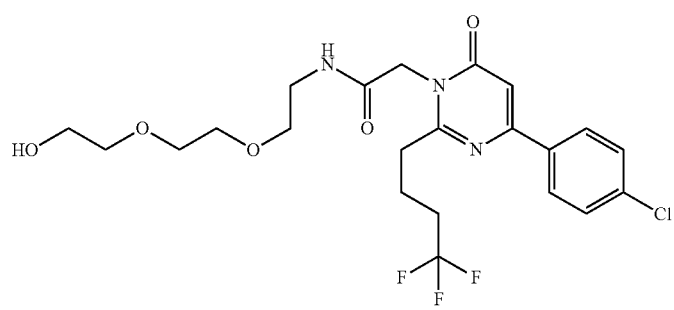 [SMILES: O=C(Cn1c(CCCC(F)(F)F)nc(-c2ccc(Cl)cc2)cc1=O)NCCOCCOCCO]
I-0141
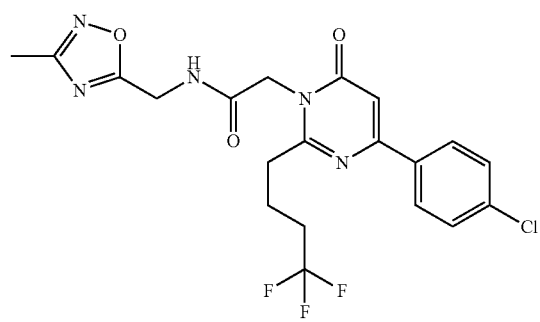 [SMILES: Cc1noc(CNC(=O)Cn2c(CCCC(F)(F)F)nc(-c3ccc(Cl)cc3)cc2=O)n1]
I-0142
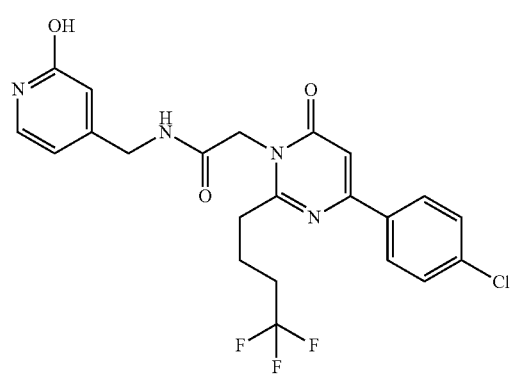 [SMILES: O=C(Cn1c(CCCC(F)(F)F)nc(-c2ccc(Cl)cc2)cc1=O)NCc1ccnc(O)c1]
I-0143
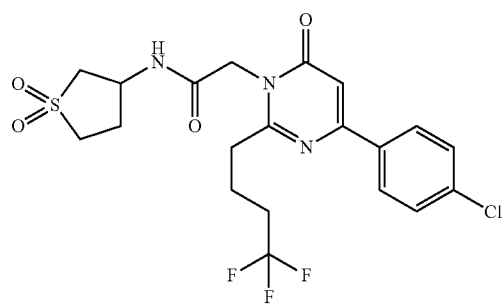 [SMILES: O=C(Cn1c(CCCC(F)(F)F)nc(-c2ccc(Cl)cc2)cc1=O)NC1CCS(=O)(=O)C1]

TABLE 24-continued
I-0144
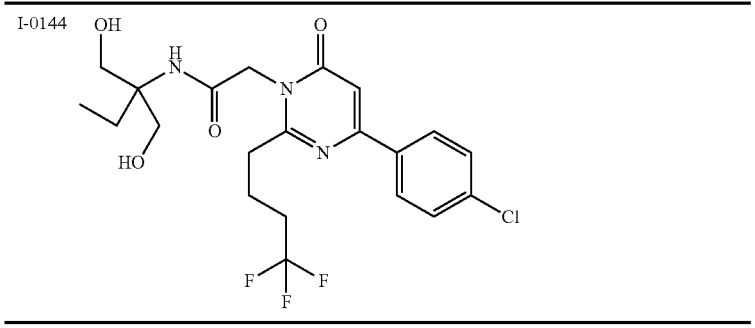
TABLE 25
I-0145
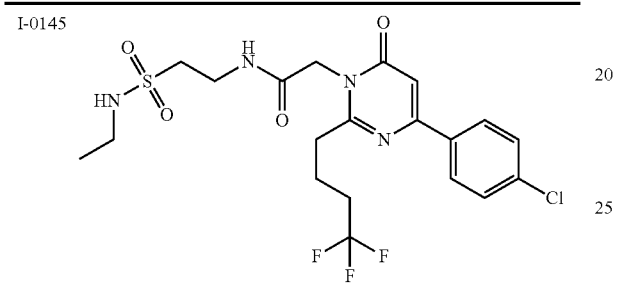
I-0146
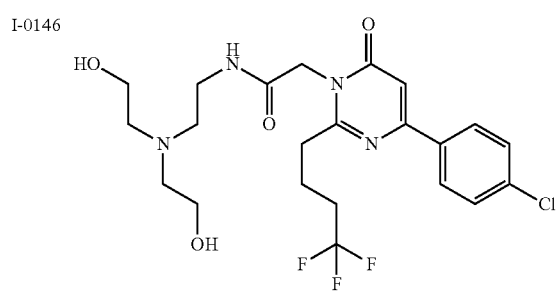
I-0147
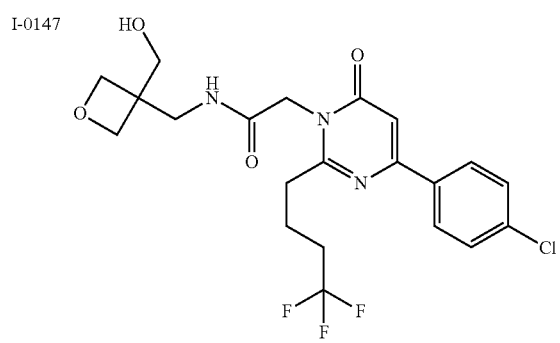
TABLE 25-continued
I-0148
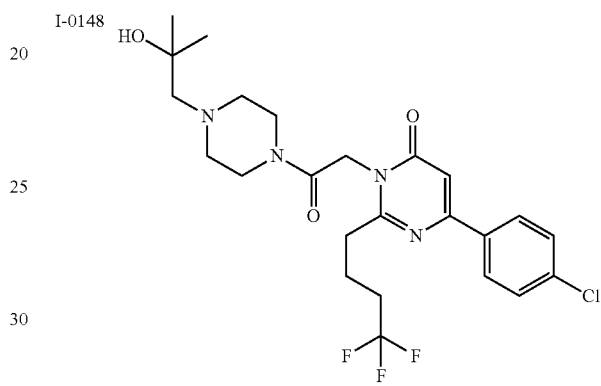
I-0149
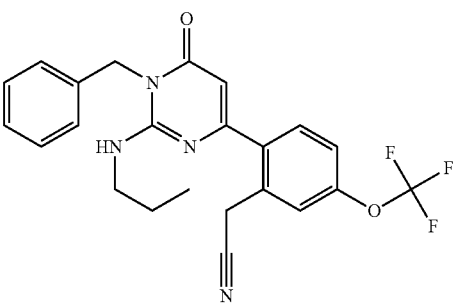 [SMILES: CCCNc1nc(-c2ccc(OC(F)(F)F)cc2CC#N)cc(=O)n1Cc1ccccc1]
I-0150
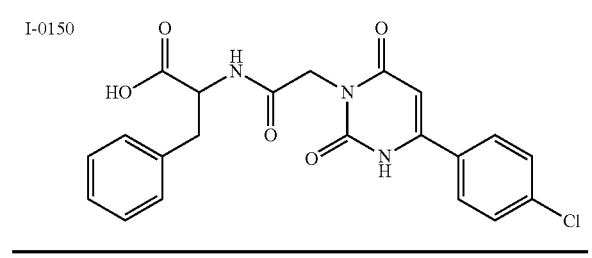

TABLE 26
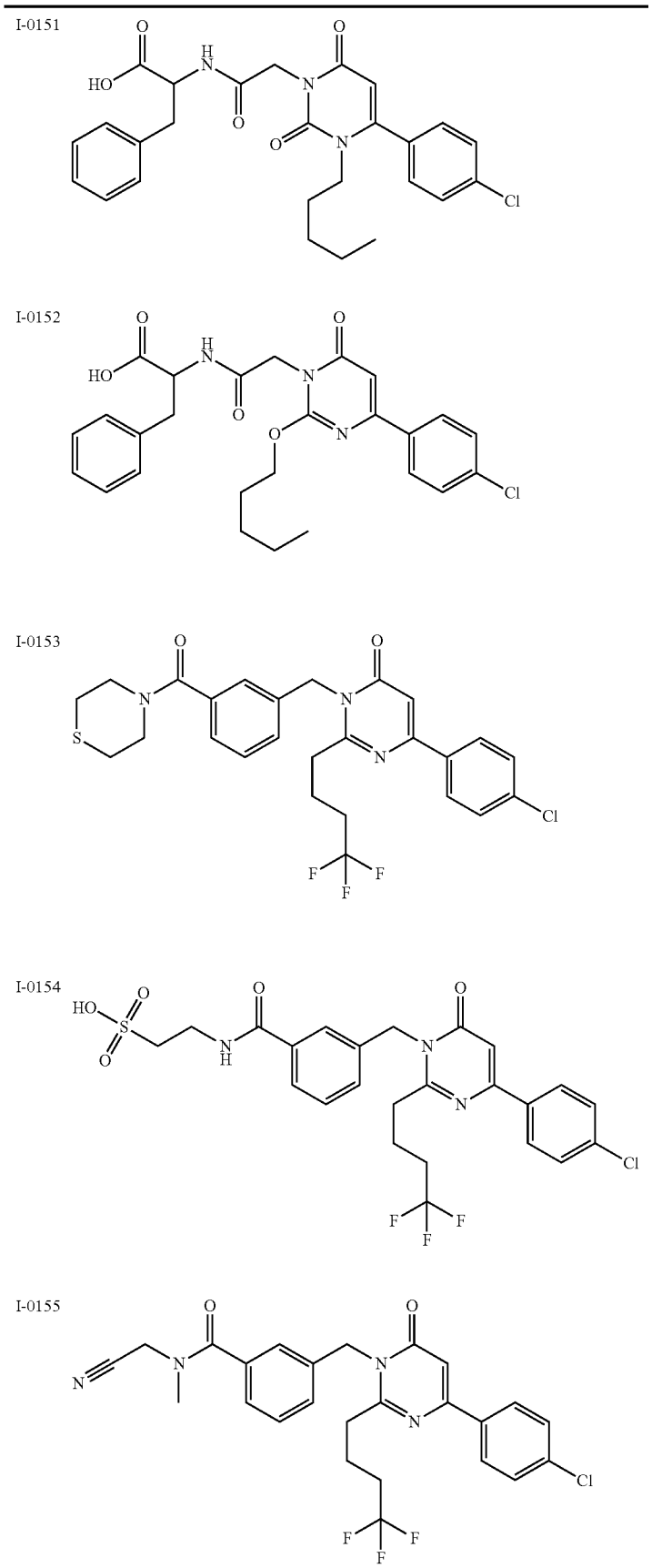

TABLE 26-continued
I-0156 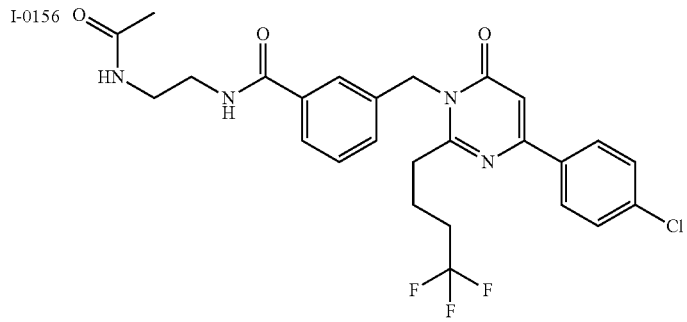
TABLE 27
I-0157 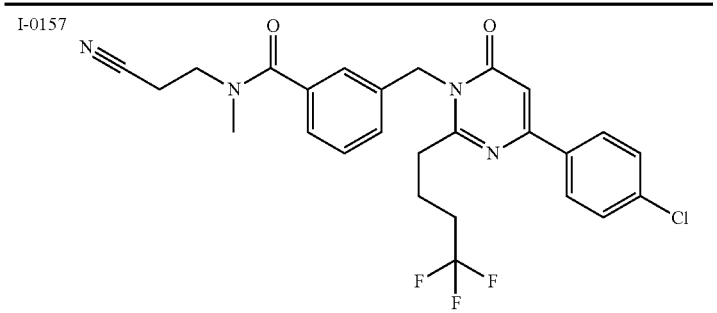
I-0158 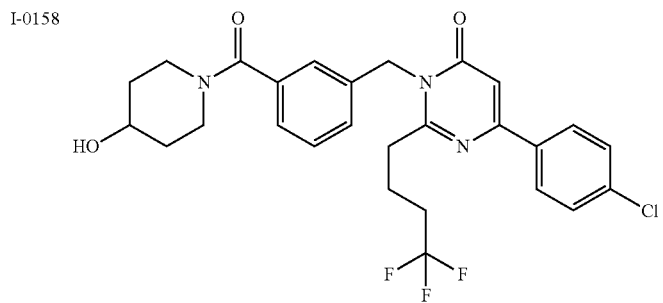
I-0159 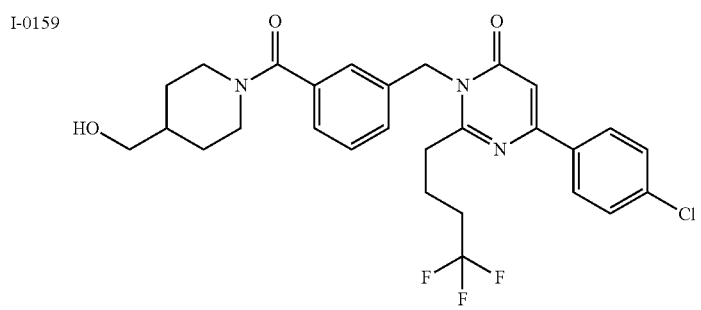
I-0160 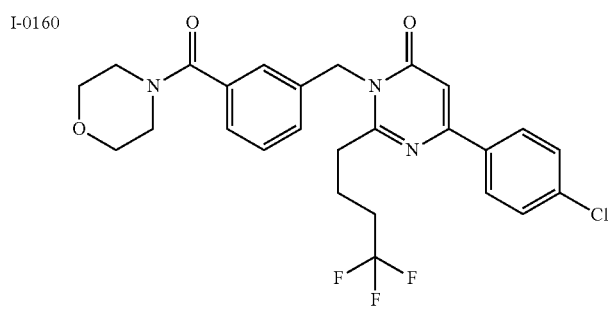

TABLE 27-continued
I-0161 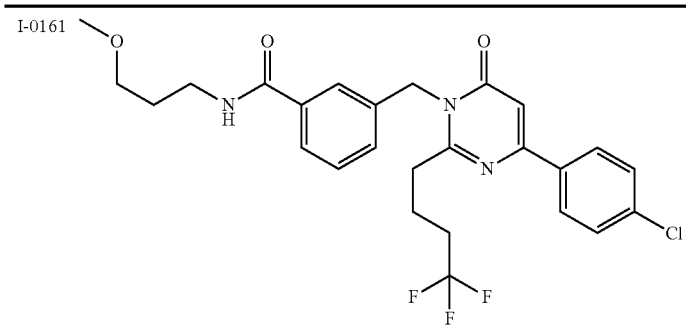
I-0162 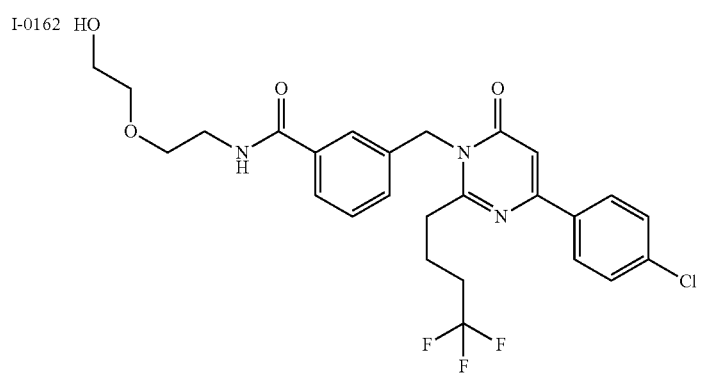
TABLE 28
I-0163 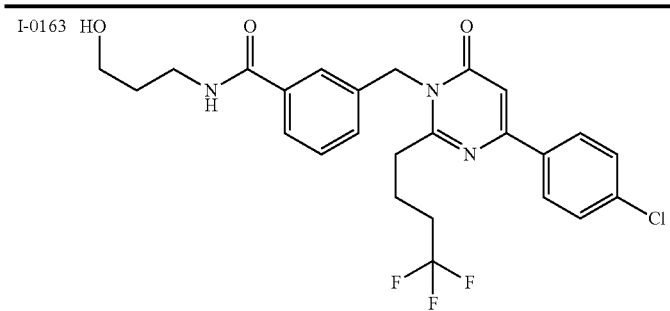
I-0164 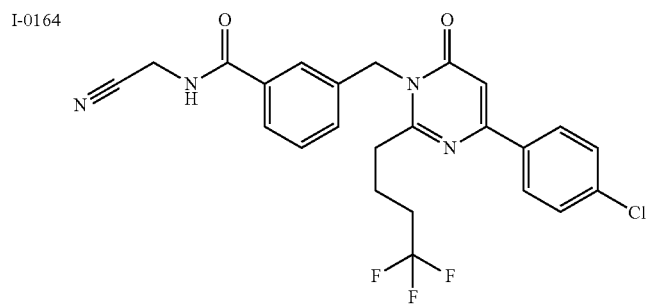

TABLE 28-continued
I-0165
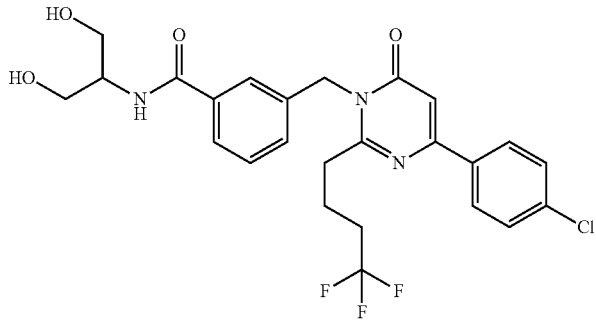 [SMILES: O=C(NC(CO)CO)c1cccc(Cn2c(CCCC(F)(F)F)nc(-c3ccc(Cl)cc3)cc2=O)c1]
I-0166
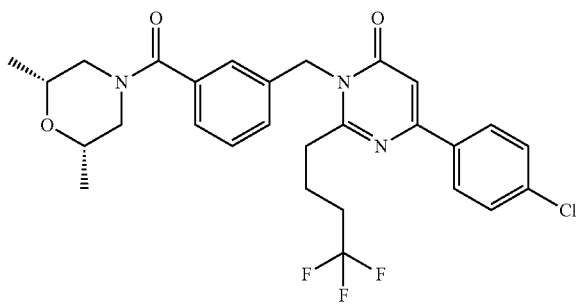 [SMILES: C[C@@H]1CN(C(=O)c2cccc(Cn3c(CCCC(F)(F)F)nc(-c4ccc(Cl)cc4)cc3=O)c2)C[C@H](C)O1]
I-0167
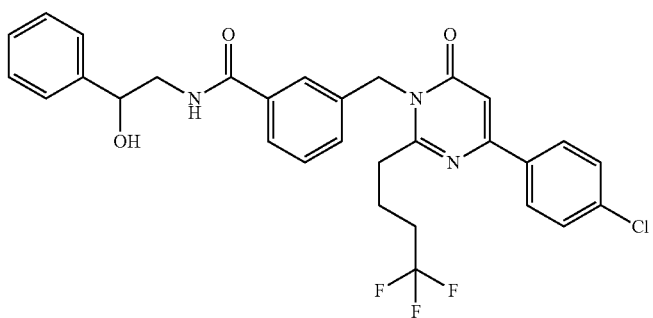 [SMILES: O=C(NCC(O)c1ccccc1)c1cccc(Cn2c(CCCC(F)(F)F)nc(-c3ccc(Cl)cc3)cc2=O)c1]
I-0168
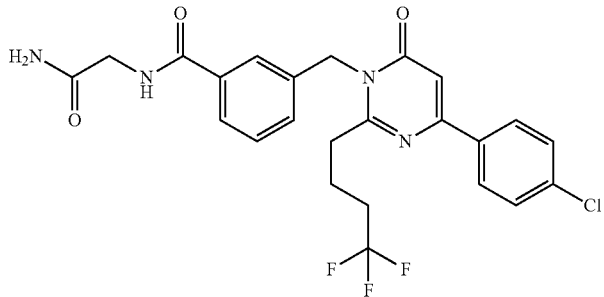 [SMILES: NC(=O)CNC(=O)c1cccc(Cn2c(CCCC(F)(F)F)nc(-c3ccc(Cl)cc3)cc2=O)c1]
TABLE 29
I-0169
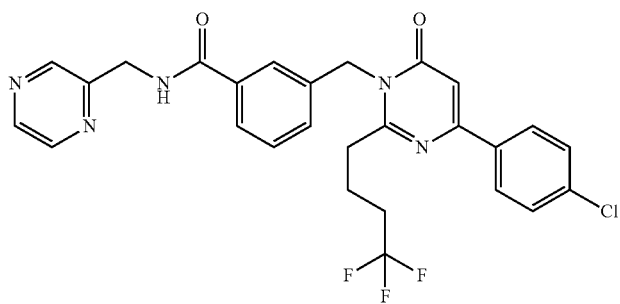 [SMILES: O=C(NCc1cnccn1)c1cccc(Cn2c(CCCC(F)(F)F)nc(-c3ccc(Cl)cc3)cc2=O)c1]

TABLE 29-continued
I-0170 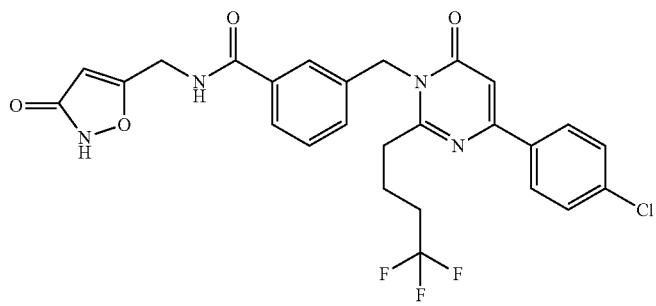 [SMILES: O=C(NCc1cc(=O)[nH]o1)c1cccc(Cn2c(CCCC(F)(F)F)nc(-c3ccc(Cl)cc3)cc2=O)c1]
I-0171 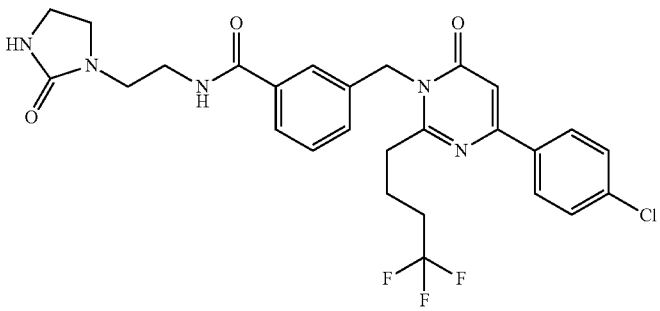 [SMILES: O=C(NCCN1CCNC1=O)c1cccc(Cn2c(CCCC(F)(F)F)nc(-c3ccc(Cl)cc3)cc2=O)c1]
I-0172 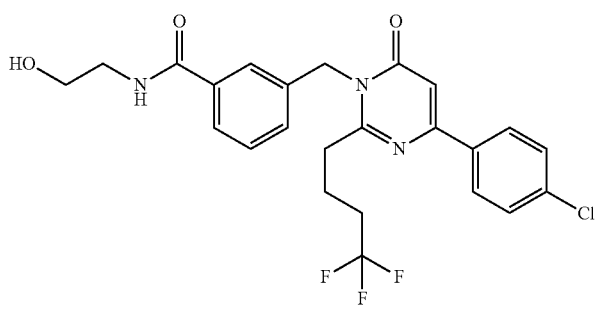 [SMILES: O=C(NCCO)c1cccc(Cn2c(CCCC(F)(F)F)nc(-c3ccc(Cl)cc3)cc2=O)c1]
I-0173 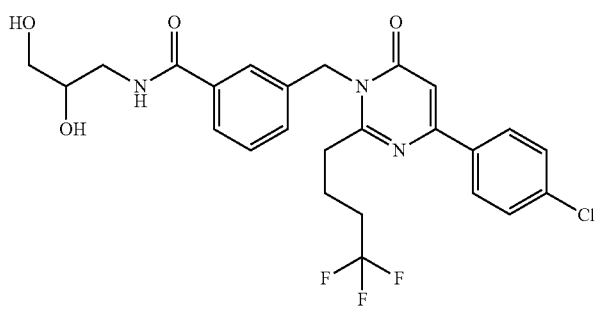 [SMILES: O=C(NCC(O)CO)c1cccc(Cn2c(CCCC(F)(F)F)nc(-c3ccc(Cl)cc3)cc2=O)c1]
I-0174 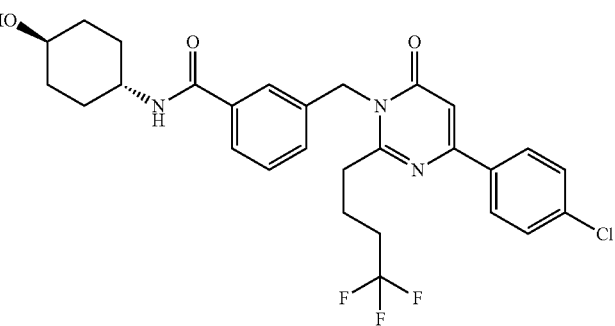

TABLE 30
I-0175 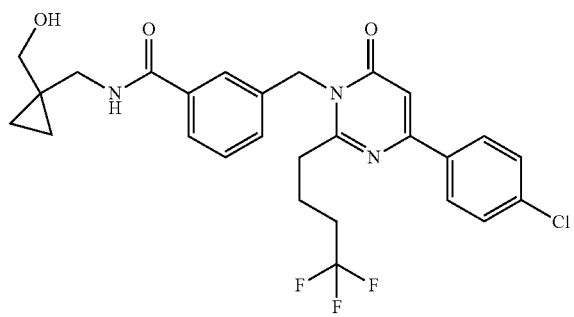 [SMILES: O=C(NCC1(CO)CC1)c1cccc(Cn2c(CCCC(F)(F)F)nc(-c3ccc(Cl)cc3)cc2=O)c1]
I-0176 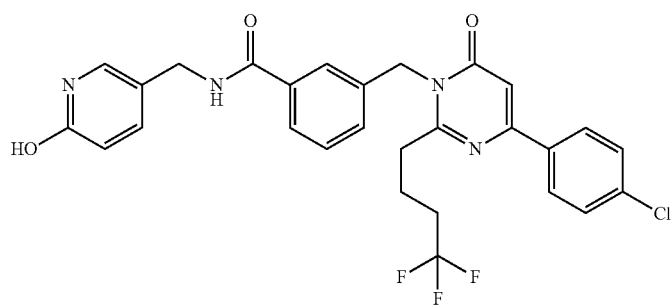 [SMILES: O=C(NCc1ccc(O)nc1)c1cccc(Cn2c(CCCC(F)(F)F)nc(-c3ccc(Cl)cc3)cc2=O)c1]
I-0177 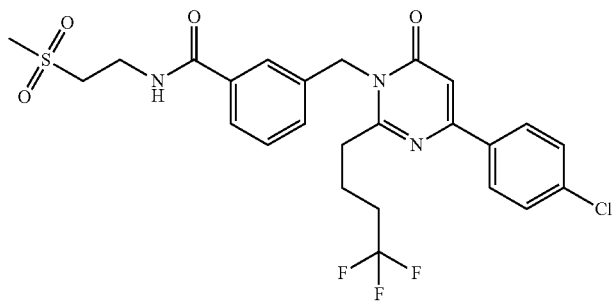 [SMILES: CS(=O)(=O)CCNC(=O)c1cccc(Cn2c(CCCC(F)(F)F)nc(-c3ccc(Cl)cc3)cc2=O)c1]
I-0178 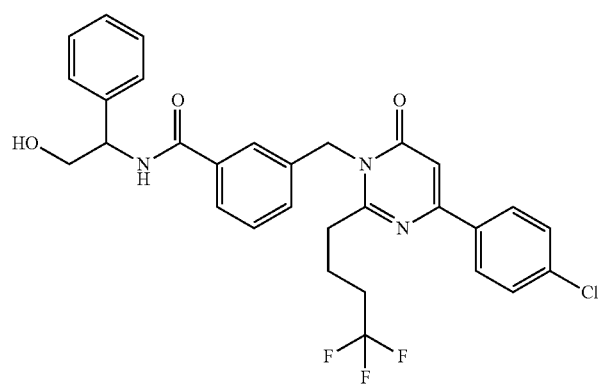 [SMILES: O=C(NC(CO)c1ccccc1)c1cccc(Cn2c(CCCC(F)(F)F)nc(-c3ccc(Cl)cc3)cc2=O)c1]
I-0179 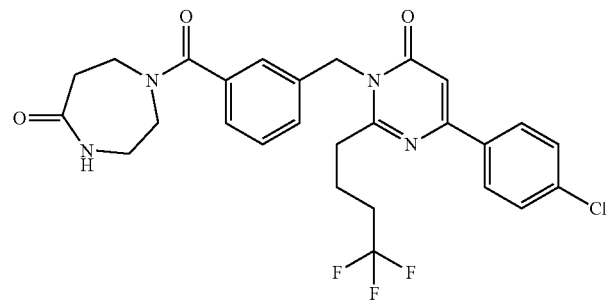 [SMILES: O=C1CCN(C(=O)c2cccc(Cn3c(CCCC(F)(F)F)nc(-c4ccc(Cl)cc4)cc3=O)c2)CCN1]

TABLE 30-continued
I-0180
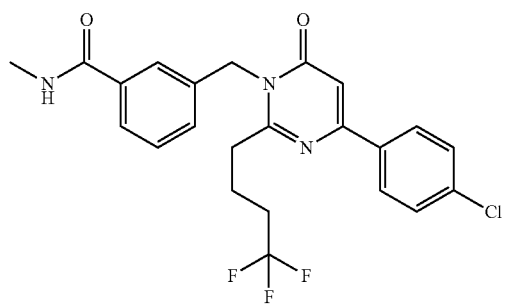 [SMILES: CNC(=O)c1cccc(Cn2c(CCCC(F)(F)F)nc(-c3ccc(Cl)cc3)cc2=O)c1]
TABLE 31
I-0181
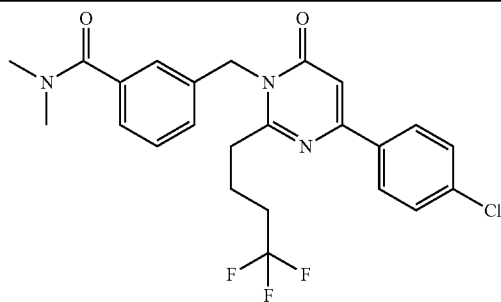
I-0182
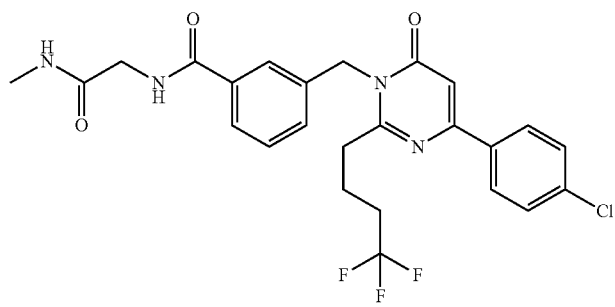 [SMILES: CNC(=O)CNC(=O)c1cccc(Cn2c(CCCC(F)(F)F)nc(-c3ccc(Cl)cc3)cc2=O)c1]
I-0183
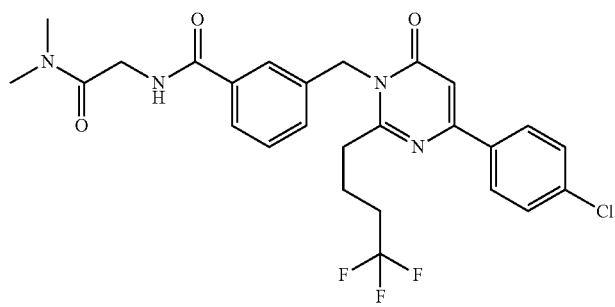 [SMILES: CN(C)C(=O)CNC(=O)c1cccc(Cn2c(CCCC(F)(F)F)nc(-c3ccc(Cl)cc3)cc2=O)c1]
I-0184
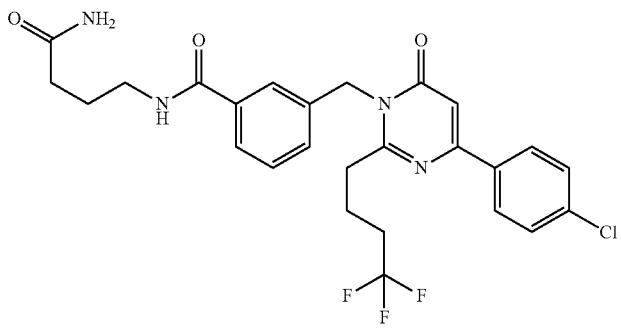 [SMILES: NC(=O)CCCNC(=O)c1cccc(Cn2c(CCCC(F)(F)F)nc(-c3ccc(Cl)cc3)cc2=O)c1]

TABLE 31-continued
I-0185 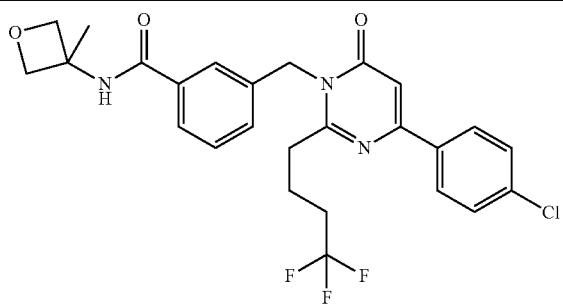
I-0186 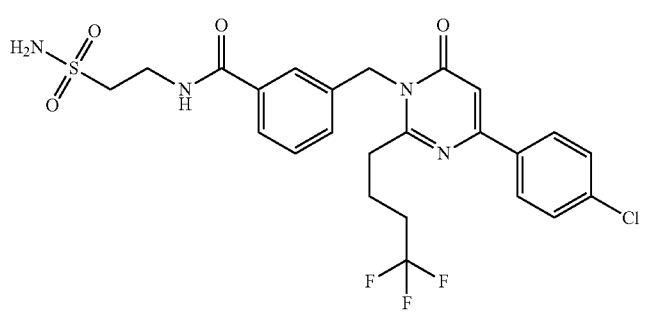 [SMILES: NS(=O)(=O)CCNC(=O)c1cccc(Cn2c(CCCC(F)(F)F)nc(-c3ccc(Cl)cc3)cc2=O)c1]
TABLE 32
I-0187 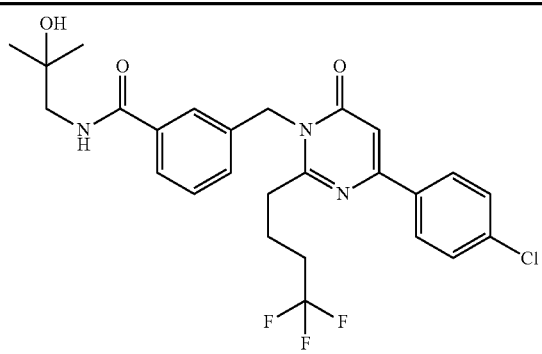
I-0188 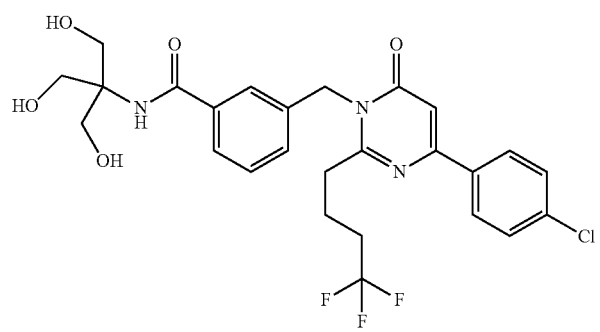 [SMILES: O=C(NC(CO)(CO)CO)c1cccc(Cn2c(CCCC(F)(F)F)nc(-c3ccc(Cl)cc3)cc2=O)c1]

TABLE 32-continued
I-0189
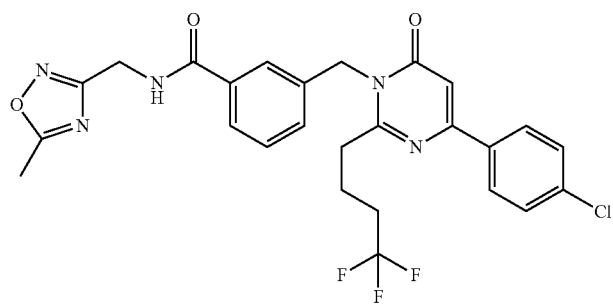 [SMILES: Cc1nc(CNC(=O)c2cccc(Cn3c(CCCC(F)(F)F)nc(-c4ccc(Cl)cc4)cc3=O)c2)no1]
I-0190
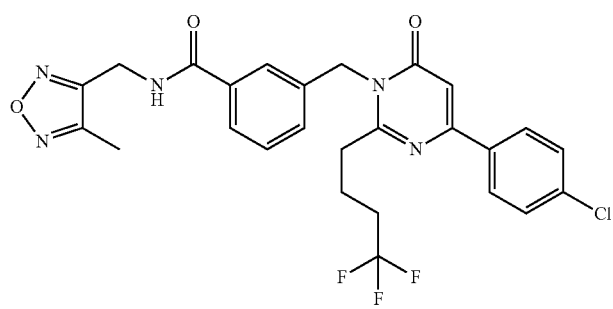 [SMILES: Cc1nonc1CNC(=O)c1cccc(Cn2c(CCCC(F)(F)F)nc(-c3ccc(Cl)cc3)cc2=O)c1]
I-0191
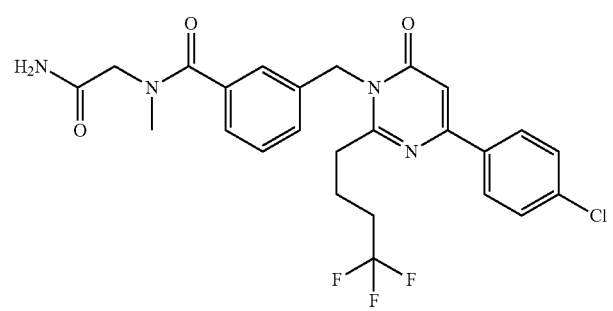 [SMILES: CN(CC(N)=O)C(=O)c1cccc(Cn2c(CCCC(F)(F)F)nc(-c3ccc(Cl)cc3)cc2=O)c1]
I-0192
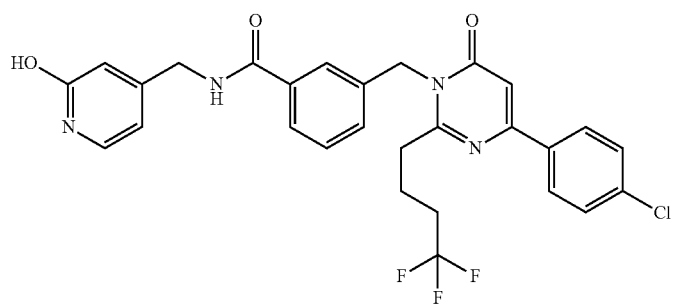 [SMILES: O=C(NCc1ccnc(O)c1)c1cccc(Cn2c(CCCC(F)(F)F)nc(-c3ccc(Cl)cc3)cc2=O)c1]
TABLE 33
I-0193
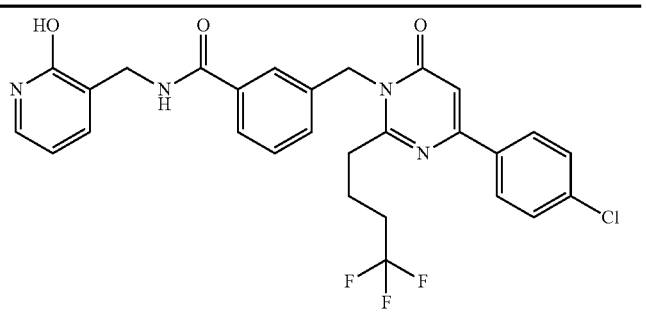

TABLE 33-continued
I-0194
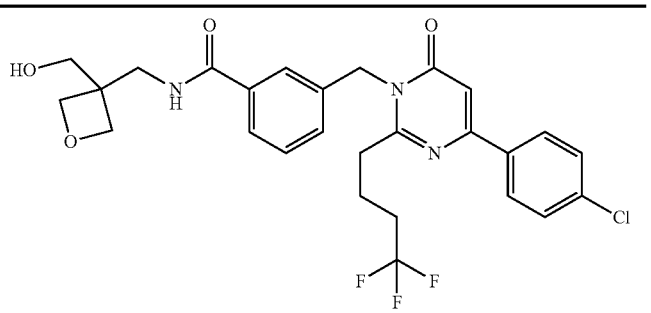
I-0195
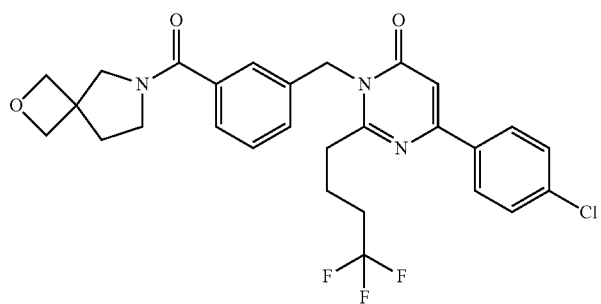 [SMILES: O=C(c1cccc(Cn2c(CCCC(F)(F)F)nc(-c3ccc(Cl)cc3)cc2=O)c1)N1CCC2(COC2)C1]
I-0196
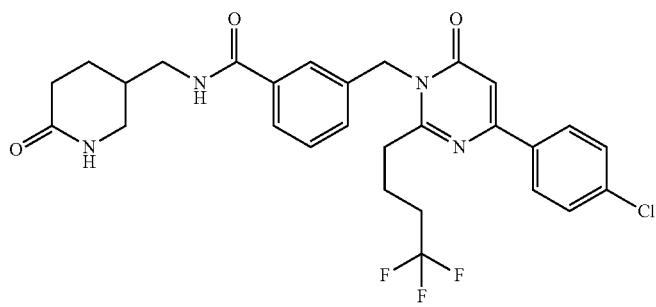 [SMILES: O=C1CCC(CNC(=O)c2cccc(Cn3c(CCCC(F)(F)F)nc(-c4ccc(Cl)cc4)cc3=O)c2)CN1]
I-0197
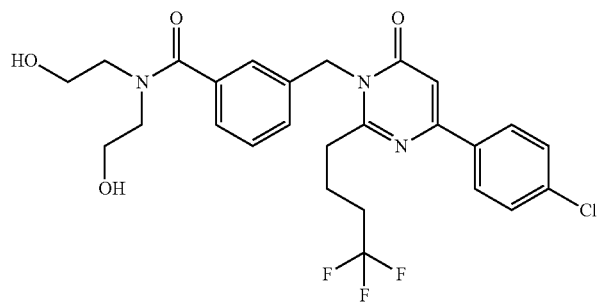 [SMILES: O=C(c1cccc(Cn2c(CCCC(F)(F)F)nc(-c3ccc(Cl)cc3)cc2=O)c1)N(CCO)CCO]
I-0198
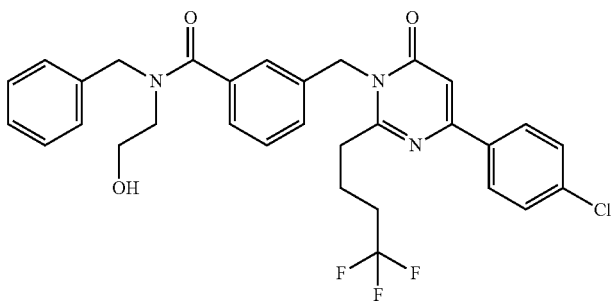 [SMILES: O=C(c1cccc(Cn2c(CCCC(F)(F)F)nc(-c3ccc(Cl)cc3)cc2=O)c1)N(CCO)Cc1ccccc1]

TABLE 34
I-0199 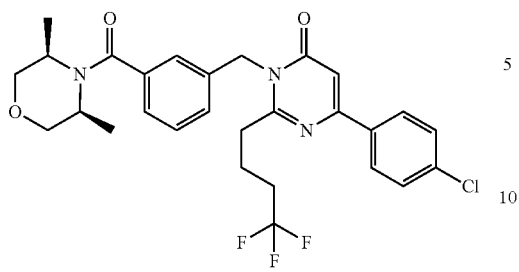
I-0200 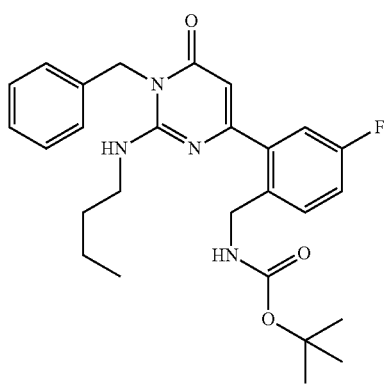 [SMILES: CCCCNc1nc(-c2cc(F)ccc2CNC(=O)OC(C)(C)C)cc(=O)n1Cc1ccccc1]
I-0201 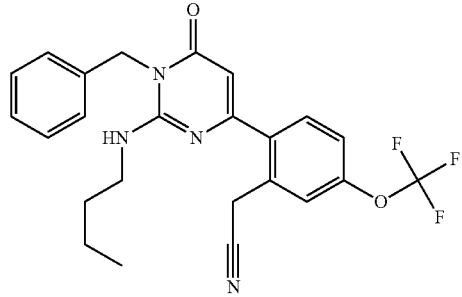 [SMILES: CCCCNc1nc(-c2ccc(OC(F)(F)F)cc2CC#N)cc(=O)n1Cc1ccccc1]
I-0202 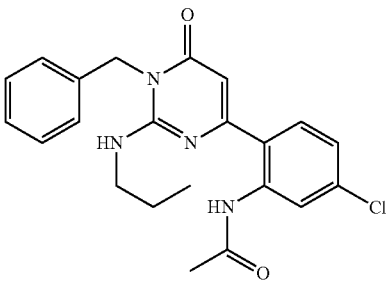 [SMILES: CCCNc1nc(-c2ccc(Cl)cc2NC(C)=O)cc(=O)n1Cc1ccccc1]
I-0203 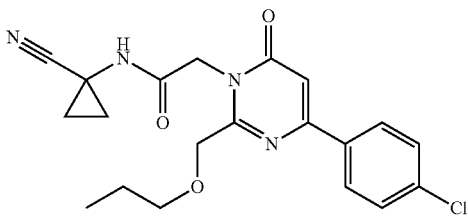 [SMILES: CCCOCc1nc(-c2ccc(Cl)cc2)cc(=O)n1CC(=O)NC1(C#N)CC1]
TABLE 34-continued
I-0204 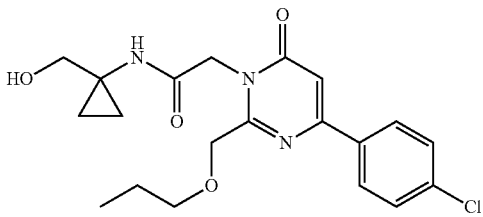 [SMILES: CCCOCc1nc(-c2ccc(Cl)cc2)cc(=O)n1CC(=O)NC1(CO)CC1]
TABLE 35
I-0205 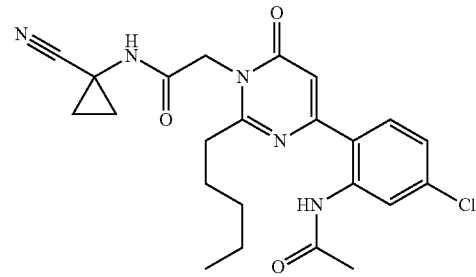 [SMILES: CCCCCc1nc(-c2ccc(Cl)cc2NC(C)=O)cc(=O)n1CC(=O)NC1(C#N)CC1]
I-0206 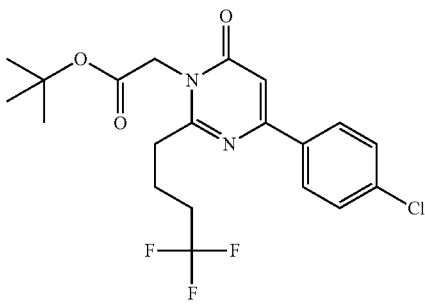 [SMILES: CC(C)(C)OC(=O)Cn1c(CCCC(F)(F)F)nc(-c2ccc(Cl)cc2)cc1=O]
I-0207 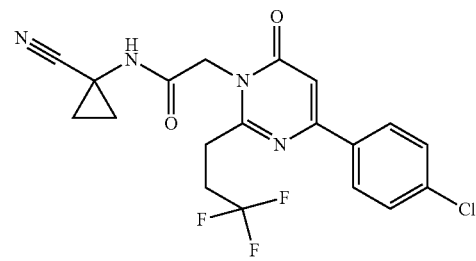 [SMILES: N#CC1(NC(=O)Cn2c(CCC(F)(F)F)nc(-c3ccc(Cl)cc3)cc2=O)CC1]
I-0208 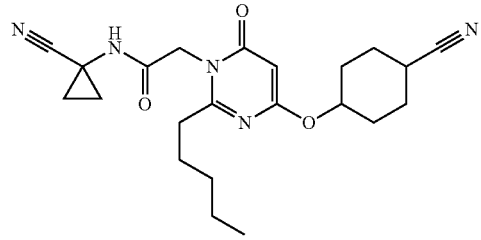 [SMILES: CCCCCc1nc(OC2CCC(C#N)CC2)cc(=O)n1CC(=O)NC1(C#N)CC1]
I-0209 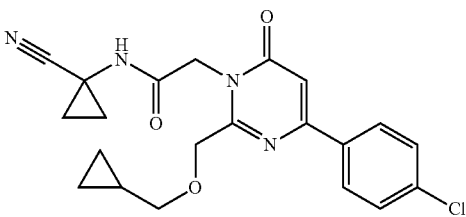 [SMILES: N#CC1(NC(=O)Cn2c(COCC3CC3)nc(-c3ccc(Cl)cc3)cc2=O)CC1]

TABLE 35-continued
I-0210 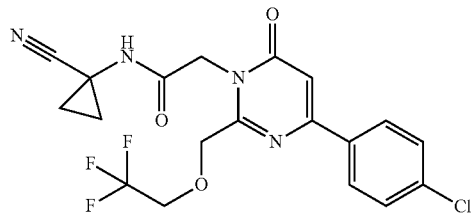 [SMILES: N#CC1(NC(=O)Cn2c(COCC(F)(F)F)nc(-c3ccc(Cl)cc3)cc2=O)CC1]
TABLE 36
I-0211 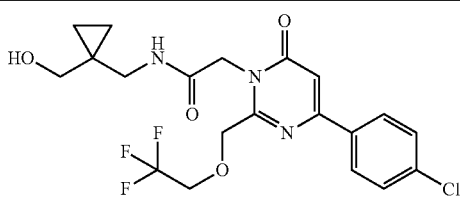
I-0212 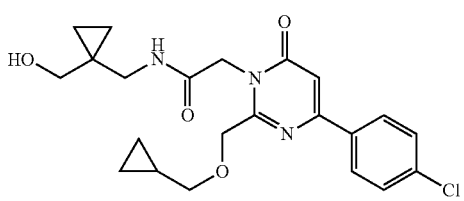 [SMILES: O=C(Cn1c(COCC2CC2)nc(-c2ccc(Cl)cc2)cc1=O)NCC1(CO)CC1]
I-0213 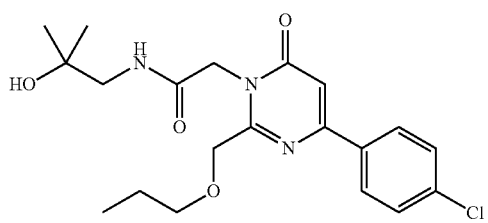
I-0214 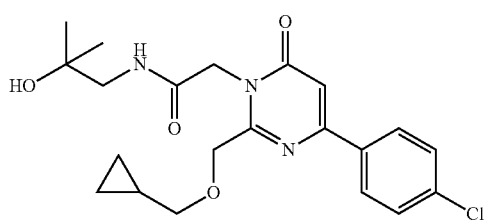 [SMILES: CC(C)(O)CNC(=O)Cn1c(COCC2CC2)nc(-c2ccc(Cl)cc2)cc1=O]
I-0215 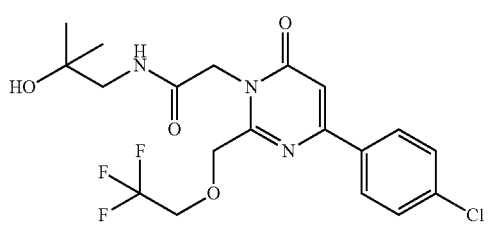 [SMILES: CC(C)(O)CNC(=O)Cn1c(COCC(F)(F)F)nc(-c2ccc(Cl)cc2)cc1=O]
I-0216 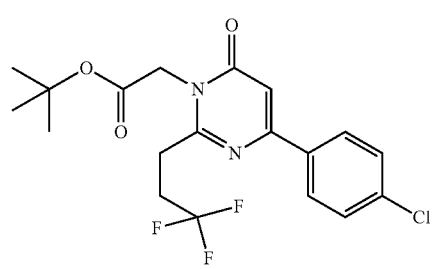 [SMILES: CC(C)(C)OC(=O)Cn1c(CCC(F)(F)F)nc(-c2ccc(Cl)cc2)cc1=O]
TABLE 37
I-0217 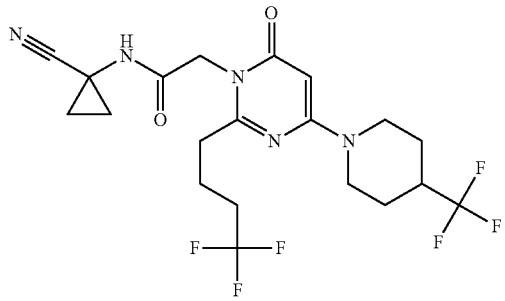 [SMILES: N#CC1(NC(=O)Cn2c(CCCC(F)(F)F)nc(N3CCC(C(F)(F)F)CC3)cc2=O)CC1]
I-0218 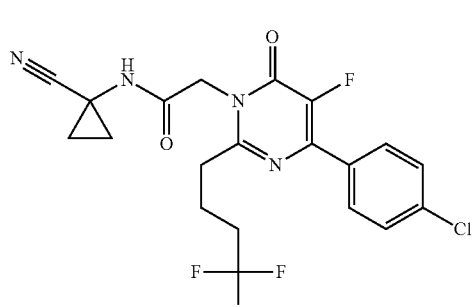
I-0219 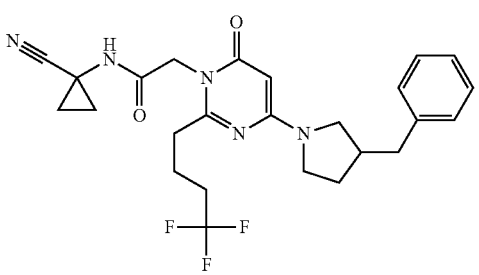 [SMILES: N#CC1(NC(=O)Cn2c(CCCC(F)(F)F)nc(N3CCC(Cc4ccccc4)C3)cc2=O)CC1]
I-0220 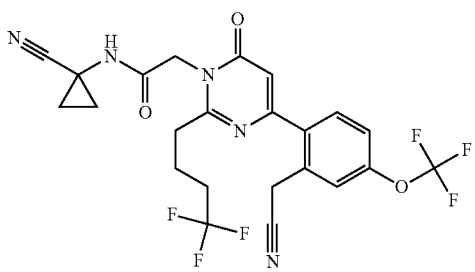 [SMILES: N#CCc1cc(OC(F)(F)F)ccc1-c1cc(=O)n(CC(=O)NC2(C#N)CC2)c(CCCC(F)(F)F)n1]
I-0221 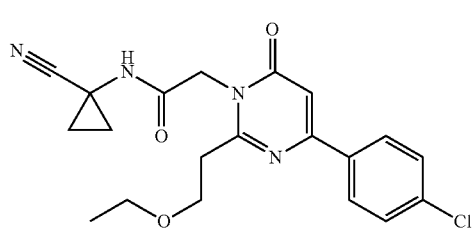 [SMILES: CCOCCc1nc(-c2ccc(Cl)cc2)cc(=O)n1CC(=O)NC1(C#N)CC1]
I-0222 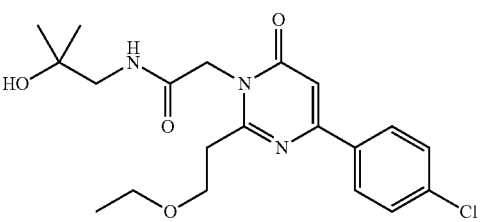 [SMILES: CCOCCc1nc(-c2ccc(Cl)cc2)cc(=O)n1CC(=O)NCC(C)(C)O]

TABLE 38
I-0223 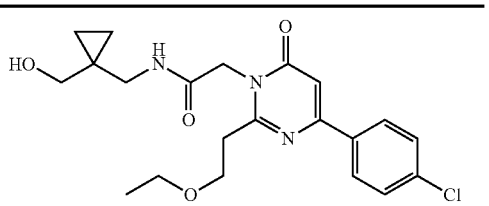
I-0224 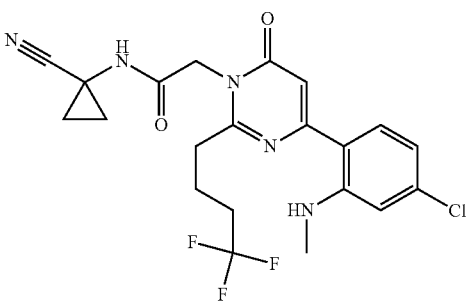 [SMILES: CNc1cc(Cl)ccc1-c1cc(=O)n(CC(=O)NC2(C#N)CC2)c(CCCC(F)(F)F)n1]
I-0225 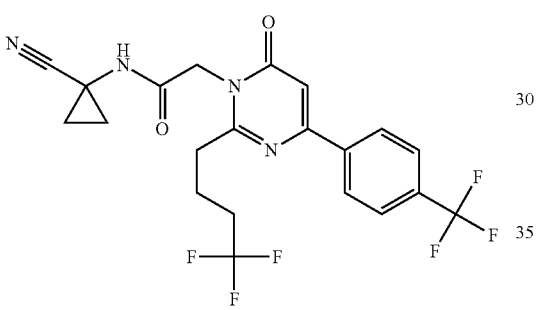
I-0226 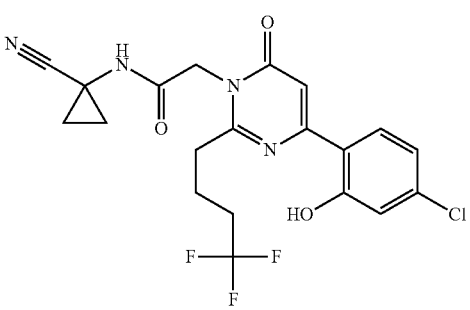 [SMILES: N#CC1(NC(=O)Cn2c(CCCC(F)(F)F)nc(-c3ccc(Cl)cc3O)cc2=O)CC1]
I-0227 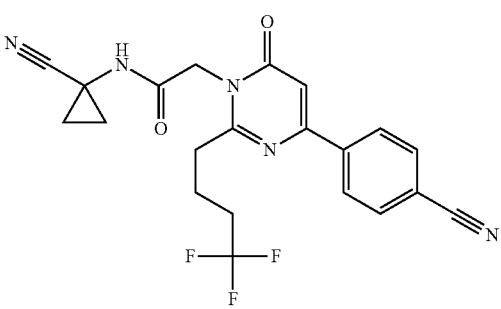 [SMILES: N#Cc1ccc(-c2cc(=O)n(CC(=O)NC3(C#N)CC3)c(CCCC(F)(F)F)n2)cc1]
TABLE 38-continued
I-0228 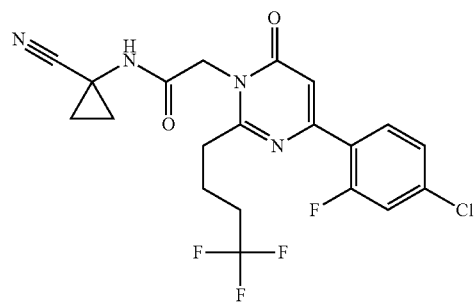
TABLE 39
I-0229 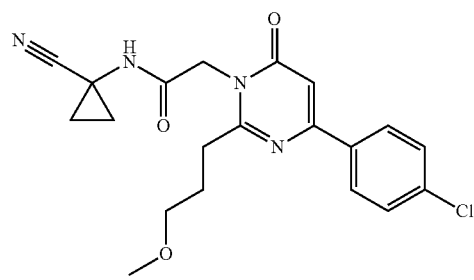 [SMILES: COCCCc1nc(-c2ccc(Cl)cc2)cc(=O)n1CC(=O)NC1(C#N)CC1]
I-0230 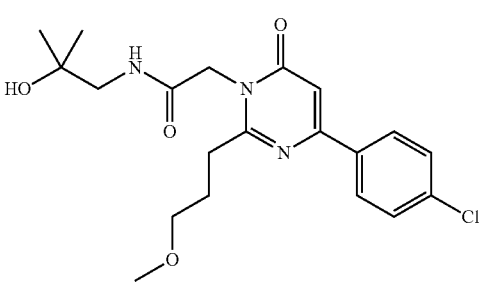 [SMILES: COCCCc1nc(-c2ccc(Cl)cc2)cc(=O)n1CC(=O)NCC(C)(C)O]
I-0231 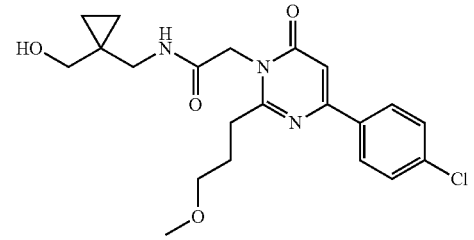 [SMILES: COCCCc1nc(-c2ccc(Cl)cc2)cc(=O)n1CC(=O)NCC1(CO)CC1]
I-0232 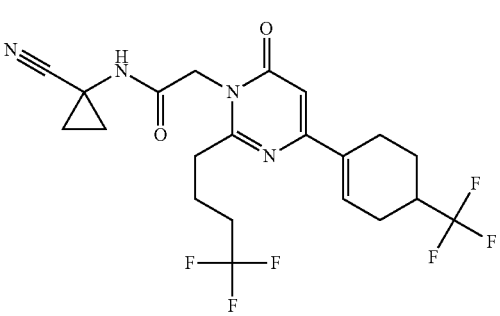 [SMILES: N#CC1(NC(=O)Cn2c(CCCC(F)(F)F)nc(C3=CCC(C(F)(F)F)CC3)cc2=O)CC1]

TABLE 39-continued
I-0233 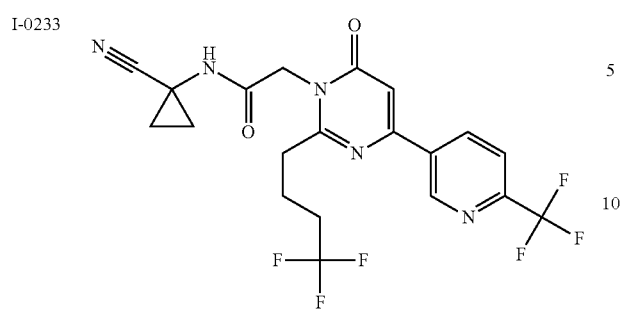
I-0234 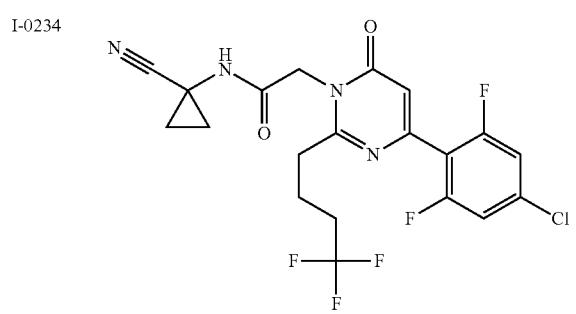
TABLE 40
I-0235 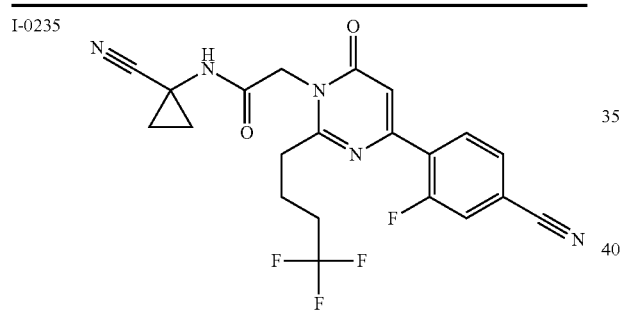
I-0236 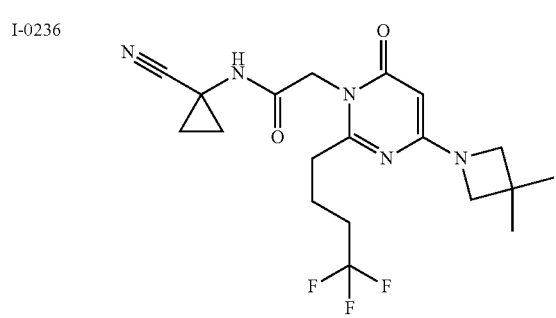
I-0237 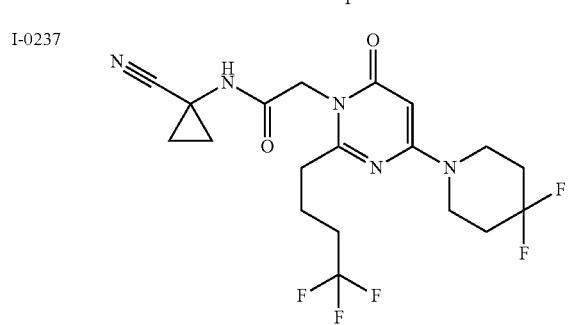
TABLE 40-continued
I-0238 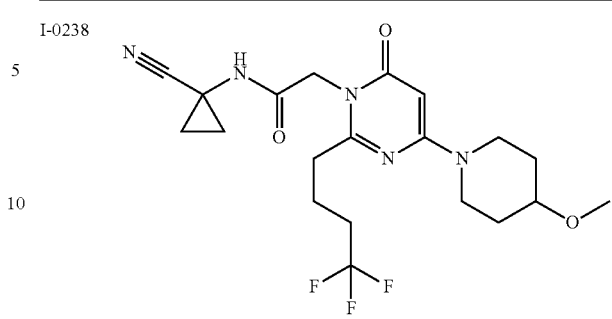
I-0239 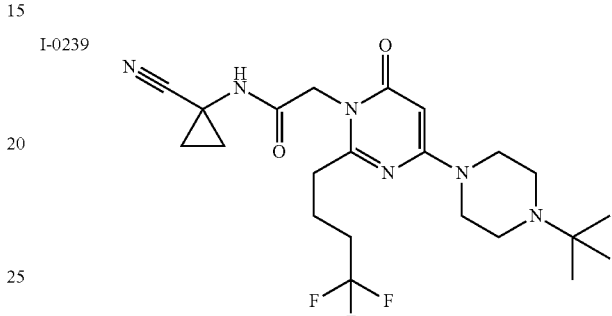
I-0240 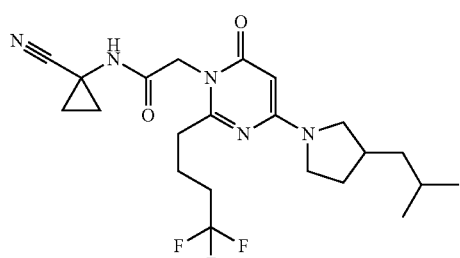
TABLE 41
I-0241 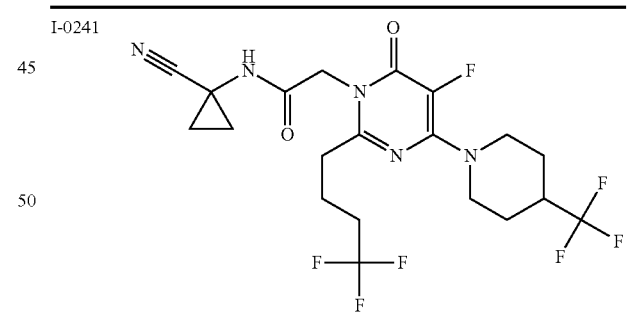
I-0242 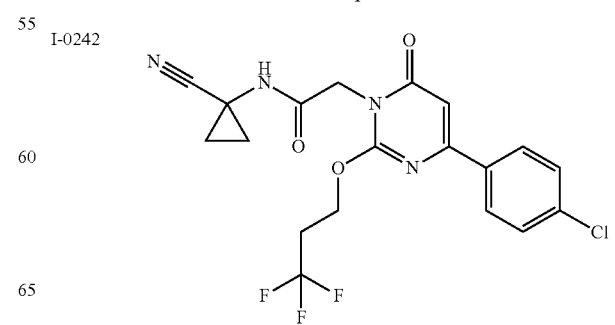

TABLE 41-continued
I-0243
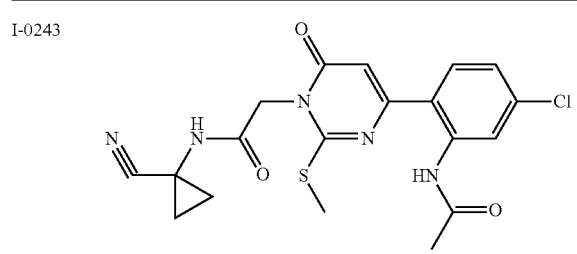
I-0244
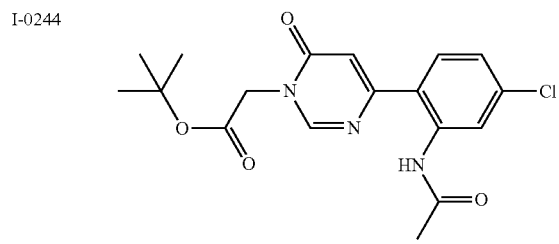
I-0245
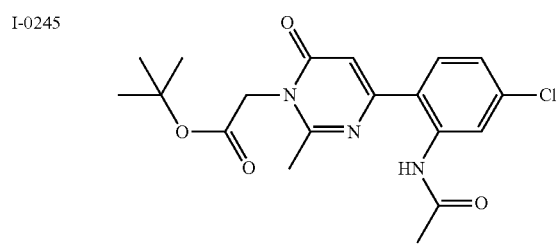
I-0246
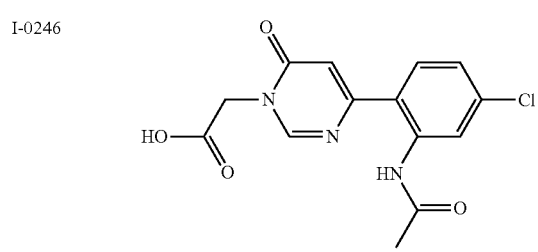
TABLE 42
1-0247
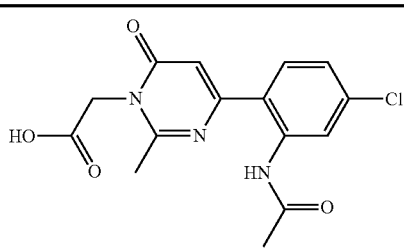
1-0248
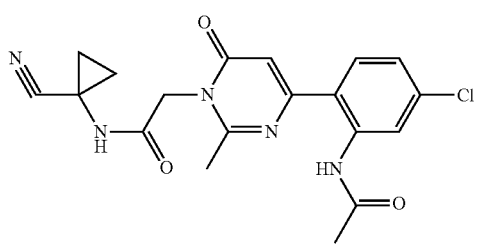 [SMILES: CC(=O)Nc1cc(Cl)ccc1-c1cc(=O)n(CC(=O)NC2(C#N)CC2)c(C)n1]
TABLE 42-continued
1-0249
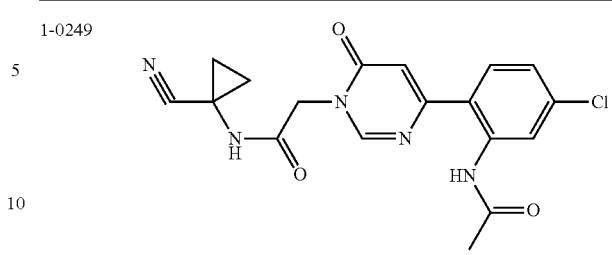
1-0250
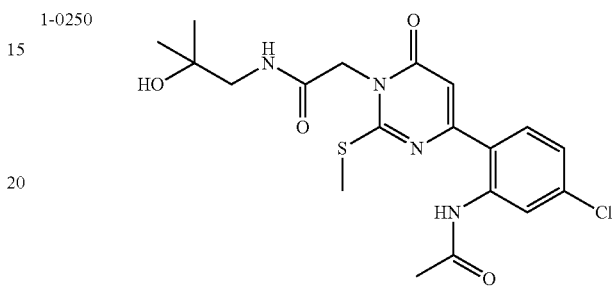
1-0251
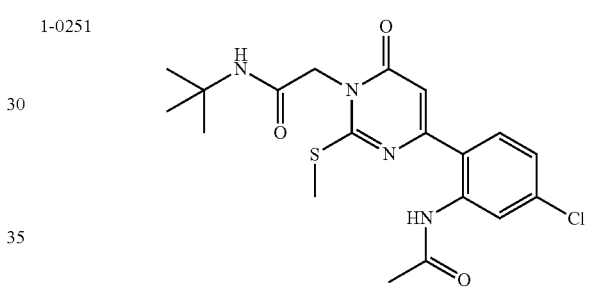
1-0252
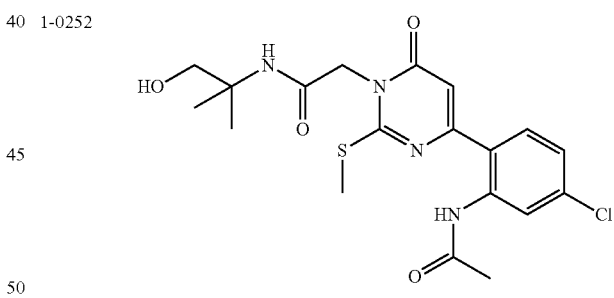
TABLE 43
I-0253
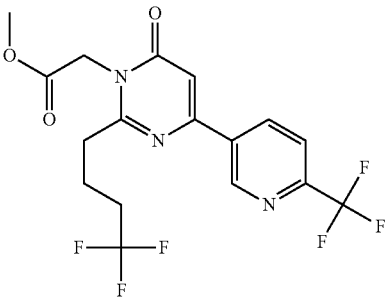 [SMILES: COC(=O)Cn1c(CCCC(F)(F)F)nc(-c2ccc(C(F)(F)F)nc2)cc1=O]

TABLE 43-continued
I-0254 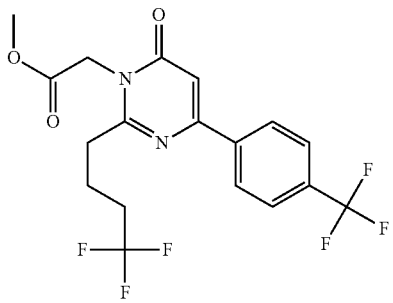 [SMILES: COC(=O)Cn1c(CCCC(F)(F)F)nc(-c2ccc(C(F)(F)F)cc2)cc1=O]
I-0255 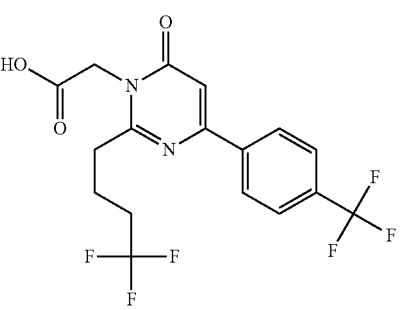 [SMILES: O=C(O)Cn1c(CCCC(F)(F)F)nc(-c2ccc(C(F)(F)F)cc2)cc1=O]
I-0256 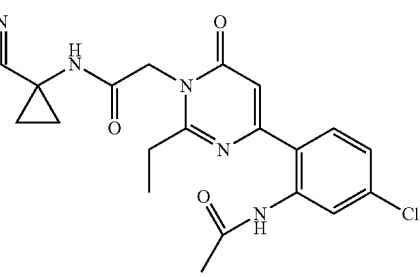
I-0257 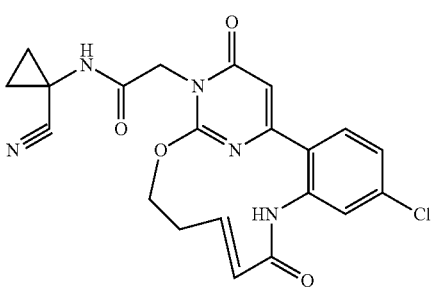 [SMILES: N#CC1(NC(=O)Cn2c3nc(cc2=O)-c2ccc(Cl)cc2NC(=O)/C=C/CCO3)CC1]
TABLE 44
I-0258 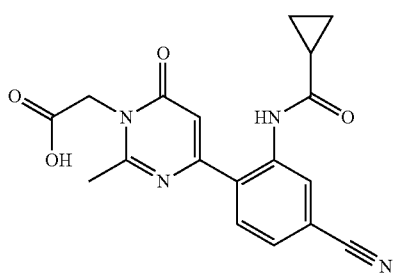 [SMILES: Cc1nc(-c2ccc(C#N)cc2NC(=O)C2CC2)cc(=O)n1CC(=O)O]
TABLE 44-continued
I-0259 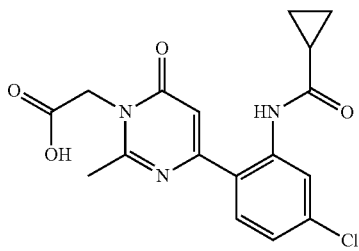 [SMILES: Cc1nc(-c2ccc(Cl)cc2NC(=O)C2CC2)cc(=O)n1CC(=O)O]
I-0260 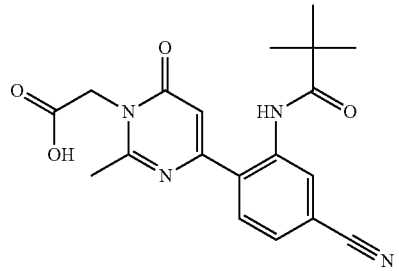 [SMILES: Cc1nc(-c2ccc(C#N)cc2NC(=O)C(C)(C)C)cc(=O)n1CC(=O)O]
I-0261 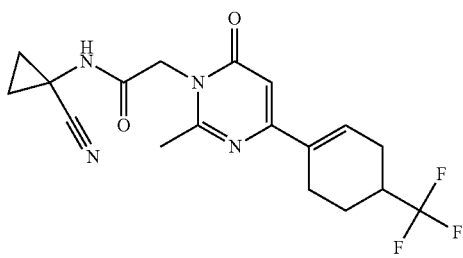 [SMILES: Cc1nc(C2=CCC(C(F)(F)F)CC2)cc(=O)n1CC(=O)NC1(C#N)CC1]
I-0262 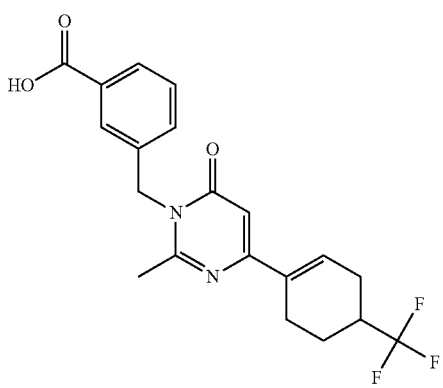 [SMILES: Cc1nc(C2=CCC(C(F)(F)F)CC2)cc(=O)n1Cc1cccc(C(=O)O)c1]
I-0263 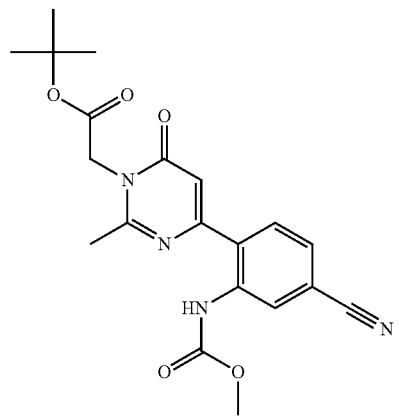 [SMILES: COC(=O)Nc1cc(C#N)ccc1-c1cc(=O)n(CC(=O)OC(C)(C)C)c(C)n1]

TABLE 45
I-0264 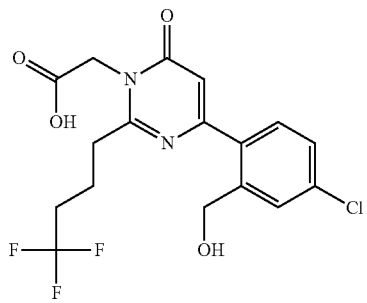 [SMILES: O=C(O)Cn1c(CCCC(F)(F)F)nc(-c2ccc(Cl)cc2CO)cc1=O]
I-0265 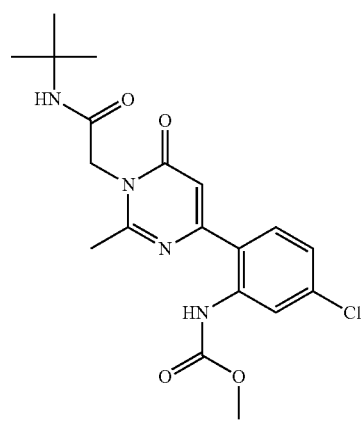
I-0266 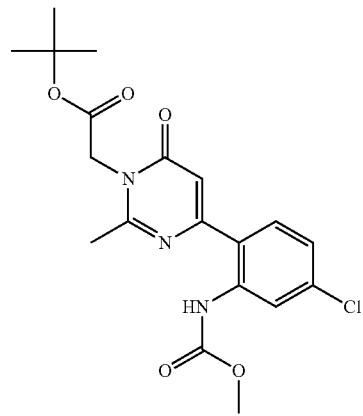 [SMILES: COC(=O)Nc1cc(Cl)ccc1-c1cc(=O)n(CC(=O)OC(C)(C)C)c(C)n1]
I-0267 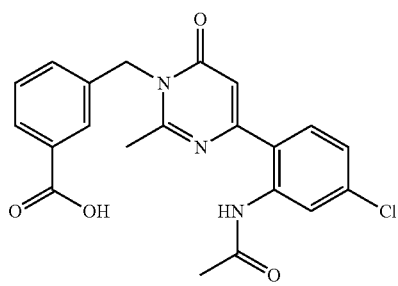 [SMILES: CC(=O)Nc1cc(Cl)ccc1-c1cc(=O)n(Cc2cccc(C(=O)O)c2)c(C)n1]
TABLE 45-continued
I-0268 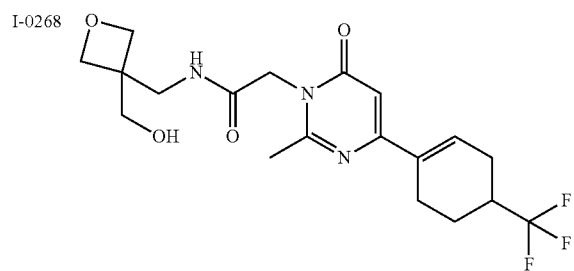
I-0269 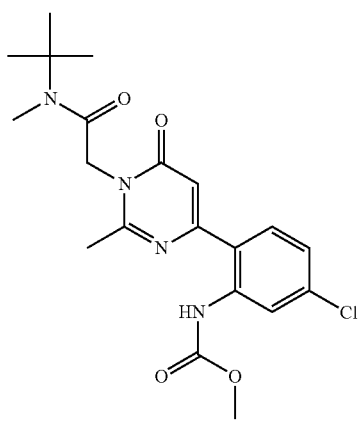 [SMILES: COC(=O)Nc1cc(Cl)ccc1-c1cc(=O)n(CC(=O)N(C)C(C)(C)C)c(C)n1]
TABLE 46
I-0270 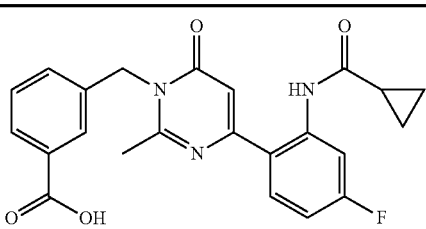
I-0271 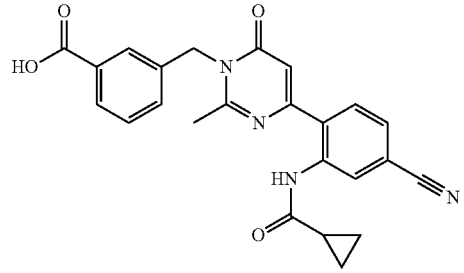 [SMILES: Cc1nc(-c2ccc(C#N)cc2NC(=O)C2CC2)cc(=O)n1Cc1cccc(C(=O)O)c1]
I-0272 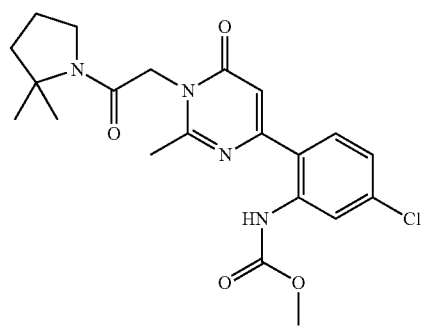 [SMILES: COC(=O)Nc1cc(Cl)ccc1-c1cc(=O)n(CC(=O)N2CCCC2(C)C)c(C)n1]

TABLE 46-continued
I-0273 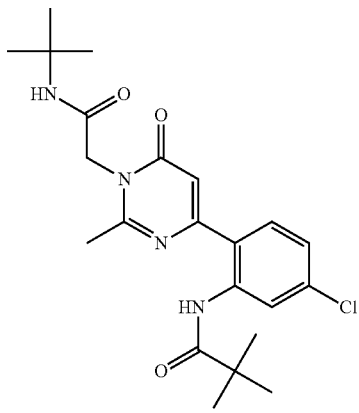 [SMILES: Cc1nc(-c2ccc(Cl)cc2NC(=O)C(C)(C)C)cc(=O)n1CC(=O)NC(C)(C)C]
I-0274 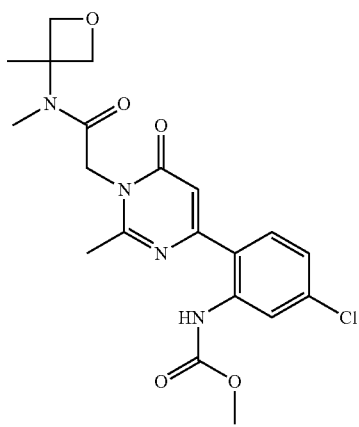 [SMILES: COC(=O)Nc1cc(Cl)ccc1-c1cc(=O)n(CC(=O)N(C)C2(C)COC2)c(C)n1]
I-0275 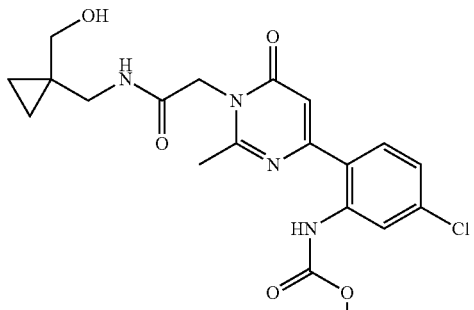
TABLE 47
I-0276 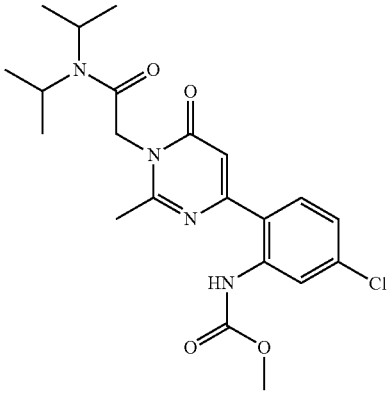 [SMILES: COC(=O)Nc1cc(Cl)ccc1-c1cc(=O)n(CC(=O)N(C(C)C)C(C)C)c(C)n1]
TABLE 47-continued
I-0277 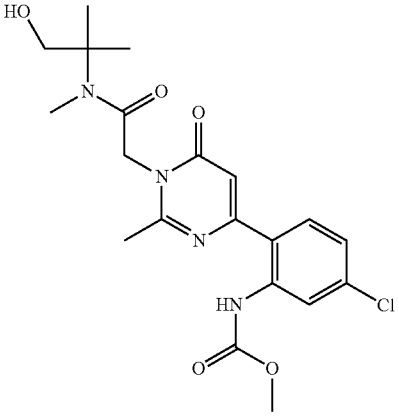 [SMILES: COC(=O)Nc1cc(Cl)ccc1-c1cc(=O)n(CC(=O)N(C)C(C)(C)CO)c(C)n1]
I-0278 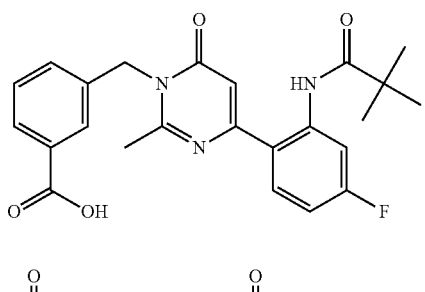
I-0279 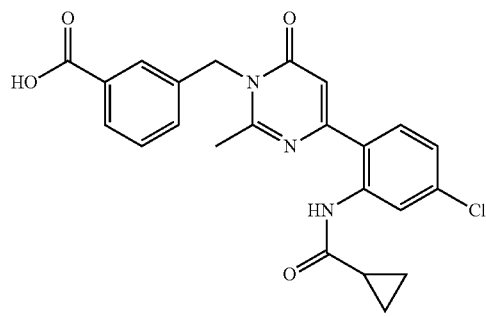 [SMILES: Cc1nc(-c2ccc(Cl)cc2NC(=O)C2CC2)cc(=O)n1Cc1cccc(C(=O)O)c1]
I-0280 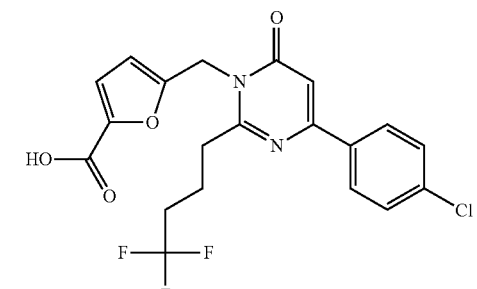
I-0281 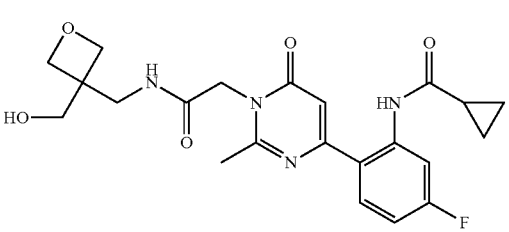 [SMILES: Cc1nc(-c2ccc(F)cc2NC(=O)C2CC2)cc(=O)n1CC(=O)NCC1(CO)COC1]

TABLE 48
I-0282 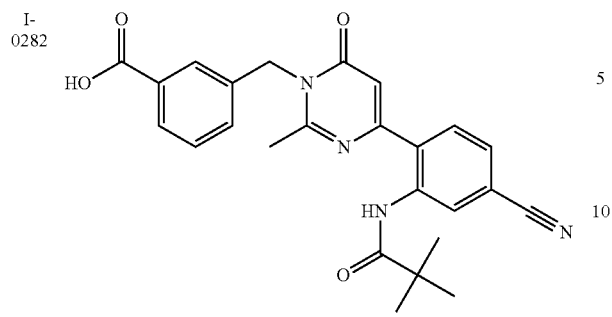
I-0283 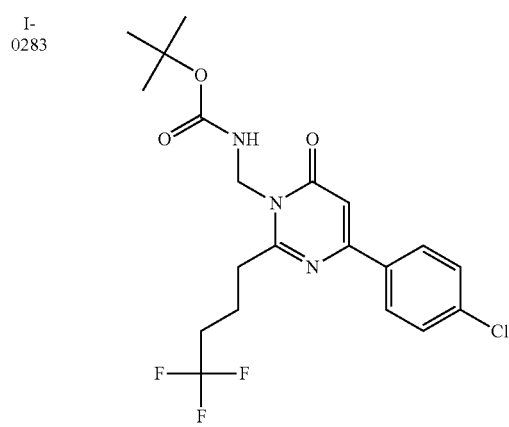
I-0284 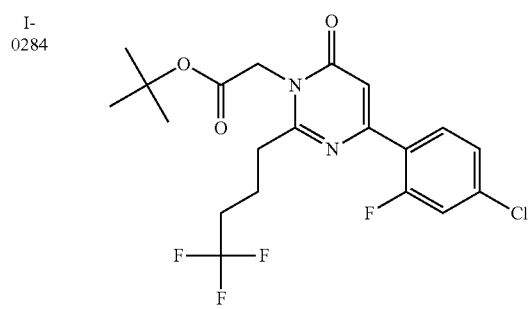
I-0285 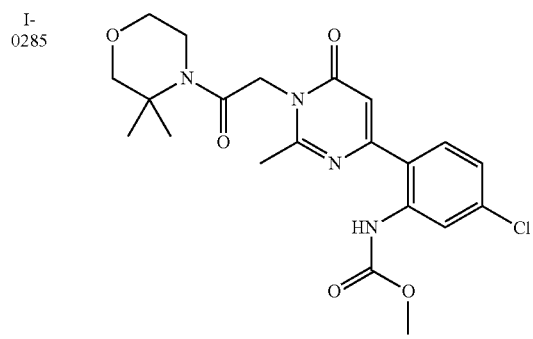
TABLE 48-continued
I-0286 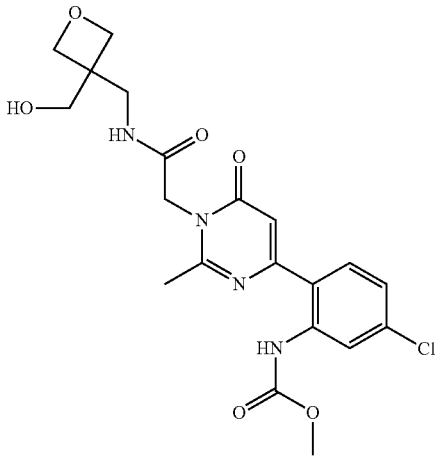 [SMILES: COC(=O)Nc1cc(Cl)ccc1-c1cc(=O)n(CC(=O)NCC2(CO)COC2)c(C)n1]
TABLE 49
I-0287 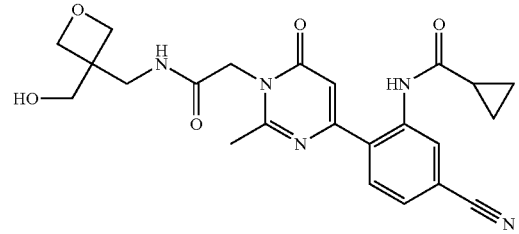 [SMILES: Cc1nc(-c2ccc(C#N)cc2NC(=O)C2CC2)cc(=O)n1CC(=O)NCC1(CO)COC1]
I-0288 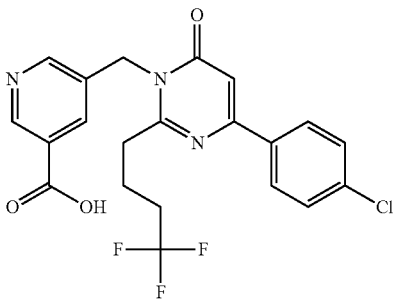 [SMILES: O=C(O)c1cncc(Cn2c(CCCC(F)(F)F)nc(-c3ccc(Cl)cc3)cc2=O)c1]
I-0289 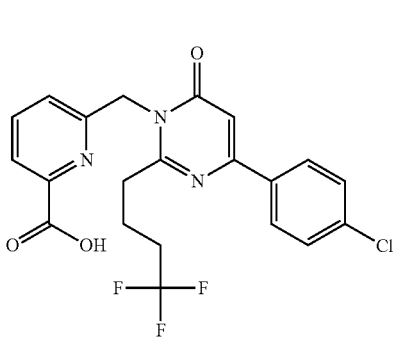 [SMILES: O=C(O)c1cccc(Cn2c(CCCC(F)(F)F)nc(-c3ccc(Cl)cc3)cc2=O)n1]

TABLE 49-continued
I-0290 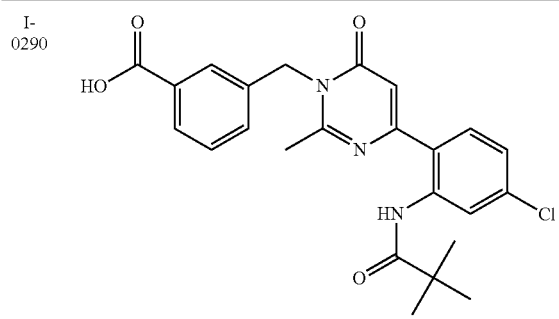
I-0291 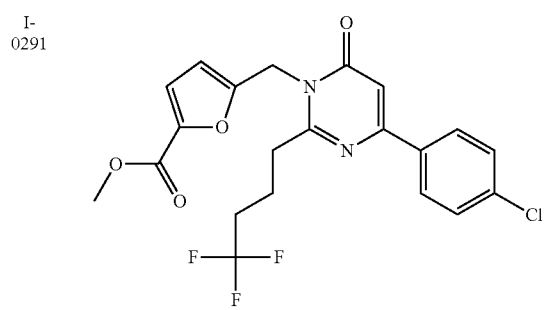
I-0292 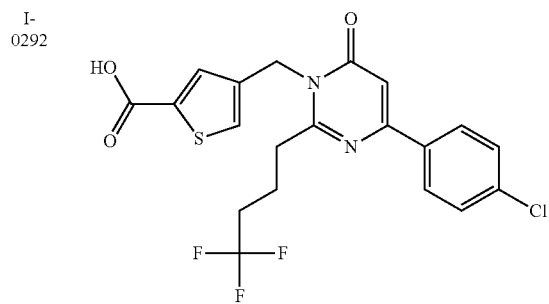
TABLE 50
I-0293 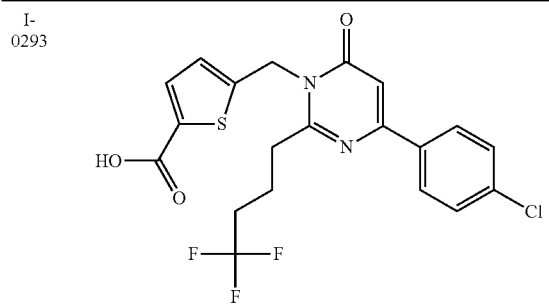
I-0294 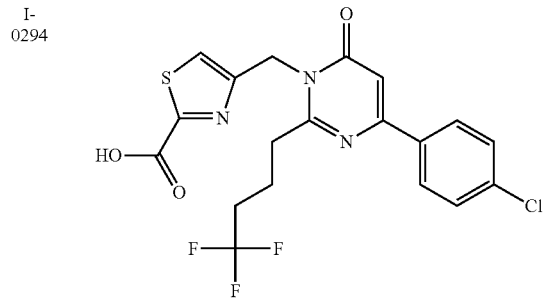
TABLE 50-continued
I-0295 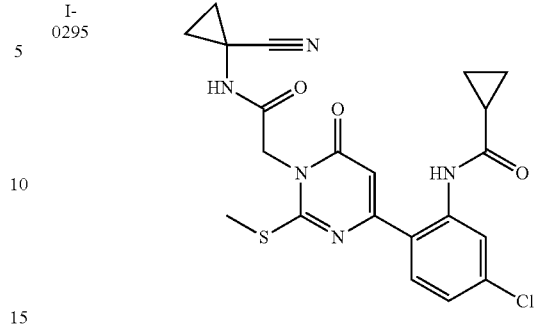
I-0296 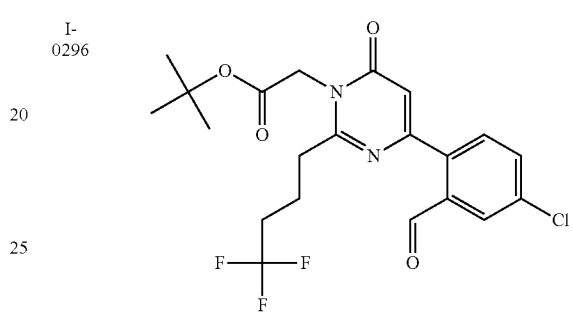
I-0297 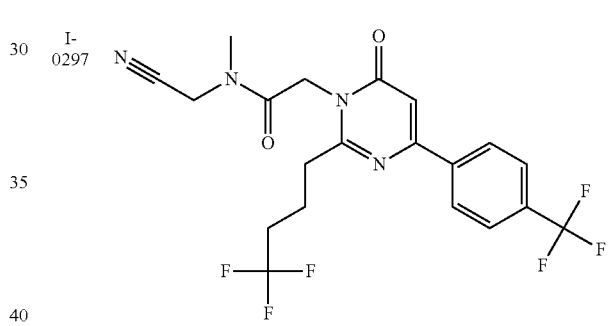
I-0298 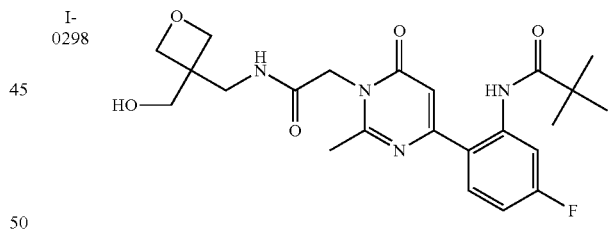
TABLE 51
I-0299 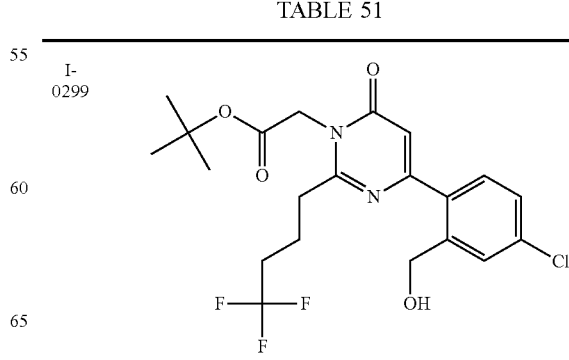

TABLE 51-continued
I-0300 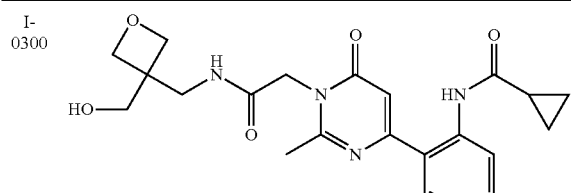
I-0301 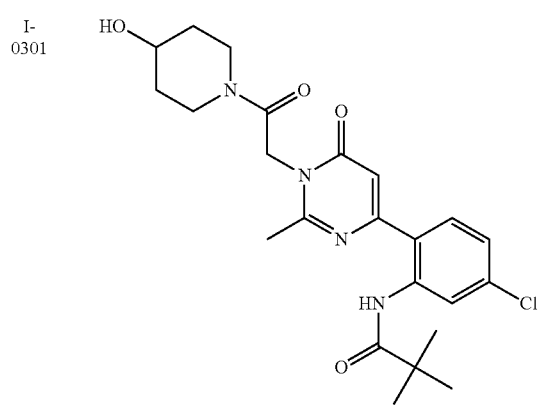
I-0302 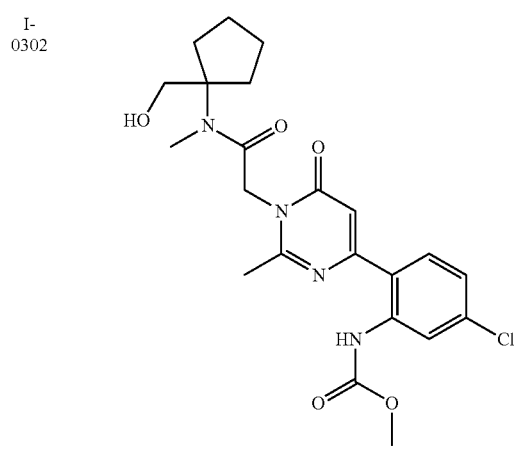
I-0303 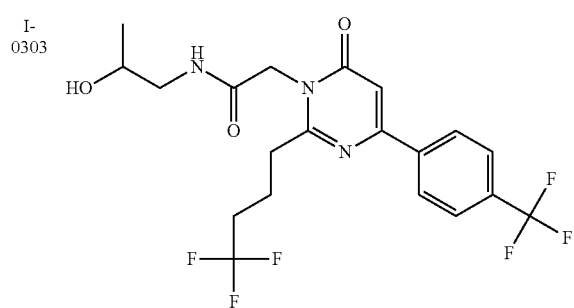
TABLE 51-continued
I-0304 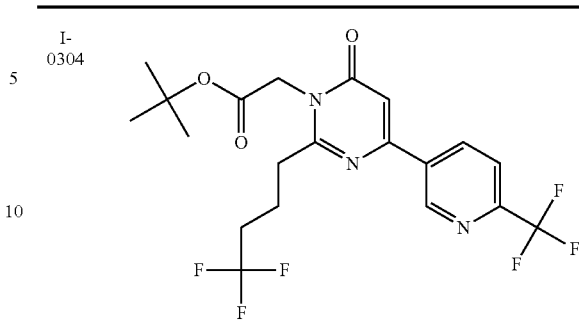
TABLE 52
I-0305 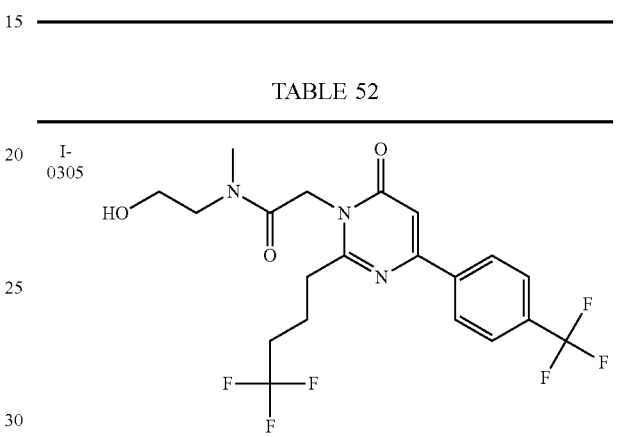
I-0306 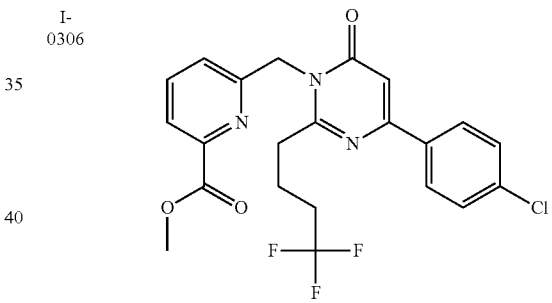
I-0307 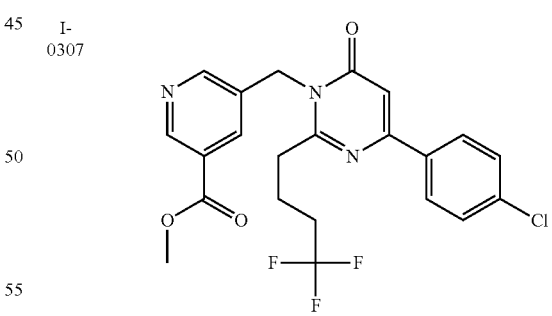
I-0308 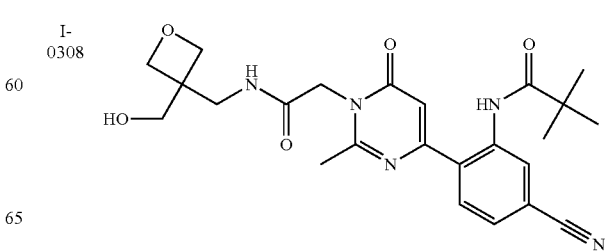

TABLE 52-continued
I-0309
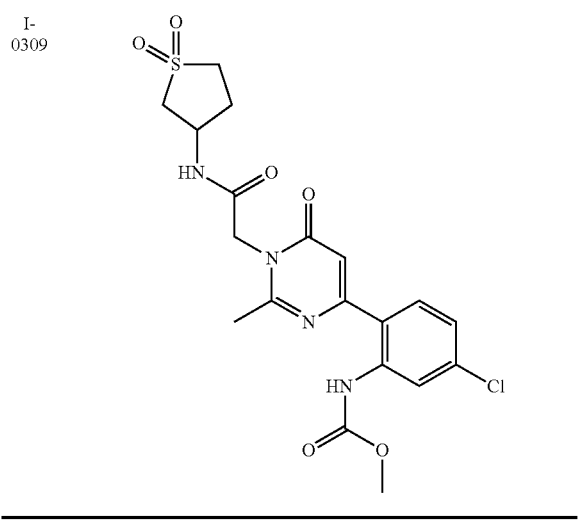
TABLE 53
I-0310
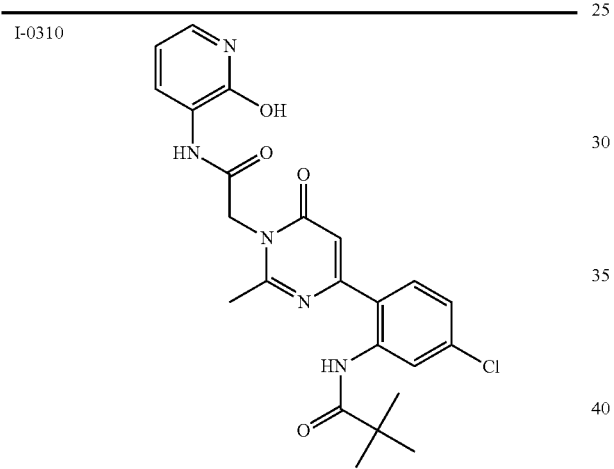
I-0311
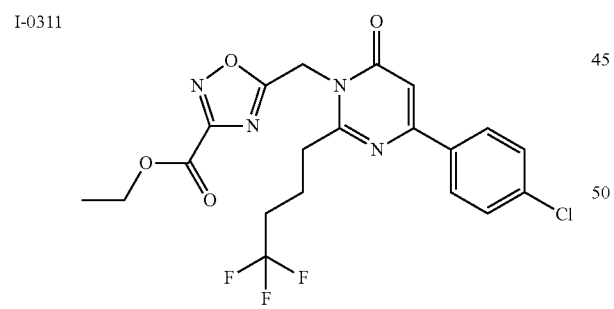
I-0312
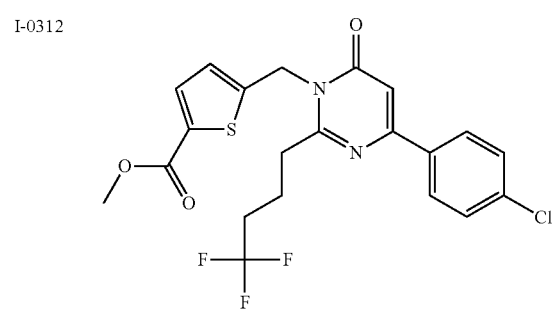
TABLE 53-continued
I-0313
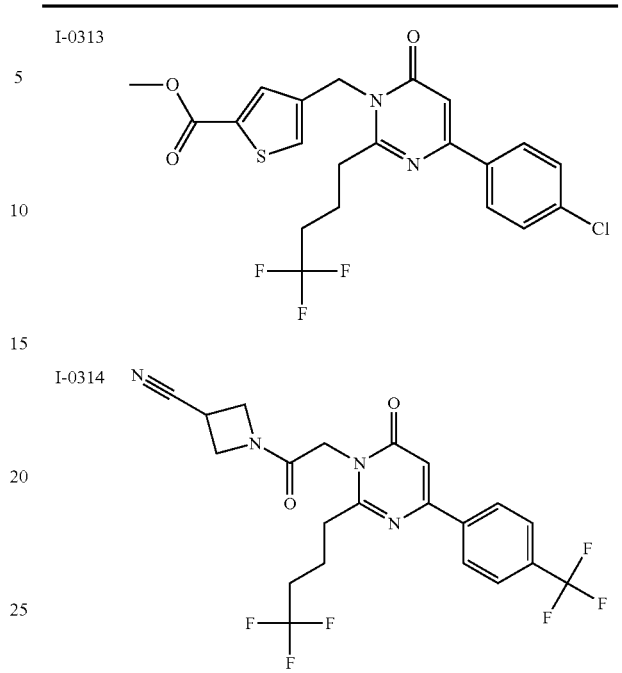
I-0314
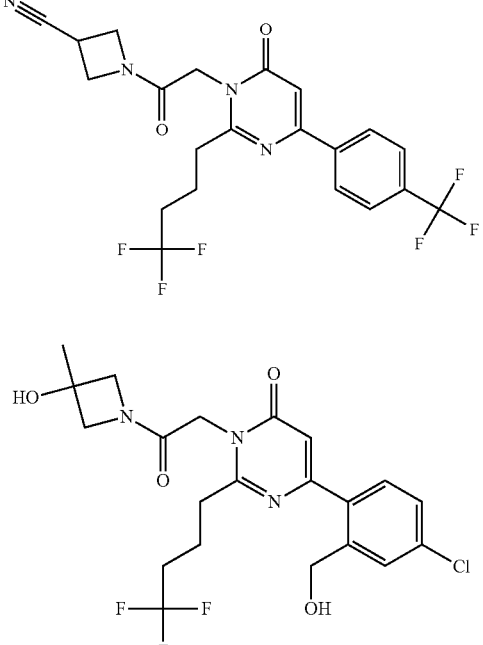
I-0315
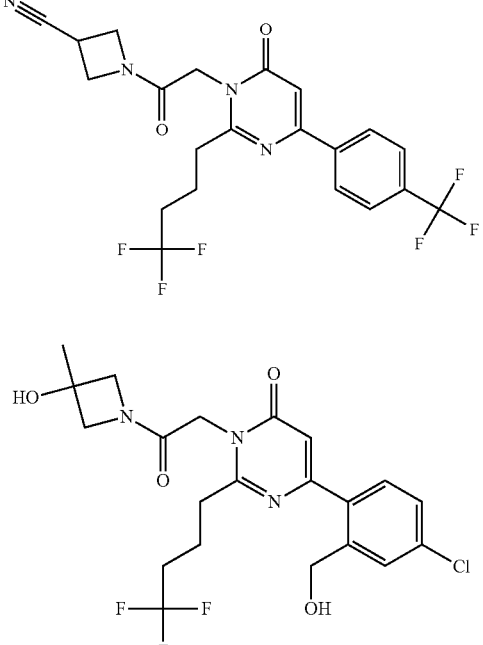
TABLE 54
I-0316
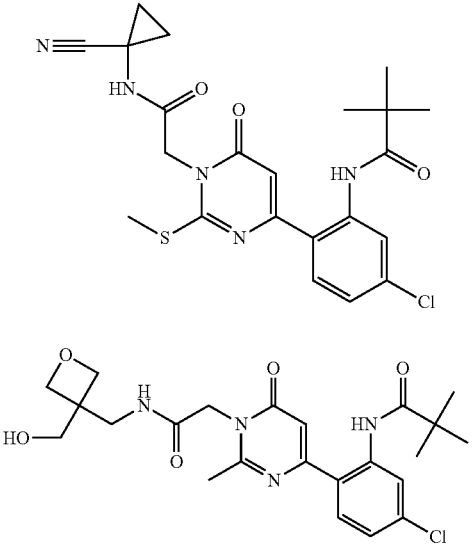
I-0317
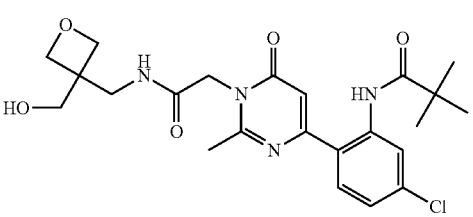 [SMILES: Cc1nc(-c2ccc(Cl)cc2NC(=O)C(C)(C)C)cc(=O)n1CC(=O)NCC1(CO)COC1]

TABLE 54-continued
I-0318 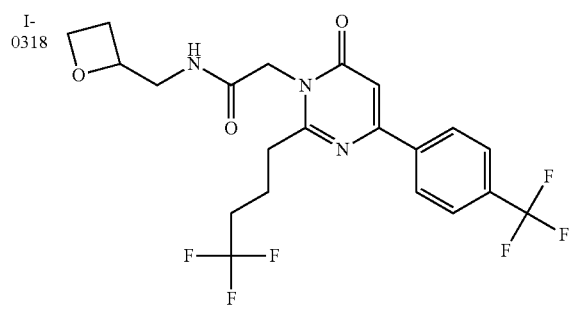
I-0319 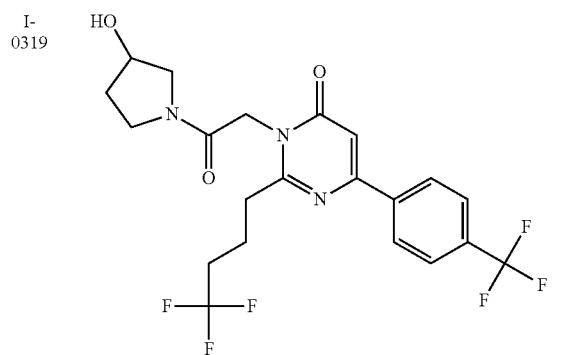
TABLE 54-continued
I-0320 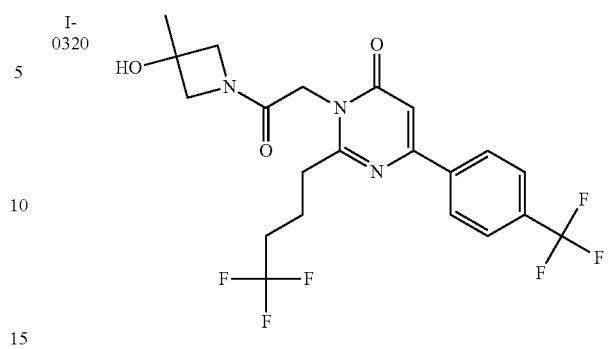
I-0321 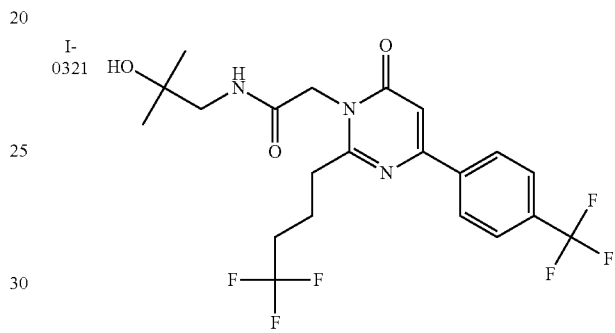
TABLE 55
I-0322 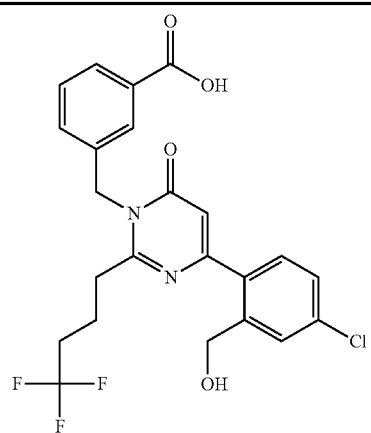
I-0323 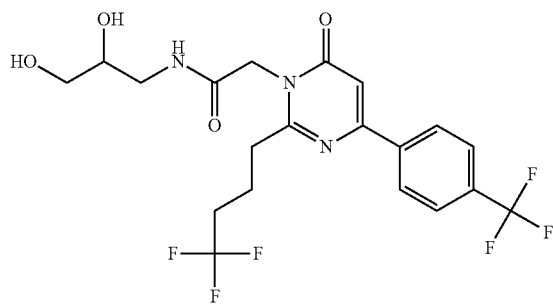 [SMILES: O=C(Cn1c(CCCC(F)(F)F)nc(-c2ccc(C(F)(F)F)cc2)cc1=O)NCC(O)CO]

TABLE 55-continued
I-0324
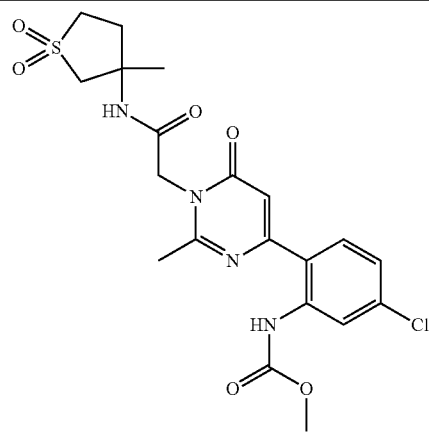
I-0325
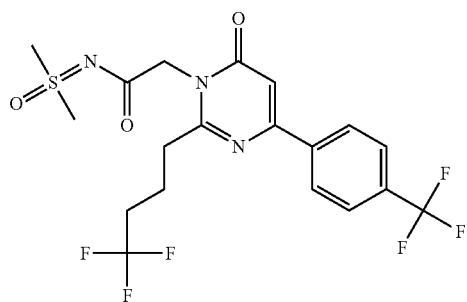 [SMILES: CS(C)(=O)=NC(=O)Cn1c(CCCC(F)(F)F)nc(-c2ccc(C(F)(F)F)cc2)cc1=O]
I-0326
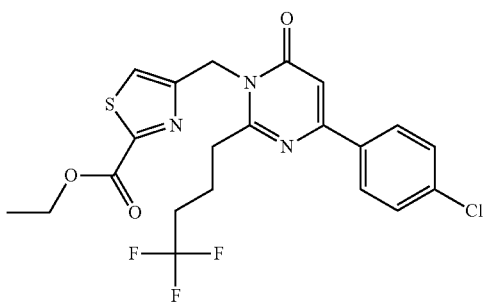 [SMILES: CCOC(=O)c1nc(Cn2c(CCCC(F)(F)F)nc(-c3ccc(Cl)cc3)cc2=O)cs1]
TABLE 56
I-0327
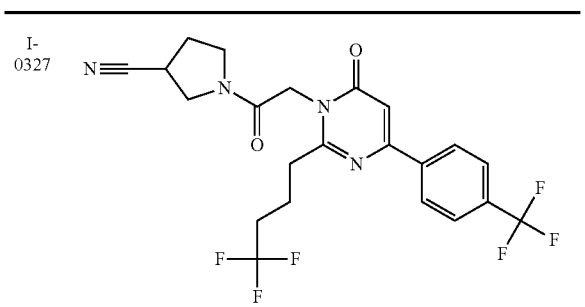
TABLE 56-continued
I-0328
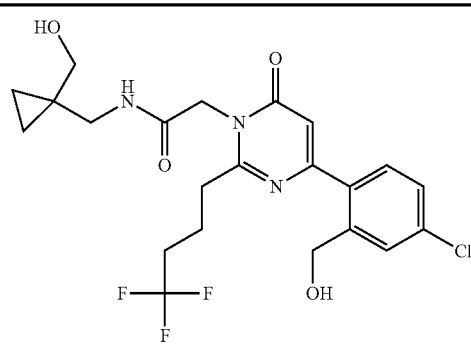

TABLE 56-continued
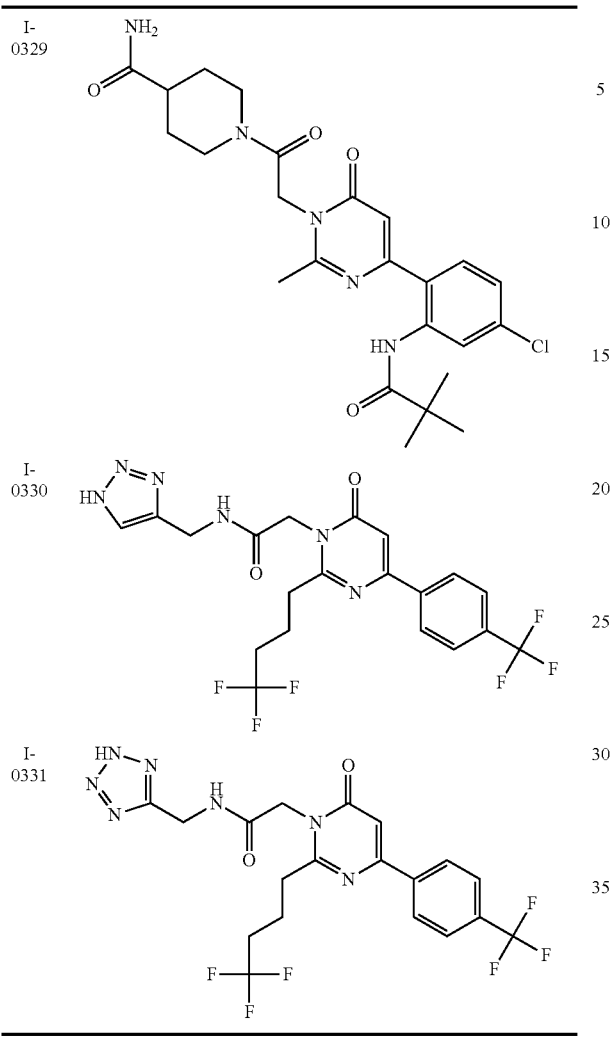
TABLE 57
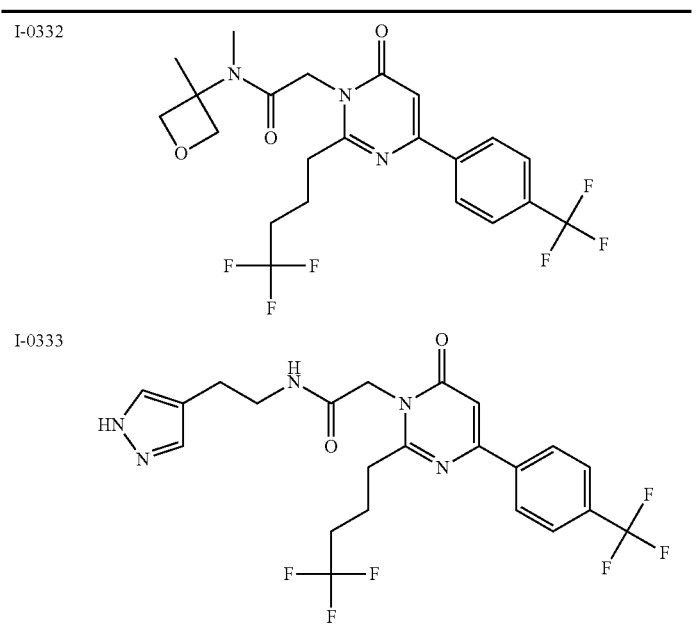

TABLE 57-continued
I-0334
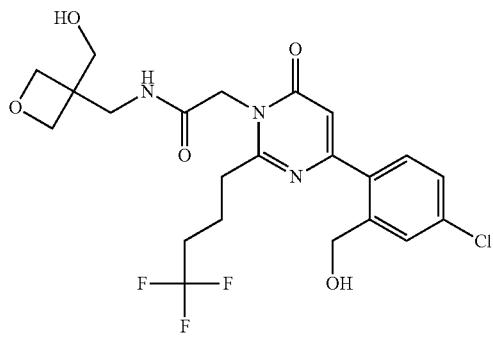 [SMILES: O=C(Cn1c(CCCC(F)(F)F)nc(-c2ccc(Cl)cc2CO)cc1=O)NCC1(CO)COC1]
I-0335
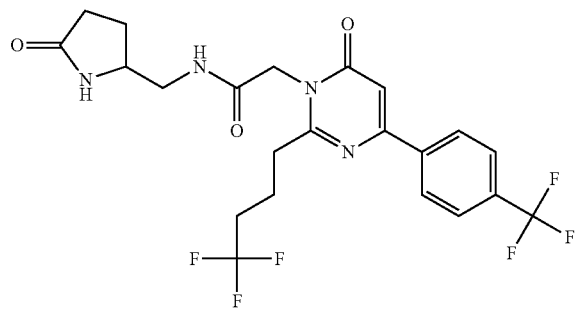 [SMILES: O=C(Cn1c(CCCC(F)(F)F)nc(-c2ccc(C(F)(F)F)cc2)cc1=O)NCC1CCC(=O)N1]
I-0336
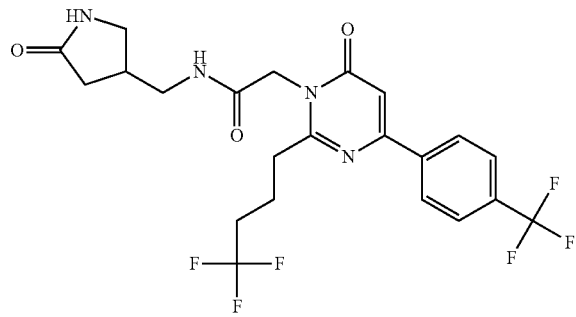 [SMILES: O=C1CC(CNC(=O)Cn2c(CCCC(F)(F)F)nc(-c3ccc(C(F)(F)F)cc3)cc2=O)CN1]
I-0337
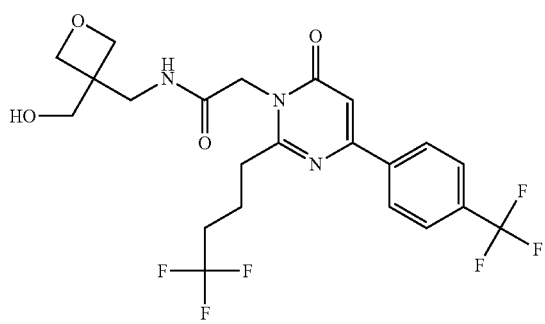 [SMILES: O=C(Cn1c(CCCC(F)(F)F)nc(-c2ccc(C(F)(F)F)cc2)cc1=O)NCC1(CO)COC1]

TABLE 58
I-0338
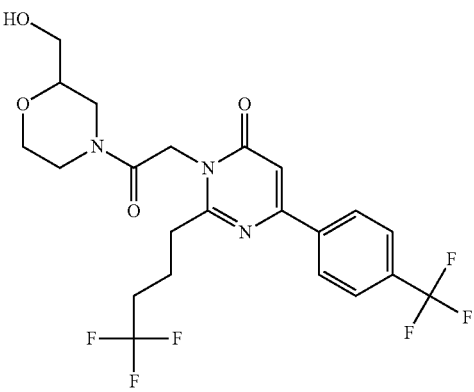 [SMILES: O=C(Cn1c(CCCC(F)(F)F)nc(-c2ccc(C(F)(F)F)cc2)cc1=O)N1CCOC(CO)C1]
I-0339
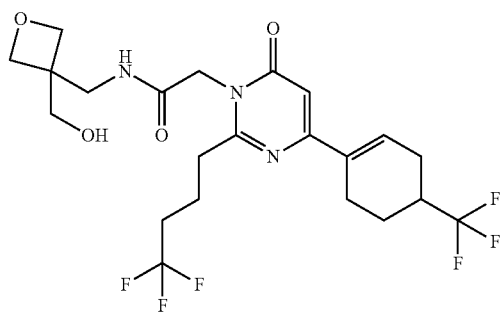 [SMILES: O=C(Cn1c(CCCC(F)(F)F)nc(C2=CCC(C(F)(F)F)CC2)cc1=O)NCC1(CO)COC1]
I-0340
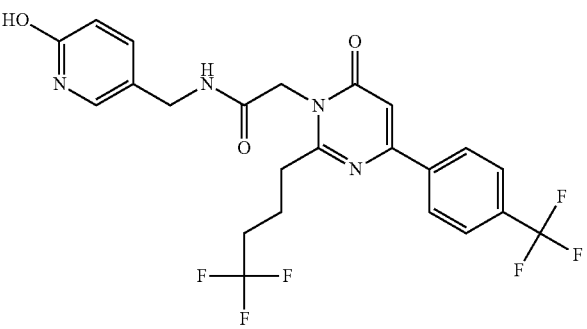 [SMILES: O=C(Cn1c(CCCC(F)(F)F)nc(-c2ccc(C(F)(F)F)cc2)cc1=O)NCc1ccc(O)nc1]
I-0341
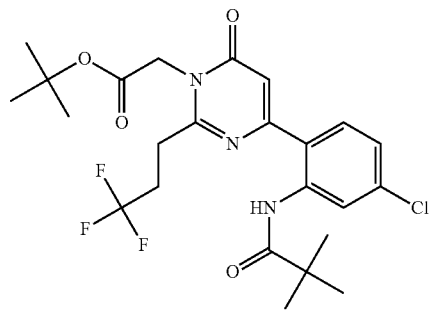 [SMILES: CC(C)(C)OC(=O)Cn1c(CCC(F)(F)F)nc(-c2ccc(Cl)cc2NC(=O)C(C)(C)C)cc1=O]

TABLE 58-continued
I-0342
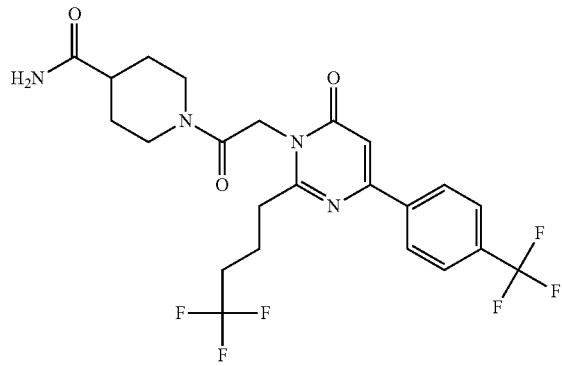 [SMILES: NC(=O)C1CCN(C(=O)Cn2c(CCCC(F)(F)F)nc(-c3ccc(C(F)(F)F)cc3)cc2=O)CC1]
TABLE 59
I-0343
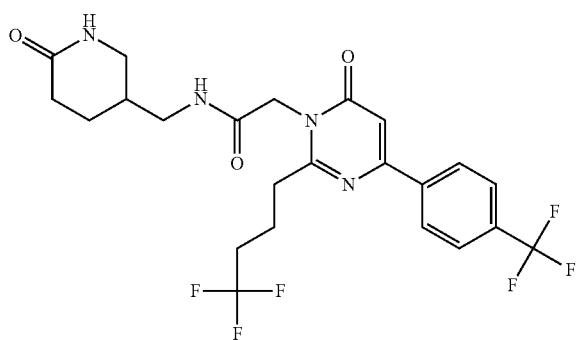 [SMILES: O=C1CCC(CNC(=O)Cn2c(CCCC(F)(F)F)nc(-c3ccc(C(F)(F)F)cc3)cc2=O)CN1]
I-0344
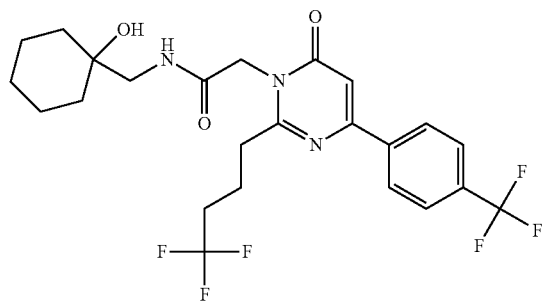 [SMILES: O=C(Cn1c(CCCC(F)(F)F)nc(-c2ccc(C(F)(F)F)cc2)cc1=O)NCC1(O)CCCCC1]
I-0345
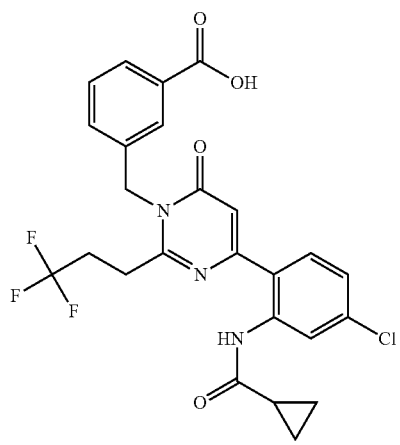 [SMILES: O=C(O)c1cccc(Cn2c(CCC(F)(F)F)nc(-c3ccc(Cl)cc3NC(=O)C3CC3)cc2=O)c1]

TABLE 59-continued
I-0346 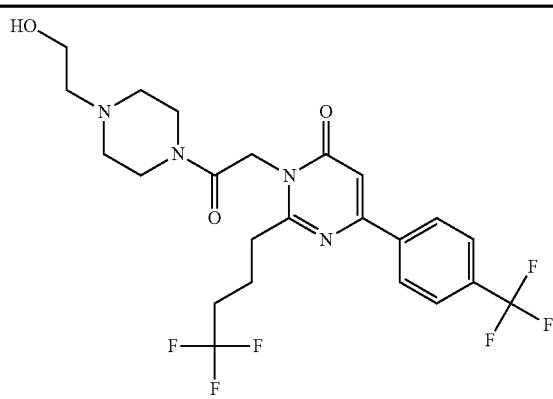
I-0347 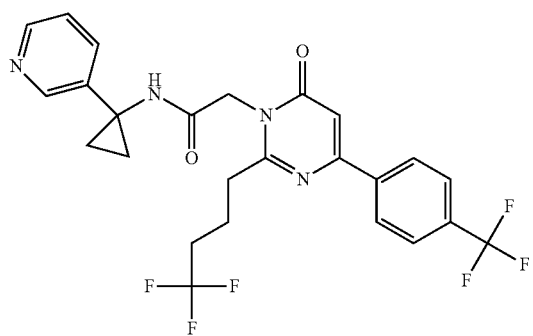 [SMILES: O=C(Cn1c(CCCC(F)(F)F)nc(-c2ccc(C(F)(F)F)cc2)cc1=O)NC1(c2cccnc2)CC1]
TABLE 60
I-0348 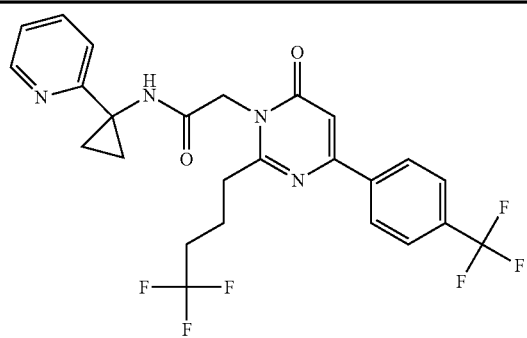
I-0349 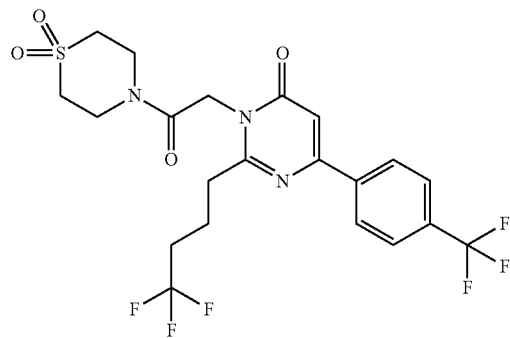 [SMILES: O=C(Cn1c(CCCC(F)(F)F)nc(-c2ccc(C(F)(F)F)cc2)cc1=O)N1CCS(=O)(=O)CC1]

TABLE 60-continued
I-0350 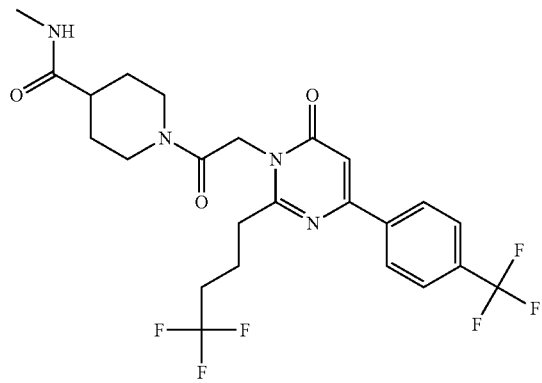 [SMILES: CNC(=O)C1CCN(C(=O)Cn2c(CCCC(F)(F)F)nc(-c3ccc(C(F)(F)F)cc3)cc2=O)CC1]
I-0351 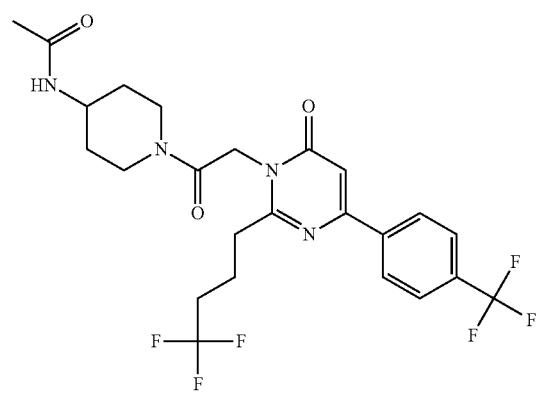 [SMILES: CC(=O)NC1CCN(C(=O)Cn2c(CCCC(F)(F)F)nc(-c3ccc(C(F)(F)F)cc3)cc2=O)CC1]
I-0352 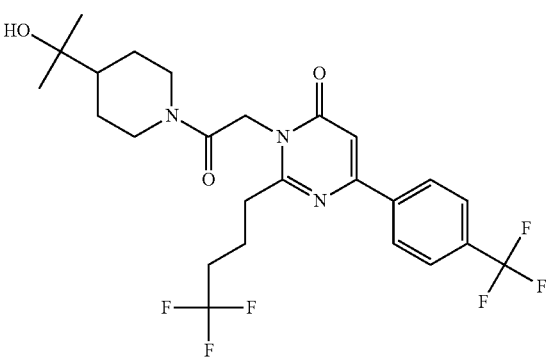 [SMILES: CC(C)(O)C1CCN(C(=O)Cn2c(CCCC(F)(F)F)nc(-c3ccc(C(F)(F)F)cc3)cc2=O)CC1]
TABLE 61
I-0353 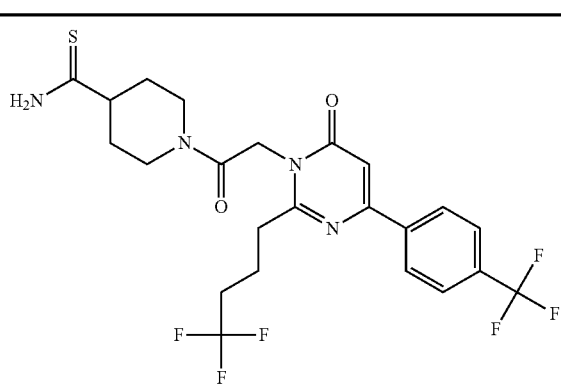

TABLE 61-continued
I-0354
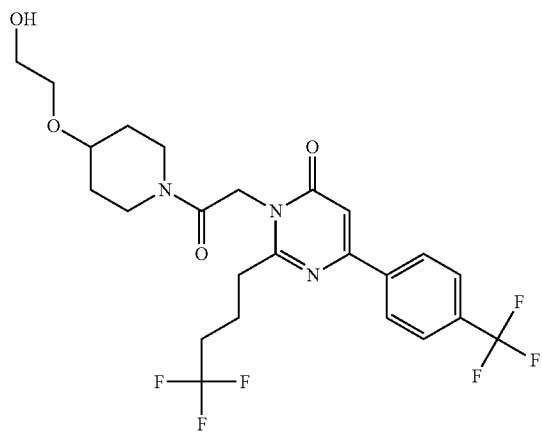 [SMILES: O=C(Cn1c(CCCC(F)(F)F)nc(-c2ccc(C(F)(F)F)cc2)cc1=O)N1CCC(OCCO)CC1]
I-0355
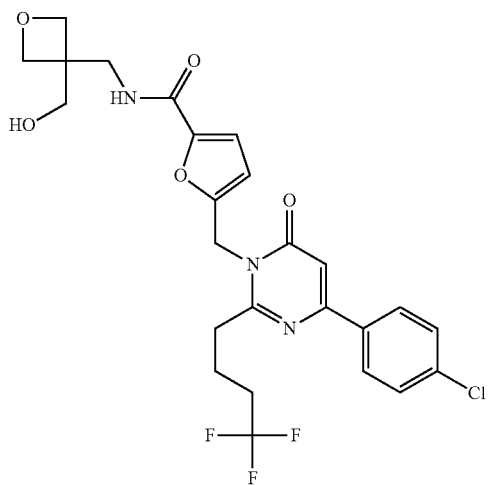 [SMILES: O=C(NCC1(CO)COC1)c1ccc(Cn2c(CCCC(F)(F)F)nc(-c3ccc(Cl)cc3)cc2=O)o1]
I-0356
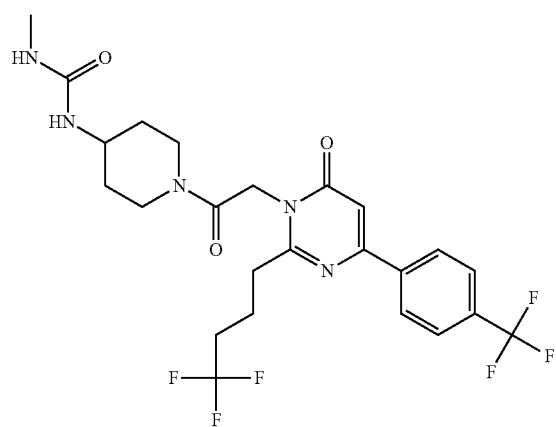 [SMILES: CNC(=O)NC1CCN(C(=O)Cn2c(CCCC(F)(F)F)nc(-c3ccc(C(F)(F)F)cc3)cc2=O)CC1]

TABLE 61-continued
I-0357
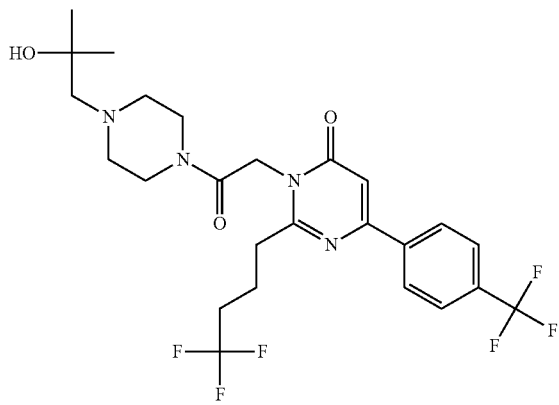 [SMILES: CC(C)(O)CN1CCN(C(=O)Cn2c(CCCC(F)(F)F)nc(-c3ccc(C(F)(F)F)cc3)cc2=O)CC1]
TABLE 62
I-0358
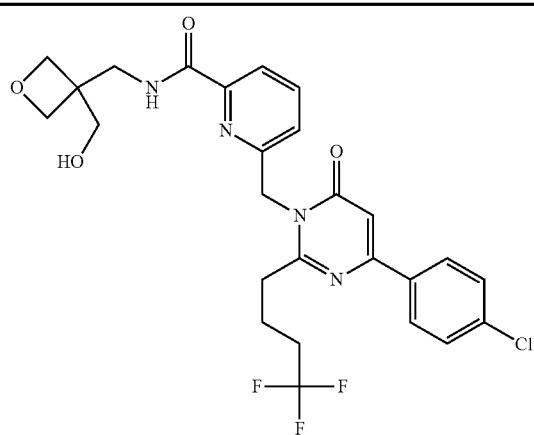
I-0359
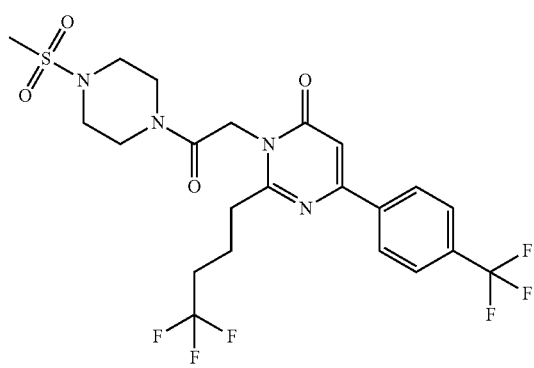 [SMILES: CS(=O)(=O)N1CCN(C(=O)Cn2c(CCCC(F)(F)F)nc(-c3ccc(C(F)(F)F)cc3)cc2=O)CC1]
I-0360
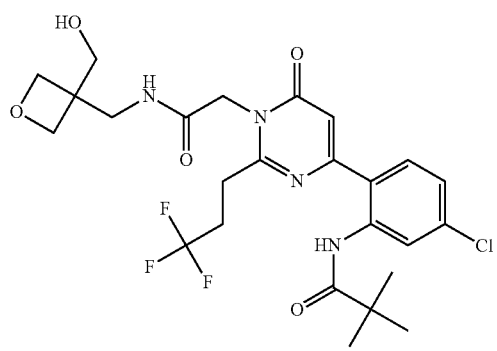 [SMILES: CC(C)(C)C(=O)Nc1cc(Cl)ccc1-c1cc(=O)n(CC(=O)NCC2(CO)COC2)c(CCC(F)(F)F)n1]

TABLE 62-continued
I-0361
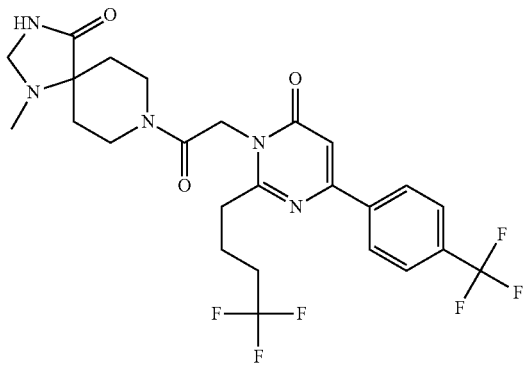 [SMILES: CN1CNC(=O)C12CCN(C(=O)Cn1c(CCCC(F)(F)F)nc(-c3ccc(C(F)(F)F)cc3)cc1=O)CC2]
I-0362
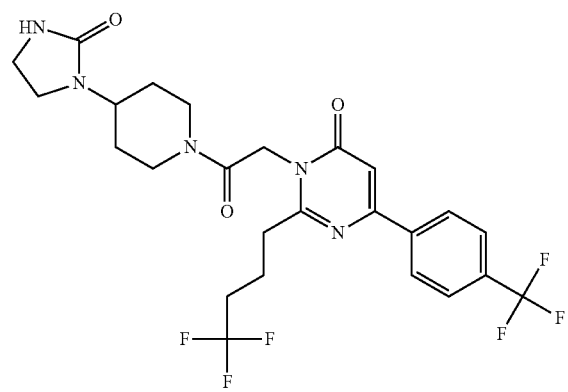 [SMILES: O=C(Cn1c(CCCC(F)(F)F)nc(-c2ccc(C(F)(F)F)cc2)cc1=O)N1CCC(N2CCNC2=O)CC1]
TABLE 63
I-0363
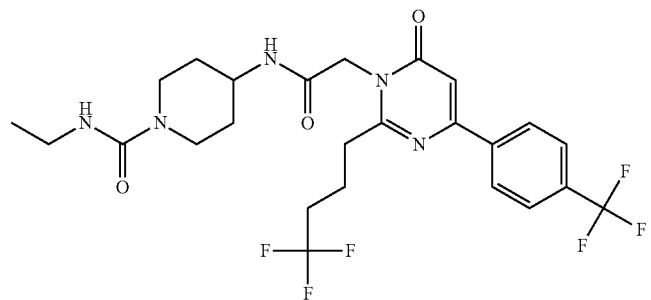 [SMILES: CCNC(=O)N1CCC(NC(=O)Cn2c(CCCC(F)(F)F)nc(-c3ccc(C(F)(F)F)cc3)cc2=O)CC1]
I-0364
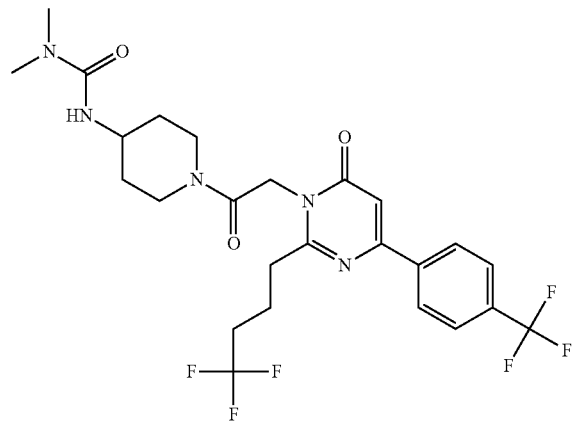 [SMILES: CN(C)C(=O)NC1CCN(C(=O)Cn2c(CCCC(F)(F)F)nc(-c3ccc(C(F)(F)F)cc3)cc2=O)CC1]

TABLE 63-continued
I-0365
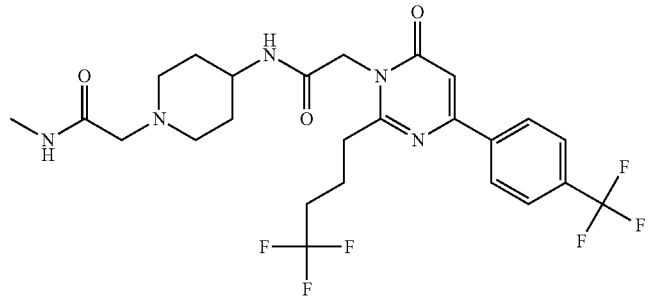 [SMILES: CNC(=O)CN1CCC(NC(=O)Cn2c(CCCC(F)(F)F)nc(-c3ccc(C(F)(F)F)cc3)cc2=O)CC1]
I-0366
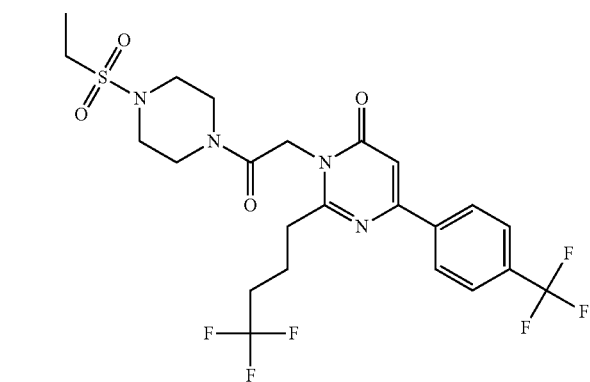 [SMILES: CCS(=O)(=O)N1CCN(C(=O)Cn2c(CCCC(F)(F)F)nc(-c3ccc(C(F)(F)F)cc3)cc2=O)CC1]
I-0367
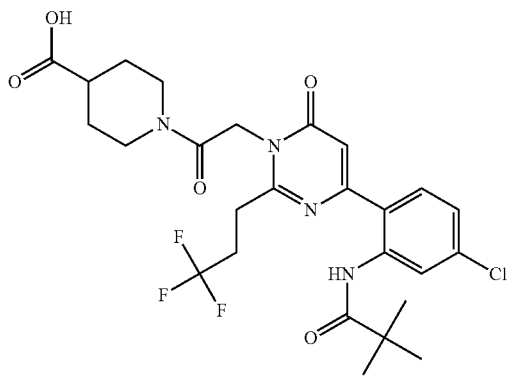 [SMILES: CC(C)(C)C(=O)Nc1cc(Cl)ccc1-c1cc(=O)n(CC(=O)N2CCC(C(=O)O)CC2)c(CCC(F)(F)F)n1]
I-0368
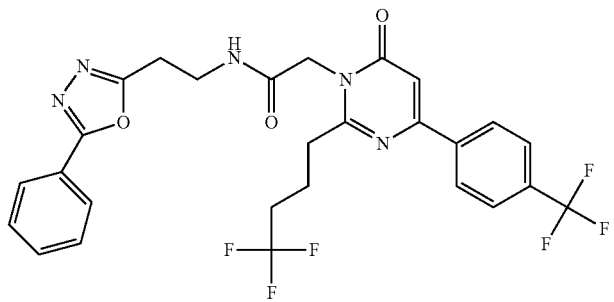 [SMILES: O=C(Cn1c(CCCC(F)(F)F)nc(-c2ccc(C(F)(F)F)cc2)cc1=O)NCCc1nnc(-c2ccccc2)o1]

TABLE 64
I-0369
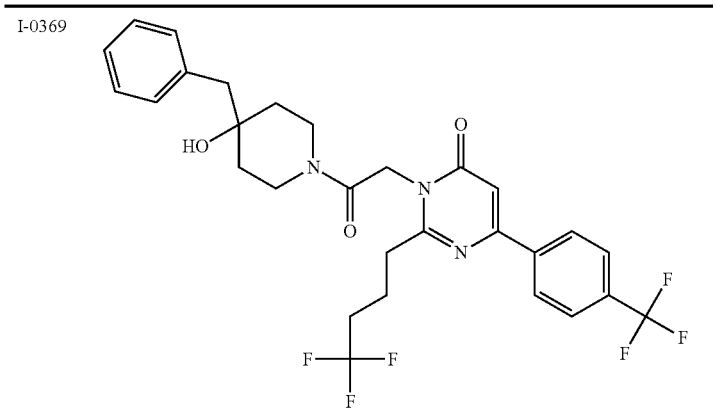
I-0370
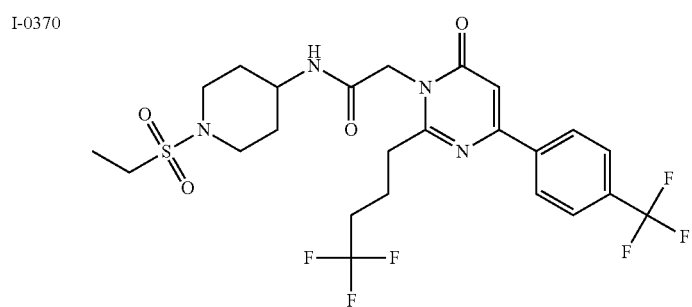
| TABLE 65 | TABLE 65-continued |
|---|---|
| I-0371 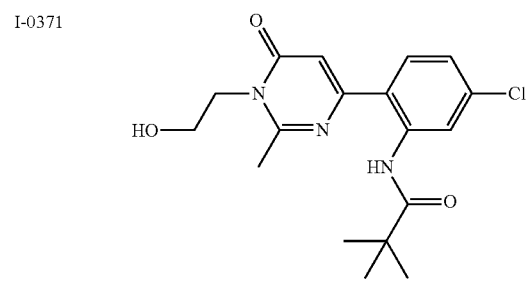 | I-0374 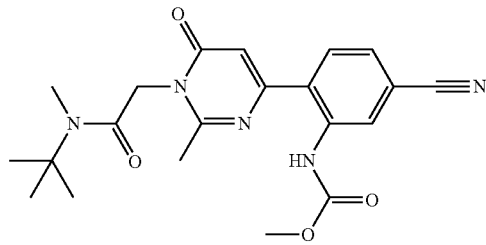 [SMILES: COC(=O)Nc1cc(C#N)ccc1-c1cc(=O)n(CC(=O)N(C)C(C)(C)C)c(C)n1] |
| I-0372 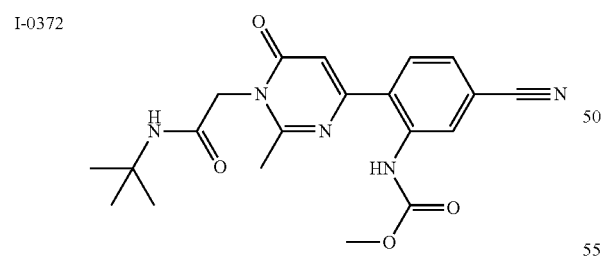 | I-0375 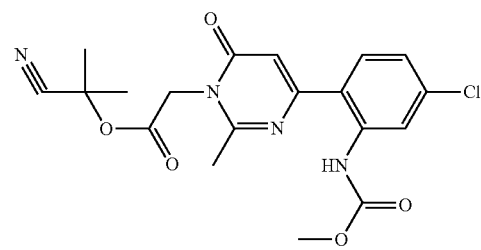 [SMILES: COC(=O)Nc1cc(Cl)ccc1-c1cc(=O)n(CC(=O)OC(C)(C)C#N)c(C)n1] |
| I-0373 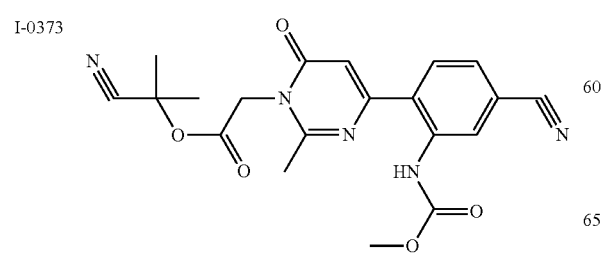 | I-0376 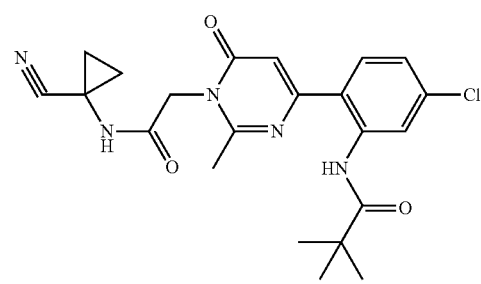 [SMILES: Cc1nc(-c2ccc(Cl)cc2NC(=O)C(C)(C)C)cc(=O)n1CC(=O)NC1(C#N)CC1] |

TABLE 66
I-0377
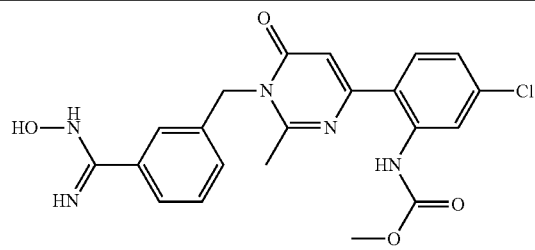
I-0378
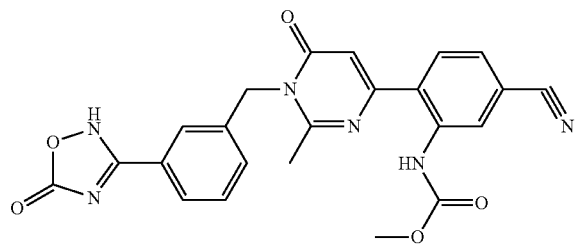 [SMILES: COC(=O)Nc1cc(C#N)ccc1-c1cc(=O)n(Cc2cccc(-c3nc(=O)o[nH]3)c2)c(C)n1]
I-0379
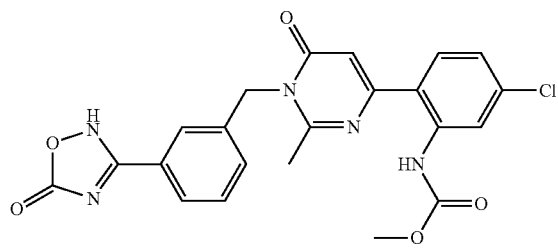 [SMILES: COC(=O)Nc1cc(Cl)ccc1-c1cc(=O)n(Cc2cccc(-c3nc(=O)o[nH]3)c2)c(C)n1]
I-0380
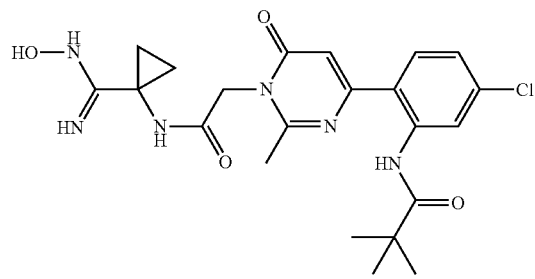 [SMILES: Cc1nc(-c2ccc(Cl)cc2NC(=O)C(C)(C)C)cc(=O)n1CC(=O)NC1(C(=N)NO)CC1]
I-0381
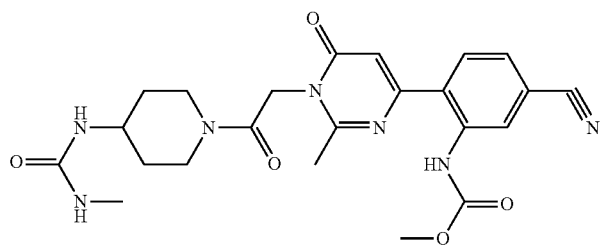 [SMILES: CNC(=O)NC1CCN(C(=O)Cn2c(C)nc(-c3ccc(C#N)cc3NC(=O)OC)cc2=O)CC1]
I-0382
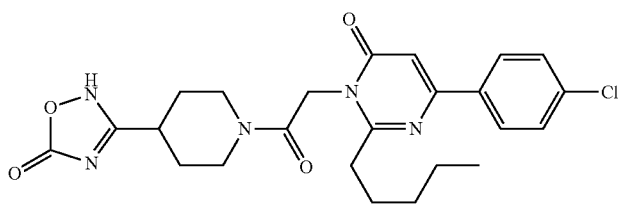 [SMILES: CCCCCc1nc(-c2ccc(Cl)cc2)cc(=O)n1CC(=O)N1CCC(c2nc(=O)o[nH]2)CC1]

TABLE 67
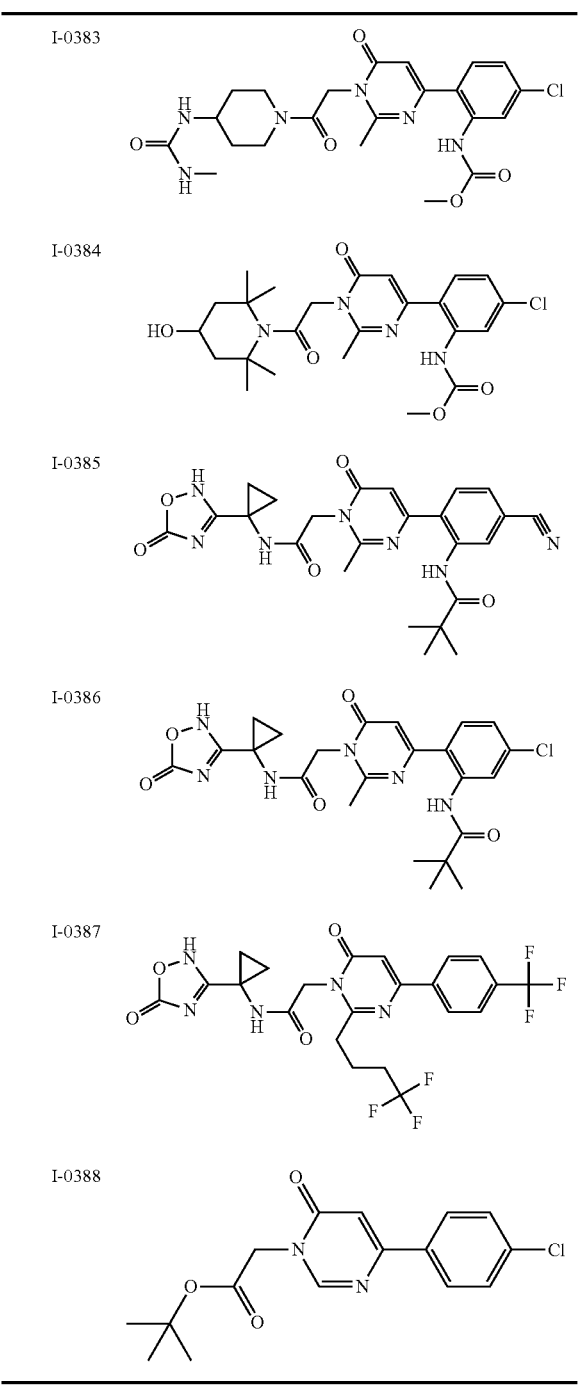
TABLE 68
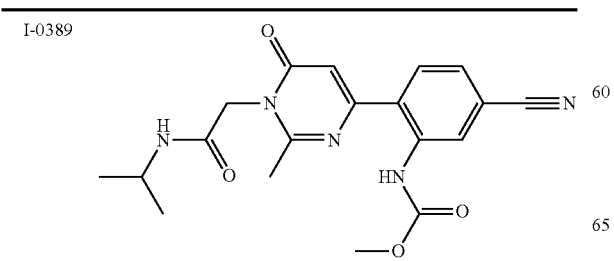
TABLE 68-continued
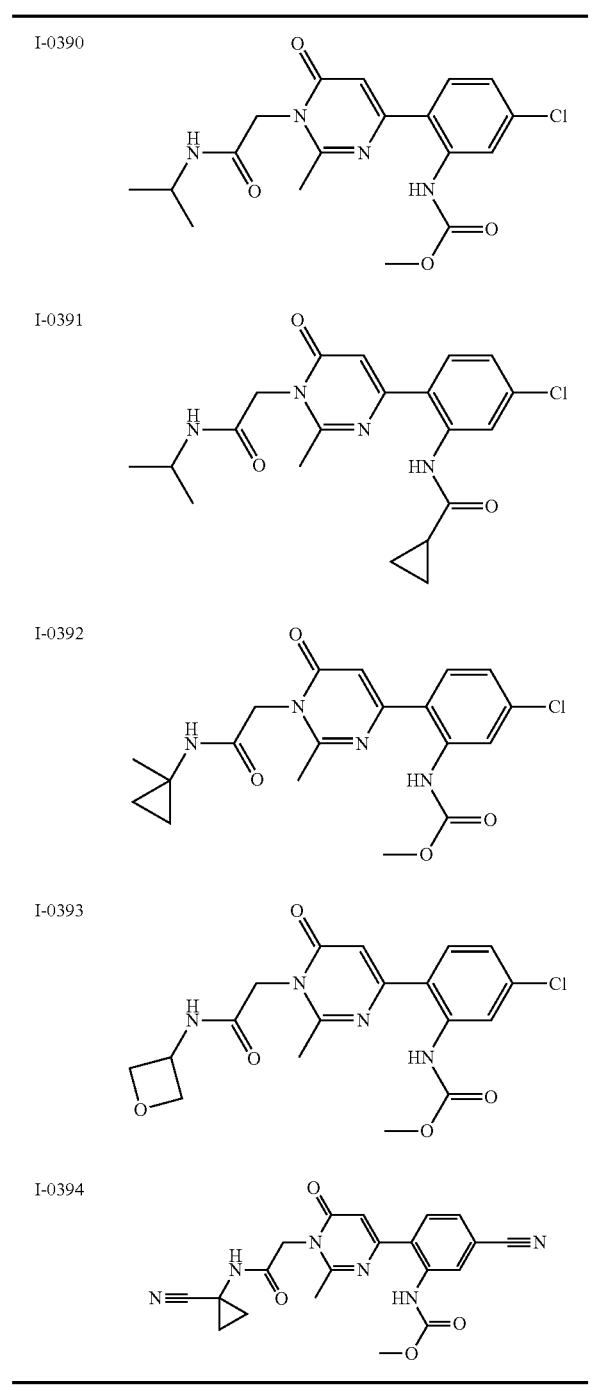
TABLE 69
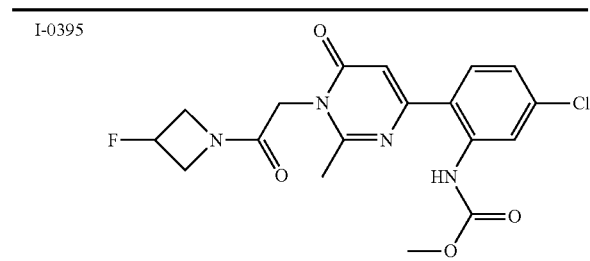

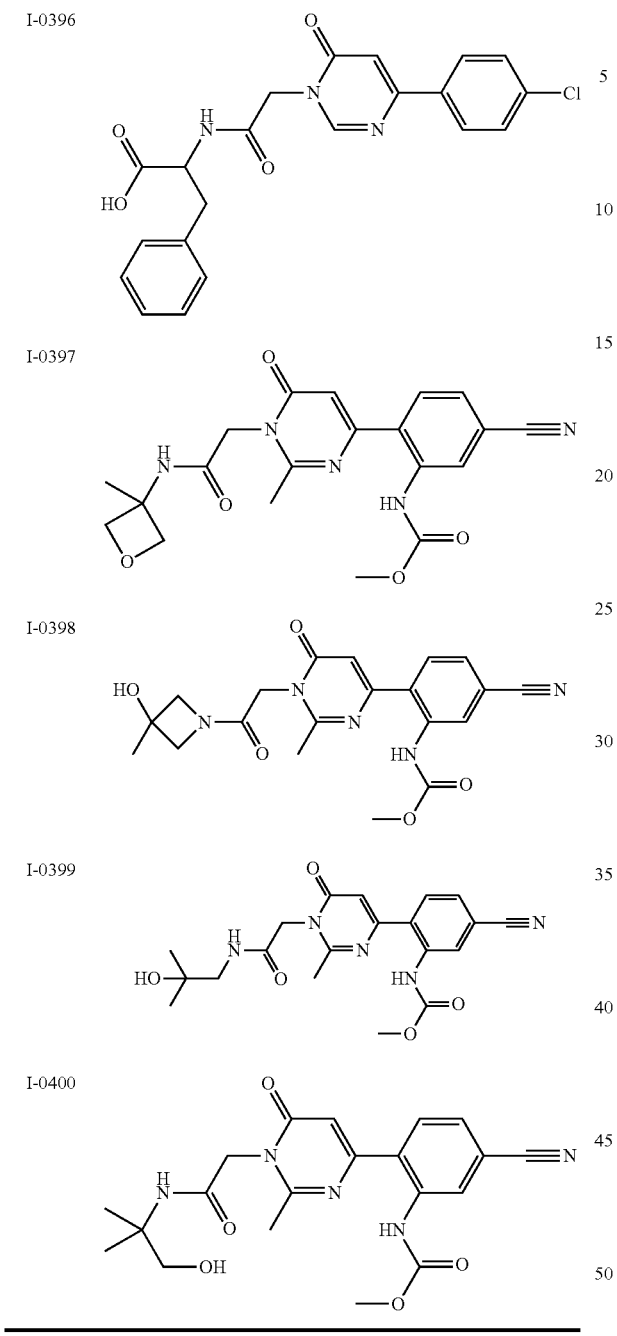
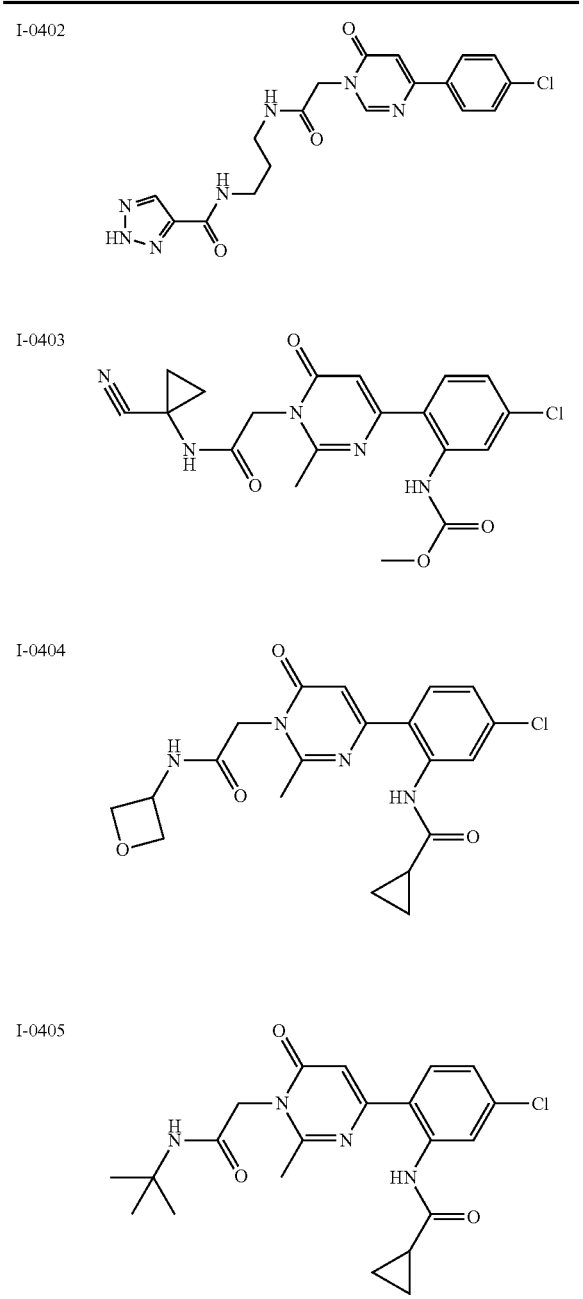

TABLE 71
I-0407 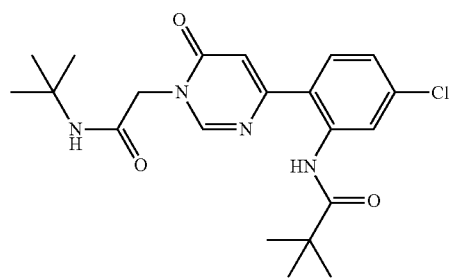 [SMILES: CC(C)(C)NC(=O)Cn1cnc(-c2ccc(Cl)cc2NC(=O)C(C)(C)C)cc1=O]
I-0408 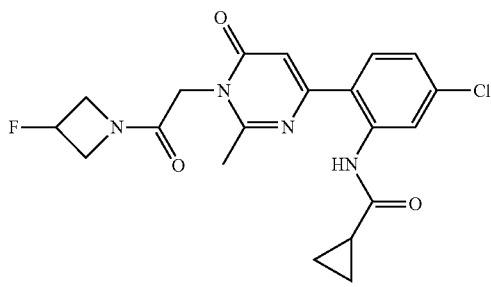 [SMILES: Cc1nc(-c2ccc(Cl)cc2NC(=O)C2CC2)cc(=O)n1CC(=O)N1CC(F)C1]
I-0409 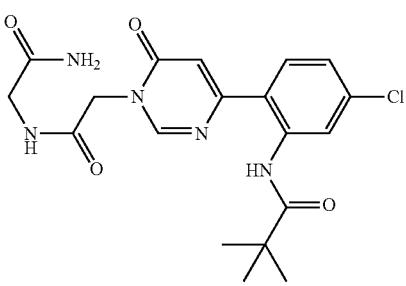 [SMILES: CC(C)(C)C(=O)Nc1cc(Cl)ccc1-c1cc(=O)n(CC(=O)NCC(N)=O)cn1]
I-0410 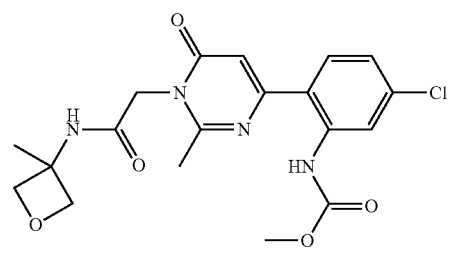 [SMILES: COC(=O)Nc1cc(Cl)ccc1-c1cc(=O)n(CC(=O)NC2(C)COC2)c(C)n1]
I-0411 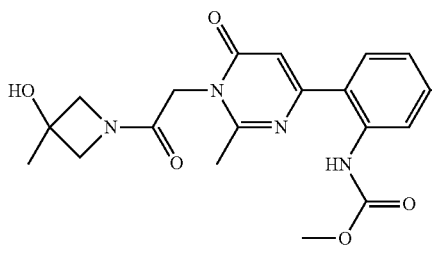
I-0412 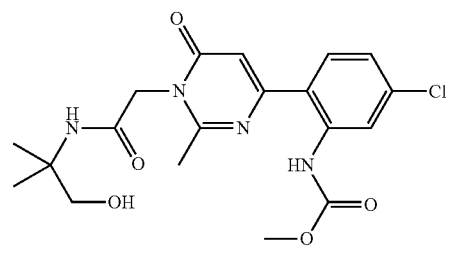 [SMILES: COC(=O)Nc1cc(Cl)ccc1-c1cc(=O)n(CC(=O)NC(C)(C)CO)c(C)n1]
TABLE 72
I-0413 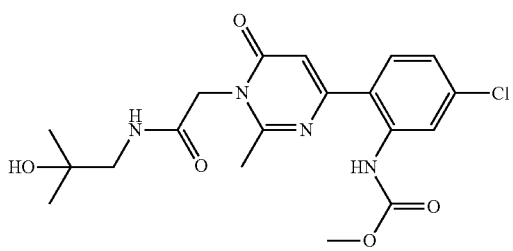 [SMILES: COC(=O)Nc1cc(Cl)ccc1-c1cc(=O)n(CC(=O)NCC(C)(C)O)c(C)n1]
I-0414 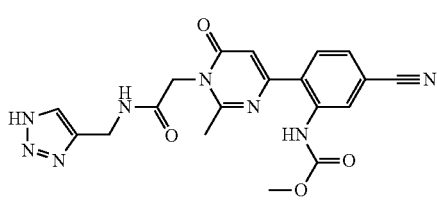 [SMILES: COC(=O)Nc1cc(C#N)ccc1-c1cc(=O)n(CC(=O)NCc2c[nH]nn2)c(C)n1]
I-0415 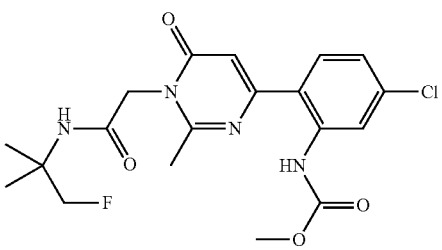 [SMILES: COC(=O)Nc1cc(Cl)ccc1-c1cc(=O)n(CC(=O)NC(C)(C)CF)c(C)n1]
I-0416 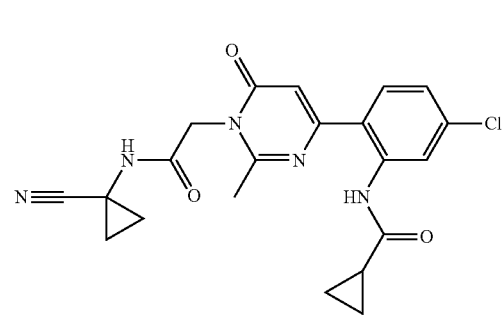 [SMILES: Cc1nc(-c2ccc(Cl)cc2NC(=O)C2CC2)cc(=O)n1CC(=O)NC1(C#N)CC1]
I-0417 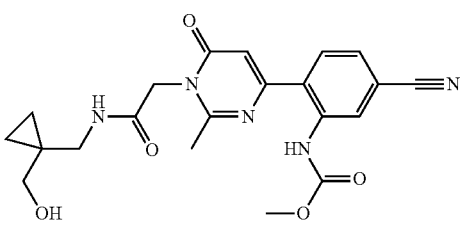 [SMILES: COC(=O)Nc1cc(C#N)ccc1-c1cc(=O)n(CC(=O)NCC2(CO)CC2)c(C)n1]
I-0418 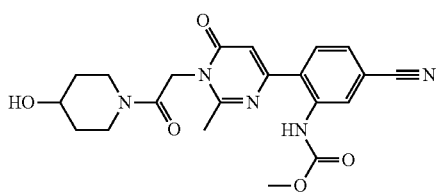 [SMILES: COC(=O)Nc1cc(C#N)ccc1-c1cc(=O)n(CC(=O)N2CCC(O)CC2)c(C)n1]

TABLE 73
I-0419 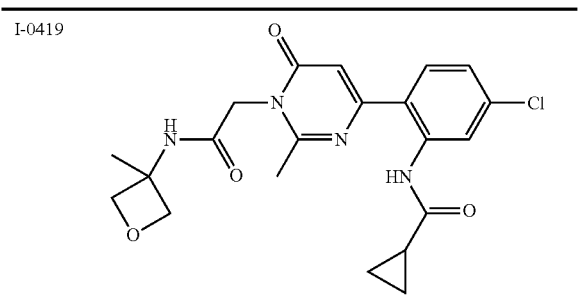
I-0420 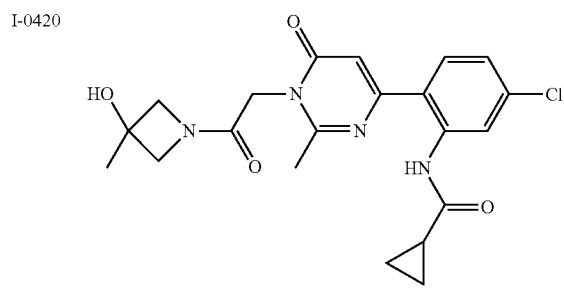
I-0421 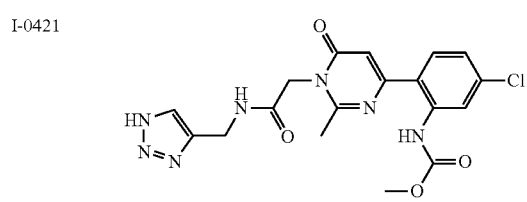
I-0422 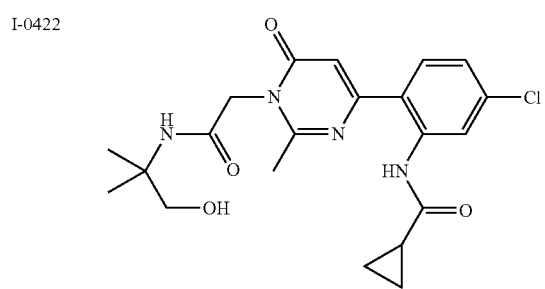
I-0423 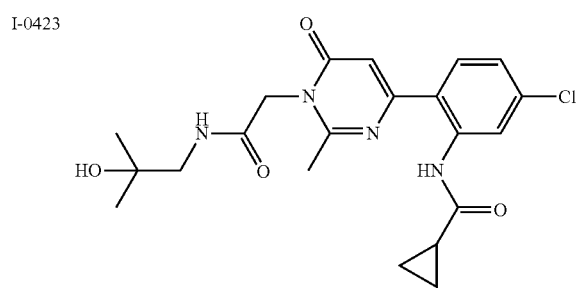
I-0424 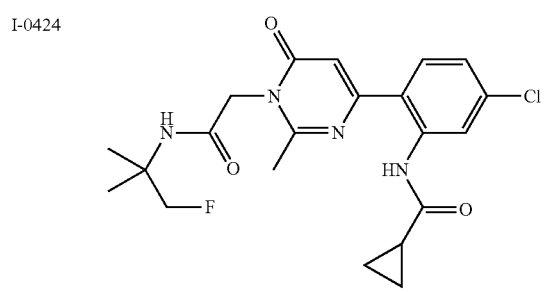
TABLE 74
I-0425 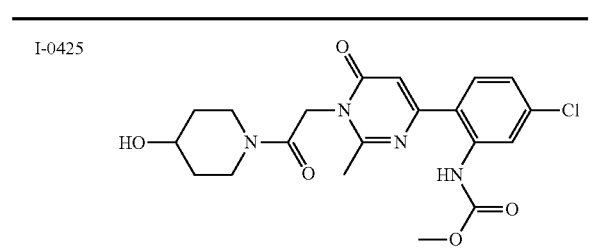
I-0426 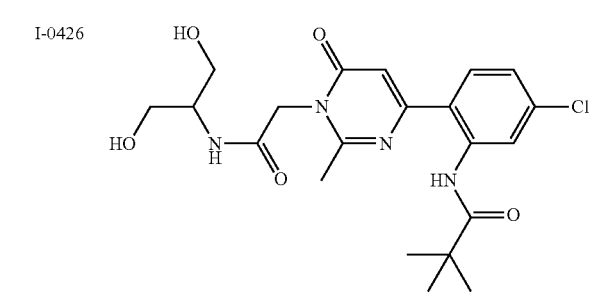
I-0427 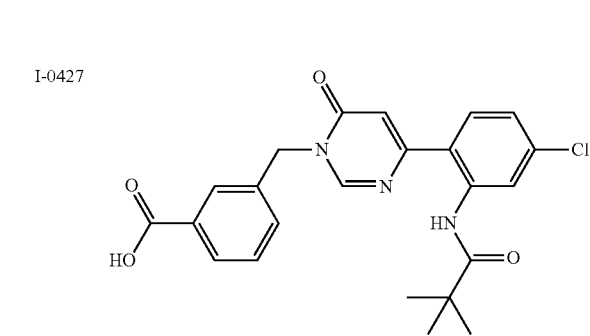
I-0428 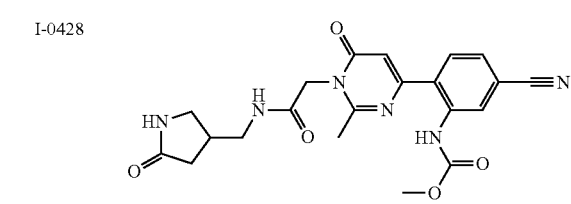
I-0429 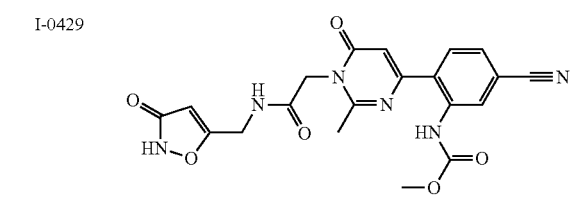
I-0430 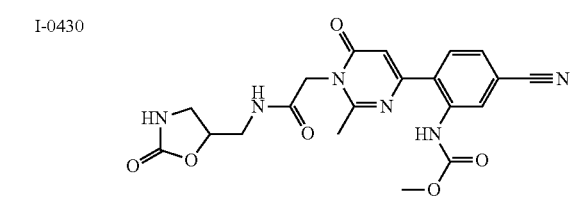

TABLE 75
I-0431 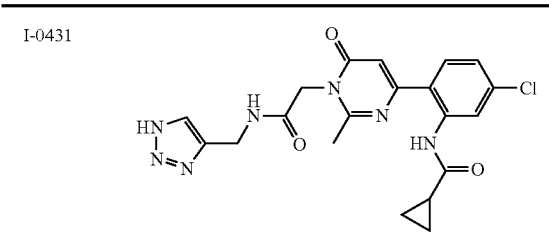
I-0432 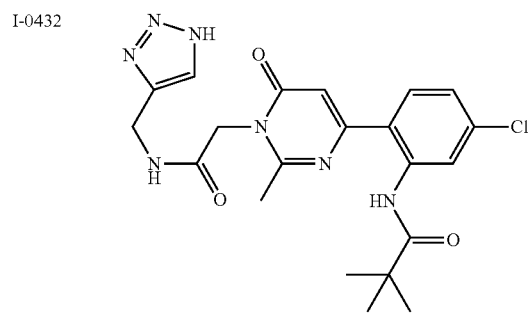
I-0433 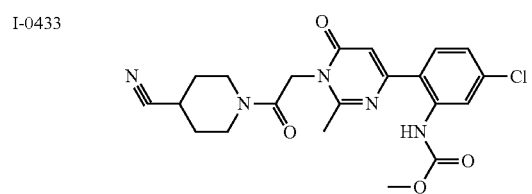
I-0434 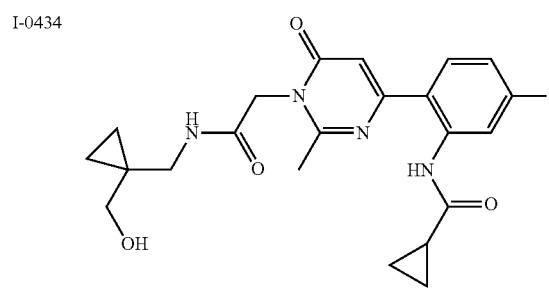
I-0435 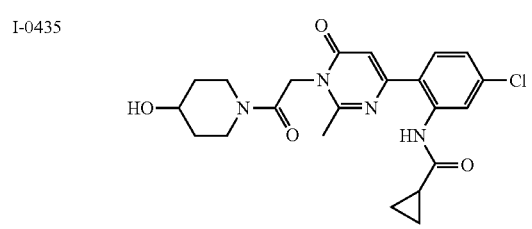
I-0436 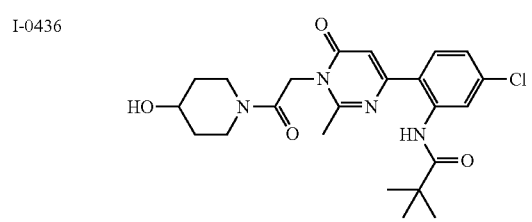
TABLE 76
I-0437 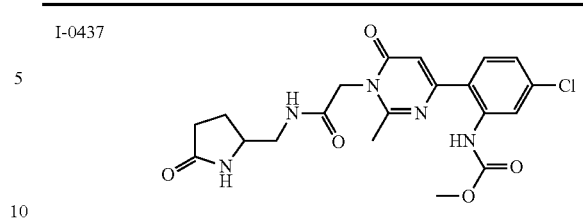
I-0438 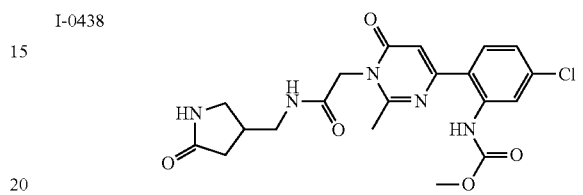
I-0439 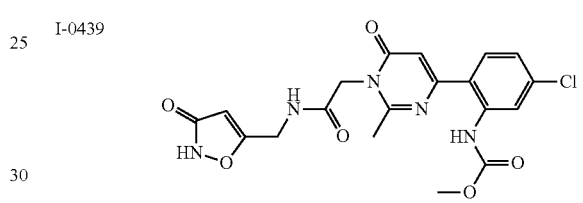
I-0440 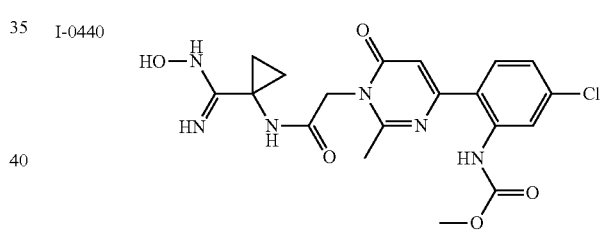
I-0441 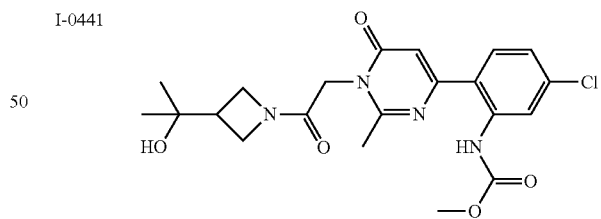
I-0442 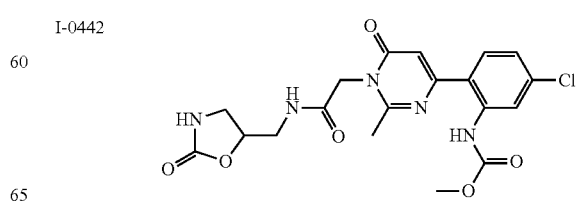

TABLE 77
I-0443
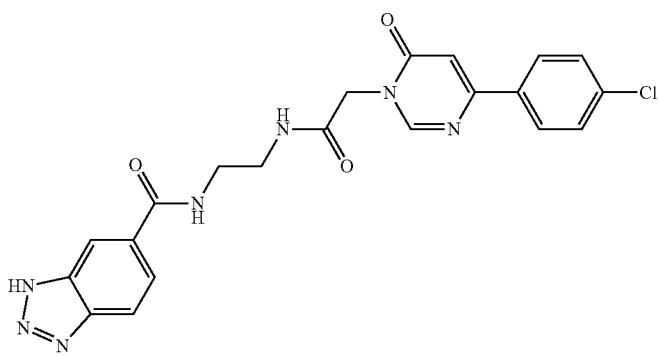 [SMILES: O=C(Cn1cnc(-c2ccc(Cl)cc2)cc1=O)NCCNC(=O)c1ccc2nn[nH]c2c1]
I-0444
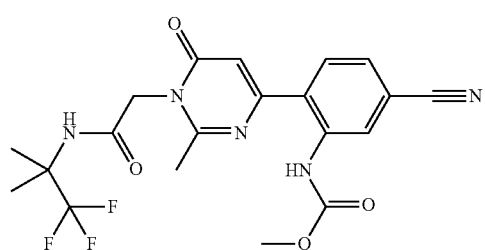 [SMILES: COC(=O)Nc1cc(C#N)ccc1-c1cc(=O)n(CC(=O)NC(C)(C)C(F)(F)F)c(C)n1]
I-0445
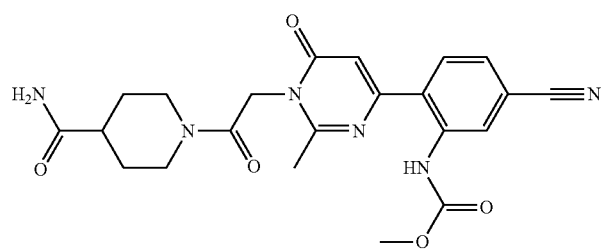 [SMILES: COC(=O)Nc1cc(C#N)ccc1-c1cc(=O)n(CC(=O)N2CCC(C(N)=O)CC2)c(C)n1]
I-0446
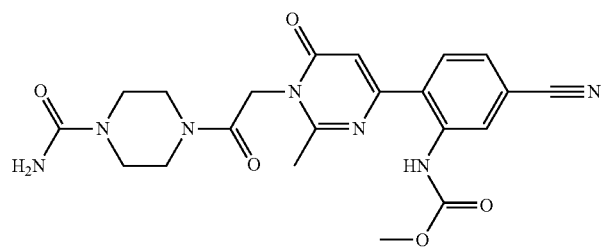 [SMILES: COC(=O)Nc1cc(C#N)ccc1-c1cc(=O)n(CC(=O)N2CCN(C(N)=O)CC2)c(C)n1]
I-0447
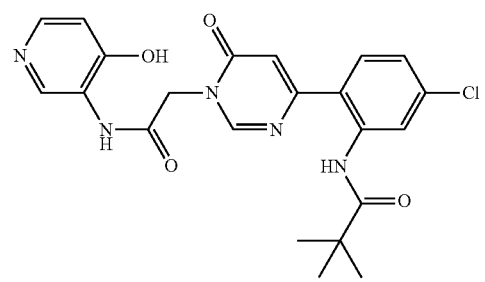 [SMILES: CC(C)(C)C(=O)Nc1cc(Cl)ccc1-c1cc(=O)n(CC(=O)Nc2cnccc2O)cn1]

TABLE 77-continued
I-0448 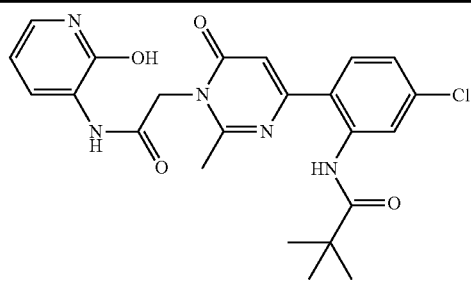
TABLE 78
I-0449 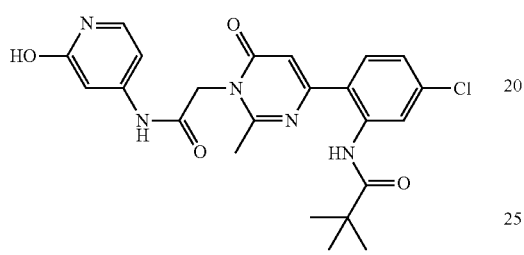
I-0450 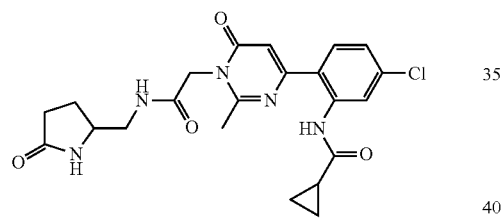
I-0451 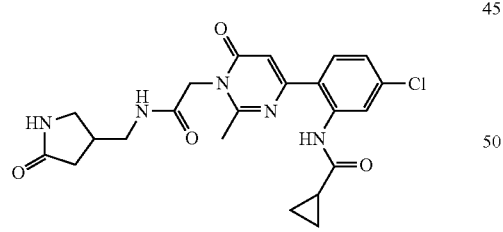
TABLE 78-continued
I-0452 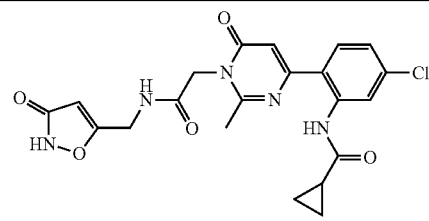
I-0453 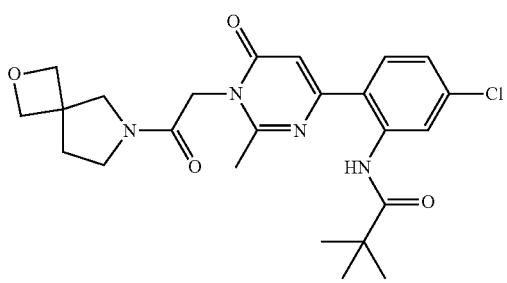 [SMILES: Cc1nc(-c2ccc(Cl)cc2NC(=O)C(C)(C)C)cc(=O)n1CC(=O)N1CCC2(COC2)C1]
I-0454 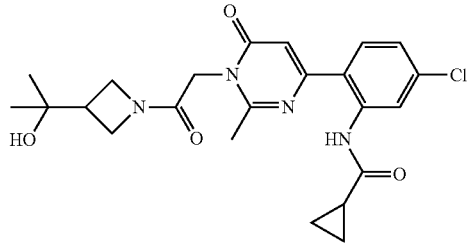 [SMILES: Cc1nc(-c2ccc(Cl)cc2NC(=O)C2CC2)cc(=O)n1CC(=O)N1CC(C(C)(C)O)C1]
TABLE 79
I-0455 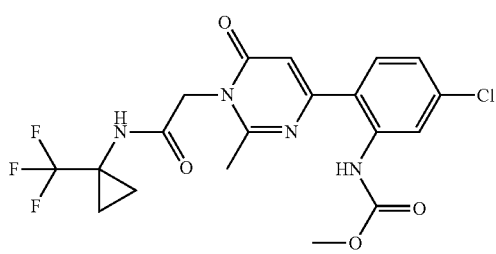 [SMILES: COC(=O)Nc1cc(Cl)ccc1-c1cc(=O)n(CC(=O)NC2(C(F)(F)F)CC2)c(C)n1]

TABLE 79-continued
I-0456
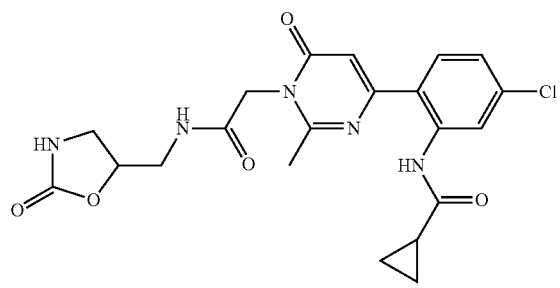 [SMILES: Cc1nc(-c2ccc(Cl)cc2NC(=O)C2CC2)cc(=O)n1CC(=O)NCC1CNC(=O)O1]
I-0457
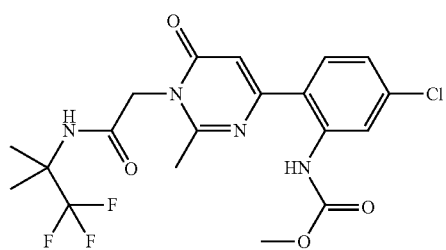 [SMILES: COC(=O)Nc1cc(Cl)ccc1-c1cc(=O)n(CC(=O)NC(C)(C)C(F)(F)F)c(C)n1]
I-0458
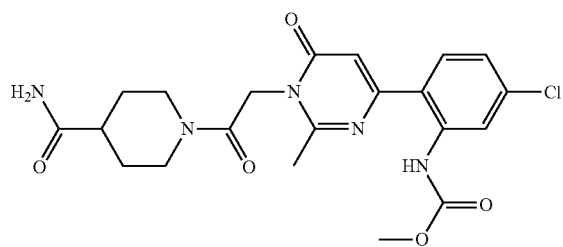 [SMILES: COC(=O)Nc1cc(Cl)ccc1-c1cc(=O)n(CC(=O)N2CCC(C(N)=O)CC2)c(C)n1]
I-0459
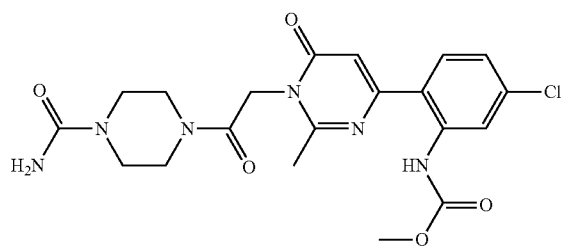 [SMILES: COC(=O)Nc1cc(Cl)ccc1-c1cc(=O)n(CC(=O)N2CCN(C(N)=O)CC2)c(C)n1]
I-0460
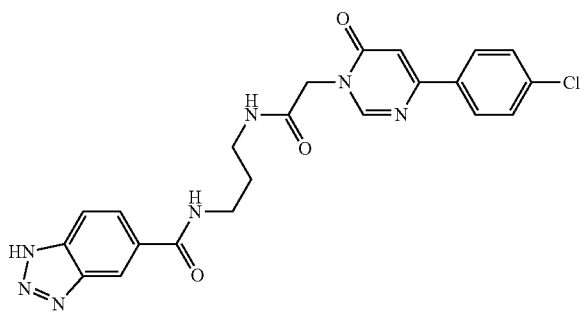 [SMILES: O=C(Cn1cnc(-c2ccc(Cl)cc2)cc1=O)NCCCNC(=O)c1ccc2[nH]nnc2c1]

TABLE 80
I-0461
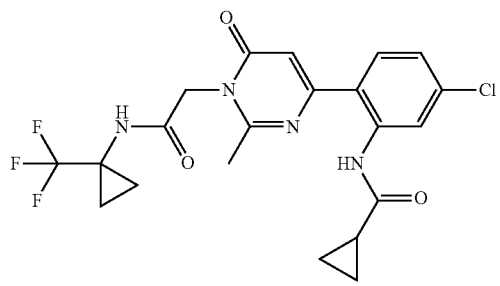 [SMILES: Cc1nc(-c2ccc(Cl)cc2NC(=O)C2CC2)cc(=O)n1CC(=O)NC1(C(F)(F)F)CC1]
I-0462
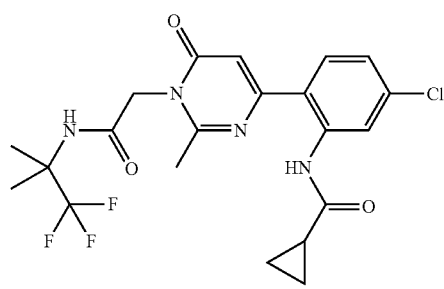 [SMILES: Cc1nc(-c2ccc(Cl)cc2NC(=O)C2CC2)cc(=O)n1CC(=O)NC(C)(C)C(F)(F)F]
I-0463
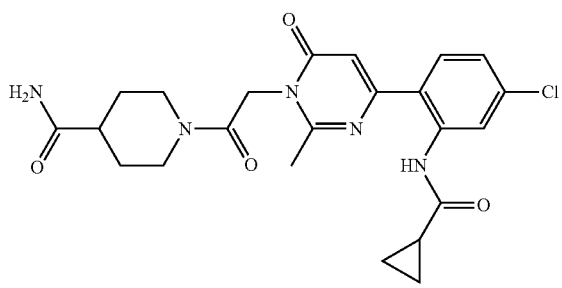 [SMILES: Cc1nc(-c2ccc(Cl)cc2NC(=O)C2CC2)cc(=O)n1CC(=O)N1CCC(C(N)=O)CC1]
I-0464
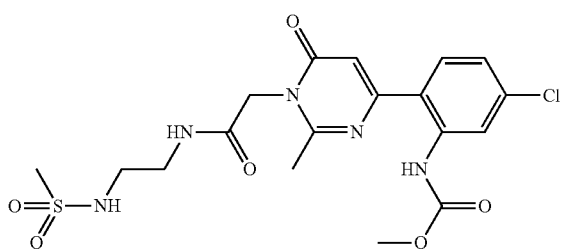 [SMILES: COC(=O)Nc1cc(Cl)ccc1-c1cc(=O)n(CC(=O)NCCNS(C)(=O)=O)c(C)n1]
I-0465
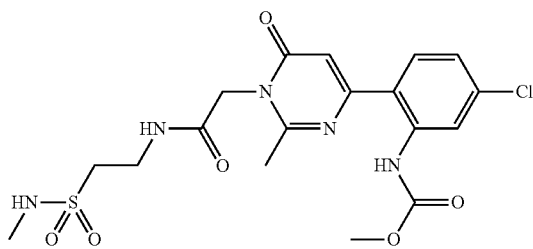 [SMILES: CNS(=O)(=O)CCNC(=O)Cn1c(C)nc(-c2ccc(Cl)cc2NC(=O)OC)cc1=O]

TABLE 80-continued
I-0466
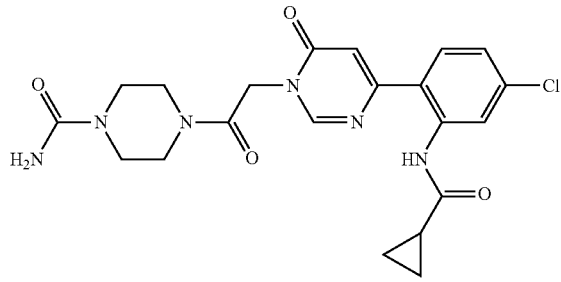 [SMILES: NC(=O)N1CCN(C(=O)Cn2cnc(-c3ccc(Cl)cc3NC(=O)C3CC3)cc2=O)CC1]
TABLE 81
I-0467
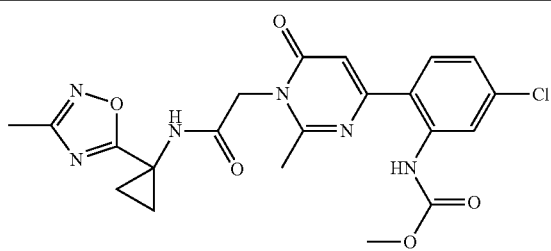
I-0468
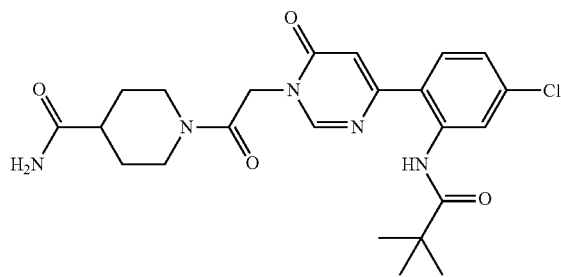 [SMILES: CC(C)(C)C(=O)Nc1cc(Cl)ccc1-c1cc(=O)n(CC(=O)N2CCC(C(N)=O)CC2)cn1]
I-0469
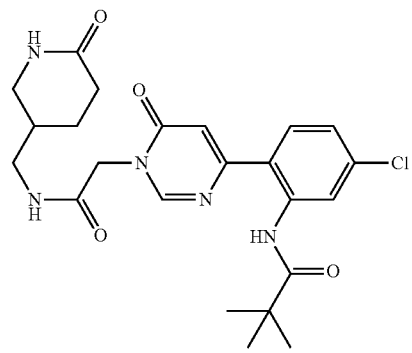 [SMILES: CC(C)(C)C(=O)Nc1cc(Cl)ccc1-c1cc(=O)n(CC(=O)NCC2CCC(=O)NC2)cn1]
I-0470
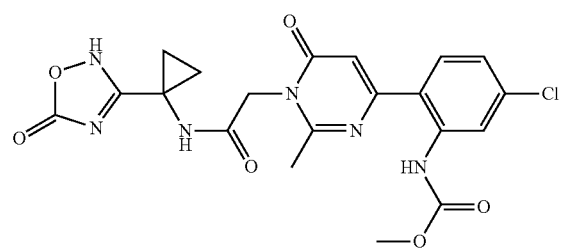 [SMILES: COC(=O)Nc1cc(Cl)ccc1-c1cc(=O)n(CC(=O)NC2(c3nc(=O)o[nH]3)CC2)c(C)n1]

TABLE 81-continued
I-0471
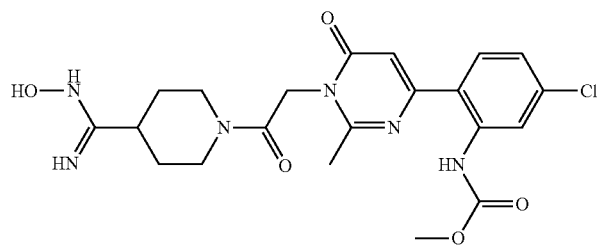 [SMILES: COC(=O)Nc1cc(Cl)ccc1-c1cc(=O)n(CC(=O)N2CCC(C(=N)NO)CC2)c(C)n1]
I-0472
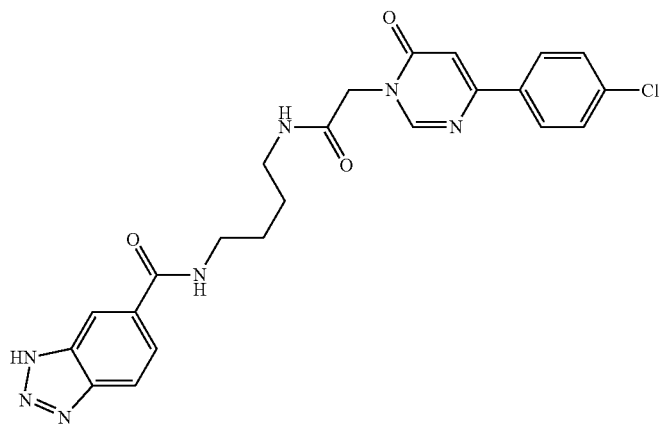 [SMILES: O=C(Cn1cnc(-c2ccc(Cl)cc2)cc1=O)NCCCCNC(=O)c1ccc2nn[nH]c2c1]
TABLE 82
I-0473
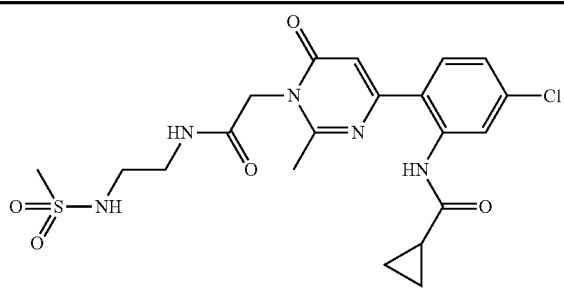
I-0474
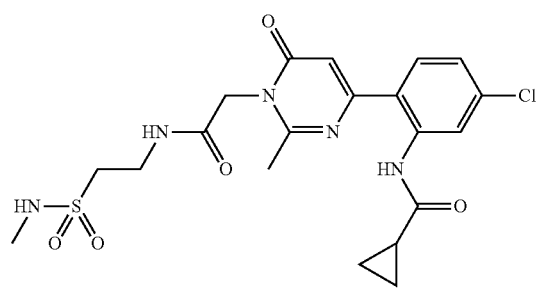 [SMILES: CNS(=O)(=O)CCNC(=O)Cn1c(C)nc(-c2ccc(Cl)cc2NC(=O)C2CC2)cc1=O]
I-0475
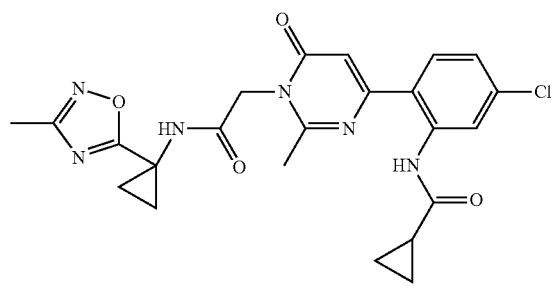 [SMILES: Cc1noc(C2(NC(=O)Cn3c(C)nc(-c4ccc(Cl)cc4NC(=O)C4CC4)cc3=O)CC2)n1]

TABLE 82-continued
I-0476
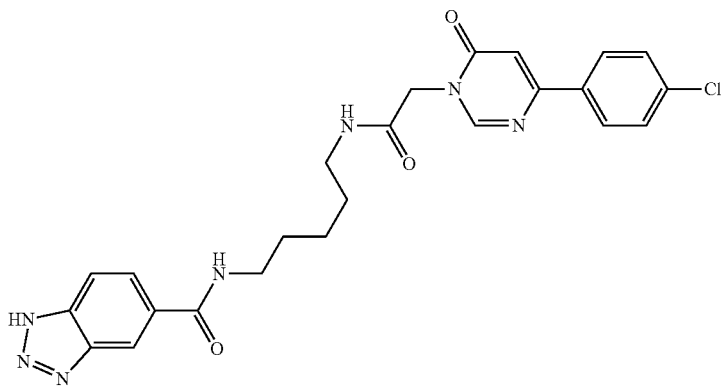 [SMILES: O=C(Cn1cnc(-c2ccc(Cl)cc2)cc1=O)NCCCCCNC(=O)c1ccc2[nH]nnc2c1]
I-0477
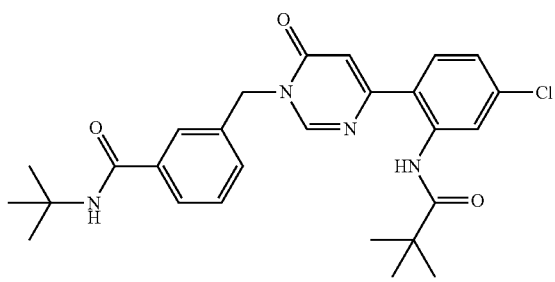 [SMILES: CC(C)(C)NC(=O)c1cccc(Cn2cnc(-c3ccc(Cl)cc3NC(=O)C(C)(C)C)cc2=O)c1]
I-0478
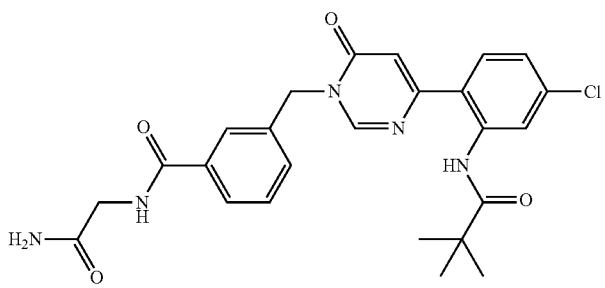 [SMILES: CC(C)(C)C(=O)Nc1cc(Cl)ccc1-c1cc(=O)n(Cc2cccc(C(=O)NCC(N)=O)c2)cn1]
TABLE 83
I-0479
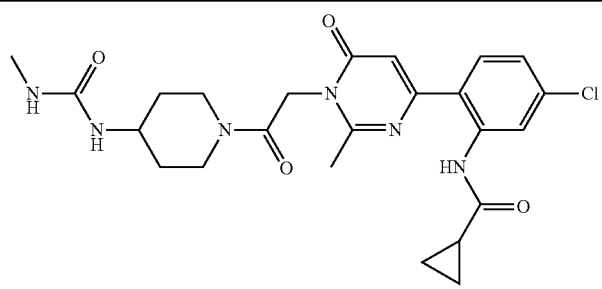
I-0480
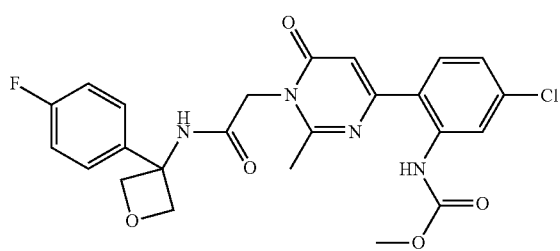 [SMILES: COC(=O)Nc1cc(Cl)ccc1-c1cc(=O)n(CC(=O)NC2(c3ccc(F)cc3)COC2)c(C)n1]

TABLE 83-continued
I-481
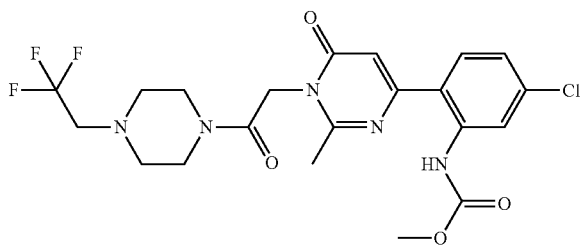 [SMILES: COC(=O)Nc1cc(Cl)ccc1-c1cc(=O)n(CC(=O)N2CCN(CC(F)(F)F)CC2)c(C)n1]
I-0482
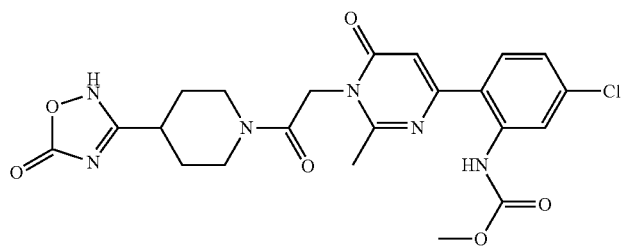 [SMILES: COC(=O)Nc1cc(Cl)ccc1-c1cc(=O)n(CC(=O)N2CCC(c3nc(=O)o[nH]3)CC2)c(C)n1]
I-0483
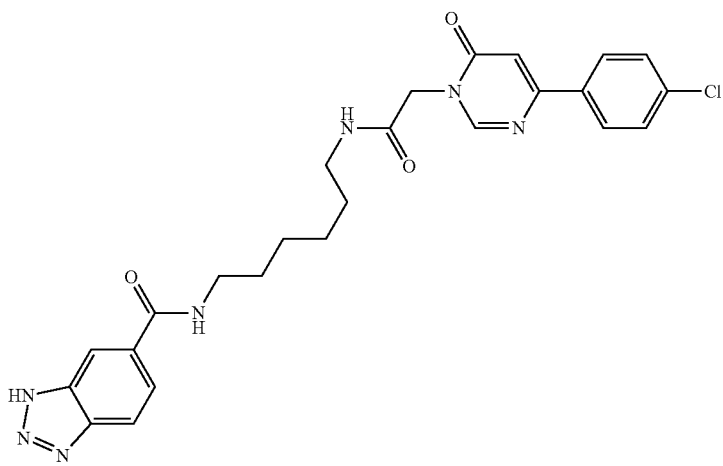 [SMILES: O=C(Cn1cnc(-c2ccc(Cl)cc2)cc1=O)NCCCCCCNC(=O)c1ccc2nn[nH]c2c1]
I-0484
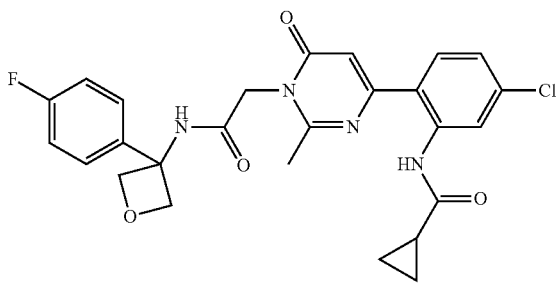 [SMILES: Cc1nc(-c2ccc(Cl)cc2NC(=O)C2CC2)cc(=O)n1CC(=O)NC1(c2ccc(F)cc2)COC1]
TABLE 84
I-0485
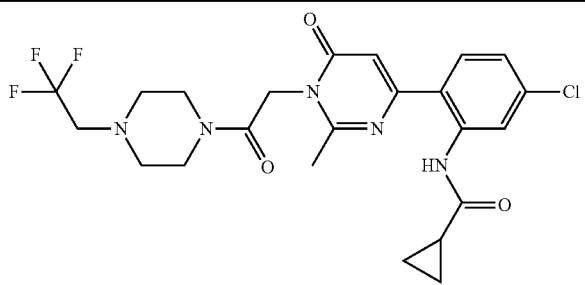

TABLE 84-continued
I-0486
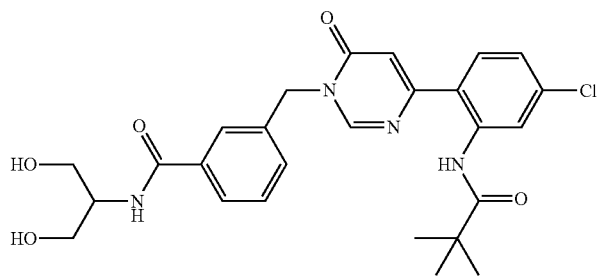 [SMILES: CC(C)(C)C(=O)Nc1cc(Cl)ccc1-c1cc(=O)n(Cc2cccc(C(=O)NC(CO)CO)c2)cn1]
I-0487
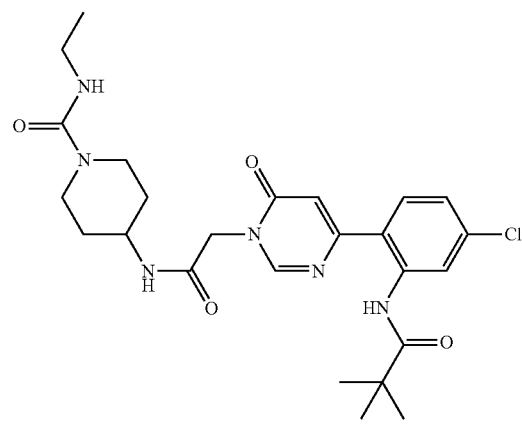 [SMILES: CCNC(=O)N1CCC(NC(=O)Cn2cnc(-c3ccc(Cl)cc3NC(=O)C(C)(C)C)cc2=O)CC1]
I-0488
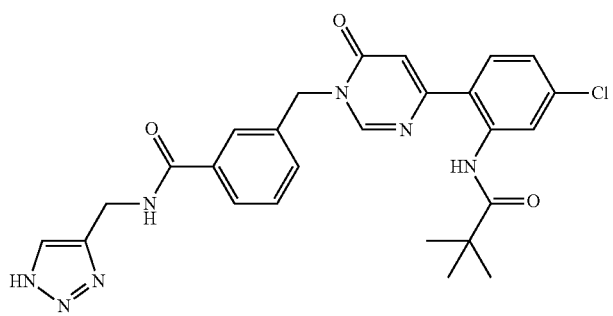 [SMILES: CC(C)(C)C(=O)Nc1cc(Cl)ccc1-c1cc(=O)n(Cc2cccc(C(=O)NCc3c[nH]nn3)c2)cn1]
I-0489
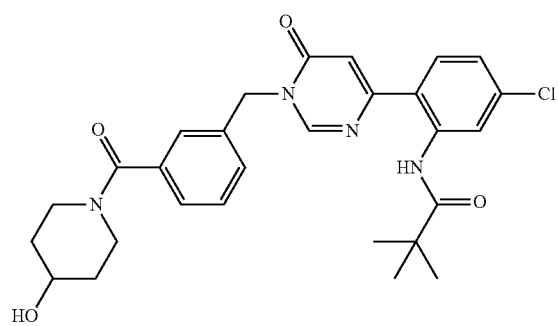 [SMILES: CC(C)(C)C(=O)Nc1cc(Cl)ccc1-c1cc(=O)n(Cc2cccc(C(=O)N3CCC(O)CC3)c2)cn1]
I-0490
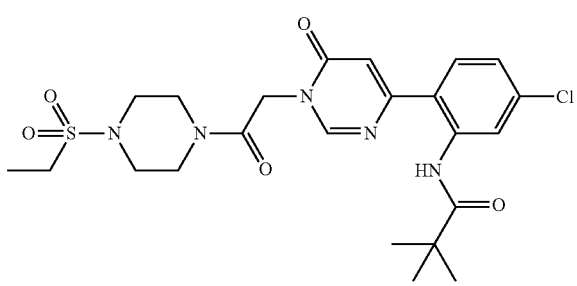 [SMILES: CCS(=O)(=O)N1CCN(C(=O)Cn2cnc(-c3ccc(Cl)cc3NC(=O)C(C)(C)C)cc2=O)CC1]

TABLE 85
I-0491
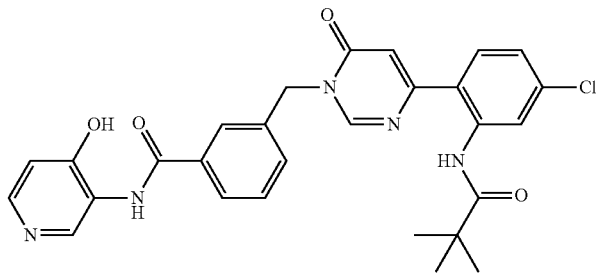 [SMILES: CC(C)(C)C(=O)Nc1cc(Cl)ccc1-c1cc(=O)n(Cc2cccc(C(=O)Nc3cnccc3O)c2)cn1]
I-0492
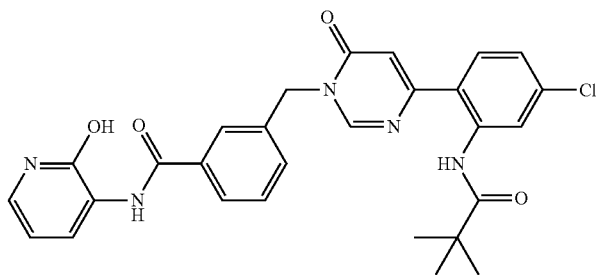 [SMILES: CC(C)(C)C(=O)Nc1cc(Cl)ccc1-c1cc(=O)n(Cc2cccc(C(=O)Nc3cccnc3O)c2)cn1]
I-0493
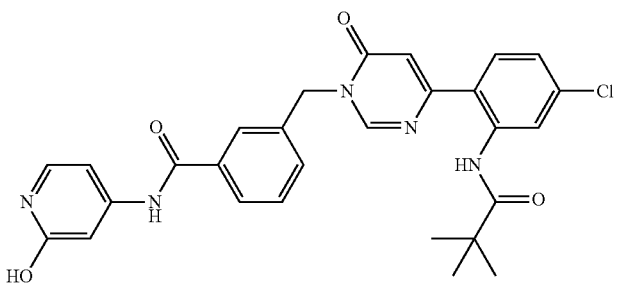 [SMILES: CC(C)(C)C(=O)Nc1cc(Cl)ccc1-c1cc(=O)n(Cc2cccc(C(=O)Nc3ccnc(O)c3)c2)cn1]
I-0494
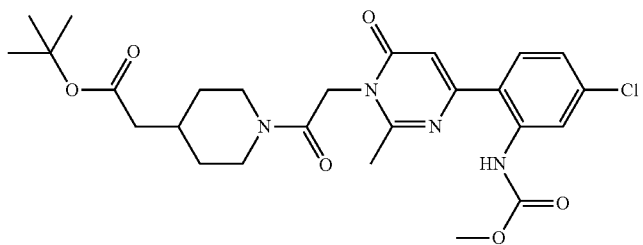 [SMILES: COC(=O)Nc1cc(Cl)ccc1-c1cc(=O)n(CC(=O)N2CCC(CC(=O)OC(C)(C)C)CC2)c(C)n1]
I-0495
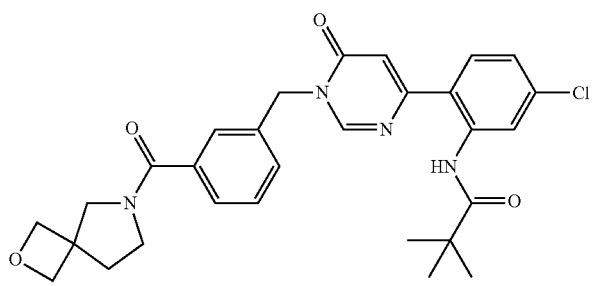 [SMILES: CC(C)(C)C(=O)Nc1cc(Cl)ccc1-c1cc(=O)n(Cc2cccc(C(=O)N3CCC4(COC4)C3)c2)cn1]

TABLE 85-continued
I-0496
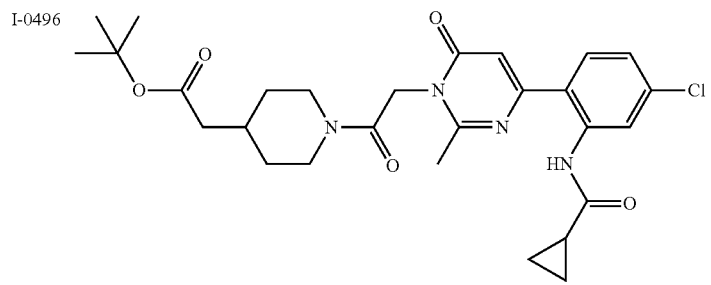
TABLE 86
I-0497
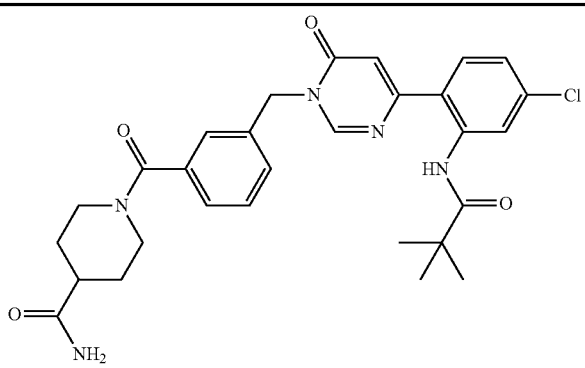
I-0498
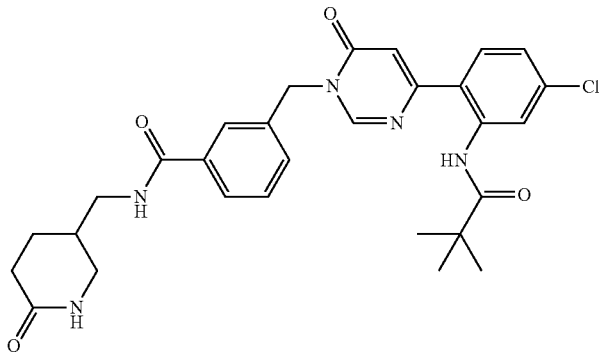 [SMILES: CC(C)(C)C(=O)Nc1cc(Cl)ccc1-c1cc(=O)n(Cc2cccc(C(=O)NCC3CCC(=O)NC3)c2)cn1]
I-0499
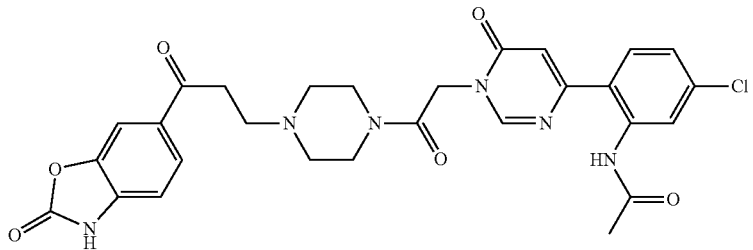 [SMILES: CC(=O)Nc1cc(Cl)ccc1-c1cc(=O)n(CC(=O)N2CCN(CCC(=O)c3ccc4[nH]c(=O)oc4c3)CC2)cn1]
I-0500
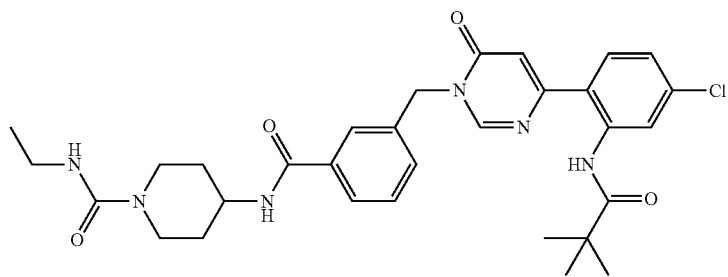 [SMILES: CCNC(=O)N1CCC(NC(=O)c2cccc(Cn3cnc(-c4ccc(Cl)cc4NC(=O)C(C)(C)C)cc3=O)c2)CC1]

TABLE 86-continued
I-0501
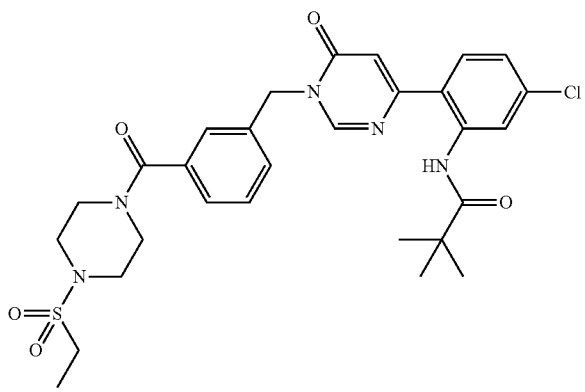 [SMILES: CCS(=O)(=O)N1CCN(C(=O)c2cccc(Cn3cnc(-c4ccc(Cl)cc4NC(=O)C(C)(C)C)cc3=O)c2)CC1]
I-0502
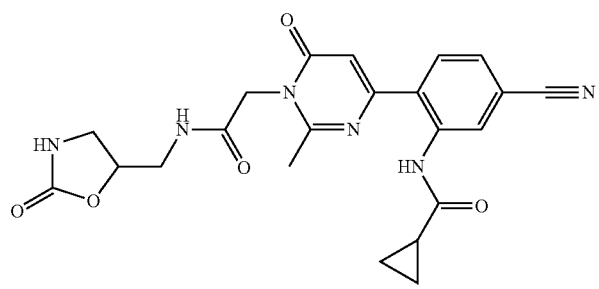
TABLE 87
I-0503
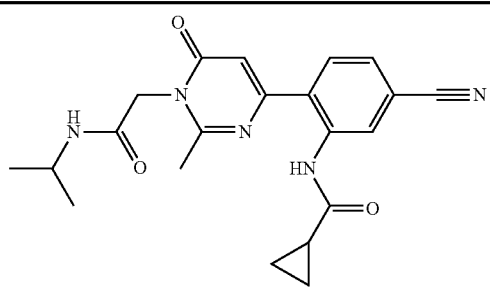
I-0504
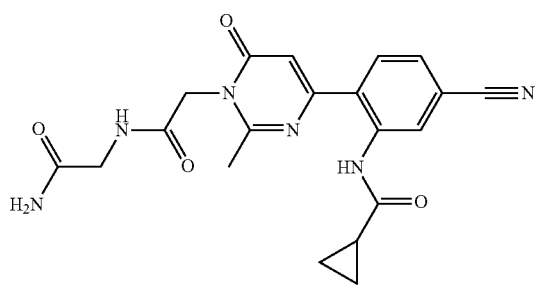 [SMILES: Cc1nc(-c2ccc(C#N)cc2NC(=O)C2CC2)cc(=O)n1CC(=O)NCC(N)=O]
I-0505
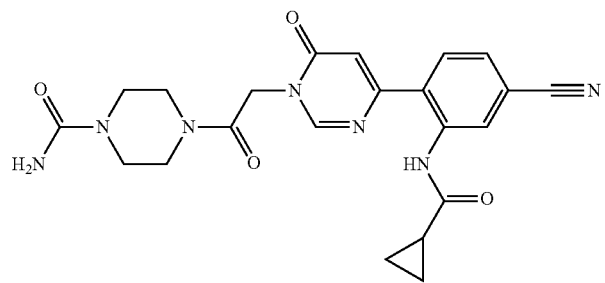 [SMILES: N#Cc1ccc(-c2cc(=O)n(CC(=O)N3CCN(C(N)=O)CC3)cn2)c(NC(=O)C2CC2)c1]

TABLE 87-continued
I-0506 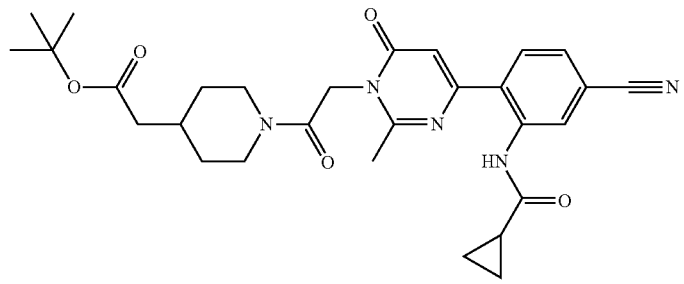 [SMILES: Cc1nc(-c2ccc(C#N)cc2NC(=O)C2CC2)cc(=O)n1CC(=O)N1CCC(CC(=O)OC(C)(C)C)CC1]
I-0507 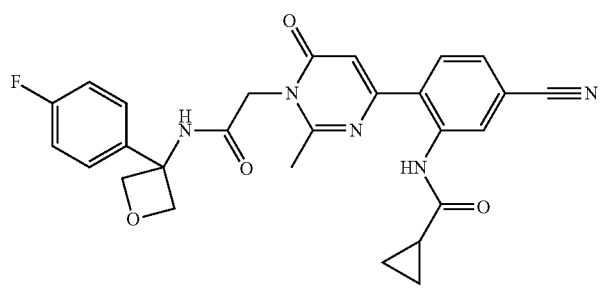 [SMILES: Cc1nc(-c2ccc(C#N)cc2NC(=O)C2CC2)cc(=O)n1CC(=O)NC1(c2ccc(F)cc2)COC1]
I-0508 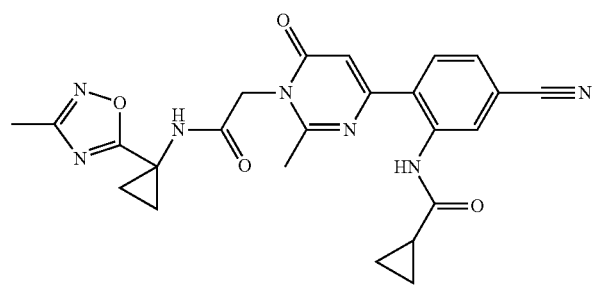 [SMILES: Cc1noc(C2(NC(=O)Cn3c(C)nc(-c4ccc(C#N)cc4NC(=O)C4CC4)cc3=O)CC2)n1]
TABLE 88
I-0509 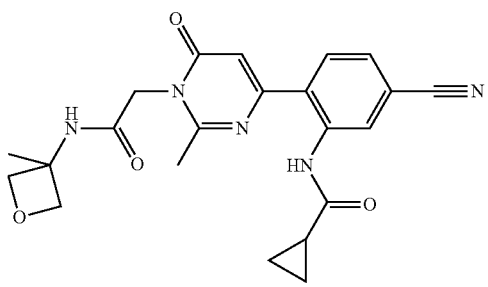 [SMILES: Cc1nc(-c2ccc(C#N)cc2NC(=O)C2CC2)cc(=O)n1CC(=O)NC1(C)COC1]
I-0510 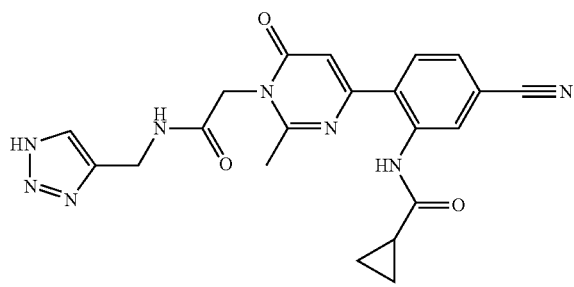 [SMILES: Cc1nc(-c2ccc(C#N)cc2NC(=O)C2CC2)cc(=O)n1CC(=O)NCc1c[nH]nn1]

TABLE 88-continued
I-0511
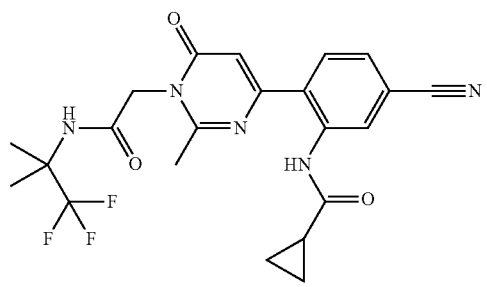 [SMILES: Cc1nc(-c2ccc(C#N)cc2NC(=O)C2CC2)cc(=O)n1CC(=O)NC(C)(C)C(F)(F)F]
I-0512
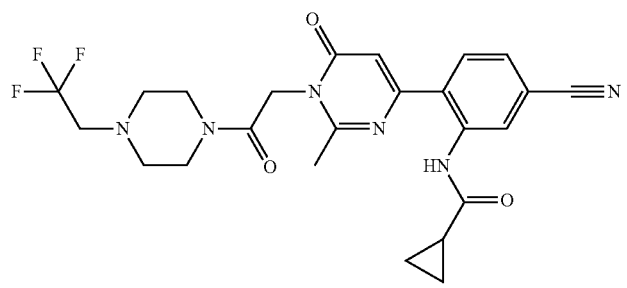 [SMILES: Cc1nc(-c2ccc(C#N)cc2NC(=O)C2CC2)cc(=O)n1CC(=O)N1CCN(CC(F)(F)F)CC1]
I-0513
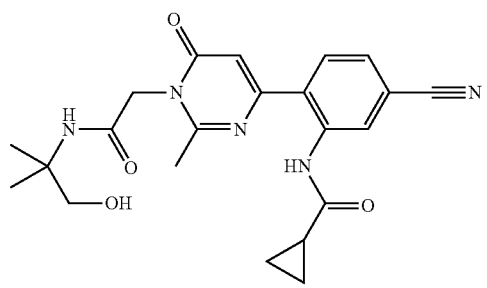 [SMILES: Cc1nc(-c2ccc(C#N)cc2NC(=O)C2CC2)cc(=O)n1CC(=O)NC(C)(C)CO]
I-0514
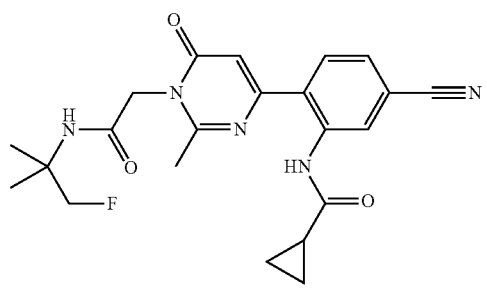 [SMILES: Cc1nc(-c2ccc(C#N)cc2NC(=O)C2CC2)cc(=O)n1CC(=O)NC(C)(C)CF]
TABLE 89
I-0515
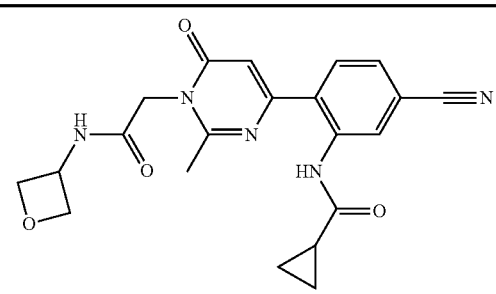

TABLE 89-continued
I-0516
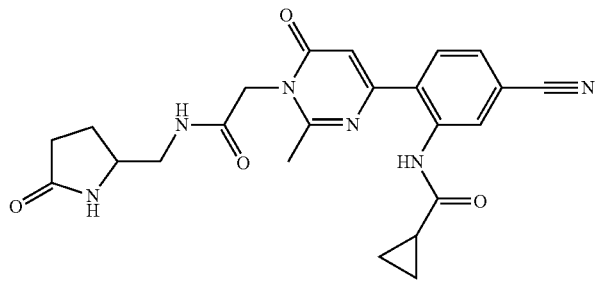 [SMILES: Cc1nc(-c2ccc(C#N)cc2NC(=O)C2CC2)cc(=O)n1CC(=O)NCC1CCC(=O)N1]
I-0517
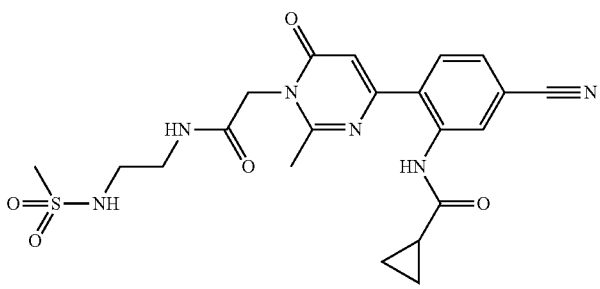 [SMILES: Cc1nc(-c2ccc(C#N)cc2NC(=O)C2CC2)cc(=O)n1CC(=O)NCCNS(C)(=O)=O]
I-0518
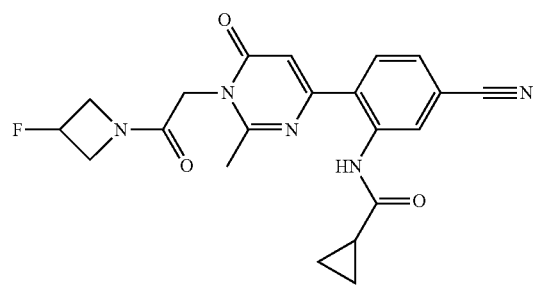 [SMILES: Cc1nc(-c2ccc(C#N)cc2NC(=O)C2CC2)cc(=O)n1CC(=O)N1CC(F)C1]
I-0519
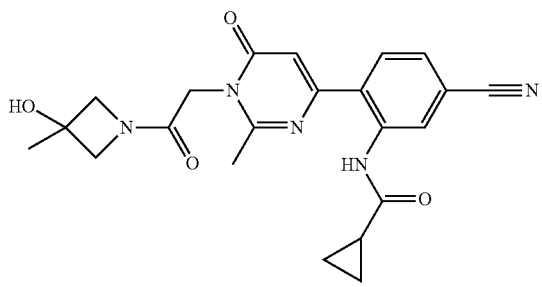 [SMILES: Cc1nc(-c2ccc(C#N)cc2NC(=O)C2CC2)cc(=O)n1CC(=O)N1CC(C)(O)C1]
I-0520
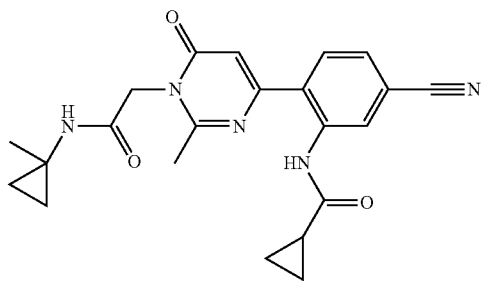 [SMILES: Cc1nc(-c2ccc(C#N)cc2NC(=O)C2CC2)cc(=O)n1CC(=O)NC1(C)CC1]

TABLE 90
I-0521
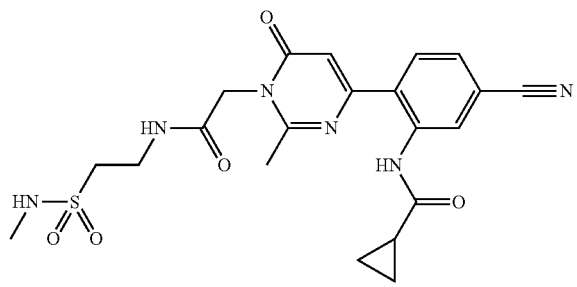 [SMILES: CNS(=O)(=O)CCNC(=O)Cn1c(C)nc(-c2ccc(C#N)cc2NC(=O)C2CC2)cc1=O]
I-0522
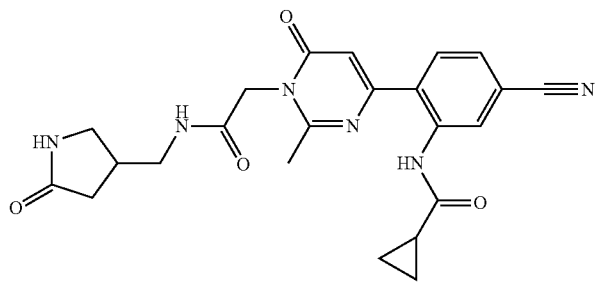 [SMILES: Cc1nc(-c2ccc(C#N)cc2NC(=O)C2CC2)cc(=O)n1CC(=O)NCC1CNC(=O)C1]
I-0523
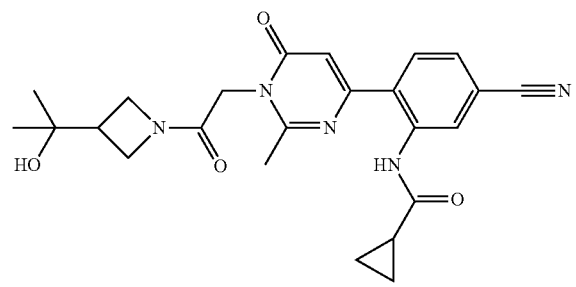 [SMILES: Cc1nc(-c2ccc(C#N)cc2NC(=O)C2CC2)cc(=O)n1CC(=O)N1CC(C(C)(C)O)C1]
I-0524
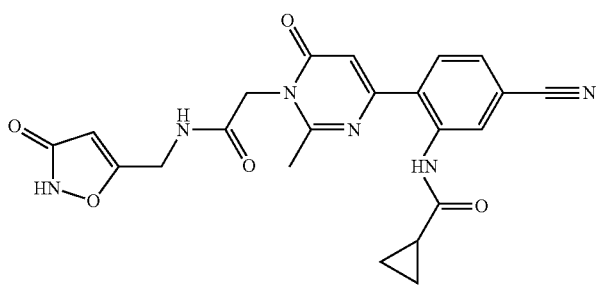 [SMILES: Cc1nc(-c2ccc(C#N)cc2NC(=O)C2CC2)cc(=O)n1CC(=O)NCc1cc(=O)[nH]o1]
I-0525
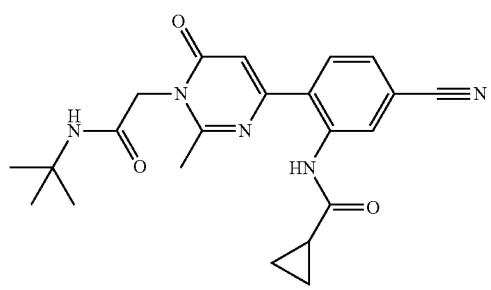 [SMILES: Cc1nc(-c2ccc(C#N)cc2NC(=O)C2CC2)cc(=O)n1CC(=O)NC(C)(C)C]

TABLE 90-continued
I-0526
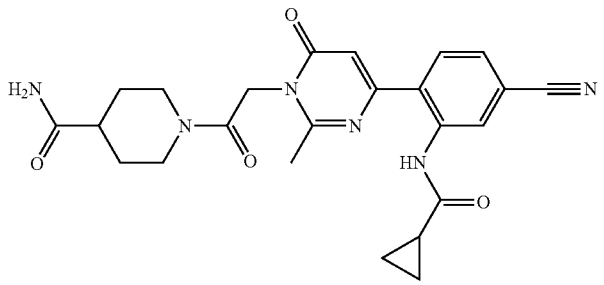 [SMILES: Cc1nc(-c2ccc(C#N)cc2NC(=O)C2CC2)cc(=O)n1CC(=O)N1CCC(C(N)=O)CC1]
TABLE 91
I-0527
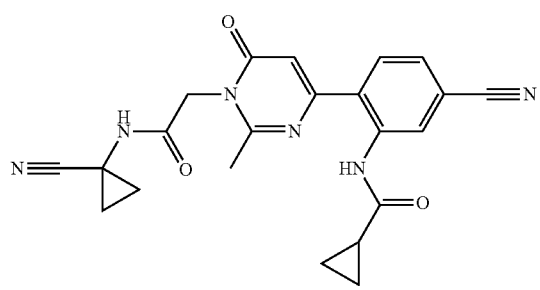 [SMILES: Cc1nc(-c2ccc(C#N)cc2NC(=O)C2CC2)cc(=O)n1CC(=O)NC1(C#N)CC1]
I-0528
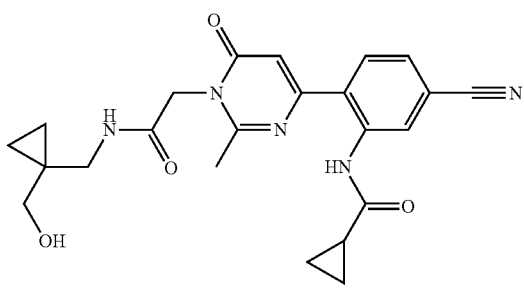 [SMILES: Cc1nc(-c2ccc(C#N)cc2NC(=O)C2CC2)cc(=O)n1CC(=O)NCC1(CO)CC1]
I-0529
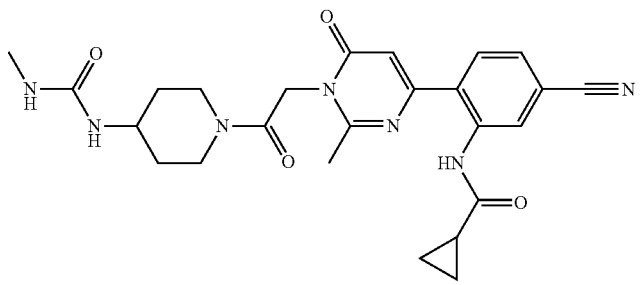 [SMILES: CNC(=O)NC1CCN(C(=O)Cn2c(C)nc(-c3ccc(C#N)cc3NC(=O)C3CC3)cc2=O)CC1]
I-0530
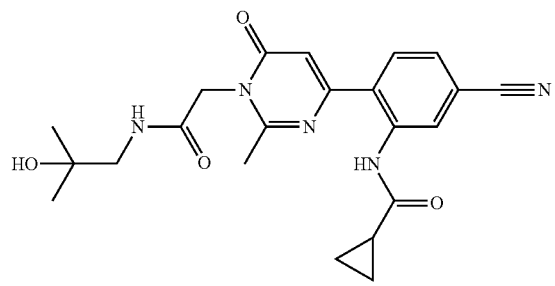 [SMILES: Cc1nc(-c2ccc(C#N)cc2NC(=O)C2CC2)cc(=O)n1CC(=O)NCC(C)(C)O]

TABLE 91-continued

I-0531

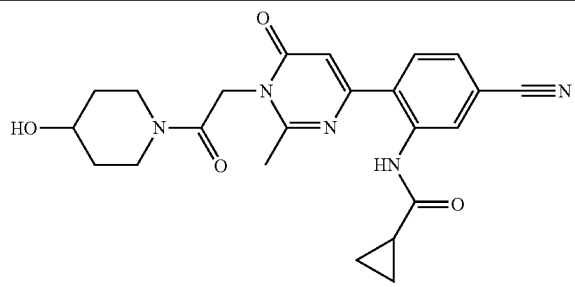

Physical constants of the compound are shown below. RT means retention time (min), MS means [M+H]$^+$.

TABLE 92

| Example No | LC/MS method | RT | MS |
|---|---|---|---|
| I-0001 | B | 2.48 | 306 |
| I-0002 | A | 1.98 | 411 |
| I-0003 | A | 1.98 | 411 |
| I-0004 |  | NMR |  |
| I-0005 | A | 2.17 | 291 |
| I-0006 | A | 2.35 | 305 |
| I-0007 | A | 2.66 | 367 |
| I-0008 | A | 2.18 | 411 |
| I-0009 | A | 2.56 | 411 |
| I-0010 | D | 2.09 | 460 |
| I-0011 | D | 2.33 | 516 |
| I-0012 | D | 1.67 | 460 |
| I-0013 | B | 2.23 | 516 |
| I-0014 | B | 2.62 | 607 |
| I-0015 | B | 2.34 | 517 |
| I-0016 | B | 2.33 | 531 |
| I-0017 | B | 2.60 | 607 |
| I-0018 | B | 2.30 | 517 |
| I-0019 | B | 2.21 | 516 |
| I-0020 | B | 2.33 | 532 |
| I-0021 | B | 2.76 | 473 |
| I-0022 | B | 2.15 | 417 |
| I-0023 | B | 2.59 | 348 |
| I-0024 | A | 2.62 | 482 |
| I-0025 | A | 2.29 | 421 |
| I-0026 | A | 2.54 | 376 |
| I-0027 | A | 2.13 | 378 |
| I-0028 | A | 2.26 | 390 |
| I-0029 | A | 2.21 | 392 |
| I-0030 | A | 2.16 | 392 |
| I-0031 | A | 2.06 | 405 |
| I-0032 | A | 1.79 | 405 |
| I-0033 | A | 2.31 | 418 |
| I-0034 | A | 2.73 | 424 |
| I-0035 | A | 2.14 | 434 |
| I-0036 | A | 2.86 | 439 |
| I-0037 | A | 2.09 | 446 |
| I-0038 | A | 2.20 | 456 |
| I-0039 | A | 2.20 | 406 |
| I-0040 | A | 2.14 | 406 |
| I-0041 | A | 2.33 | 469 |
| I-0042 | A | 2.29 | 446 |
| I-0043 | A | 2.28 | 448 |
| I-0044 | A | 2.17 | 420 |
| I-0045 | A | 2.35 | 460 |
| I-0046 | A | 2.65 | 522 |
| I-0047 | A | 2.59 | 522 |
| I-0048 | A | 1.86 | 461 |
| I-0049 | A | 2.41 | 446 |
| I-0050 | A | 2.40 | 434 |
| I-0051 | A | 2.30 | 420 |
| I-0052 | A | 2.04 | 422 |
| I-0053 | A | 2.57 | 522 |
| I-0054 | A | 2.46 | 469 |
| I-0055 | A | 2.01 | 449 |
| I-0056 | A | 2.24 | 420 |
| I-0057 | A | 2.36 | 446 |
| I-0058 | A | 2.14 | 462 |
| I-0059 | A | 2.12 | 503 |
| I-0060 | A | 2.23 | 484 |
| I-0061 | A | 2.46 | 482 |
| I-0062 | A | 2.57 | 474 |
| I-0063 | A | 2.35 | 460 |
| I-0064 | A | 2.21 | 434 |
| I-0065 | A | 2.12 | 392 |
| I-0066 | A | 2.23 | 432 |
| I-0067 | A | 2.23 | 448 |
| I-0068 | A | 2.23 | 432 |
| I-0069 | A | 2.16 | 418 |
| I-0070 | A | 2.35 | 434 |
| I-0071 | A | 2.21 | 432 |
| I-0072 | A | 2.45 | 486 |
| I-0073 | A | 2.28 | 432 |
| I-0074 | B | 2.91 | 425 |
| I-0075 | A | 2.55 | 486 |
| I-0076 | A | 2.78 | 480 |
| I-0077 | A | 2.67 | 441 |
| I-0078 | A | 2.17 | 443 |
| I-0079 | A | 2.38 | 401 |
| I-0080 | A | 2.29 | 387 |

TABLE 93

| Example No | LC/MS method | RT | MS |
|---|---|---|---|
| I-0081 | A | 2.25 | 452 |
| I-0082 | A | 2.12 | 431 |
| I-0083 | A | 2.13 | 442 |
| I-0084 | A | 2.36 | 404 |
| I-0085 | A | 2.33 | 373 |
| I-0086 | A | 2.32 | 418 |
| I-0087 | A | 2.64 | 438 |
| I-0088 | A | 2.56 | 469 |
| I-0089 | A | 2.33 | 451 |
| I-0090 | A | 2.39 | 399 |
| I-0091 | A | 2.24 | 416 |
| I-0092 | A | 2.54 | 469 |
| I-0093 | A | 2.23 | 466 |
| I-0094 | A | 2.19 | 440 |
| I-0095 | A | 2.58 | 432 |
| I-0096 | A | 2.19 | 406 |
| I-0097 | A | 2.12 | 445 |
| I-0098 | A | 2.24 | 406 |
| I-0099 | A | 2.71 | 441 |
| I-0100 | A | 2.82 | 480 |
| I-0101 | A | 2.01 | 496 |
| I-0102 | A | 2.83 | 452 |
| I-0103 | A | 2.75 | 438 |
| I-0104 | A | 2.18 | 443 |
| I-0105 | B | 1.89 | 369 |

TABLE 93-continued

| Example No | LC/MS method | RT | MS |
|---|---|---|---|
| I-0106 | B | 1.79 | 342 |
| I-0107 | B | 2.13 | 548 |
| I-0108 | B | 1.78 | 303 |
| I-0109 | B | 2.34 | 389 |
| I-0110 | B | 2.13 | 374 |
| I-0111 | B | 2.63 | 465 |
| I-0112 | B | 2.33 | 451 |
| I-0113 | A | 2.48 | 460 |
| I-0114 | A | 2.44 | 434 |
| I-0115 | A | 1.85 | 495 |
| I-0116 | A | 2.07 | 495 |
| I-0117 | A | 1.99 | 462 |
| I-0118 | A | 2.07 | 485 |
| I-0119 | A | 2.10 | 432 |
| I-0120 | A | 2.15 | 471 |
| I-0121 | A | 2.02 | 486 |
| I-0122 | A | 1.86 | 515 |
| I-0123 | A | 2.31 | 439 |
| I-0124 | A | 2.18 | 458 |
| I-0125 | A | 2.45 | 472 |
| I-0126 | A | 2.03 | 445 |
| I-0127 | A | 2.13 | 459 |
| I-0128 | A | 2.16 | 528 |
| I-0129 | A | 1.78 | 528 |
| I-0130 | A | 2.03 | 488 |
| I-0131 | A | 1.77 | 487 |
| I-0132 | A | 2.00 | 462 |
| I-0133 | A | 2.07 | 481 |
| I-0134 | A | 2.17 | 446 |
| I-0135 | A | 1.97 | 478 |
| I-0136 | A | 1.95 | 496 |
| I-0137 | A | 2.22 | 427 |
| I-0138 | A | 1.80 | 496 |
| I-0139 | A | 2.10 | 474 |
| I-0140 | A | 2.05 | 506 |
| I-0141 | A | 2.28 | 470 |
| I-0142 | A | 1.99 | 481 |
| I-0143 | A | 2.19 | 492 |
| I-0144 | A | 2.16 | 476 |
| I-0145 | A | 2.26 | 509 |
| I-0146 | A | 1.72 | 505 |
| I-0147 | A | 2.04 | 474 |
| I-0148 | A | 1.82 | 515 |
| I-0149 | A | 2.51 | 444 |
| I-0150 | A | 1.61 | 428 |
| I-0151 | A | 2.39 | 498 |
| I-0152 | A | 2.63 | 498 |
| I-0153 | A | 2.65 | 536 |
| I-0154 | A | 1.96 | 558 |
| I-0155 | A | 2.52 | 503 |
| I-0156 | A | 2.23 | 535 |
| I-0157 | A | 2.46 | 517 |
| I-0158 | A | 2.27 | 534 |
| I-0159 | A | 2.31 | 548 |
| I-0160 | A | 2.45 | 520 |

TABLE 94

| Example No | LC/MS method | RT | MS |
|---|---|---|---|
| I-0161 | A | 2.50 | 522 |
| I-0162 | A | 2.26 | 538 |
| I-0163 | A | 2.29 | 508 |
| I-0164 | A | 2.47 | 489 |
| I-0165 | A | 2.16 | 524 |
| I-0166 | A | 2.65 | 548 |
| I-0167 | A | 2.57 | 570 |
| I-0168 | A | 2.19 | 507 |
| I-0169 | A | 2.36 | 542 |
| I-0170 | A | 2.35 | 547 |
| I-0171 | A | 2.23 | 562 |
| I-0172 | A | 2.25 | 494 |
| I-0173 | A | 2.17 | 524 |
| I-0174 | A | 2.34 | 548 |

TABLE 94-continued

| Example No | LC/MS method | RT | MS |
|---|---|---|---|
| I-0175 | A | 2.42 | 534 |
| I-0176 | A | 2.18 | 557 |
| I-0177 | A | 2.35 | 556 |
| I-0178 | A | 2.56 | 570 |
| I-0179 | A | 2.17 | 547 |
| I-0180 | A | 2.40 | 464 |
| I-0181 | A | 2.48 | 478 |
| I-0182 | A | 2.24 | 522 |
| I-0183 | A | 2.35 | 535 |
| I-0184 | A | 2.20 | 535 |
| I-0185 | A | 2.45 | 520 |
| I-0186 | A | 2.29 | 557 |
| I-0187 | A | 2.38 | 522 |
| I-0188 | A | 2.19 | 554 |
| I-0189 | A | 2.46 | 546 |
| I-0190 | A | 2.62 | 546 |
| I-0191 | A | 2.19 | 521 |
| I-0192 | A | 2.19 | 557 |
| I-0193 | A | 2.25 | 557 |
| I-0194 | A | 2.27 | 550 |
| I-0195 | A | 2.37 | 546 |
| I-0196 | A | 2.20 | 561 |
| I-0197 | A | 2.16 | 538 |
| I-0198 | A | 2.60 | 584 |
| I-0199 | A | 2.62 | 548 |
| I-0200 | A | 2.67 | 482 |
| I-0201 | A | 2.63 | 458 |
| I-0202 | A | 2.35 | 412 |
| I-0203 | B | 2.05 | 401 |
| I-0204 | B | 1.88 | 406 |
| I-0205 | A | 2.11 | 456 |
| I-0206 | A | 2.79 | 431 |
| I-0207 | A | 2.20 | 425 |
| I-0208 | A | 1.85 | 412 |
| I-0209 | B | 2.04 | 413 |
| I-0210 | B | 2.02 | 441 |
| I-0211 | B | 1.92 | 460 |
| I-0212 | B | 1.94 | 432 |
| I-0213 | B | 1.93 | 408 |
| I-0214 | B | 1.92 | 420 |
| I-0215 | B | 1.91 | 448 |
| I-0216 | A | 2.75 | 417 |
| I-0217 | A | 2.09 | 480 |
| I-0218 | A | 2.38 | 457 |
| I-0219 | A | 2.34 | 488 |
| I-0220 | A | 2.21 | 528 |
| I-0221 | B | 1.93 | 401 |
| I-0222 | B | 1.81 | 408 |
| I-0223 | B | 1.82 | 420 |
| I-0224 | A | 2.35 | 468 |
| I-0225 | A | 2.33 | 473 |
| I-0226 | A | 2.22 | 455 |
| I-0227 | A | 1.94 | 430 |
| I-0228 | A | 2.30 | 457 |
| I-0229 | B | 1.85 | 401 |
| I-0230 | B | 1.74 | 408 |
| I-0231 | B | 1.75 | 420 |
| I-0232 | A | 2.31 | 477 |
| I-0233 | A | 2.08 | 474 |
| I-0234 | A | 2.23 | 475 |
| I-0235 | A | 1.97 | 448 |
| I-0236 | A | 2.05 | 412 |
| I-0237 | A | 1.99 | 448 |
| I-0238 | A | 1.78 | 442 |
| I-0239 | A | 1.20 | 469 |
| I-0240 | A | 2.53 | 454 |

TABLE 95

| Example No | LC/MS method | RT | MS |
|---|---|---|---|
| I-0241 | A | 2.18 | 498 |
| I-0242 | B | 2.02 | 441 |

TABLE 95-continued

| Example No | LC/MS method | RT | MS |
|---|---|---|---|
| I-0243 | B | 1.66 | 432 |
| I-0244 | A | 1.91 | 378 |
| I-0245 | B | 2.00 | 392 |
| I-0246 | B | 1.21 | 321 |
| I-0247 | B | 1.33 | 336 |
| I-0248 | B | 1.46 | 400 |
| I-0249 | B | 1.32 | 386 |
| I-0250 | B | 1.58 | 439 |
| I-0251 | B | 1.90 | 422 |
| I-0252 | B | 1.64 | 439 |
| I-0253 | A | 2.22 | 424 |
| I-0254 | B | 2.37 | 423 |
| I-0255 | B | 2.18 | 409 |
| I-0256 | B | 1.17 | 414 |
| I-0257 | B | 1.77 | 440 |

TABLE 96

| Example No | LC/MS method | RT | MS |
|---|---|---|---|
| I-0258 | E | 1.42 | 353 |
| I-0259 | B | 1.63 | 362 |
| I-0260 | B | 1.57 | 369 |
| I-0261 | B | 1.77 | 381 |
| I-0262 | B | 2.00 | 393 |
| I-0263 | B | 2.04 | 399 |
| I-0264 | E | 1.85 | 406 |
| I-0265 | B | 2.03 | 407 |
| I-0266 | B | 2.31 | 408 |
| I-0267 | B | 1.70 | 412 |
| I-0268 | B | 1.53 | 416 |
| I-0269 | B | 2.14 | 421 |
| I-0270 | B | 1.80 | 422 |
| I-0271 | B | 1.75 | 429 |
| I-0272 | B | 2.12 | 433 |
| I-0273 | B | 2.22 | 433 |
| I-0274 | B | 1.75 | 435 |
| I-0275 | B | 1.64 | 435 |
| I-0276 | B | 2.24 | 435 |
| I-0277 | E | 1.89 | 437 |
| I-0278 | B | 1.98 | 438 |
| I-0279 | B | 2.00 | 438 |
| I-0280 | A | 2.30 | 441 |
| I-0281 | B | 1.34 | 445 |
| I-0282 | B | 1.92 | 445 |
| I-0283 | E | 2.69 | 446 |
| I-0284 | B | 2.72 | 449 |
| I-0285 | B | 1.99 | 449 |
| I-0286 | B | 1.50 | 451 |
| I-0287 | B | 1.24 | 452 |
| I-0288 | A | 2.16 | 452 |
| I-0289 | A | 2.29 | 452 |
| I-0290 | B | 2.16 | 454 |
| I-0291 | A | 2.62 | 455 |
| I-0292 | A | 2.47 | 457 |
| I-0293 | A | 2.41 | 457 |
| I-0294 | A | 2.23 | 458 |
| I-0295 | B | 1.89 | 457 |
| I-0296 | B | 2.50 | 459 |
| I-0297 | A | 2.37 | 461 |
| I-0298 | B | 1.54 | 461 |
| I-0299 | B | 2.35 | 461 |
| I-0300 | E | 1.60 | 461 |
| I-0301 | E | 1.89 | 461 |
| I-0302 | E | 2.02 | 463 |
| I-0303 | A | 2.13 | 466 |
| I-0304 | B | 2.49 | 466 |
| I-0305 | A | 2.13 | 466 |
| I-0306 | A | 2.55 | 466 |
| I-0307 | A | 2.46 | 466 |
| I-0308 | B | 1.44 | 468 |
| I-0309 | B | 1.61 | 469 |
| I-0310 | B | 1.88 | 470 |

TABLE 96-continued

| Example No | LC/MS method | RT | MS |
|---|---|---|---|
| I-0311 | A | 2.60 | 471 |
| I-0312 | A | 2.76 | 471 |
| I-0313 | A | 2.74 | 471 |
| I-0314 | A | 2.35 | 473 |
| I-0315 | B | 1.69 | 474 |
| I-0316 | B | 2.03 | 474 |
| I-0317 | B | 1.70 | 477 |
| I-0318 | A | 2.21 | 478 |
| I-0319 | A | 2.11 | 478 |
| I-0320 | A | 2.17 | 478 |
| I-0321 | A | 2.20 | 480 |
| I-0322 | B | 2.03 | 481 |
| I-0323 | A | 1.99 | 482 |
| I-0324 | B | 1.72 | 483 |
| I-0325 | B | 2.15 | 484 |
| I-0326 | A | 2.71 | 486 |
| I-0327 | A | 2.32 | 487 |
| I-0328 | B | 1.74 | 488 |
| I-0329 | E | 1.84 | 488 |
| I-0330 | A | 2.09 | 489 |
| I-0331 | A | 2.12 | 490 |
| I-0332 | A | 2.33 | 492 |
| I-0333 | A | 2.13 | 502 |
| I-0334 | B | 1.61 | 504 |
| I-0335 | A | 2.07 | 505 |
| I-0336 | A | 2.03 | 505 |
| I-0337 | A | 2.08 | 508 |

TABLE 97

| Example No | LC/MS method | RT | MS |
|---|---|---|---|
| I-0338 | A | 2.14 | 508 |
| I-0339 | B | 2.00 | 512 |
| I-0340 | A | 2.02 | 515 |
| I-0341 | B | 2.68 | 516 |
| I-0342 | A | 2.11 | 519 |
| I-0343 | A | 2.04 | 519 |
| I-0344 | A | 2.44 | 520 |
| I-0345 | B | 2.18 | 520 |
| I-0346 | A | 1.81 | 521 |
| I-0347 | A | 1.92 | 525 |
| I-0348 | A | 2.17 | 525 |
| I-0349 | A | 2.28 | 526 |
| I-0350 | A | 2.15 | 533 |
| I-0351 | A | 2.16 | 533 |
| I-0352 | A | 2.33 | 534 |
| I-0353 | A | 2.30 | 535 |
| I-0354 | A | 2.19 | 536 |
| I-0355 | A | 2.14 | 540 |
| I-0356 | A | 2.14 | 548 |
| I-0357 | A | 1.87 | 549 |
| I-0358 | A | 2.12 | 551 |
| I-0359 | A | 2.32 | 555 |
| I-0360 | B | 1.97 | 559 |
| I-0361 | A | 1.99 | 560 |
| I-0362 | A | 2.18 | 560 |
| I-0363 | A | 2.19 | 562 |
| I-0364 | A | 2.22 | 562 |
| I-0365 | A | 1.80 | 562 |
| I-0366 | A | 2.38 | 569 |
| I-0367 | B | 2.13 | 571 |
| I-0368 | A | 2.47 | 580 |
| I-0369 | A | 2.57 | 582 |
| I-0370 | A | 2.35 | 583 |
| I-0371 | B | 1.82 | 364 |
| I-0372 | B | 1.75 | 398 |
| I-0373 | B | 1.79 | 410 |
| I-0374 | B | 1.86 | 412 |
| I-0375 | B | 2.08 | 419 |
| I-0376 | B | 1.93 | 442 |
| I-0377 | E | 1.54 | 443 |
| I-0378 | B | 1.76 | 459 |
| I-0379 | B | 2.03 | 468 |

TABLE 97-continued

| Example No | LC/MS method | RT | MS |
|---|---|---|---|
| I-0380 | B | 1.34 | 475 |
| I-0381 | B | 1.30 | 482 |
| I-0382 | B | 2.30 | 486 |
| I-0383 | B | 1.57 | 491 |
| I-0384 | B | 1.37 | 491 |
| I-0385 | B | 1.61 | 492 |
| I-0386 | B | 1.85 | 501 |
| I-0387 | E | 2.23 | 532 |
| I-0388 | A | 2.12 | 321 |
| I-0389 | A | 1.52 | 384 |
| I-0390 | A | 1.83 | 393 |
| I-0391 | A | 1.78 | 403 |
| I-0392 | A | 1.84 | 405 |
| I-0393 | A | 1.58 | 407 |
| I-0394 | A | 1.46 | 407 |
| I-0395 | A | 1.74 | 409 |
| I-0396 | A | 1.81 | 412 |
| I-0397 | A | 1.35 | 412 |
| I-0398 | A | 1.27 | 412 |
| I-0399 | A | 1.31 | 414 |
| I-0400 | A | 1.39 | 414 |
| I-0401 | A | 1.80 | 415 |
| I-0402 | A | 1.36 | 416 |
| I-0403 | B | 1.74 | 416 |
| I-0404 | A | 1.55 | 417 |
| I-0405 | A | 2.01 | 417 |
| I-0406 | A | 1.41 | 418 |
| I-0407 | A | 2.30 | 419 |
| I-0408 | A | 1.70 | 419 |
| I-0409 | A | 1.68 | 420 |
| I-0410 | A | 1.67 | 421 |
| I-0411 | A | 1.57 | 421 |
| I-0412 | A | 1.70 | 423 |
| I-0413 | A | 1.62 | 423 |
| I-0414 | A | 1.23 | 423 |
| I-0415 | A | 2.03 | 425 |
| I-0416 | A | 1.75 | 426 |
| I-0417 | A | 1.34 | 426 |
| I-0418 | A | 1.27 | 426 |
| I-0419 | A | 1.63 | 431 |
| I-0420 | A | 1.54 | 431 |
| I-0421 | A | 1.53 | 432 |
| I-0422 | A | 1.66 | 433 |
| I-0423 | A | 1.58 | 433 |
| I-0424 | A | 1.98 | 435 |
| I-0425 | A | 1.58 | 435 |
| I-0426 | A | 1.66 | 437 |
| I-0427 | E | 2.09 | 439 |
| I-0428 | A | 1.18 | 439 |
| I-0429 | A | 1.33 | 439 |
| I-0430 | A | 1.20 | 441 |
| I-0431 | A | 1.50 | 442 |
| I-0432 | A | 1.76 | 444 |
| I-0433 | B | 1.80 | 444 |
| I-0434 | A | 1.61 | 445 |
| I-0435 | A | 1.54 | 445 |
| I-0436 | A | 1.83 | 447 |
| I-0437 | A | 1.50 | 448 |
| I-0438 | A | 1.47 | 448 |
| I-0439 | A | 1.65 | 448 |
| I-0440 | B | 1.21 | 449 |
| I-0441 | A | 1.65 | 449 |
| I-0442 | A | 1.52 | 450 |
| I-0443 | A | 1.36 | 452 |
| I-0444 | A | 1.93 | 452 |
| I-0445 | A | 1.23 | 453 |
| I-0446 | A | 1.21 | 454 |
| I-0447 | A | 1.75 | 456 |
| I-0448 | A | 1.97 | 456 |
| I-0449 | A | 1.80 | 456 |
| I-0450 | A | 1.48 | 458 |
| I-0451 | A | 1.44 | 458 |
| I-0452 | A | 1.61 | 458 |
| I-0453 | A | 1.89 | 459 |
| I-0454 | A | 1.62 | 459 |
| I-0455 | A | 2.07 | 459 |
| I-0456 | A | 1.49 | 460 |
| I-0457 | A | 2.22 | 461 |
| I-0458 | A | 1.54 | 462 |
| I-0459 | A | 1.52 | 463 |
| I-0460 | A | 1.44 | 466 |
| I-0461 | A | 2.01 | 469 |
| I-0462 | A | 2.17 | 471 |
| I-0463 | A | 1.51 | 472 |
| I-0464 | A | 1.60 | 472 |
| I-0465 | A | 1.64 | 472 |
| I-0466 | A | 1.49 | 473 |
| I-0467 | A | 1.82 | 473 |
| I-0468 | A | 1.78 | 474 |
| I-0469 | A | 1.73 | 474 |
| I-0470 | B | 1.67 | 475 |
| I-0471 | B | 1.22 | 477 |
| I-0472 | A | 1.45 | 480 |
| I-0473 | A | 1.57 | 482 |
| I-0474 | A | 1.61 | 482 |
| I-0475 | A | 1.78 | 483 |
| I-0476 | A | 1.52 | 494 |
| I-0477 | A | 2.58 | 495 |
| I-0478 | A | 1.92 | 496 |
| I-0479 | A | 1.55 | 501 |
| I-0480 | A | 2.07 | 501 |
| I-0481 | A | 2.08 | 502 |
| I-0482 | B | 1.71 | 503 |
| I-0483 | A | 1.58 | 508 |
| I-0484 | A | 2.03 | 511 |

TABLE 98

| Example No | LC/MS method | RT | MS |
|---|---|---|---|
| I-0485 | A | 2.03 | 512 |
| I-0486 | A | 1.90 | 513 |
| I-0487 | A | 1.92 | 517 |
| I-0488 | A | 2.01 | 520 |
| I-0489 | A | 2.01 | 523 |
| I-0490 | A | 2.09 | 524 |
| I-0491 | A | 1.99 | 532 |
| I-0492 | A | 2.22 | 532 |
| I-0493 | A | 2.02 | 532 |
| I-0494 | A | 2.40 | 533 |
| I-0495 | A | 2.13 | 535 |
| I-0496 | A | 2.36 | 543 |
| I-0497 | A | 1.97 | 550 |
| I-0498 | A | 1.96 | 550 |
| I-0499 | B | 1.13 | 579 |
| I-0500 | A | 2.11 | 593 |
| I-0501 | A | 2.29 | 600 |
| I-0502 | A | 1.18 | 451 |
| I-0503 | A | 1.49 | 394 |
| I-0504 | A | 1.10 | 409 |
| I-0505 | A | 1.19 | 464 |
| I-0506 | A | 2.12 | 534 |
| I-0507 | A | 1.76 | 502 |
| I-0508 | A | 1.49 | 474 |
| I-0509 | A | 1.33 | 422 |
| I-0510 | A | 1.23 | 433 |
| I-0511 | A | 1.90 | 462 |
| I-0512 | A | 1.77 | 503 |
| I-0513 | A | 1.37 | 424 |
| I-0514 | A | 1.69 | 426 |
| I-0515 | A | 1.24 | 408 |
| I-0516 | A | 1.19 | 449 |
| I-0517 | A | 1.27 | 473 |
| I-0518 | A | 1.38 | 410 |
| I-0519 | A | 1.24 | 422 |
| I-0520 | A | 1.50 | 406 |
| I-0521 | A | 1.30 | 473 |
| I-0522 | A | 1.15 | 449 |
| I-0523 | A | 1.34 | 450 |
| I-0524 | A | 1.31 | 449 |
| I-0525 | A | 1.73 | 408 |
| I-0526 | A | 1.22 | 463 |
| I-0527 | A | 1.43 | 417 |

TABLE 98-continued

| Example No | LC/MS method | RT | MS |
|---|---|---|---|
| I-0528 | A | 1.31 | 436 |
| I-0529 | A | 1.26 | 492 |
| I-0530 | A | 1.29 | 424 |
| I-0531 | A | 1.25 | 436 |

NMR data of Compound I-0004:

$^1$H-NMR (CDCl$_3$) δ 8.02 (m, 2H), 7.35 (m, 3H), 7.29 (d, J=1.0 Hz, 2H), 7.27 (d, J=0.7 Hz, 2H), 6.44 (s, 1H), 5.27 (s, 2H), 4.62 (t, J=4.9 Hz, 1H), 3.41 (td, J=6.9, 5.3 Hz, 2H), 1.45 (m, 2H), 1.19 (m, 2H), 1.04 (m, 2H), 0.82 (t, J=7.3 Hz, 3H).

Test Example 1

Evaluation of Aoutotaxin Inhibitor

Solution A containing 25 mM Tris-HCl buffer (pH7.5), 100 mM NaCl, 5 mM MgCl2, and 0.1% BSA was prepared. Mouse autotaxin enzyme (purchased from R&D system) was diluted with Solution A, and 5 µl of which was added to a solution of test compound in DMSO. Furthermore, 5 µl of 0.5 µM TG-mTMP in Solution A was added and allowed react at room temperature for 2 hours. 5 µl of 150 mM EDTA in Solution A was added to quench the reaction, and a fluorescent dye TokyoGreen, which was produced by the reaction, was detected. The fluorescence was detected using ViewLux (PerkinElmer, Inc.) with an excitation wavelength of 480 nm and a fluorescence wavelength of 540 nm.

The percent inhibition of the test compound was calculated by assuming the sample with no test compound as 0% inhibition and the test sample with no enzyme as 100% inhibition, and the percent inhibitions at different concentrations of the test compound were plotted to obtain a concentration-dependent curve. The IC50 value, which is the concentration of the test compound that resulted in 50% inhibition, was determined from the curve.

[Chemical Formula 127]

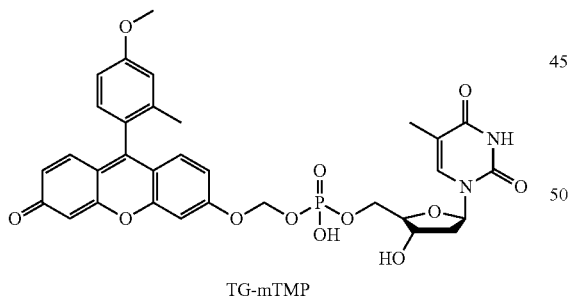

TG-mTMP

Test Example 2

Evaluation of Autotaxin Inhibitor

Solution B containing 100 mM Tris-HCl buffer (pH7.5), 150 mM NaCl, 5 mM MgCl2, and 0.05% Triton X-100 was prepared. Human autotaxin enzyme (purchased from R&D System) was diluted with Solution B, and 2.5 µl of which was added to a solution of test compound in DMSO. Furthermore, 2.5 µl of 200 µM 18:0 Lyso PC (purchased from Avanti Polar Lipids) in Solution B was added and allowed to react at room temperature for 2 hours. After completion of the reaction, 15 µl of the coline assay reagent. (100 mM Tris-HCl buffer (pH7.5), 5 mM. MgCl2, 77 µg/ml coline oxidase, 10 µg/ml peroxydase, 25µM 10-acetyl-3,7-dihydroxyphenoxazine, and excess autotaxin inhibitor) was added and allowed to react at room temperature for 20 minutes. The fluorescent dye Resorufin, which was produced by the reaction, was detected. The fluorescence was detected using ViewLux (PerkinElmer, Inc.) with a excitation wavelength of 531 nm and a fluorescence wavelength of 598 nm.

The percent inhibition of the test compound was calculated by assuming the sample with no test compound as 0% inhibition and the sample with no enzyme as 100% inhibition, and the percent inhibitions at different concentrations of the test compound were plotted to obtain a concentration-dependent curve. The IC$_{50}$ value, which is the concentration of the test compound that resulted in 50% inhibition, was determined from the curve.

The results obtained by the test method described the above Test Example 3 are shown in the following tables.

A:IC50<10 nM, B:10 nM≤IC50<100 nM, C:100 nM≤IC50<1000 nM, D:1000 nM≤IC50

TABLE 99

| Example No | Inhibitor activity |
|---|---|
| I-0001 | D |
| I-0002 | C |
| I-0003 | C |
| I-0004 | D |
| I-0005 | D |
| I-0006 | D |
| I-0007 | D |
| I-0008 | C |
| I-0009 | B |
| I-0010 | C |
| I-0011 | D |
| I-0012 | B |
| I-0013 | C |
| I-0014 | C |
| I-0015 | B |
| I-0016 | C |
| I-0017 | C |
| I-0018 | C |
| I-0019 | D |
| I-0020 | C |
| I-0021 | C |
| I-0022 | B |
| I-0023 | B |
| I-0024 | A |
| I-0025 | C |
| I-0026 | B |
| I-0027 | C |
| I-0028 | B |
| I-0029 | C |
| I-0030 | C |
| I-0031 | C |
| I-0032 | C |
| I-0033 | B |
| I-0034 | C |
| I-0035 | B |
| I-0036 | C |
| I-0037 | C |
| I-0038 | C |
| I-0039 | B |
| I-0040 | B |
| I-0041 | B |
| I-0042 | A |
| I-0043 | B |
| I-0044 | A |
| I-0045 | A |
| I-0046 | B |
| I-0047 | C |

TABLE 99-continued

| Example No | Inhibitor activity |
|---|---|
| I-0048 | A |
| I-0049 | C |
| I-0050 | C |
| I-0051 | A |
| I-0052 | A |
| I-0053 | B |
| I-0054 | C |
| I-0055 | A |
| I-0056 | A |
| I-0057 | B |
| I-0058 | D |
| I-0059 | B |
| I-0060 | B |
| I-0061 | B |
| I-0062 | B |
| I-0063 | A |
| I-0064 | A |
| I-0065 | B |
| I-0066 | D |
| I-0067 | C |
| I-0068 | D |
| I-0069 | B |
| I-0070 | A |
| I-0071 | A |
| I-0072 | A |
| I-0073 | A |
| I-0074 | D |
| I-0075 | D |
| I-0076 | C |
| I-0077 | C |
| I-0078 | D |
| I-0079 | B |
| I-0080 | B |
| I-0081 | B |
| I-0082 | C |
| I-0083 | D |
| I-0084 | B |
| I-0085 | B |
| I-0086 | C |
| I-0087 | B |
| I-0088 | B |
| I-0089 | B |
| I-0090 | B |
| I-0091 | D |
| I-0092 | C |
| I-0093 | B |
| I-0094 | B |
| I-0095 | B |
| I-0096 | C |
| I-0097 | C |
| I-0098 | B |
| I-0099 | D |
| I-0100 | C |
| I-0101 | B |
| I-0102 | C |
| I-0103 | B |
| I-0104 | C |
| I-0105 | C |
| I-0106 | D |
| I-0107 | D |
| I-0108 | D |
| I-0109 | B |
| I-0110 | D |
| I-0111 | B |
| I-0112 | B |
| I-0113 | B |
| I-0114 | B |
| I-0115 | D |
| I-0116 | B |
| I-0117 | B |
| I-0118 | B |
| I-0119 | B |
| I-0120 | A |

TABLE 100

| Example No | Inhibitor activity |
|---|---|
| I-0121 | C |
| I-0122 | C |
| I-0123 | B |
| I-0124 | B |
| I-0125 | B |
| I-0126 | C |
| I-0127 | C |
| I-0128 | B |
| I-0129 | C |
| I-0130 | B |
| I-0131 | B |
| I-0132 | C |
| I-0133 | B |
| I-0134 | A |
| I-0135 | B |
| I-0136 | C |
| I-0137 | B |
| I-0138 | A |
| I-0139 | B |
| I-0140 | C |
| I-0141 | B |
| I-0142 | C |
| I-0143 | B |
| I-0144 | B |
| I-0145 | B |
| I-0146 | C |
| I-0147 | B |
| I-0148 | C |
| I-0149 | C |
| I-0150 | D |
| I-0151 | C |
| I-0152 | B |
| I-0153 | B |
| I-0154 | B |
| I-0155 | C |
| I-0156 | C |
| I-0157 | B |
| I-0158 | B |
| I-0159 | A |
| I-0160 | B |
| I-0161 | C |
| I-0162 | C |
| I-0163 | C |
| I-0164 | C |
| I-0165 | C |
| I-0166 | C |
| I-0167 | C |
| I-0168 | C |
| I-0169 | C |
| I-0170 | B |
| I-0171 | C |
| I-0172 | C |
| I-0173 | C |
| I-0174 | C |
| I-0175 | C |
| I-0176 | C |
| I-0177 | C |
| I-0178 | C |
| I-0179 | B |
| I-0180 | C |
| I-0181 | B |
| I-0182 | C |
| I-0183 | B |
| I-0184 | C |
| I-0185 | C |
| I-0186 | C |
| I-0187 | C |
| I-0188 | C |
| I-0189 | C |
| I-0190 | C |
| I-0191 | C |
| I-0192 | B |
| I-0193 | C |
| I-0194 | C |
| I-0195 | A |
| I-0196 | B |
| I-0197 | C |

TABLE 100-continued

| Example No | Inhibitor activity |
|---|---|
| I-0198 | C |
| I-0199 | B |
| I-0200 | D |
| I-0201 | C |
| I-0202 | C |
| I-0203 | C |
| I-0204 | C |
| I-0205 | B |
| I-0206 | A |
| I-0207 | D |
| I-0208 | D |
| I-0209 | B |
| I-0210 | B |
| I-0211 | B |
| I-0212 | C |
| I-0213 | C |
| I-0214 | C |
| I-0215 | B |
| I-0216 | C |
| I-0217 | B |
| I-0218 | C |
| I-0219 | C |
| I-0220 | B |
| I-0221 | B |
| I-0222 | C |
| I-0223 | C |
| I-0224 | C |
| I-0225 | A |
| I-0226 | C |
| I-0227 | A |
| I-0228 | A |
| I-0229 | C |
| I-0230 | C |
| I-0231 | C |
| I-0232 | A |
| I-0233 | B |
| I-0234 | B |
| I-0235 | A |
| I-0236 | D |
| I-0237 | C |
| I-0238 | C |
| I-0239 | D |
| I-0240 | C |

TABLE 101

| Example No | Inhibitor activity |
|---|---|
| I-0241 | D |
| I-0242 | C |
| I-0243 | B |
| I-0244 | B |
| I-0245 | A |
| I-0246 | D |
| I-0247 | D |
| I-0248 | B |
| I-0249 | C |
| I-0250 | B |
| I-0251 | B |
| I-0252 | B |
| I-0253 | C |
| I-0254 | B |
| I-0255 | D |
| I-0256 | B |
| I-0257 | B |

TABLE 102

| Example No | Inhibitor Activity |
|---|---|
| I-0258 | D |
| I-0259 | D |
| I-0260 | D |
| I-0261 | C |
| I-0262 | C |
| I-0263 | A |
| I-0264 | D |
| I-0265 | B |
| I-0266 | A |
| I-0267 | A |
| I-0268 | D |
| I-0269 | B |
| I-0270 | B |
| I-0271 | A |
| I-0272 | B |
| I-0273 | B |
| I-0274 | B |
| I-0275 | B |
| I-0276 | B |
| I-0277 | B |
| I-0278 | B |
| I-0279 | A |
| I-0280 | B |
| I-0281 | C |
| I-0282 | A |
| I-0283 | C |
| I-0284 | B |
| I-0285 | B |
| I-0286 | B |
| I-0287 | B |
| I-0288 | B |
| I-0289 | C |
| I-0290 | A |
| I-0291 | B |
| I-0292 | B |
| I-0293 | B |
| I-0294 | B |
| I-0295 | B |
| I-0296 | C |
| I-0297 | B |
| I-0298 | C |
| I-0299 | A |
| I-0300 | B |
| I-0301 | B |
| I-0302 | B |
| I-0303 | B |
| I-0304 | B |
| I-0305 | B |
| I-0306 | B |
| I-0307 | C |
| I-0308 | B |
| I-0309 | B |
| I-0310 | B |
| I-0311 | C |
| I-0312 | C |
| I-0313 | C |
| I-0314 | B |
| I-0315 | D |
| I-0316 | B |
| I-0317 | B |
| I-0318 | B |
| I-0319 | C |
| I-0320 | C |
| I-0321 | B |
| I-0322 | B |
| I-0323 | B |
| I-0324 | B |
| I-0325 | B |
| I-0326 | B |
| I-0327 | B |
| I-0328 | B |
| I-0329 | B |
| I-0330 | B |
| I-0331 | A |
| I-0332 | B |
| I-0333 | B |
| I-0334 | B |

TABLE 102-continued

| Example No | Inhibitor Activity |
|---|---|
| I-0335 | B |
| I-0336 | B |
| I-0337 | B |
| I-0338 | B |
| I-0339 | B |
| I-0340 | C |
| I-0341 | C |
| I-0342 | B |
| I-0343 | C |
| I-0344 | B |
| I-0345 | B |
| I-0346 | B |
| I-0347 | B |
| I-0348 | B |
| I-0349 | B |
| I-0350 | B |
| I-0351 | C |
| I-0352 | B |
| I-0353 | B |
| I-0354 | B |
| I-0355 | C |
| I-0356 | A |
| I-0357 | C |
| I-0358 | B |
| I-0359 | B |
| I-0360 | C |
| I-0361 | B |
| I-0362 | B |
| I-0363 | B |
| I-0364 | C |
| I-0365 | C |
| I-0366 | C |
| I-0367 | B |
| I-0368 | B |
| I-0369 | C |
| I-0370 | C |
| I-0371 | D |
| I-0372 | B |
| I-0373 | B |

TABLE 103

| Example No | Inhibitor Activity |
|---|---|
| I-0374 | B |
| I-0375 | A |
| I-0376 | B |
| I-0377 | B |
| I-0378 | A |
| I-0379 | A |
| I-0380 | B |
| I-0381 | B |
| I-0382 | B |
| I-0383 | B |
| I-0384 | D |
| I-0385 | B |
| I-0386 | B |
| I-0387 | B |
| I-0388 | D |
| I-0389 | B |
| I-0390 | B |
| I-0391 | B |
| I-0392 | B |
| I-0393 | B |
| I-0394 | A |
| I-0395 | C |
| I-0396 | D |
| I-0397 | B |
| I-0398 | C |
| I-0399 | B |
| I-0400 | B |
| I-0401 | B |
| I-0402 | D |
| I-0403 | B |
| I-0404 | B |
| I-0405 | B |
| I-0406 | B |
| I-0407 | B |
| I-0408 | C |
| I-0409 | C |
| I-0410 | A |
| I-0411 | C |
| I-0412 | A |
| I-0413 | B |
| I-0414 | A |
| I-0415 | A |
| I-0416 | B |
| I-0417 | B |
| I-0418 | B |
| I-0419 | B |
| I-0420 | C |
| I-0421 | A |
| I-0422 | B |
| I-0423 | B |
| I-0424 | B |
| I-0425 | B |
| I-0426 | D |
| I-0427 | B |
| I-0428 | B |
| I-0429 | A |
| I-0430 | B |
| I-0431 | B |
| I-0432 | B |
| I-0433 | B |
| I-0434 | B |
| I-0435 | B |
| I-0436 | C |
| I-0437 | B |
| I-0438 | B |
| I-0439 | A |
| I-0440 | B |
| I-0441 | C |
| I-0442 | B |
| I-0443 | D |
| I-0444 | A |
| I-0445 | A |
| I-0446 | B |
| I-0447 | C |
| I-0448 | C |
| I-0449 | C |
| I-0450 | B |
| I-0451 | B |
| I-0452 | B |
| I-0453 | D |
| I-0454 | C |
| I-0455 | B |
| I-0456 | B |
| I-0457 | A |
| I-0458 | A |
| I-0459 | B |
| I-0460 | D |
| I-0461 | B |
| I-0462 | B |
| I-0463 | B |
| I-0464 | B |
| I-0465 | A |
| I-0466 | B |
| I-0467 | B |
| I-0468 | B |
| I-0469 | C |
| I-0470 | A |
| I-0471 | B |
| I-0472 | D |
| I-0473 | B |
| I-0474 | B |
| I-0475 | B |
| I-0476 | D |
| I-0477 | C |
| I-0478 | C |
| I-0479 | B |

TABLE 103-continued

| Example No | Inhibitor Activity |
|---|---|
| I-0480 | B |
| I-0481 | B |
| I-0482 | A |
| I-0483 | C |
| I-0484 | B |
| I-0485 | B |
| I-0486 | C |
| I-0487 | C |
| I-0488 | C |
| I-0489 | B |
| I-0490 | C |
| I-0491 | C |
| I-0492 | B |
| I-0493 | D |
| I-0494 | A |
| I-0495 | B |
| I-0496 | B |
| I-0497 | B |
| I-0498 | C |
| I-0499 | C |
| I-0500 | B |
| I-0501 | B |

Test Example 4

CYP Inhibition Test

Using commercially available pooled human hepatic microsome, the compound was tested to assess inhibitory effect on the typical substrate metabolism reactions of human main five CYP enyme forms (CYP1A2, 2C9, 2C19, 2D6, 3A4), specifically, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6) terfenedine hydroxylation (CYP3A4).

The reaction conditions were as follows.
Substrates:
 0.5 μmol/L ethoxyresorufin (CYP1A2),
 100 μmol/L tolbutamide
 50 μmol/L S-mephenitoin (CYP2C19),
 5 μmol/L dextromethorphan (CYP2D6),
 1 μmol/L terfenadine (CYP3A4);
Reaction Time: 15 minutes;
Reaction Temperature: 37° C.;
Enzyme: pooled human hepatic microsome 0.2 mg protein/mL;
Concentration of Test Compound: 1, 5, 10, 20 μmol/L (four points).

A test sample, which contains the substrate, humen hepatic microsome and test compound at the amounts as described above in 50 mM Hepes buffer, was added to a 96-well plate. The cofoator NADPH was added to initiate metabolism reaction. After the incubation at 37° C. for 15 minutes, a methanol/acetonitrile=1/1 (v/v) solution was added to stop the reaction. After centrifugation at 3000 rpm for 15 minutes, resotufin (CYP1A2 metabolite) in the supernatant was quantified by fluorescent multilabel counter. Tributamide hydroxide (CYP2C9 metabolite), mephenyloin 4' hydroxide (CYP2C19 metabolite), dextromethorphan (CYP2D6 metabolite) and terfenadine alcohol (CYP3A4 metabolite) were determined by LC/MS/MS.

Only DMSO, which was the solvent for the test compound, was added to the reaction system as the control (100%). For each concentration of the test compound, the remaining activity (%) was calculated, and the IC50 was calculated by reverse presumption by a logistic model using the concentration and the inhibition rate.

Test Example 5

Evaluation of Metabolism Stability

Metabolism stability evaluation by human hapatic microsomes: To a tris-HCl buffer (pH7.4) was added NADPH (final concentration 1 mM, the case of oxi dative matabolism), human hepatic microsomes (final concentration 0.5 mg protein/ml) and the test compound (final concentration 2 μM), the mixture was reacted at 37° C. for 0 minute and 30 minutes. In the case of glucuronidation, UDPGA (final concentration 5 mM) was added instead of NADPH. After the reaction was stopped by adding double volume of the reaction solution of acetonitrile/methanol=1/1 (v/v), the compound into the centrifugal supernatant was measured by HP LC. The loss amount due to metabolic reactions was calculated by comparing between value of 0 minute and 30 minute to confirm the metabolic stability of the compound of the present invention.

Test Example 6

Powder Solubility Test

Appropriate quantity of the test compound was put in a suitable container and 200 μL of JP-1 solution (water was added to 2.0 g of sodium chloride and 7.0 mL of hydrochloric acid to reach 1000 mL), JP-2 solution (500 mL of water was added to 500 mL of phosphate buffer with a pH6.8), or 20 mmol/L TCA (sodium taurocholate)/JP-2 solution (water was added to 1.08 g of TCA to reach 1.00 mL) was independently added to each container. When total amount was dissolved after adding the test reagent, the test compound was added appropriately. The container was sealed and shaken at 37° C. for 1 hour. The solution was filtered and 100 μL of methanol was added to 100 μL of each filtrate to dilute two-fold. The dilution rate was changed as necessary. After checking that there is no bubble and deposit, the container was sealed and shaken. The test compound was measured using HPLC by absolute calibration curve method.

Test Example 7

DMSO Method, Solubility Test

The solubility of the compound o the present invention was determined under 1% DMSO addition condition. A 10 mmol/L solution of the compound was prepared with DMSO, and 2 μL of the solution of the compound of the present invention was added, respectively, to 198 μL of JP-1 solution or JP-2 solution. After leaving to stand at 25° C. for 16 hours, the mixture was filtered under reduced pressure. The filtrate was ten-fold diluted with methanol/water=1/1 (v/v) and the compound concentration in the filtrate was measured with LC/MS by the absolute calibration method.
Compound II-0054 JP 1: >50 μmol/L, JP2: >50 μmol/L
Compound II-0076 JP 1: >50 μmol/L, JP2: >50 μmol/L
Compound II-0168 JP 1: 48.3 μmol/L, JP2: >50 μmol/L
Compound II-0175 JP 1: 45.7 μmol/L, JP2: >50 μmol/L
Compound II-0208 JP 1: 49.9 μmol/L, JP2: >50 μmol/L

Test Example 8

BA Test

Material and method for experiments to evaluate oral absorption
(1) Experimental animals: mice or SD rats were used.
(2) Rearing condition: mice or SD rats were allowed free access to solid feed and sterilized tap water.
(3) Setting of dosage and grouping: Oral administration and intravenous administration were performed with the predetermined dosage. Grouping was set as below. (Dosage was changed per compound)
Oral administration 1 to 30 mg/kg (n=2 to 3)
Intravenous administration 0.5 to 10 mg/kg (n=2 to 3)
(4) Preparation of administration solutions: Oral administration was performed as solution or suspension. Intravenous administration was performed after solubilization.
(5) Routes of administration: Oral administration was performed mandatory into the stomach by oral sonde. Intravenous administration was performed from caudal vein by syringes with needle.
(6) Evaluation items: Blood was collected serially and concentration of the compound of the present invention was calculated from AUCs of the oral administration group and the intravenous administration group.
(7) Statistical analysis: About transition of concentration of the compound of the present invention in plasma, the area under the plasma concentration versus time curve (AUC) was calculated by non-linear least-squares method program, Win Nonlin (registered trademark), and bioavailability (BA) of the compound of the present, invention was calculated from AUCs of the oral administration group and the intravenous administration group.

Test Example 9

Metabolism Stability Test

Using commercially available pooled hum an hepatic microsomes, the compound of the present invention was reacted for a constant time, and a remaining rate was calculated by comparing a reacted sample and an unreacted sample, thereby, a degree of metabolism in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1(v/v), mixed an centrifuged at 3000 rpm for 15 minutes. The compound of the present invention in the supernatant was quantified by LC/MS/MS, and a remaining amount of the compound o the present invention after the reaction was calculated, letting the compound amount at 0 minute reaction time to be 100%. Indeed, hydrolysis reaction was performed in the presence of 5 mM UDP-glucuronic acid instead of NADPH, followed by similar operation.

Test Example 10

CYP3A4 Fluorescent MBI Test

The CYP3A4 fluorescent MBI test is a test of investigating enhancement of CYP3A4 inhibition of a compound of the present invention by a metabolism reaction, and the test was performed using, as CYP3A4 enzyme expressed in *Escherichia coli* and employing, as an index, a reaction in which 7-benzyloxytrifluoromethylcoumarin (7-BFC) is debenzylated by the CYP3A4 enzyme to produce a metabolite, 7-hydroxytrifluoromethylcouomarin (7-HFC) emitting fluorescent light.

The reaction conditions were as follows: substrate, 5.6 μmol/L 7-BFC; pre-reaction time, 0 or 30 minutes; reaction time, 15 minutes; reaction temperature, 25° C. (room temperature); CYP3A4 content (expressed in *Escherichia* pre-reaction 62.5 pmol/mL, at reaction 6.25 pmol/mL (at 10-fold dilution); test drug concentration of the compound of the present invention, 0.625, 1.25, 2.5, 5, 10, 20 μmol/L (6 points).

An enzyme in a K-Pi buffer (pH7.4) and a solution of the solution of the present invention as a pre-reaction solution were added to a 96-well plate at the above composition of the pre-reaction, a part of it was transferred to another 96-well plate so that it was 1/10 diluted with a substrate and a K-Pi buffer, NADPH as a co-factor was added to initiate a reaction as an index (without preincubation) and, after a predetermined time of a reaction, acetonitrile/0.5 mol/L Tris(trishydroxyaminomethane)=4/1(V/V) was added to stop the reaction. In addition, NADPH was added to a remaining preincubation solution to initiate a preincubation (with preincubation) and, after a predetermined time of a preincubation, a part was transferred to another plate so that it was 1/10 diluted with a substrate and a K-Pi buffer to initiate a reaction as an index. After a predetermined time of a reaction, acetonitrile/0.5 mol/L Tris(trishydroxyaminomethane)=4/1(V/V) was added to stop the reaction. For the plate on which each index reaction had been performed, a fluorescent value of 7-HFC which is a metabolite was measured with a fluorescent plate reader. (Ex=420 nm, Em=535 nm)

Addition of only DMSO which is a solvent dissolving the compound of the present invention to a reaction system was adopted as a control (100%), remaining activity (%) was calculated at each concentration of the compound of the present invention added as the solution, and $IC_{50}$ was calculated by reverse-presumption by a logistic model using a concentration and an inhibition rate. When a difference between $IC_{50}$ value was 5 μmol/L or more, this was defined as (+) and, when the difference was 3 μmol/L or less, this was defined as (−).

Test Example 11

Fluctuation Ames Test

Mutagenicity of compounds of the present invention was evaluated.

20 μL of freezing-stored rat typhoid *bacillus* (*Salmonella typhimurium* TA98 strain, TA100 strain) is inoculated on 10 mL of a liquid nutrient medium (2.5% Oxoid nutrient broth No. 2), and this was cultured before shaking at 37° C. for 10 hours. 9 mL of a bacterial solution of the TA98 strain was centrifuged (2000×g, 10 minutes) to remove a culturing solution. The bacteria was suspended in 9 mL of a Micro F buffer ($K_2HPO_4$: 3.5 g/L, $KH_2PO_1$: 1 g/L, $(NH_4)_2SO_1$: 1 g/L, trisodium citrate dehydrate: 0.25 g/L, $MgSO_4 \cdot 7H_2O$: 0.1 g/L), the suspension was added to 1.10 mL of an Exposure medium (Micro F buffer containing Biotin: 8 μg/mL, histidine: 0.2 μg/mL, glucose: 8 mg/mL). The TA100 strain was added to 120 mL of the Exposure medium relative to 3.16 mL of the bacterial solution to prepare a test bacterial solution. Each 12 μL of DMSO solution of a compound of the present invention (several stage dilution from maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under the non-metabolism activating condition, 40 μg/mL of 2-aminoanthracene DMSO solution for the TA98 strain, 20 μg/mL of 2-aminoanthracene DMSO solution for the TA100 strain under the metabolism activating condition as a positive control, and 588 μL of the test bacterial solution (a mixed solution of 498 μl of the test bacterial solution and 90 μL of S9 mix under the metabolism activating condition) were mixed, and this was shaking-cultured at 37° C. for 90 minutes. 460 μL of the bacterial solution exposed to a compound of the present invention was mixed with 2300 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which has obtained the proliferation ability by mutation of an amino acid (histidine) synthesizing enzyme gene turns from purple to yellow due to a pH change, the bacterium proliferation well which has turned to yellow in 48 wells per dose is counted, and was assessed by comparing with a negative control group. (−) means that mutagenicity is negative and (+) is positive.

Test Example 12 hERG Test

For the purpose of assessing risk of an electrocardiogram QT interval prolongation of the compound of the present invention, effects of the compound of the present invention on delayed rectifier K+ current ($I_{Kr}$), which plays an important role in the ventricular repolarization process, was studied using HEK293 cells expressing human ether-a-go-go related gene (hERG) channel.

After a cell was retained at a membrane potential of −80 mV by whole cell patch clamp method using an automated patch clamp system (PatchXpress 7000 A, AxonInstruments Inc.), $I_{Kr}$ induced by depolarization pulse stimulation at +40 mV for 2 seconds further reporlarization pulse stimulation at −50 mV for 2 seconds, is recorded. After the generated current was stabilized, extracellular solution (NaCl: 135 mmol/L, KCl: 5.4 mmol/L, $NaH_2PO_4$: 0.3 mmol/L, $CaCl_2$, $2H_2O$: 1.8 mmol/L, $MgCl_2$ $6H_2O$: 1 mmol/L, Glucose: 10 mmol/L, HEPES (4-(2-hydroxyethyl)-1-piperazineethane-sulfonic acid, 4-(2-hydroxyethyl)-1-piperazinethanesulfonic acid): 10 mmol/L, pH=7.4), in which the compound of the present invention had been dissolved at an objective concentration, was applied to the cell at room temperature for 10 minutes.

From the recording $I_{Kr}$, an absolute value of the tail peak current was measured based on the current value at the resting membrane potential using analysis software (DataXpress ver.1, Molecular Devices Corporation). Further, the % inhibition relative to the tail peak current before application of the compound of the present invention was calculated, and compared with the vehicle-applied group (0.1% dimethyl sulfoxide solution) to assess influence of the compound of the present invention on $I_{Kr}$.

FORMULATION EXAMPLES

The following Formulation Examples are only exemplified and not intended to limit the scope of the invention.

Formulation Example 1

Tablets

| Compound of formula (I) | 15 mg |
|---|---|
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

The above ingredients except calcium stearate are uniformly mixed and milled to granylate, and dried to obtain a suitable size of granules. Then, the granules are added with calcium stearate and compressed to form a tablet.

Formulation Examples 2

Capsules

| Compound of formula (I) | 10 mg |
|---|---|
| Magnesium stearate | 10 mg |
| Lactose | 80 mg |

The above ingredients are mixed uniformly to obtain powders or fine granules, which are then filled in a capsule.

Formulation Examples 3

Granules

| Compound of formula (I) | 30 g |
|---|---|
| Lactose | 265 g |
| Magnesium stearate | 5 g |

The above ingredients are mixed uniformaly and compressed. The compressed mixture is milled, granylated and sirved to obtain the desired size of granules.

INDUSTRIAL APPLICABILITY

The present invention is applicable in the pharmaceutical field, for example, in the development and production of medicaments for the treatment of fibrotic diseases.

The invention claimed is:
1. A compound of formula (Ia), or a pharmaceutically acceptable salt thereof:

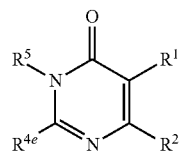

wherein:
R¹ is hydrogen,
R² is a group represented by the formula:

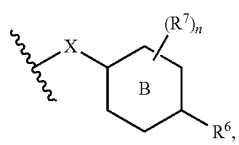

wherein:
X is a single bond or O,
Ring B is a benzene ring, a 6-membered aromatic heterocycle, a 6-membered non-aromatic carbocycle or a 6-membered non-aromatic heterocycle,
R⁶ is halogen, cyano, or substituted or unsubstituted alkyloxy,
R⁷ is each independently, substituted or unsubstituted alkyl, substituted or unsubstituted amino, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl or substituted or unsubstituted alkynylsulfonyl,
n is integer of 0 to 4,
R⁴ᵃ is substituted or unsubstituted alkyl,
R⁵ is a group represented by formula: R¹¹—(C(R¹⁰ᵃ)(R¹⁰ᵇ))m-,
wherein
R¹⁰ᵃ is each independently hydrogen, halogen or substituted or unsubstituted alkyl,
R¹⁰ᵇ is each independently hydrogen, halogen or substituted or unsubstituted alkyl,
m is integer of 1 to 6,
R¹¹ is substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl, or substituted or unsubstituted sulfamoyl.

2. The compound according to claim 1, wherein R⁴ᵃ is alkyl optionally substituted with one or more substitutent(s) selected from Substituent group α, alkenyl optionally substituted with one or more substitutent(s) selected from the Substituent group α, alkynyl optionally substituted with one or more substitutent(s) selected from the Substituent group α, alkylamino optionally substituted with one or more substitutent(s) selected from the Substituent group α, alkenylamino optionally substituted with one or more substitutent(s) selected from the Substituent group α, alkynylamino optionally substituted with one or more substitutent(s) selected from the Substituent group α, alkyloxy optionally substituted with one or more substitutent(s) selected from the Substituent group α, alkenyloxy optionally substituted with one or more substitutent(s) selected from the Substituent group α, alkynyloxy optionally substituted with one or more substitutent(s) selected from the Substituent group α, alkylthio optionally substituted with one or more substitutent(s) selected from the Substituent group α, alkenylthio optionally substituted with one or more substitutent(s) selected from the Substituent group α, or alkynylthio optionally substituted with one or more substitutent(s) selected from the Substituent group α,
wherein the one or more substitutent(s) of Substituent group α is selected from the group consisting of cyano, halogen, substituted or unsubstituted alkyloxy, substituted or unsubstituted alkenyloxy, substituted or unsubstituted alkynyloxy, substituted or unsubstituted non-aromatic carbocyclylalkyloxy, substituted or unsubstituted aromatic carbocyclylalkyloxy, substituted or unsubstituted non-aromatic heterocyclylalkyloxy and substituted or unsubstituted aromatic heterocyclylalkyloxy,
or its pharmaceutically acceptable salt.

3. The compound according to claim 1, wherein R¹¹ is substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl or substituted or unsubstituted sulfamoyl, or its pharmaceutically acceptable salt.

4. The compound according to claim 1, wherein R¹¹ is substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl or substituted or unsubstituted sulfamoyl, or its pharmaceutically acceptable salt.

5. The compound according to claim 1, wherein $R^{11}$ is carbamoyl optionally substituted with one or more substitutent(s) selected from the group consisting of substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl and substituted or unsubstituted non-aromatic heterocyclyl, or its pharmaceutically acceptable salt.

6. A pharmaceutical composition comprising the compound according to claim 1 or its pharmaceutically acceptable salt as an active ingredient and a pharmaceutical additive.

7. A method for the treatment of a disease related to autotaxin, comprising administering an effective amount of the compound according to claim 1 or a pharmaceutically acceptable salt thereof to a patient in need thereof,
wherein the disease is selected from the group consisting of urinary extraction failure, chronic kidney disease, renal fibrosis, interstitial pneumonitis, pulmonary fibrosis, scleroderma, pain, fibromyalgia, rheumatoid arthritis, angiogenesis, cancer, formation, growth and propagation of tumor, arteriosclerosis, an ocular disease, choroidal neovascularization, diabetic retinopathy, an inflammatory disease, arthritis, neurodegeneration, restenosis, wound healing, transplant rejection and endometriosis.

8. A pharmaceutical composition comprising the compound according to claim 2 or its pharmaceutically acceptable salt as an active ingredient and a pharmaceutical additive.

9. A pharmaceutical composition comprising the compound according to claim 3 or its pharmaceutically acceptable salt as an active ingredient and a pharmaceutical additive.

10. A pharmaceutical composition comprising the compound according to claim 4 or its pharmaceutically acceptable salt as an active ingredient and a pharmaceutical additive.

11. A pharmaceutical composition comprising the compound according to claim 5 or its pharmaceutically acceptable salt as an active ingredient and a pharmaceutical additive.

12. A method for the treatment of a disease related to autotaxin, comprising administering an effective amount of the compound according to claim 2 or a pharmaceutically acceptable salt thereof to a patient in need thereof,
wherein the disease is selected from the group consisting of urinary extraction failure, chronic kidney disease, renal fibrosis, interstitial pneumonitis, pulmonary fibrosis, scleroderma, pain, fibromyalgia, rheumatoid arthritis, angiogenesis, cancer, formation, growth and propagation of tumor, arteriosclerosis, an ocular disease, choroidal neovascularization, diabetic retinopathy, an inflammatory disease, arthritis, neurodegeneration, restenosis, wound healing, transplant rejection and endometriosis.

13. A method for the treatment of a disease related to autotaxin, comprising administering an effective amount of the compound according to claim 3 or a pharmaceutically acceptable salt thereof to a patient in need thereof,
wherein the disease is selected from the group consisting of urinary extraction failure, chronic kidney disease, renal fibrosis, interstitial pneumonitis, pulmonary fibrosis, scleroderma, pain, fibromyalgia, rheumatoid arthritis, angiogenesis, cancer, formation, growth and propagation of tumor, arteriosclerosis, an ocular disease, choroidal neovascularization, diabetic retinopathy, an inflammatory disease, arthritis, neurodegeneration, restenosis, wound healing, transplant rejection and endometriosis.

14. A method for the treatment of a disease related to autotaxin, comprising administering an effective amount of the compound according to claim 4 or a pharmaceutically acceptable salt thereof to a patient in need thereof,
wherein the disease is selected from the group consisting of urinary extraction failure, chronic kidney disease, renal fibrosis, interstitial pneumonitis, pulmonary fibrosis, scleroderma, pain, fibromyalgia, rheumatoid arthritis, angiogenesis, cancer, formation, growth and propagation of tumor, arteriosclerosis, an ocular disease, choroidal neovascularization, diabetic retinopathy, an inflammatory disease, arthritis, neurodegeneration, restenosis, wound healing, transplant rejection and endometriosis.

15. A method for the prevention or treatment of a disease related to autotaxin, comprising administering an effective amount of the compound according to claim 5 or a pharmaceutically acceptable salt thereof to a patient in need thereof,
wherein the disease is selected from the group consisting of urinary extraction failure, chronic kidney disease, renal fibrosis, interstitial pneumonitis, pulmonary fibrosis, scleroderma, pain, fibromyalgia, rheumatoid arthritis, angiogenesis, cancer, formation, growth and propagation of tumor, arteriosclerosis, an ocular disease, choroidal neovascularization, diabetic retinopathy, an inflammatory disease, arthritis, neurodegeneration, restenosis, wound healing, transplant rejection and endometriosis.

16. A method for the treatment of a disease related to autotaxin, comprising administering an effective amount of the compound according to claim 1 or a pharmaceutically acceptable salt thereof to a patient in need thereof,
wherein the disease is selected from the group consisting of urinary extraction failure, interstitial lung disease, fibroid lung, renal fibrosis, hepatic fibrosis, pachyderma, pain, fibromyalgia syndrome, arthritis, rheumatism, disseminated sclerosis and endometriosis.

* * * * *